(12) United States Patent
Taramino et al.

(10) Patent No.: US 9,115,203 B2
(45) Date of Patent: Aug. 25, 2015

(54) PLANTS WITH ALTERED ROOT ARCHITECTURE, RELATED CONSTRUCTS AND METHODS INVOLVING GENES ENCODING EXOSTOSIN FAMILY POLYPEPTIDES AND HOMOLOGS THEREOF

(75) Inventors: Graziana Taramino, Wilmington, DE (US); Hajime Sakai, Newark, DE (US); Scott V Tingey, Rockdale, TX (US); Stanley Luck, Wilmington, DE (US); Dwight Tomes, Grimes, IA (US); Xiaomu Niu, Johnston, IA (US)

(73) Assignees: E I DU PONT DE NEMOURS AND COMPANY, Wilmington, DE (US); PIONEER HI-BRED INTERNATIONAL INC, Johnston, IA (US)

( * ) Notice: Subject to any disclaimer, the term of this patent is extended or adjusted under 35 U.S.C. 154(b) by 1345 days.

(21) Appl. No.: 12/908,397

(22) Filed: Oct. 20, 2010

(65) Prior Publication Data

US 2011/0035822 A1  Feb. 10, 2011

Related U.S. Application Data

(63) Continuation of application No. 12/261,411, filed on Oct. 30, 2008, now abandoned.

(60) Provisional application No. 60/984,028, filed on Oct. 31, 2007.

(51) Int. Cl.
  *C12N 15/82* (2006.01)
  *C07K 14/415* (2006.01)

(52) U.S. Cl.
  CPC .......... *C07K 14/415* (2013.01); *C12N 15/8201* (2013.01); *C12N 15/8261* (2013.01); *C12N 15/8271* (2013.01)

(58) Field of Classification Search
  None
  See application file for complete search history.

(56) References Cited

U.S. PATENT DOCUMENTS

| | | | |
|---|---|---|---|
| 6,344,601 | B1 | 2/2002 | Chug et al. |
| 7,214,786 | B2 | 5/2007 | Kovalic et al. |
| 2004/0016432 | A1 | 1/2004 | Genger et al. |
| 2004/0214272 | A1 | 10/2004 | La Rosa et al. |
| 2004/0216190 | A1 | 10/2004 | Kovalic |
| 2005/0057473 | A1 | 3/2005 | Hsu et al. |
| 2005/0059154 | A1 | 3/2005 | Beeckman et al. |
| 2005/0223429 | A1 | 10/2005 | Frankard et al. |

FOREIGN PATENT DOCUMENTS

| | | |
|---|---|---|
| JP | 2005185101 | 7/2005 |
| WO | 2004106531 A1 | 12/2004 |

OTHER PUBLICATIONS

Kano-Murakami et al (1993, FEBS 334:365-368).*
Bowie et al, Science 247:1306-1310, 1990.*
McConnell et al, Nature 411 (6838):709-713, 2001.*
EBI Database Accession No. AQD60511, Rice cDNA-encoded protein SEQ ID No. 54370, XP002512140, Jun. 12, 2008.
Database WPI Week 200558, Thomas Scientific, London, AN 2005-566181, XP002512141, Jul. 14, 2005.
Gabriela C. Pagnussat et al., Genetic and molecular identification of genes required for female gametophyle development and fuction in *Arabidopsis*, Development (Cambridge), Feb. 3, 2005, vol. 132, No. 3, pp. 603-614.
Michael Madson et al., The MUR3 Gene of *Arabidopsis* Encodes a Xyloglucan Galactosyltransferase, The Plant Cell, Jul. 2003, vol. 15, No. 7, pp. 1662-1670.
Lopez-Bucio et al., The Role of Nutrient Availability in Regulating Root Architecture, Current Opinion in Plant Biology, 2003, vol. 6:280-287.
J. E. Malamy, Intrinsic and Environmental Response Pathways That Regulate Root System Architecture, Plant Cell and Environment, 2005, vol. 28:67-77.
Hochholdinger et al., Genetic Dissection of Root Formation in Maize (*Zea mays*) Reveals Root-Type Specific Developmental Programmes, Annals of Botany, 2004, vol. 93;359-368.
National Center for Biotechnology Information General Identifier No. 15228598, May 22, 2008.
National Center for Biotechnology Information General Identifier No. 115476598, Feb. 14, 2008, H. Ohyanagi et al., The Rice Annotation Project Database (RAP-DB): Hub for *Oryza sativa* Ssp. Japonica Genome Information.
National Center for Biotechnology Information General Identifier No. 115487106, Feb. 14, 2008, H. Ohyanagi et al., The Rice Annotation Project Database (RAP-DB): Hub for *Oryza Sativa* Ssp. Japonica Genome Information.
National Center for Biotechnology Information General Identifier No. 115452759, Feb. 14, 2008, H. Ohyanagi et al., The Rice Annotation Project Database (RAP-DB): Hub for *Oryza Sativa* Ssp. Japonica Genome Information.
National Center for Biotechnology Information General Identifier No. 15441893, Feb. 14, 2008, H. Ohyanagi et al., The Rice Annotation Project Database (RAP-DB); Hub for *Oryza sativa* Ssp. Japonica Genome Information.
Pritchard et al., Inference of Population Structure Using Multilocus Genotype Data, Genetics, 2000, vol. 155:945-959.
U.S. Appl. No. 10/489,500, filed Sep. 30, 2004.
Press et al., Numerical Recipes in C: The Art of Scientific Computing, Second Edition, 2002, Cambridge University Press, New York, USA, pp. 620-628.

* cited by examiner

*Primary Examiner* — Stuart F Baum

(57) ABSTRACT

Isolated polynucleotides and polypeptides and recombinant DNA constructs particularly useful for altering root structure of plants, compositions (such as plants or seeds) comprising these recombinant DNA constructs, and methods utilizing these recombinant DNA constructs. The recombinant DNA construct comprises a polynucleotide operably linked to a promoter functional in a plant, wherein said polynucleotide encodes a polypeptide useful for altering plant root architecture.

14 Claims, 26 Drawing Sheets

Modified Hoagland's solutions -
16X concentrations for semi-hydroponics maize growth.

| Nutrient | 1 mM KNO$_3$ | 2 mM KNO$_3$ | 3 mM KNO$_3$ | 4 mM KNO$_3$ |
|---|---|---|---|---|
| KNO$_3$ | 16 mM | 32 mM | 48 mM | 64 mM |
| KCl | 48 mM | 32 mM | 16 mM | ----- |
| KH$_2$PO$_4$ | 11 mM | 11 mM | 11 mM | 11 mM |
| MgSO$_4$ | 16 mM | 16 mM | 16 mM | 16 mM |
| CaCl$_2 \cdot$2H$_2$O | 16 mM | 16 mM | 16 mM | 16 mM |
| Sprint 330 | 1.6 g/L | 1.6 g/L | 1.6 g/L | 1.6 g/L |
| H$_3$BO$_3$ | 24 μM | 24 μM | 24 μM | 24 μM |
| 5 mM MnCl$_2 \cdot$4H$_2$O | 8 μM | 8 μM | 8 μM | 8 μM |
| 5 mM ZnSO$_4 \cdot$7 H$_2$O | 8 M | 8 μM | 8 μM | 8 μM |
| 0.5 mM CuSO$_4 \cdot$5 H$_2$O | 800 nM | 800 nM | 800 nM | 800 nM |
| 0.5 mM H$_2$MoO$_4 \cdot$H$_2$O | 800 nM | 800 nM | 800 nM | 800 nM |

Dilute 16X with tap water and determine the pH of the final mixture.
Add 3-12 mL H$_2$SO$_4$ if the pH is above 6.5.
Optimum pH is 5.0 - 5.5

Fig. 18

The effect of different nitrate concentrations on the growth and development of Gaspe Bay Flint derived maize lines (see Example 10C).

| [nitrate] | root (g dwt) | shoot (g dwt) | total vegetative (g dwt) | ear & husk (g dwt) | tassel (g dwt) | tiller # | tiller (g dwt) |
|---|---|---|---|---|---|---|---|
| 1 week after emergence | | | | | | | |
| 1 mM | 0.070a | 0.105b | 0.175b | | | | |
| 2 mM | 0.073a | 0.137ab | 0.209ab | | | | |
| 3 mM | 0.056a | 0.120ab | 0.176ab | | | | |
| 4 mM | 0.074a | 0.157a | 0.231a | | | | |
| 2 weeks after emergence | | | | | | | |
| 1 mM | 0.331ab | 0.544c | 0.875c | | | | |
| 2 mM | 0.266b | 0.951b | 1.217b | | | | |
| 3 mM | 0.352a | 1.171a | 1.523a | | | | |
| 4 mM | 0.303ab | 1.209a | 1.512a | | | | |
| 3 weeks after emergence | | | | | | | |
| 1 mM | 0.757a | 1.283b | 2.040b | 0.379c | 0.239c | 0.8c | 0.080b |
| 2 mM | 0.785a | 2.033a | 2.819a | 0.718a | 0.363bc | 2.3 | 0.506a |
| 3 mM | 0.664a | 1.911a | 2.574a | 0.451bc | 0.403ab | 2.8ab | 0.441a |
| 4 mM | 0.845a | 2.129a | 2.974a | 0.650ab | 0.506a | 3.3a | 0.688a |
| 4 weeks after emergence | | | | | | | |
| 1 mM | 0.842b | 2.010b | 2.852b | 1.318b | 0.677b | * | * |
| 2 mM | 1.493a | 3.772a | 5.265a | 3.130a | 1.018a | * | * |
| 3 mM | 1.232ab | 3.563a | 4.795a | 3.060a | 0.875ab | * | * |
| 4 mM | 1.010b | 2.943a | 3.952a | 2.787a | 0.891ab | * | * |

* Tillers removed 3 weeks after emergence
Means with similar letters are not different by protected Least Significant Difference (LSD) (0.05)

PLANTS WITH ALTERED ROOT ARCHITECTURE, RELATED CONSTRUCTS AND METHODS INVOLVING GENES ENCODING EXOSTOSIN FAMILY POLYPEPTIDES AND HOMOLOGS THEREOF

CROSS REFERENCE TO RELATED APPLICATIONS

This application is a continuation of U.S. patent application Ser. No. 12/261,411, filed Oct. 30, 2008, which claims the benefit of U.S. Provisional Application No. 60/984,028, filed Oct. 31, 2007, the entire content of each is herein incorporated by reference.

REFERENCE TO SEQUENCE LISTING SUBMITTED ELECTRONICALLY

The official copy of the sequence listing is submitted electronically via EFS-Web as an ASCII formatted sequence listing with a file named "20141205_BB1572USCNT_SubstituteSequenceListing.txt" created on Dec. 5, 2014, and having a size of 405 kilobytes. The sequence listing contained in this ASCII formatted document is part of the specification and is herein incorporated by reference in its entirety.

FIELD OF THE INVENTION

The field of invention relates to plant breeding and genetics and, in particular, relates to recombinant DNA constructs useful in plants for altering root architecture.

BACKGROUND OF THE INVENTION

Water and nutrient availability limit plant growth in all but a very few natural ecosystems. They limit yield in most agricultural ecosystems. Plant roots serve important functions such as water and nutrient uptake, anchorage of the plants in the soil and the establishment of biotic interactions at the rhizosphere. Elucidation of the genetic regulation of plant root development and function is therefore the subject of considerable interest in agriculture and ecology.

The root system originates from a primary root that develops during embryogenesis. The primary root produces secondary roots, which in turn produce tertiary roots. All secondary, tertiary, quaternary and further roots are referred to as lateral roots. Many plants, including maize, can also produce shoot borne roots, from consecutive under-ground nodes (crown roots) or above-ground nodes (brace roots). Three major processes affect the overall architecture of the root system. First, cell division at the primary root meristem enables indeterminate growth by adding new cells to the root. Second, lateral root formation increases the exploratory capacity of the root system. Third, root-hair formation increases the total surface of primary and lateral roots (Lopez-Bucio et al., Current Opinion in Plant Biology (2003) 6:280-287). In maize mutants have been isolated that are missing only a subset of root types. In *Arabidopsis*, mutations in root patterning genes such as SHORTROOT and SCARECROW, which show developmental defects in primary and lateral roots, have been identified (J. E. Malamy, Plant, Cell and Environment (2005) 28: 67-77).

A number of maize mutants affected specifically in root development have been identified (Hochholdinger et al 2004, Annals of Botany 93:359-368). The recessive mutants rtcs and rt1 forms no, or fewer, crown and brace roots, while the primary and lateral roots are not affected. In the recessive mutants des21, lateral seminal roots and root hairs are absent. Root hairs are lacking in the recessive mutant rthl-3. The mutants lrt1 and rum1 are affected before lateral root initiation and mutants slr1 and slr2 are impaired in lateral root elongation. Intrinsic response pathways that determine root system architecture include hormones, cell cycle regulators and regulatory genes. Water stress and nutrient availability belong to the environmental response pathways that determine root system architecture.

U.S. Application No. 2005-57473 filed Feb. 14, 2005 (U.S. Patent Publication No. 2005/223429 A1 published Oct. 6, 2005) concerns the use of *Arabidopsis* cytokinin oxidase genes to alter cytokinin levels in plants and stimulate root growth.

U.S. Pat. No. 6,344,601 (issued Feb. 5, 2002) concerns the under- or overexpression of profilin in a plant cell to alter plant growth habit, e.g. a reduced root and root hair system, delay in the onset of flowering.

WO2004/US16432 (filed May 21, 2004 (WO2004/106531 published Dec. 9, 2004) concerns the use of methods to manipulate the growth rate and/or yield and/or architecture by over expression of cis-prenyltransferase.

U.S. Application No. 2004/489500 filed Sep. 30, 2004 (U.S. Patent Publication No. 2005/059154 A1 published Mar. 13, 2005) concerns methods to modify cell number, architecture and yield using over expression of the transcription factor E2F in plants.

Activation tagging can be utilized to identify genes with the ability to affect a trait. This approach has been used in the model plant species *Arabidopsis thaliana* (Weigel et al., 2000, Plant Physiol. 122:1003-1013).

Insertions of transcriptional enhancer elements can dominantly activate and/or elevate the expression of nearby endogenous genes.

SUMMARY OF THE INVENTION

The present invention includes:

In one embodiment, an isolated polynucleotide comprising a nucleic acid sequence encoding an EXST or EXST-like polypeptide having an amino acid sequence of at least 80% sequence identity, when compared to SEQ ID NO:15, or 31, or of at least 95%, when compared to SEQ ID NO:25, based on the Clustal V method of alignment, or a full complement of said nucleic acid sequence.

In a second embodiment, an isolated polynucleotide comprising a nucleic acid sequence encoding an EXST or EXST-like polypeptide having an amino acid sequence of at least 85% sequence identity, when compared to SEQ ID NO:15, or 31 based on the Clustal V method of alignment, or a full complement of said nucleic acid sequence.

In a third embodiment, an isolated polynucleotide comprising a nucleic acid sequence encoding an EXST or EXST-like polypeptide having an amino acid sequence of at least 90% sequence identity, when compared to SEQ ID NO:15, or 31 based on the Clustal V method of alignment, or a full complement of said nucleic acid sequence.

In a fourth embodiment, an isolated polynucleotide comprising a nucleic acid sequence encoding an EXST or EXST-like polypeptide having an amino acid sequence of at least 95% sequence identity, when compared to SEQ ID NO:15, or 31 based on the Clustal V method of alignment, or a full complement of said nucleic acid sequence.

In a fifth embodiment, an isolated polynucleotide comprising a nucleic acid sequence encoding an EXST or EXST-like polypeptide, wherein the amino acid sequence of the polypeptide comprises SEQ ID NO: 15, 25, or 31.

In a sixth embodiment, an isolated polynucleotide comprising a nucleic acid sequence encoding an EXST or EXST-like polypeptide, wherein the nucleic acid sequence comprises SEQ ID NO: 14, 24, or 30.

In further embodiments, vectors and recombinant constructs comprising any of the foregoing polynucleotides and cells comprising the recombinant constructs.

In additional embodiments, methods for transforming a cell with any of the foregoing the polynucleotides and for producing and regenerating a transformed plant comprising any of the foregoing polynucleotides.

In another embodiment, a plant comprising in its genome a recombinant DNA construct comprising a polynucleotide operably linked to at least one regulatory element, wherein said polynucleotide encodes a polypeptide having an amino acid sequence of at least 50% sequence identity, based on the Clustal V method of alignment, when compared to SEQ ID NO: 15, 17, 19, 21, 23, 25, 27, 29, 31, or 34, and wherein said plant exhibits altered root architecture when compared to a control plant not comprising said recombinant DNA construct.

In another embodiment, a plant comprising in its genome a recombinant DNA construct comprising:

(a) a polynucleotide operably linked to at least one regulatory element, wherein said polynucleotide encodes a polypeptide having an amino acid sequence of at least 50% sequence identity, based on the Clustal V method of alignment, when compared to SEQ ID NO: 15, 17, 19, 21, 23, 25, 27, 29, 31, or 34, or (b) a suppression DNA construct comprising at least one regulatory element operably linked to: (i) all or part of: (A) a nucleic acid sequence encoding a polypeptide having an amino acid sequence of at least 50% sequence identity, based on the Clustal V method of alignment, when compared to SEQ ID NO: 15, 17, 19, 21, 23, 25, 27, 29, 31, or 34, or (B) a full complement of the nucleic acid sequence of (b)(i)(A); or (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a EXST or EXST-like polypeptide, and wherein said plant exhibits an alteration of at least one agronomic characteristic when compared to a control plant not comprising said recombinant DNA construct.

In another embodiment, a method of altering root architecture in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO: 15, 17, 19, 21, 23, 25, 27, 29, 31, or 34; and (b) regenerating a transgenic plant from the regenerable plant cell after step (a), wherein the transgenic plant comprises in its genome the recombinant DNA construct and exhibits altered root architecture when compared to a control plant not comprising the recombinant DNA construct; and optionally, (c) obtaining a progeny plant derived from the transgenic plant, wherein said progeny plant comprises in its genome the recombinant DNA construct and exhibits altered root architecture when compared to a control plant not comprising the recombinant DNA construct.

In another embodiment, a method of evaluating root architecture in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO: 15, 17, 19, 21, 23, 25, 27, 29, 31, or 34, (b) regenerating a transgenic plant from the regenerable plant cell after step (a), wherein the transgenic plant comprises in its genome the recombinant DNA construct; and (c) evaluating root architecture of the transgenic plant compared to a control plant not comprising the recombinant DNA construct; and optionally, (d) obtaining a progeny plant derived from the transgenic plant, wherein the progeny plant comprises in its genome the recombinant DNA construct; and optionally, (e) evaluating root architecture of the progeny plant compared to a control plant not comprising the recombinant DNA construct.

In another embodiment, a method of evaluating root architecture in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO: 15, 17, 19, 21, 23, 25, 27, 29, 31, or 34 (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) evaluating root architecture of the progeny plant compared to a control plant not comprising the recombinant DNA construct.

In another embodiment, a method of determining an alteration of an agronomic characteristic in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO: 15, 17, 19, 21, 23, 25, 27, 29, 31, or 34 (b) regenerating a transgenic plant from the regenerable plant cell after step (a), wherein the transgenic plant comprises in its genome the recombinant DNA construct; and (c) determining whether the transgenic plant exhibits an alteration of at least one agronomic characteristic when compared to a control plant not comprising the recombinant DNA construct; and optionally, (d) obtaining a progeny plant derived from the transgenic plant, wherein the progeny plant comprises in its genome the recombinant DNA construct; and optionally, (e) determining whether the progeny plant exhibits an alteration of at least one agronomic characteristic when compared to a control plant not comprising the recombinant DNA construct.

In another embodiment, a method of determining an alteration of an agronomic characteristic in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO: 15, 17, 19, 21, 23, 25, 27, 29, 31, or 34 (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) determining whether the progeny plant exhibits an alteration of at least one agronomic characteristic when compared to a control plant not comprising the recombinant DNA construct.

In another embodiment, a method of determining an alteration of an agronomic characteristic in a plant, comprising:

(a) introducing into a regenerable plant cell a suppression DNA construct comprising at least one regulatory element operably linked to:
  (i) all or part of: (A) a nucleic acid sequence encoding a polypeptide having an amino acid sequence of at least 50% sequence identity, based on the Clustal V method of alignment, when compared to SEQ ID NO: 15, 17, 19, 21, 23, 25, 27, 29, 31, or 34, or (B) a full complement of the nucleic acid sequence of (b)(i)(A); or
  (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a EXST or EXST-like polypeptide;
(b) regenerating a transgenic plant from the regenerable plant cell after step (a), wherein the transgenic plant comprises in its genome the suppression DNA construct; and
(c) determining whether the transgenic plant exhibits an alteration of at least one agronomic characteristic when compared to a control plant not comprising the suppression DNA construct;
and optionally, (d) obtaining a progeny plant derived from the transgenic plant, wherein the progeny plant comprises in its genome the suppression DNA construct; and optionally, (e) determining whether the progeny plant exhibits an alteration of at least one agronomic characteristic when compared to a control plant not comprising the suppression DNA construct.

In another embodiment, a method of determining an alteration of an agronomic characteristic in a plant, comprising:

(a) introducing into a regenerable plant cell a suppression DNA construct comprising at least one regulatory element operably linked to:
  (i) all or part of: (A) a nucleic acid sequence encoding a polypeptide having an amino acid sequence of at least 50% sequence identity, based on the Clustal V method of alignment, when compared to SEQ ID NO: 15, 17, 19, 21, 23, 25, 27, 29, 31, or 34, or (B) a full complement of the nucleic acid sequence of (b)(i)(A); or
  (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a EXST or EXST-like polypeptide;
(b) regenerating a transgenic plant from the regenerable plant cell after step (a), wherein the transgenic plant comprises in its genome the suppression DNA construct and exhibits altered root architecture when compared to a control plant not comprising the suppression DNA construct;
(c) obtaining a progeny plant derived from the transgenic plant, wherein the progeny plant comprises in its genome the suppression DNA construct; and (d) determining whether the progeny plant exhibits an alteration of at least one agronomic characteristic when compared to a control plant not comprising the suppression DNA construct.

In another embodiment, a method of altering root architecture in a plant, comprising:

(a) introducing into a regenerable plant cell a suppression DNA construct comprising at least one regulatory element operably linked to:
  (i) all or part of: (A) a nucleic acid sequence encoding a polypeptide having an amino acid sequence of at least 50% sequence identity, based on the Clustal V method of alignment, when compared to SEQ ID NO: 15, 17, 19, 21, 23, 25, 27, 29, 31, or 34, or (B) a full complement of the nucleic acid sequence of (b)(i)(A); or
  (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a EXST or EXST-like polypeptide; and
(b) regenerating a transgenic plant from the regenerable plant cell after step (a), wherein the transgenic plant comprises in its genome the suppression DNA construct and wherein the transgenic plant exhibits altered root architecture when compared to a control plant not comprising the suppression DNA construct; and
optionally, (c) obtaining a progeny plant derived from the transgenic plant, wherein said progeny plant comprises in its genome the recombinant DNA construct and wherein the progeny plant exhibits altered root architecture when compared to a control plant not comprising the suppression DNA construct.

In another embodiment, a method of evaluating root architecture in a plant, comprising:

(a) introducing into a regenerable plant cell a suppression DNA construct comprising at least one regulatory element operably linked to:
  (i) all or part of: (A) a nucleic acid sequence encoding a polypeptide having an amino acid sequence of at least 50% sequence identity, based on the Clustal V method of alignment, when compared to SEQ ID NO: 15, 17, 19, 21, 23, 25, 27, 29, 31, or 34, or (B) a full complement of the nucleic acid sequence of (b)(i)(A); or
  (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a EXST or EXST-like polypeptide;
(b) regenerating a transgenic plant from the regenerable plant cell after step (a), wherein the transgenic plant comprises in its genome the suppression DNA construct; and
(c) evaluating root architecture of the transgenic plant compared to a control plant not comprising the suppression DNA construct;
and optionally, (d) obtaining a progeny plant derived from the transgenic plant, wherein the progeny plant comprises in its genome the suppression DNA construct; and optionally, (e) evaluating root architecture of the progeny plant compared to a control plant not comprising the suppression DNA construct.

In another embodiment, a method of evaluating root architecture in a plant, comprising:
   (a) introducing into a regenerable plant cell a suppression DNA construct comprising at least one regulatory element operably linked to:
      (i) all or part of: (A) a nucleic acid sequence encoding a polypeptide having an amino acid sequence of at least 50% sequence identity, based on the Clustal V method of alignment, when compared to SEQ ID NO: 15, 17, 19, 21, 23, 25, 27, 29, 31, or 34, or (B) a full complement of the nucleic acid sequence of (b)(i)(A); or
      (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a EXST or EXST-like polypeptide;
   (b) regenerating a transgenic plant from the regenerable plant cell after step (a), wherein the transgenic plant comprises in its genome the suppression DNA construct;
   (c) obtaining a progeny plant derived from the transgenic plant, wherein the progeny plant comprises in its genome the suppression DNA construct; and
   (d) evaluating root architecture of the progeny plant compared to a control plant not comprising the suppression DNA construct.

In another aspect, this invention also concerns a method of mapping genetic variations related to controlling embryo/endosperm size during seed development and/or altering oil phenotypes in plants comprising:
   (a) crossing two plant varieties; and
   (b) evaluating genetic variations with respect to:
      (i) a nucleic acid sequence selected from the group consisting of SEQ ID NO: 14, 16, 18, 20, 22, 24, 26, 28, 30 or 33; or
      (ii) a nucleic acid sequence encoding a polypeptide selected from the group consisting of SEQ ID NO: 15; 17, 19, 21, 23, 25, 27, 29, 31 or 34
   in progeny plants resulting from the cross of step (a) wherein the evaluation is made using a method selected from the group consisting of: RFLP analysis, SNP analysis, and PCR-based analysis.

In another embodiment, this invention concerns a method of molecular breeding to obtain altered embryo/endosperm size during seed development and/or altered oil phenotypes in plants comprising:
   (a) crossing two plant varieties; and
   (b) evaluating genetic variations with respect to:
      (i) a nucleic acid sequence selected from the group consisting of SEQ ID NO: 14, 16, 18, 20, 22, 24, 26, 28, 30 or 33; or
      (ii) a nucleic acid sequence encoding a polypeptide selected from the group consisting of SEQ ID NO: 15; 17, 19, 21, 23, 25, 27, 29, 31 or 34;
   in progeny plants resulting from the cross of step (a) wherein the evaluation is made using a method selected from the group consisting of: RFLP analysis, SNP analysis, and PCR-based analysis.

Also included in the present invention is any progeny of the above plants, any seeds of the above plants, and cells from any of the above plants and progeny.

A method of producing seed that can be sold as a product offering with altered root architecture comprising any of the preceding preferred methods, and further comprising obtaining seeds from said progeny plant, wherein said seeds comprise in their genome said recombinant DNA construct.

BRIEF DESCRIPTION OF THE FIGURES AND SEQUENCE LISTINGS

The invention can be more fully understood from the following detailed description and the accompanying drawings and Sequence Listing which form a part of this application.

Figure 15A:
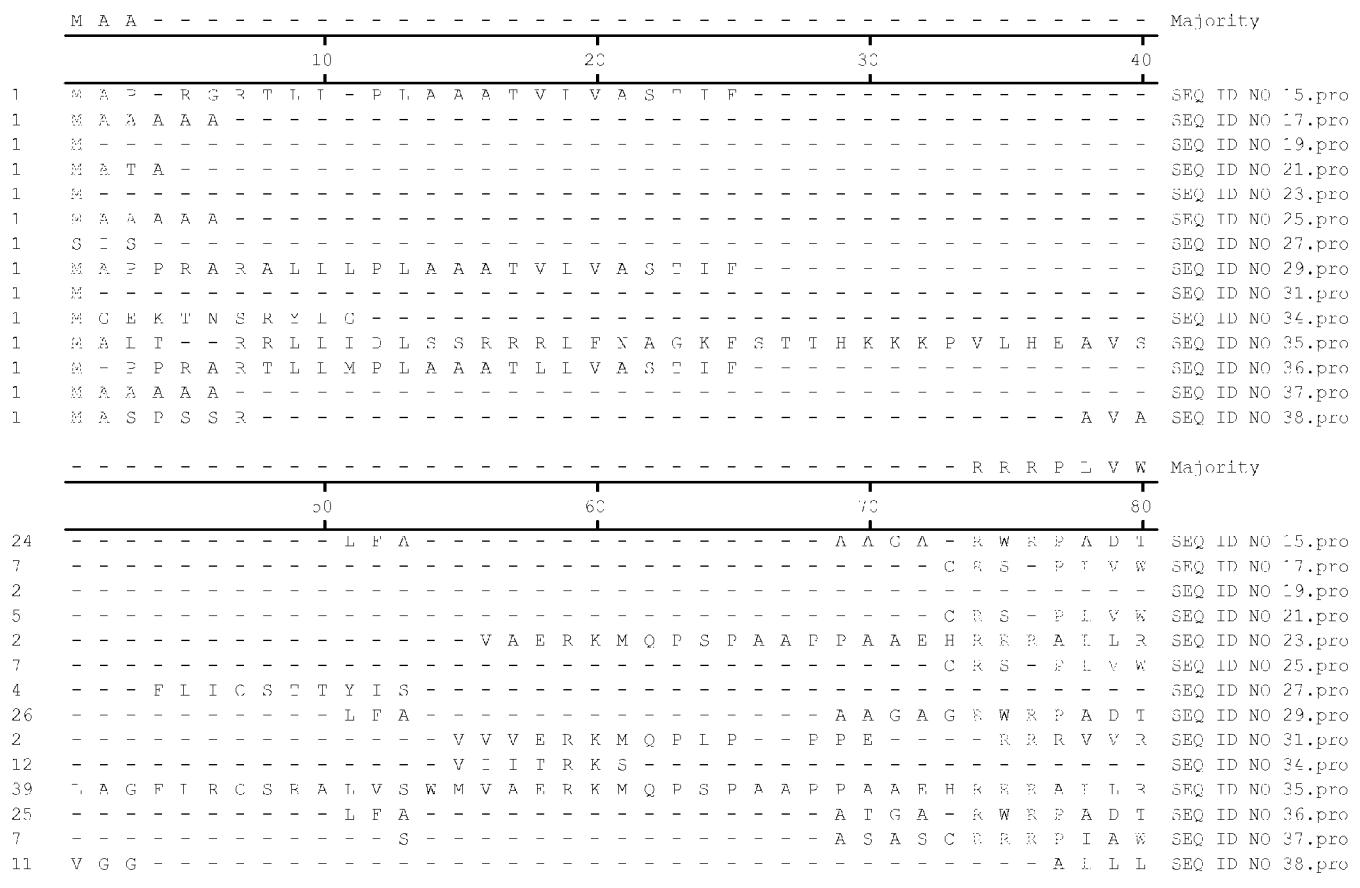
Figure 15B:
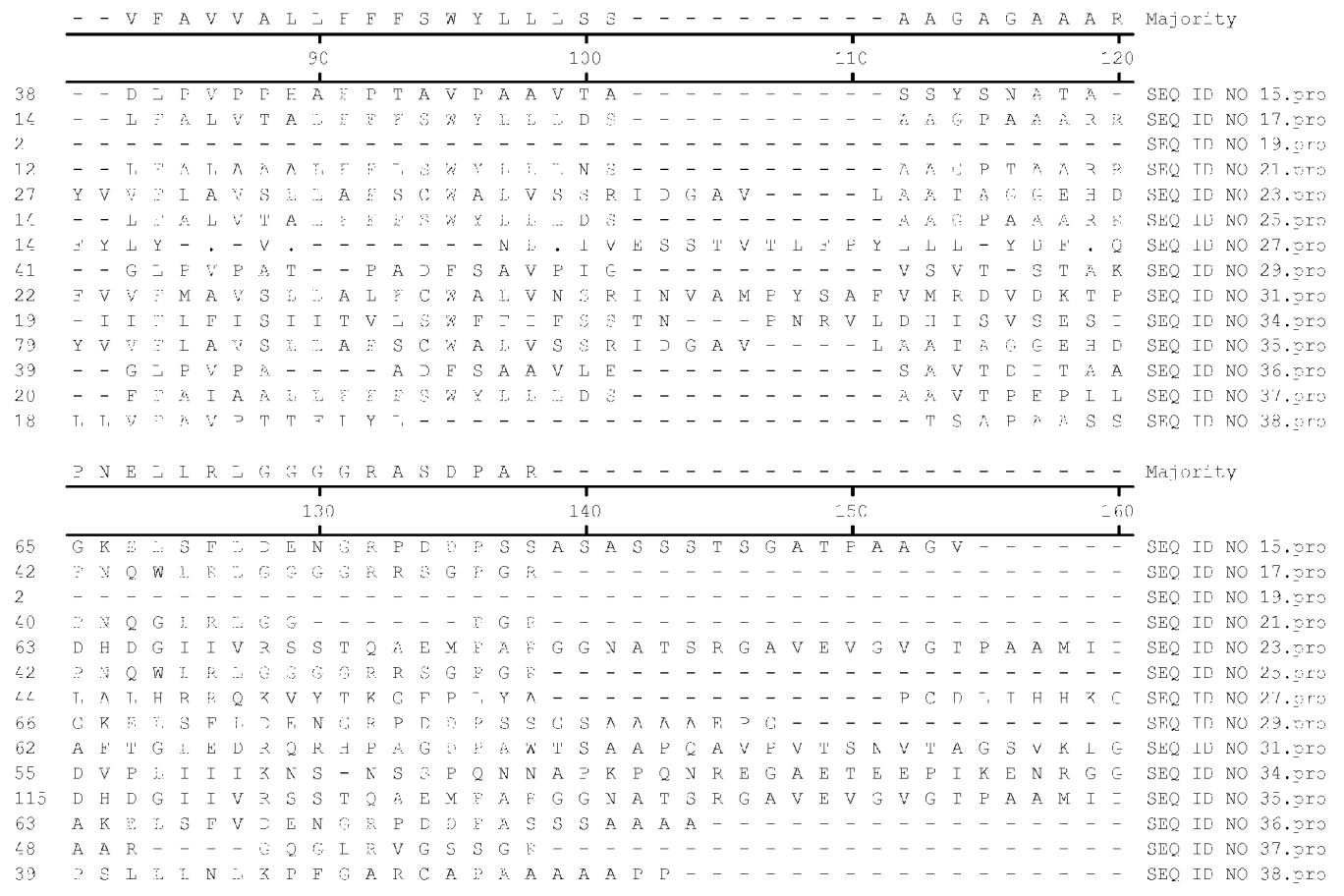
Figure 15C:
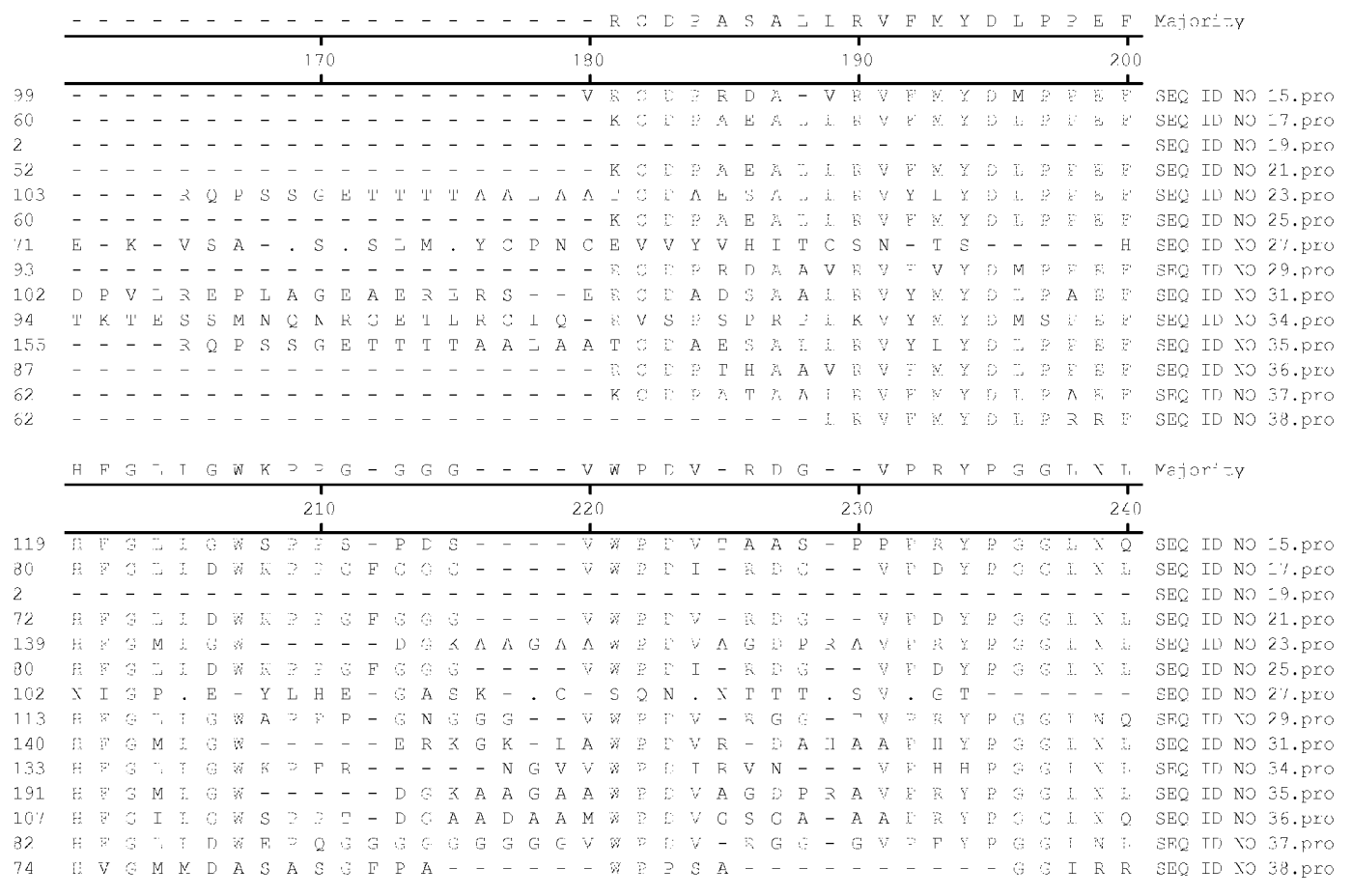
Figure 15D:
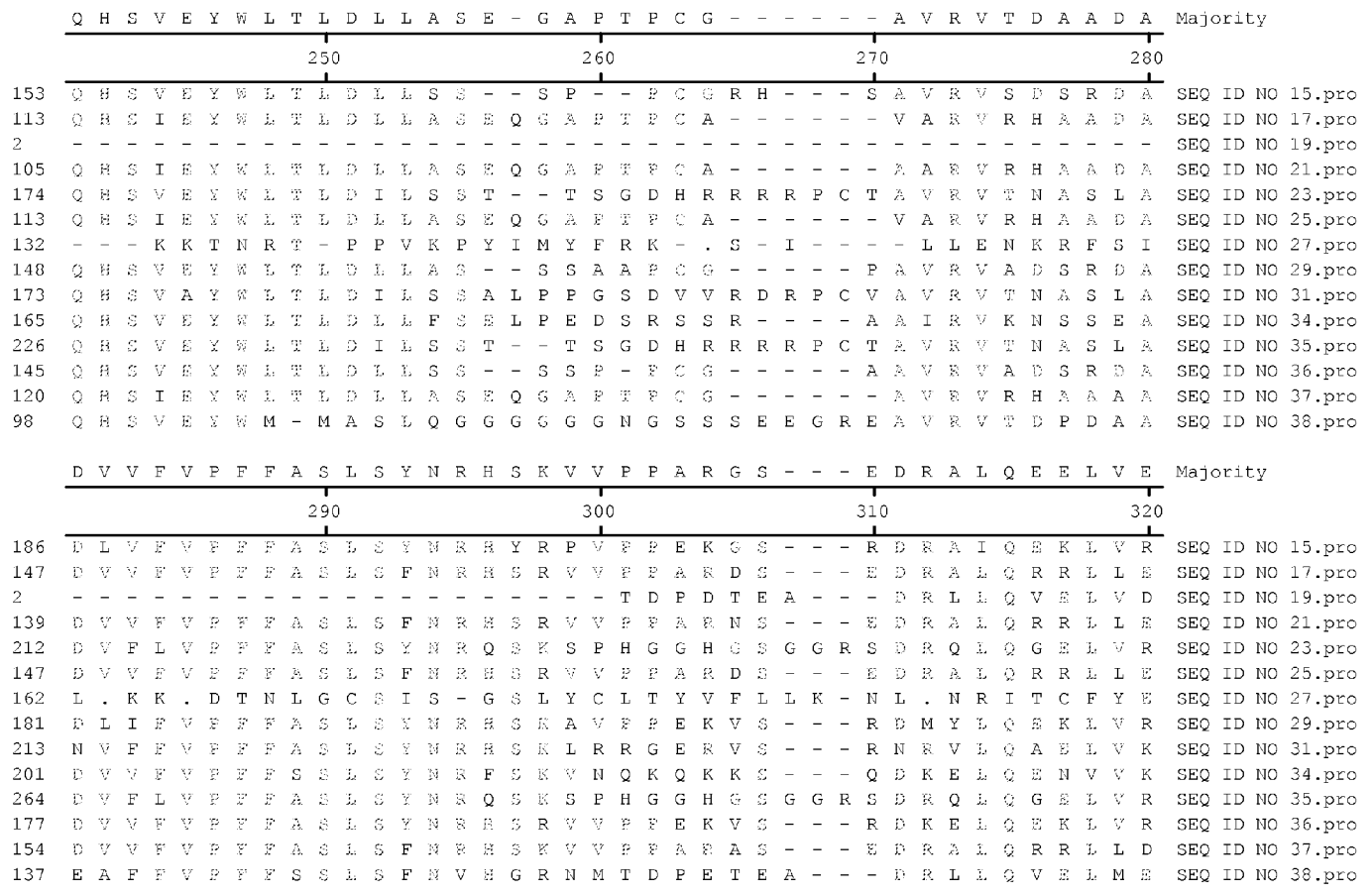
Figure 15E:
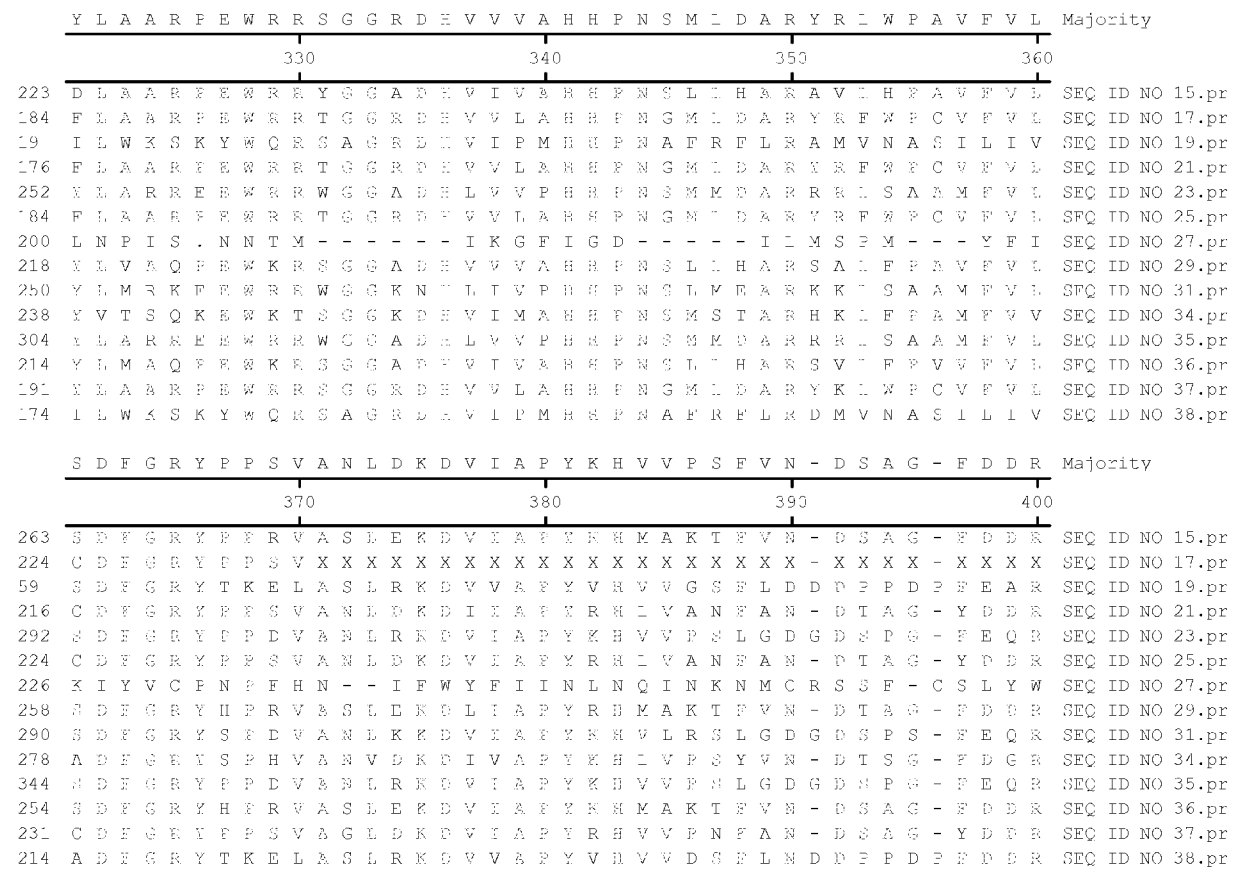
Figure 15F:
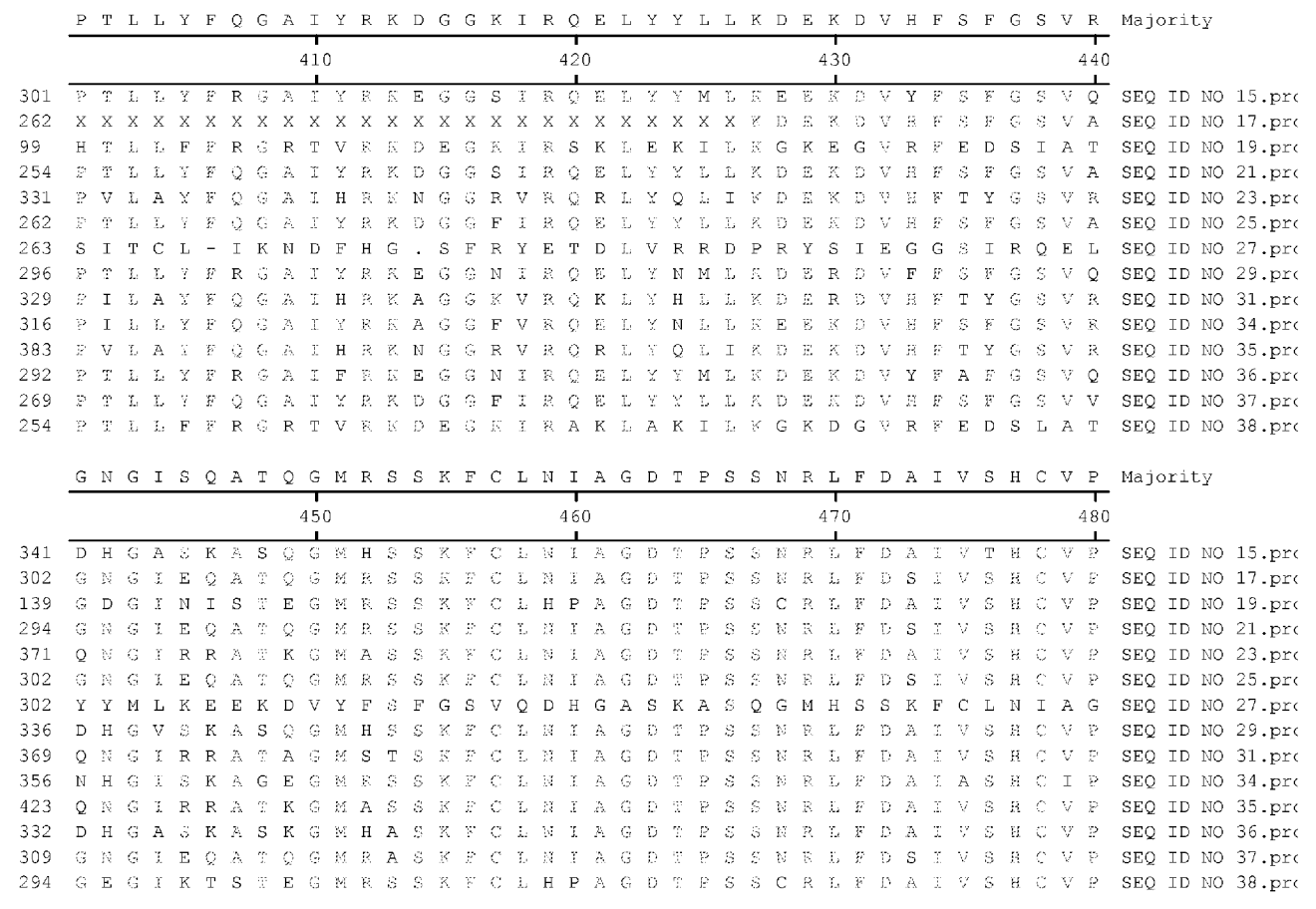
Figure 15G:
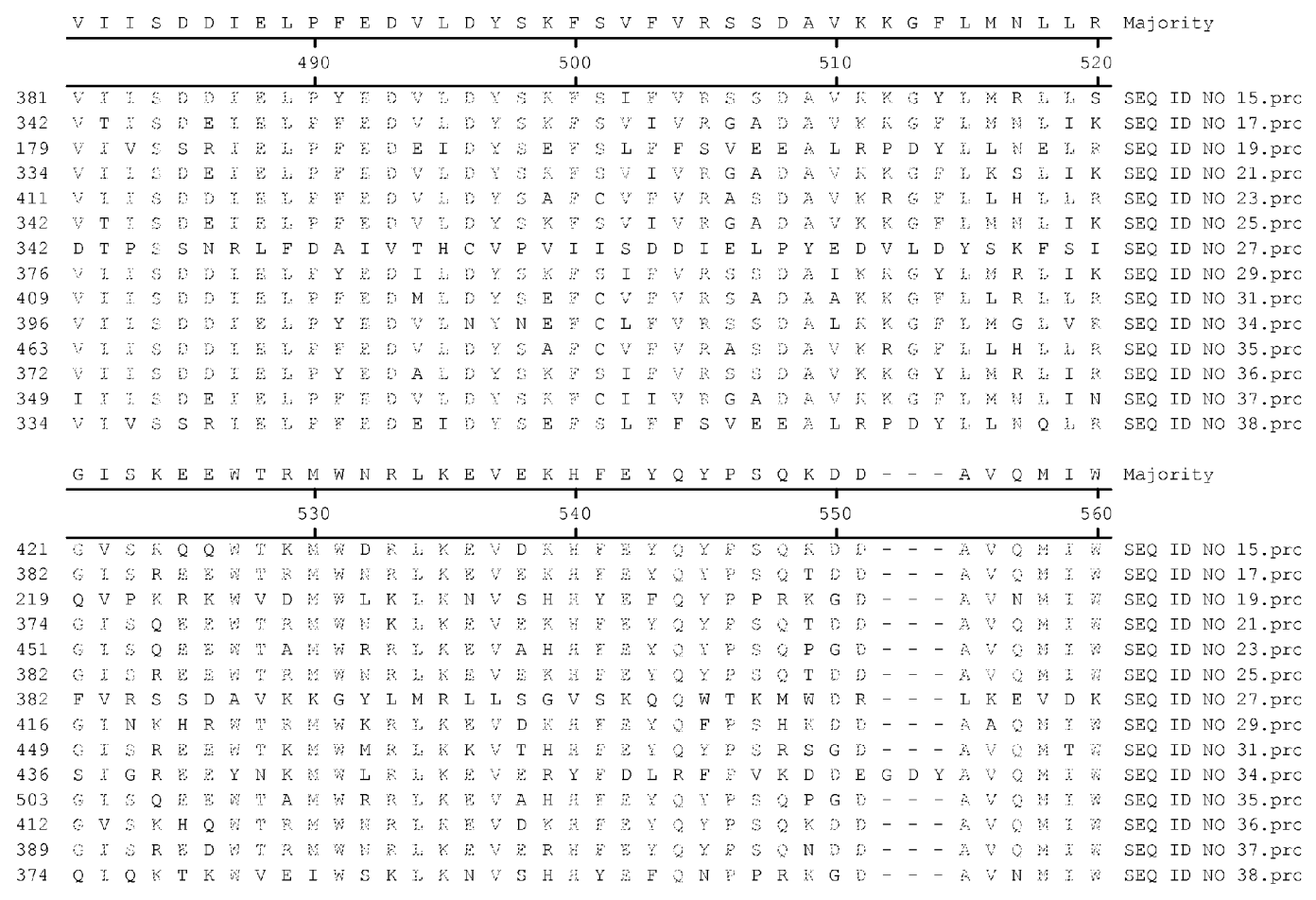
Figure 15H:
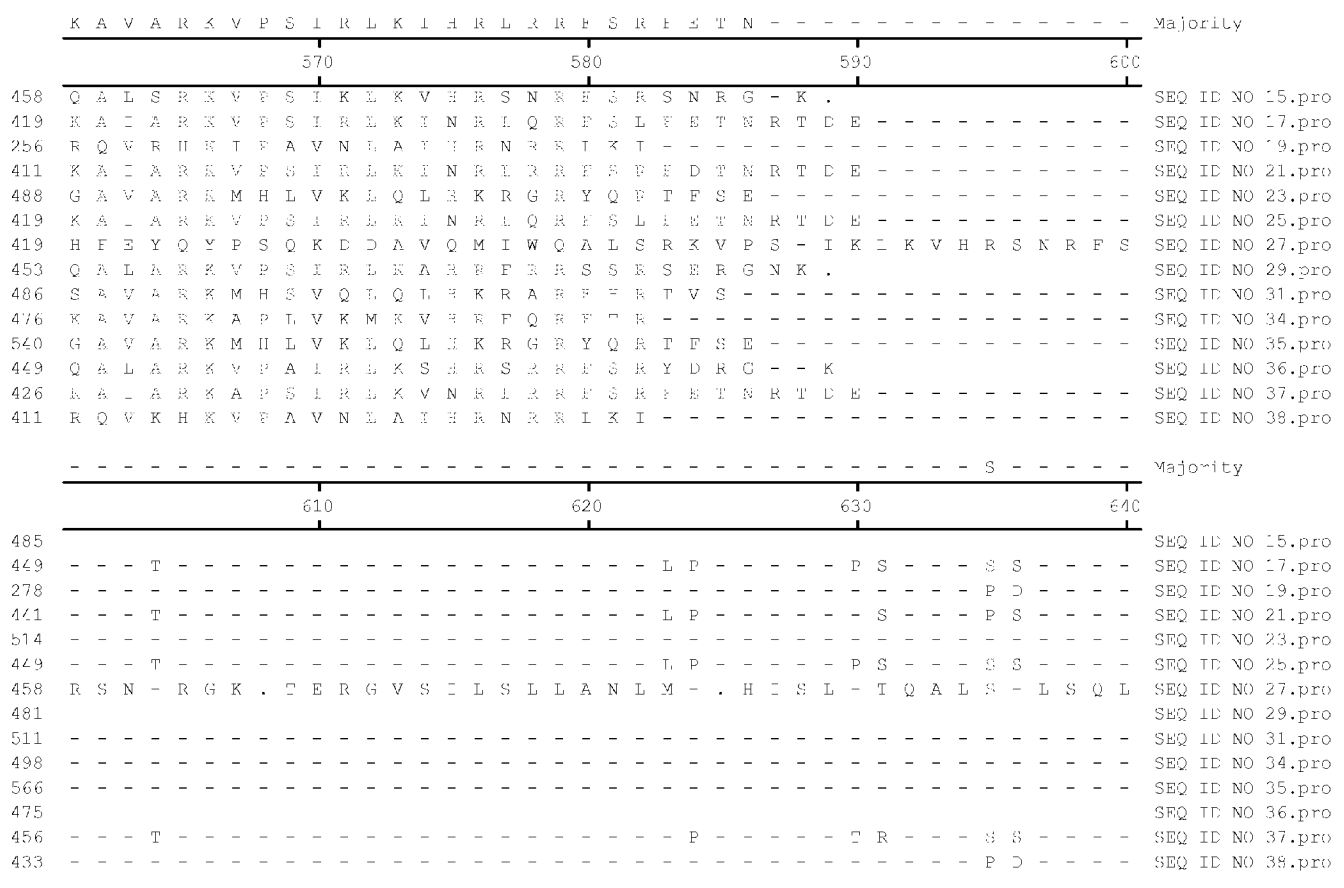
Figure 15I:
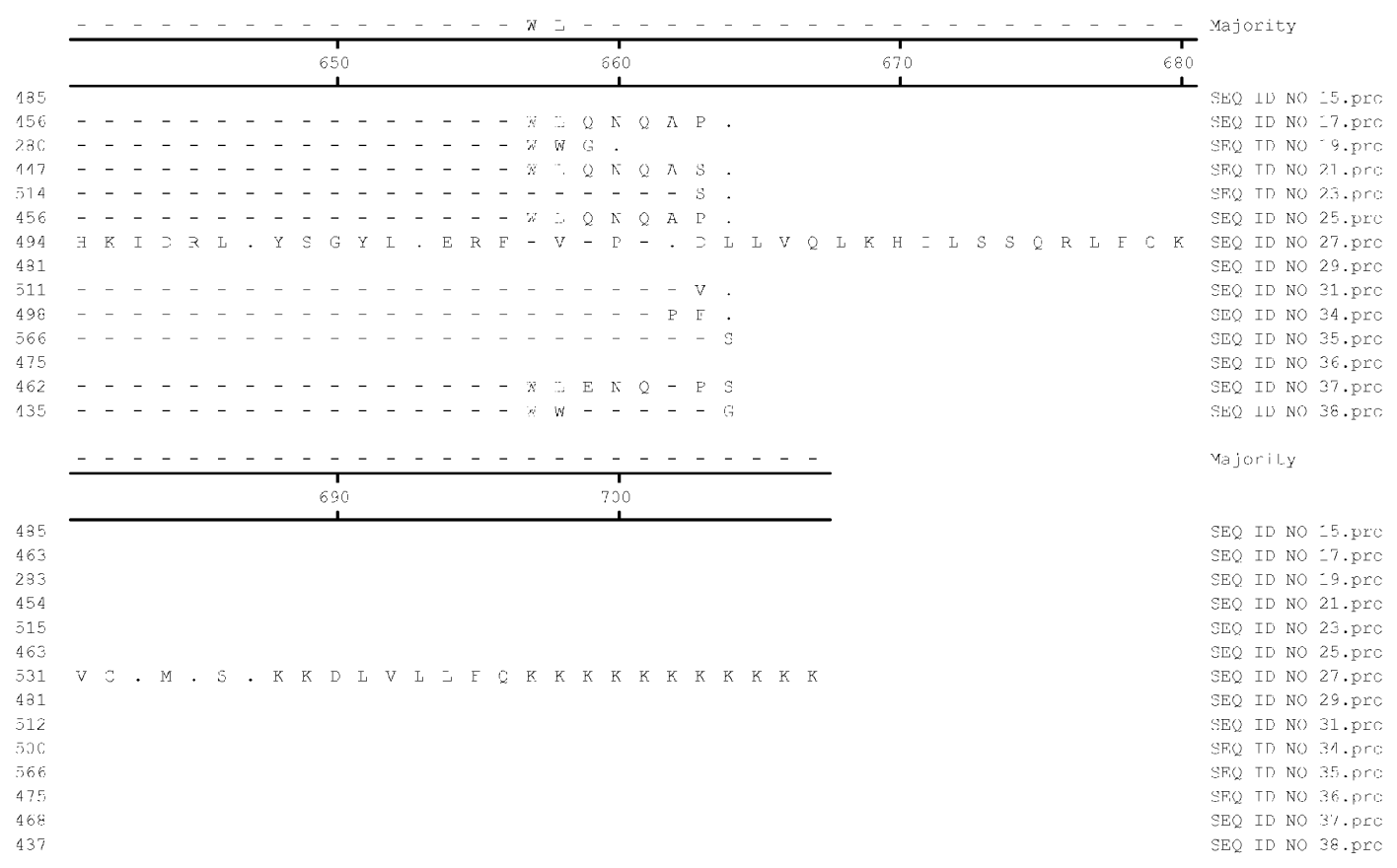

FIGS. 15A-15I show the multiple alignment of the full length amino acid sequences of SEQ ID NOs: 15, 17, 19, 21, 23, 25, 27, 29, 31, 34, and SEQ ID NOs:35, 36, 37, and 38. Residues that match the Consensus sequence exactly are shaded. The consensus sequence (SEQ ID NO:49) is shown above each alignment. The consensus residues are determined by a straight majority.

Figure 16:
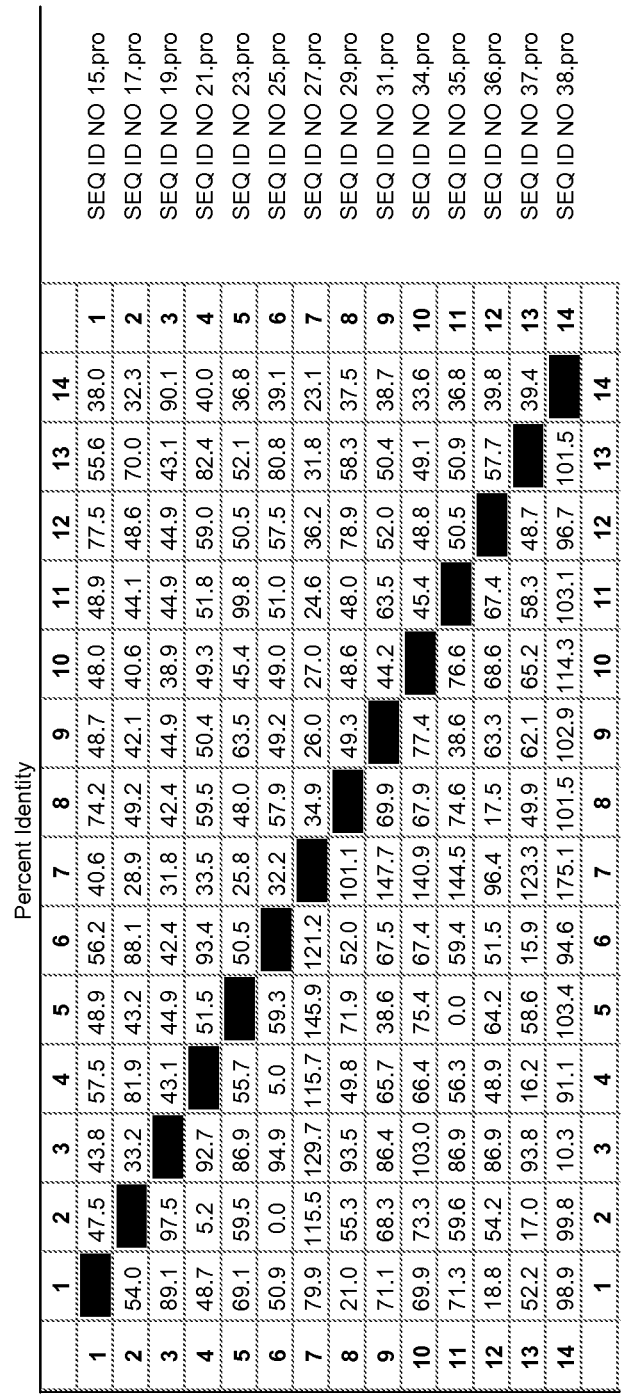

FIG. 16 shows a chart of the percent sequence identity and the divergence values for each pair of amino acid sequences of the EXST homologs displayed in FIGS. 15A-15I.

FIG. 17 is the growth medium used for semi-hydroponics maize growth in Example 17.

FIG. 18 is a chart setting forth data relating to the effect of different nitrate concentrations on the growth and development of Gaspe Flint derived maize lines in Example 17.

The sequence descriptions and Sequence Listing attached hereto comply with the rules governing nucleotide and/or amino acid sequence disclosures in patent applications as set forth in 37 C.F.R. §1.821-1.825.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

SEQ ID NO:1 pHSbarENDs2
SEQ ID NO:2 pDONR™/Zeo
SEQ ID NO:3 pDONR™221
SEQ ID NO:4 pBC-yellow
SEQ ID NO:5 PHP27840
SEQ ID NO:6 PHP23236
SEQ ID NO:7 PHP10523
SEQ ID NO:8 PHP23235
SEQ ID NO:9 PHP20234
SEQ ID NO:10 PHP28529
SEQ ID NO:11 PHP28408
SEQ ID NO:12 PHP22020
SEQ ID NO:13 PHP29635

Contig of: lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence listing.

TABLE 1

EXST and EXST-like proteins

| Protein | Clone Designation | SEQ ID NO: (Amino Acid) | SEQ ID NO: (Nucleotide) |
|---|---|---|---|
| EXST-like | Contig of:<br>cfp5n.pk007.k11<br>cfp5n.pk007.k11.f<br>cfp6n.pk005.i1 | 14 | 15 |
| EXST-like | Contig of:<br>cfp3n.pk069.l15<br>cfp3n.pk069.l15.f<br>p0127.cntdd86ra<br>p0127.cntdd86ra.f | 16 | 17 |
| EXST-like | my.ceb1.pk0010.e5 | 18 | 19 |
| EXST-like | cfp6n.pk002.a5:fis | 20 | 21 |
| EXST-like | rls24.pk0026.h11:fis | 22 | 23 |
| EXST-like | p0127.cntdd86ra:fis | 24 | 25 |
| EXST-like | cfp5n.pk007.k11:fis | 26 | 27 |
| EXST-like | esl1c.pk006.l19:fis | 28 | 29 |
| EXST-like | cfp1n.pk002.o16.f:fis | 30 | 31 |

SEQ ID NO:32 is the nucleotide sequence of the *Arabidopsis thaliana* embryo sac development arrest 5 (EDA5, Exostosin Family protein or EXST protein, NCBI GI NO: 15228598, At3g03650).

SEQ ID NO:33 is the ORF corresponding to nucleotides 245-1744 of SEQ ID NO:32.

SEQ ID NO:34 corresponds to the protein sequence (NCBI GI NO: 15228598) encoded by SEQ ID NO:33

SEQ ID NO:35 corresponds to NCBI GI NO:115476598 (*Oryza sativa*).
SEQ ID NO:36 corresponds to NCBI GI NO:115487106 (*Oryza sativa*).
SEQ ID NO:37 corresponds to NCBI GI NO:115452759 (*Oryza sativa*).
SEQ ID NO:38 corresponds to NCBI GI NO:115441893 (*Oryza sativa*).
SEQ ID NO:39 is the attB1 sequence.
SEQ ID NO:40 is the attB2 sequence.
SEQ ID NO:41 is the forward primer VC062 in Example 9.
SEQ ID NO:42 is the reverse primer VC063 in Example 9.
SEQ ID NO:43 PHOXS2a-FRT87(ni)m.
SEQ ID NO:44 is the maize NAS2 promoter.
SEQ ID NO:45 is the GOS2 promoter.
SEQ ID NO:46 is the ubiquitin promoter.
SEQ ID NO:47 is the S2A promoter.
SEQ ID NO:48 is the PINII terminator.

DETAILED DESCRIPTION OF PREFERRED EMBODIMENTS

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

The term "root architecture" refers to the arrangement of the different parts that comprise the root. The terms "root architecture", "root structure", "root system" or "root system architecture" are used interchangeably herewithin.

In general, the first root of a plant that develops from the embryo is called the primary root. In most dicots, the primary root is called the taproot. This main root grows downward and gives rise to branch (lateral) roots. In monocots the primary root of the plant branches, giving rise to a fibrous root system.

The term "altered root architecture" refers to aspects of alterations of the different parts that make up the root system at different stages of its development compared to a reference or control plant. It is understood that altered root architecture encompasses alterations in one or more measurable parameters, including but not limited to, the diameter, length, number, angle or surface of one or more of the root system parts, including but not limited to, the primary root, lateral or branch root, adventitious root, and root hairs, all of which fall within the scope of this invention. These changes can lead to an overall alteration in the area or volume occupied by the root. The reference or control plant does not comprise in its genome the recombinant DNA construct or heterologous construct.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Agronomic characteristics" is a measurable parameter including but not limited to greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, stalk lodging, plant height, ear length, and harvest index.

"Exostosin Family", "at-Exostosin Family, exst, at-exst are used interchangeably herewithin and refer to the *Arabidopsis thaliana* locus, AT3G03650 (SEQ ID NO:32).

EXST refers to the protein (SEQ ID NO:34) encoded by the ORF (SEQ ID NO:33 of AT3G03650 (SEQ ID NO:32).

"exst-like" refers to nucleotide homologs from different species, such as corn and soybean, of the *Arabidopsis thaliana* "exostosin family" locus, AT3G03650 (SEQ ID NO:32) and includes without limitation any of the nucleotide sequences of SEQ ID NOs:14, 16, 18, 20, 22, 24, 26, 28, and 30.

"EXST-like" refers to protein homologs from different species, such as corn and soybean, of the *Arabidopsis thaliana* "EXOSTOSIN FAMILY" polypeptide (SEQ ID NO:34) and includes without limitation any of the amino acid sequences of SEQ ID NOs: 15, 17, 19, 21, 23, 25, 27, 29, and 31.

"Environmental conditions" refer to conditions under which the plant is grown, such as the availability of water, availability of nutrients (for example nitrogen), or the presence of disease.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation "Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Transgenic plant" includes reference to a plant which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase I.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably, and refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) *CABIOS.* 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. *Molecular Cloning: A Laboratory Manual; Cold Spring Harbor Laboratory Press: Cold Spring Harbor,* 1989 (hereinafter "Sambrook").

Turning now to preferred embodiments:

Preferred embodiments include isolated polynucleotides and polypeptides, recombinant DNA constructs, compositions (such as plants or seeds) comprising these recombinant DNA constructs, and methods utilizing these recombinant DNA constructs.

Preferred Isolated Polynucleotides and Polypeptides

The present invention includes the following preferred isolated polynucleotides and polypeptides:

An isolated polynucleotide comprising: (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 21, 23, 25, 27, 29, 31, or 34; or (ii) a full complement of the nucleic acid sequence of (i). Any of the foregoing isolated polynucleotides may be utilized in any recombinant DNA constructs (including suppression DNA constructs) of the present invention. The polypeptide is preferably a EXST or EXST-like protein.

An isolated polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 21, 23, 25, 27, 29, 31, or 34. The polypeptide is preferably a EXST or EXST-like protein.

An isolated polynucleotide comprising (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 21, 23, 25, 27, 29, 31, or 34, or (ii) a full complement of the nucleic acid sequence of (i). Any of the foregoing isolated polynucleotides may be utilized in any recombinant DNA constructs (including suppression DNA constructs) of the present invention. The isolated polynucleotide encodes a EXST or EXST-like protein.

Preferred Recombinant DNA Constructs and Suppression DNA Constructs.

In one aspect, the present invention includes recombinant DNA constructs (including suppression DNA constructs).

In one preferred embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 21, 23, 25, 27, 29, 31, or 34, or (ii) a full complement of the nucleic acid sequence of (i).

In another preferred embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 21, 23, 25, 27, 29, 31, or 34, or (ii) a full complement of the nucleic acid sequence of (i).

FIGS. 15A-15I show the multiple alignment of the amino acid sequences of SEQ ID NOs: 15, 17, 19, 21, 23, 25, 27, 29, 31, 34, and SEQ ID NOs:35, 36, 37, and 38. The multiple alignment of the sequences was performed using the Megalign® program of the LASERGENE® bioinformatics computing suite (DNASTAR® Inc., Madison, Wis.); in particular, using the Clustal V method of alignment (Higgins and Sharp (1989) *CABIOS*. 5:151-153) with the multiple alignment default parameters of GAP PENALTY=10 and GAP LENGTH PENALTY=10, and the pairwise alignment default parameters of KTUPLE=1, GAP PENALTY=3, WINDOW=5 and DIAGONALS SAVED=5.

FIG. 16 shows the percent sequence identity and the divergence values for each pair of amino acids sequences displayed in FIGS. 15A-15I.

In another preferred embodiment, a recombinant DNA construct comprises a polynucleotide operably linked to at least one regulatory sequence (e.g., a promoter functional in a plant), wherein said polynucleotide encodes a EXST or EXST-like protein.

In another aspect, the present invention includes suppression DNA constructs.

A suppression DNA construct preferably comprises at least one regulatory sequence (preferably a promoter functional in a plant) operably linked to (a) all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 21, 23, 25, 27, 29, 31, or 34, or (ii) a full complement of the nucleic acid sequence of (a)(i); or (b) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a EXST or EXST-like protein; or (c) all or part of (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 21, 23, 25, 27, 29, 31, or 34, or (ii) a full complement of the nucleic acid sequence of (c)(i). The suppression DNA construct preferably comprises a cosuppression construct, antisense construct, viral-suppression construct, hairpin suppression construct, stem-loop suppression construct, double-stranded RNA-producing construct, RNAi construct, or small RNA construct (e.g., an siRNA construct or an miRNA construct).

It is understood, as those skilled in the art will appreciate, that the invention encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The term "suppression" includes lower, reduce, decline, decrease, inhibit, eliminate or prevent. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target protein.

"Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target protein. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al. (1998) *Plant J.* 16:651-659; and Gura (2000) *Nature* 404:804-808).

Another variation describes the use of plant viral sequences to direct the suppression of proximal mRNA encoding sequences (PCT Publication WO 98/36083 published on Aug. 20, 1998).

Previously described is the use of "hairpin" structures that incorporate all, or part, of an mRNA encoding sequence in a complementary orientation that results in a potential "stem-loop" structure for the expressed RNA (PCT Publication WO 99/53050 published on Oct. 21, 1999). In this case the stem is formed by polynucleotides corresponding to the gene of interest inserted in either sense or anti-sense orientation with respect to the promoter and the loop is formed by some polynucleotides of the gene of interest, which do not have a complement in the construct. This increases the frequency of cosuppression or silencing in the recovered transgenic plants. For review of hairpin suppression see Wesley, S. V. et al. (2003) Methods in Molecular Biology, Plant Functional Genomics: Methods and Protocols 236:273-286.

A construct where the stem is formed by at least 30 nucleotides from a gene to be suppressed and the loop is formed by a random nucleotide sequence has also effectively been used for suppression (PCT Publication No. WO 99/61632 published on Dec. 2, 1999).

The use of poly-T and poly-A sequences to generate the stem in the stem-loop structure has also been described (PCT Publication No. WO 02/00894 published Jan. 3, 2002).

Yet another variation includes using synthetic repeats to promote formation of a stem in the stem-loop structure. Transgenic organisms prepared with such recombinant DNA fragments have been shown to have reduced levels of the protein encoded by the nucleotide fragment forming the loop as described in PCT Publication No. WO 02/00904, published 3 Jan. 2002.

RNA interference refers to the process of sequence-specific post-transcriptional gene silencing in animals mediated by short interfering RNAs (siRNAs) (Fire et al., Nature 391: 806 1998). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., Trends Genet. 15:358 1999). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Berstein et al., Nature 409:363, 2001). Short interfering RNAs derived from dicer activity are typically about 21 to about 23 nucleotides in length and comprise about 19 base pair duplexes (Elbashir et al., Genes Dev. 15:188, 2001). Dicer has also been implicated in the excision of 21- and 22-nucleotide small temporal RNAs (stRNAs) from precursor RNA of conserved structure that are implicated in translational control (Hutvagner et al., Science 293:834, 2001). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex (Elbashir et al., Genes Dev. 15:188, 2001). In addition, RNA interference can also involve small RNA (e.g., miRNA) mediated gene silencing, presumably through cellular mechanisms that regulate chromatin structure and thereby prevent transcription of target gene sequences (see, e.g., Allshire, Science 297:1818-1819, 2002; Volpe et al., Science 297:1833-1837, 2002; Jenuwein, Science 297:2215-

2218, 2002; and Hall et al., Science 297:2232-2237, 2002). As such, miRNA molecules of the invention can be used to mediate gene silencing via interaction with RNA transcripts or alternately by interaction with particular gene sequences, wherein such interaction results in gene silencing either at the transcriptional or post-transcriptional level.

RNAi has been studied in a variety of systems. Fire et al. (Nature 391:806, 1998) were the first to observe RNAi in *C. elegans*. Wianny and Goetz (Nature Cell Biol. 2:70, 1999) describe RNAi mediated by dsRNA in mouse embryos. Hammond et al. (Nature 404:293, 2000) describe RNAi in *Drosophila* cells transfected with dsRNA. Elbashir et al., (Nature 411:494, 2001) describe RNAi induced by introduction of duplexes of synthetic 21-nucleotide RNAs in cultured mammalian cells including human embryonic kidney and HeLa cells.

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

It is thought that sequence complementarity between small RNAs and their RNA targets helps to determine which mechanism, RNA cleavage or translational inhibition, is employed. It is believed that siRNAs, which are perfectly complementary with their targets, work by RNA cleavage. Some miRNAs have perfect or near-perfect complementarity with their targets, and RNA cleavage has been demonstrated for at least a few of these miRNAs. Other miRNAs have several mismatches with their targets, and apparently inhibit their targets at the translational level. Again, without being held to a particular theory on the mechanism of action, a general rule is emerging that perfect or near-perfect complementarity causes RNA cleavage, whereas translational inhibition is favored when the miRNA/target duplex contains many mismatches. The apparent exception to this is microRNA 172 (miR172) in plants. One of the targets of miR172 is APETALA2 (AP2), and although miR172 shares near-perfect complementarity with AP2 it appears to cause translational inhibition of AP2 rather than RNA cleavage.

MicroRNAs (miRNAs) are noncoding RNAs of about 19 to about 24 nucleotides (nt) in length that have been identified in both animals and plants (Lagos-Quintana et al., Science 294:853-858 2001, Lagos-Quintana et al., Curr. Biol. 12:735-739, 2002; Lau et al., Science 294:858-862, 2001; Lee and Ambros, Science 294:862-864, 2001; Llave et al., Plant Cell 14:1605-1619, 2002; Mourelatos et al., Genes. Dev. 16:720-728, 2002; Park et al., Curr. Biol. 12:1484-1495, 2002; Reinhart et al., Genes. Dev. 16:1616-1626, 2002). They are processed from longer precursor transcripts that range in size from approximately 70 to 200 nt, and these precursor transcripts have the ability to form stable hairpin structures. In animals, the enzyme involved in processing miRNA precursors is called Dicer, an RNAse III-like protein (Grishok et al., Cell 106:23-34, 2001; Hutvagner et al., Science 293:834-838, 2001; Ketting et al., Genes. Dev. 15:2654-2659, 2001). Plants also have a Dicer-like enzyme, DCL1 (previously named CARPEL FACTORY/SHORT INTEGUMENTS1/SUS-PENSOR1), and recent evidence indicates that it, like Dicer, is involved in processing the hairpin precursors to generate mature miRNAs (Park et al., Curr. Biol. 12:1484-1495, 2002; Reinhart et al., Genes. Dev. 16:1616-1626, 2002). Furthermore, it is becoming clear from recent work that at least some miRNA hairpin precursors originate as longer polyadenylated transcripts, and several different miRNAs and associated hairpins can be present in a single transcript (Lagos-Quintana et al., Science 294:853-858, 2001; Lee et al., EMBO J. 21:4663-4670, 2002). Recent work has also examined the selection of the miRNA strand from the dsRNA product arising from processing of the hairpin by DICER (Schwartz, et al., Cell 115:199-208, 2003). It appears that the stability (i.e. G:C vs. A:U content, and/or mismatches) of the two ends of the processed dsRNA affects the strand selection, with the low stability end being easier to unwind by a helicase activity. The 5' end strand at the low stability end is incorporated into the RISC complex, while the other strand is degraded.

MicroRNAs appear to regulate target genes by binding to complementary sequences located in the transcripts produced by these genes. In the case of lin-4 and let-7, the target sites are located in the 3' UTRs of the target mRNAs (Lee et al., Cell 75:843-854, 1993; Wightman et al., Cell 75:855-862, 1993; Reinhart et al., Nature 403:901-906, 2000; Slack et al., Mol. Cell. 5:659-669, 2000), and there are several mismatches between the lin-4 and let-7 miRNAs and their target sites. Binding of the lin-4 or let-7 miRNA appears to cause downregulation of steady-state levels of the protein encoded by the target mRNA without affecting the transcript itself (Olsen and Ambros, Dev. Biol. 216:671-680, 1999). On the other hand, recent evidence suggests that miRNAs can in some cases cause specific RNA cleavage of the target transcript within the target site, and this cleavage step appears to require 100% complementarity between the miRNA and the target transcript (Hutvagner and Zamore, Science 297:2056-2060, 2002; Llave et al., Plant Cell 14:1605-1619, 2002). It seems likely that miRNAs can enter at least two pathways of target gene regulation: Protein downregulation when target complementarity is <100%, and RNA cleavage when target complementarity is 100%. MicroRNAs entering the RNA cleavage pathway are analogous to the 21-25 nt short interfering RNAs (siRNAs) generated during RNA interference (RNAi) in animals and posttranscriptional gene silencing (PTGS) in plants (Hamilton and Baulcombe 1999; Hammond et al., 2000; Zamore et al., 2000; Elbashir et al., 2001), and likely are incorporated into an RNA-induced silencing complex (RISC) that is similar or identical to that seen for RNAi.

Identifying the targets of miRNAs with bioinformatics has not been successful in animals, and this is probably due to the fact that animal miRNAs have a low degree of complementarity with their targets. On the other hand, bioinformatic approaches have been successfully used to predict targets for plant miRNAs (Llave et al., Plant Cell 14:1605-1619 2002; Park et al., Curr. Biol. 12:1484-1495 2002; Rhoades et al., Cell 110:513-520 2002), and thus it appears that plant miRNAs have higher overall complementarity with their putative targets than do animal miRNAs. Most of these predicted target transcripts of plant miRNAs encode members of transcription factor families implicated in plant developmental patterning or cell differentiation.

A recombinant DNA construct (including a suppression DNA construct) of the present invention preferably comprises at least one regulatory sequence.

A preferred regulatory sequence is a promoter.

A number of promoters can be used in recombinant DNA constructs (and suppression DNA constructs) of the present invention. The promoters can be selected based on the desired outcome, and may include constitutive, tissue-specific, cell specific, inducible, or other promoters for expression in the host organism.

High level, constitutive expression of the candidate gene under control of the 35S or UBI promoter may have pleiotropic effects, although Candidate gene efficacy may be estimated when driven by a constitutive promoter.

Use of tissue-specific and/or stress-specific expression may eliminate undesirable effects but retain the ability to alter root architecture. This effect has been observed in *Arabidopsis* (Kasuga et al. (1999) Nature Biotechnol. 17:287-291).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., Nature 313:810-812 (1985)); rice actin (McElroy et al., Plant Cell 2:163-171 (1990)); ubiquitin (UBI) (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)); ALS promoter (U.S. Pat. No. 5,659,026), the maize GOS2 promoter (WO0020571 A2, published Apr. 1, 2000) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the invention, it may be desirable to use a tissue-specific or developmentally regulated promoter.

A preferred tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present invention which causes the desired temporal and spatial expression.

Promoters which are seed or embryo specific and may be useful in the invention include soybean Kunitz trysin inhibitor (Kti3, Jofuku and Goldberg, Plant Cell 1:1079-1093 (1989)), patatin (potato tubers) (Rocha-Sosa, M., et al. (1989) EMBO J. 8:23-29), convicilin, vicilin, and legumin (pea cotyledons) (Rerie, W. G., et al. (1991) Mol. Gen. Genet. 259: 149-157; Newbigin, E. J., et al. (1990) Planta 180:461-470; Higgins, T. J. V., et al. (1988) Plant. Mol. Biol. 11:683-695), zein (maize endosperm) (Schemthaner, J. P., et al. (1988) EMBO J. 7:1249-1255), phaseolin (bean cotyledon) (Segupta-Gopalan, C., et al. (1985) Proc. Natl. Acad. Sci. U.S.A. 82:3320-3324), phytohemagglutinin (bean cotyledon) (Voelker, T. et al. (1987) EMBO J. 6:3571-3577), B-conglycinin and glycinin (soybean cotyledon) (Chen, Z-L, et al. (1988) EMBO J. 7:297-302), glutelin (rice endosperm), hordein (barley endosperm) (Marris, C., et al. (1988) Plant Mol. Biol. 10:359-366), glutenin and gliadin (wheat endosperm) (Colot, V., et al. (1987) EMBO J. 6:3559-3564), and sporamin (sweet potato tuberous root) (Hattori, T., et al. (1990) Plant Mol. Biol. 14:595-604). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al., Bio/Technology 7:L929-932 (1989)), bean lectin and bean beta-phaseolin promoters to express luciferase (Riggs et al., Plant Sci. 63:47-57 (1989)), and wheat glutenin promoters to express chloramphenicol acetyl transferase (Colot et al., EMBO J. 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Preferred promoters include the following: 1) the stress-inducible RD29A promoter (Kasuga et al. (1999) Nature Biotechnol. 17:287-91); 2) the barley promoter, B22E; expression of B22E is specific to the pedicel in developing maize kernels ("Primary Structure of a Novel Barley Gene Differentially Expressed in Immature Aleurone Layers". Klemsdal, S. S. et al., Mol. Gen. Genet. 228(1/2):9-16 (1991)); and 3) maize promoter, Zag2 ("Identification and molecular characterization of ZAG1, the maize homolog of the *Arabidopsis* floral homeotic gene AGAMOUS", Schmidt, R. J. et al., Plant Cell 5(7):729-737 (1993)). "Structural characterization, chromosomal localization and phylogenetic evaluation of two pairs of AGAMOUS-like MADS-box genes from maize", Theissen et al., Gene 156(2): 155-166 (1995); NCBI GenBank Accession No. X80206)). Zag2 transcripts can be detected 5 days prior to pollination to 7 to 8 days after pollination (DAP), and directs expression in the carpel of developing female inflorescences and Ciml which is specific to the nucleus of developing maize kernels. Ciml transcript is detected 4 to 5 days before pollination to 6 to 8 DAP. Other useful promoters include any promoter which can be derived from a gene whose expression is maternally associated with developing female florets.

Additional preferred promoters for regulating the expression of the nucleotide sequences of the present invention in plants are vascular element specific or stalk-preferred promoters. Such stalk-preferred promoters include the alfalfa S2A promoter (GenBank Accession No. EF030816; Abrahams et al., Plant Mol. Biol. 27:513-528 (1995)) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B., Biochemistry of Plants 15:1-82 (1989). (Put this with the other constitutive promoter description.)

Preferred promoters may include: RIP2, mLIP15, ZmCOR1, Rab17, CaMV 35S, RD29A, B22E, Zag2, SAM synthetase, ubiquitin (SEQ ID NO:46), CaMV 19S, nos, Adh, sucrose synthase, R-allele, root cell promoter, the vascular tissue specific promoters S2A (Genbank accession number EF030816; SEQ ID NO:47) and S2B (Genbank accession number EF030817) and the constitutive promoter GOS2 (SEQ ID NO:45) from *Zea mays*. Other preferred promoters include root preferred promoters, such as the maize NAS2 promoter (SEQ ID NO:44), the maize Cyclo promoter (US 2006/0156439, published Jul. 13, 2006), the maize ROOT-MET2 promoter (WO05063998, published Jul. 14, 2005), the CR1BIO promoter (WO06055487, published May 26, 2006), the CRWAQ81 (WO05035770, published Apr. 21, 2005) and the maize ZRP2.47 promoter (NCBI accession number: U38790, gi: 1063664).

A "substantial portion" of a nucleotide sequence comprises a nucleotide sequence that is sufficient to afford putative identification of the promoter that the nucleotide sequence comprises. Nucleotide sequences can be evaluated either manually, by one skilled in the art, or using computer-based sequence comparison and identification tools that employ algorithms such as BLAST (Basic Local Alignment Search Tool; Altschul et al. (1993) *J. Mol. Biol.* 215:403-410). In general, a sequence of thirty or more contiguous nucleotides is necessary in order to putatively identify a promoter nucleic acid sequence as homologous to a known promoter. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

Recombinant DNA constructs (and suppression DNA constructs) of the present invention may also include other regulatory sequences, including but not limited to, translation leader sequences, introns, and polyadenylation recognition sequences. In another preferred embodiment of the present invention, a recombinant DNA construct of the present invention further comprises an enhancer or silencer.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell. Biol.* 8:4395-4405 (1988); Callis et al., *Genes Dev.* 1:1183-1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, New York (1994).

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

A translation leader sequence is a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. Molecular Biotechnology 3:225 (1995)).

In another preferred embodiment of the present invention, a recombinant DNA construct of the present invention further comprises an enhancer or silencer.

Any plant can be selected for the identification of regulatory sequences and genes to be used in creating recombinant DNA constructs and suppression DNA constructs of the present invention. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini. Particularly preferred plants for the identification of regulatory sequences are *Arabidopsis*, corn, wheat, soybean, and cotton.

Preferred Compositions

A preferred composition of the present invention is a plant comprising in its genome any of the recombinant DNA constructs (including any of the suppression DNA constructs) of the present invention (such as those preferred constructs discussed above). Preferred compositions also include any progeny of the plant, and any seed obtained from the plant or its progeny, wherein the progeny or seed comprises within its genome the recombinant DNA construct (or suppression DNA construct). Progeny includes subsequent generations obtained by self-pollination or out-crossing of a plant. Progeny also includes hybrids and inbreds.

Preferably, in hybrid seed propagated crops, mature transgenic plants can be self-pollinated to produce a homozygous inbred plant. The inbred plant produces seed containing the newly introduced recombinant DNA construct (or suppression DNA construct). These seeds can be grown to produce plants that would exhibit altered root (or plant) architecture, or used in a breeding program to produce hybrid seed, which can be grown to produce plants that would exhibit altered root (or plant) architecture. Preferably, the seeds are maize.

Preferably, the plant is a monocotyledonous or dicotyledonous plant, more preferably, a maize or soybean plant, even more preferably a maize plant, such as a maize hybrid plant or a maize inbred plant. The plant may also be sunflower, sorghum, castor bean, grape, canola, wheat, alfalfa, cotton, rice, barley or millet.

Preferably, the recombinant DNA construct is stably integrated into the genome of the plant.

Particularly preferred embodiments include but are not limited to the following preferred embodiments:

1. A plant (preferably a maize or soybean plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 21, 23, 25, 27, 29, 31, or 34, and wherein said plant exhibits an altered root architecture when compared to a control plant not comprising said recombinant DNA construct. Preferably, the plant further exhibits an alteration of at least one agronomic characteristic when compared to the control plant.

2. A plant (preferably a maize or soybean plant) comprising in its genome:
a recombinant DNA construct comprising:
(a) a polynucleotide operably linked to at least one regulatory element, wherein said polynucleotide encodes a polypeptide having an amino acid sequence of at least 50% sequence identity, based on the Clustal V method of alignment, when compared to SEQ ID NO: 15, 17, 19, 21, 23, 25, 27, 29, 31, or 34, or
(b) a suppression DNA construct comprising at least one regulatory element operably linked to:
(i) all or part of: (A) a nucleic acid sequence encoding a polypeptide having an amino acid sequence of at least 50% sequence identity, based on the Clustal V method of alignment, when compared to SEQ ID NO: 15, 17, 19, 21, 23, 25, 27, 29, 31, or 34, or (B) a full complement of the nucleic acid sequence of (b)(i)(A); or
(ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a EXST or EXST-like polypeptide, and wherein said plant exhibits an alteration of at least one agronomic characteristic when compared to a control plant not comprising said recombinant DNA construct.

3. A plant (preferably a maize or soybean plant) comprising in its genome a recombinant DNA construct comprising a polynucleotide operably linked to at least one regulatory sequence, wherein said polynucleotide encodes a EXST or EXST-like protein, and wherein said plant exhibits an altered root architecture when compared to a control plant not comprising said recombinant DNA construct. Preferably, the plant further exhibits an alteration of at least one agronomic characteristic.

Preferably, the EXST protein is from *Arabidopsis thaliana, Zea mays, Glycine max, Glycine tabacina, Glycine soja* or *Glycine tomentella*.

4. A plant (preferably a maize or soybean plant) comprising in its genome a suppression DNA construct comprising at least one regulatory element operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a EXST or EXST-like protein, and wherein said plant exhibits an alteration of at least one agronomic characteristic when compared to a control plant not comprising said recombinant DNA construct.

5. A plant (preferably a maize or soybean plant) comprising in its genome a suppression DNA construct comprising at least one regulatory element operably linked to all or part of (a) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 21, 23, 25, 27, 29, 31, or 34, or (b) a full complement of the nucleic acid sequence of (a), and wherein said plant exhibits an alteration of at least one agronomic characteristic when compared to a control plant not comprising said recombinant DNA construct.

6. Any progeny of the above plants in preferred embodiments 1-5, any seeds of the above plants in preferred embodiments 1-5, any seeds of progeny of the above plants in preferred embodiments 1-5, and cells from any of the above plants in preferred embodiments 1-5 and progeny thereof.

In any of the foregoing preferred embodiments 1-6 or any other embodiments of the present invention, the recombinant DNA construct (or suppression DNA construct) preferably comprises at least a promoter that is functional in a plant as a preferred regulatory sequence.

In any of the foregoing preferred embodiments 1-6 or any other embodiments of the present invention, the alteration of at least one agronomic characteristic is either an increase or decrease, preferably an increase.

In any of the foregoing preferred embodiments 1-6 or any other embodiments of the present invention, the at least one agronomic characteristic is preferably selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, stalk lodging, plant height, ear length and harvest index. Yield, greenness, biomass and root lodging are particularly preferred agronomic characteristics for alteration (preferably an increase).

In any of the foregoing preferred embodiments 1-6 or any other embodiments of the present invention, the plant preferably exhibits the alteration of at least one agronomic characteristic irrespective of the environmental conditions, for example, water and nutrient availability, when compared to a control plant.

One of ordinary skill in the art is familiar with protocols for determining alteration in plant root architecture. For example, transgenic maize plants can be assayed for changes in root architecture at seedling stage, flowering time or maturity. Alterations in root architecture can be determined by counting the nodal root numbers of the top 3 or 4 nodes of the greenhouse grown plants or the width of the root band. "Root band" refers to the width of the mat of roots at the bottom of a pot at plant maturity. Other measures of alterations in root architecture include, but are not limited to, the number of lateral roots, average root diameter of nodal roots, average root diameter of lateral roots, number and length of root hairs.

The extent of lateral root branching (e.g. lateral root number, lateral root length) can be determined by sub-sampling a complete root system, imaging with a flat-bed scanner or a digital camera and analyzing with WinRHIZO™ software (Regent Instruments Inc.).

Data taken on root phenotype are subjected to statistical analysis, normally a t-test to compare the transgenic roots with that of non-transgenic sibling plants. One-way ANOVA may also be used in cases where multiple events and/or constructs are involved in the analysis.

The Examples below describe some representative protocols and techniques for detecting alterations in root architecture.

One can also evaluate alterations in root architecture by the ability of the plant to increase yield in field testing when compared, under the same conditions, to a control or reference plant.

One can also evaluate alterations in root architecture by the ability of the plant to maintain substantial yield (preferably at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under stress conditions (e.g., nutrient over-abundance or limitation, water over-abundance or limitation, presence of disease), when compared to the yield of a control or reference plant under non-stressed conditions.

Alterations in root architecture can also be measured by determining the resistance to root lodging of the transgenic plants compared to reference or control plants.

One of ordinary skill in the art would readily recognize a suitable control or reference plant to be utilized when assessing or measuring an agronomic characteristic or phenotype of a transgenic plant in any embodiment of the present invention in which a control or reference plant is utilized (e.g., compositions or methods as described herein). For example, by way of non-limiting illustrations:

1. Progeny of a transformed plant which is hemizygous with respect to a recombinant DNA construct (or suppression DNA construct), such that the progeny are segregating into plants either comprising or not comprising the recombinant DNA construct (or suppression DNA construct): the progeny comprising the recombinant DNA construct (or suppression DNA construct) would be typically measured relative to the progeny not comprising the recombinant DNA construct (or suppression DNA construct) (i.e., the progeny not comprising the recombinant DNA construct (or suppression DNA construct) is the control or reference plant).

2. Introgression of a recombinant DNA construct (or suppression DNA construct) into an inbred line, such as in maize, or into a variety, such as in soybean: the introgressed line would typically be measured relative to the parent inbred or variety line (i.e., the parent inbred or variety line is the control or reference plant).

3. Two hybrid lines, where the first hybrid line is produced from two parent inbred lines, and the second hybrid line is produced from the same two parent inbred lines except that one of the parent inbred lines contains a recombinant DNA construct (or suppression DNA construct): the second hybrid line would typically be measured relative to the first hybrid line (i.e., the parent inbred or variety line is the control or reference plant).

4. A plant comprising a recombinant DNA construct (or suppression DNA construct): the plant may be assessed or measured relative to a control plant not comprising the recombinant DNA construct (or suppression DNA construct) but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct (or suppression DNA construct). There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

Furthermore, one of ordinary skill in the art would readily recognize that a suitable control or reference plant to be utilized when assessing or measuring an agronomic characteristic or phenotype of a transgenic plant would not include a plant that had been previously selected, via mutagenesis or transformation, for the desired agronomic characteristic or phenotype.

Preferred Methods

Preferred methods include but are not limited to methods for altering root architecture in a plant, methods for evaluating alteration of root architecture in a plant, methods for altering an agronomic characteristic in a plant, methods for determining an alteration of an agronomic characteristic in a plant, and methods for producing seed. Preferably, the plant is a monocotyledonous or dicotyledonous plant, more preferably, a maize or soybean plant, even more preferably a maize plant. The plant may also be sunflower, sorghum, castor bean, canola, wheat, alfalfa, cotton, rice, barley or millet. The seed is preferably a maize or soybean seed, more preferably a maize seed, and even more preferably, a maize hybrid seed or maize inbred seed.

Particularly preferred methods include but are not limited to the following:

A method of altering root architecture of a plant, comprising: (a) introducing into a regenerable plant cell a recombinant DNA construct comprising a polynucleotide operably linked to at least one regulatory sequence (preferably a promoter functional in a plant), wherein the polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 21, 23, 25, 27, 29, 31, or 34; and (b) regenerating a transgenic plant from the regenerable plant cell after step (a), wherein the transgenic plant comprises in its genome the recombinant DNA construct and exhibits altered root architecture when compared to a control plant not comprising the recombinant DNA construct. The method may further comprise (c) obtaining a progeny plant derived from the transgenic plant, wherein said progeny plant comprises in its genome the recombinant DNA construct and exhibits altered root architecture when compared to a control plant not comprising the recombinant DNA construct.

A method of altering root architecture in a plant, comprising: (a) introducing into a regenerable plant cell a suppression DNA construct comprising at least one regulatory sequence (preferably a promoter functional in a plant) operably linked to:

(i) all or part of: (A) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 21, 23, 25, 27, 29, 31, or 34, or (B) a full complement of the nucleic acid sequence of (a)(i)(A); or (ii) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a EXST or EXST-like polypeptide; and (b) regenerating a transgenic plant from the regenerable plant cell after step (a), wherein the transgenic plant comprises in its genome the recombinant DNA construct and exhibits an altered root architecture when compared to a control plant not comprising the suppression DNA construct. The method may further comprise (c) obtaining a progeny plant derived from the transgenic plant, wherein said progeny plant comprises in its genome the recombinant DNA construct and exhibits altered root architecture when compared to a control plant not comprising the suppression DNA construct.

A method of evaluating altered root architecture in a plant, comprising (a) introducing into a regenerable plant cell a recombinant DNA construct comprising a polynucleotide operably linked to at least on regulatory sequence (preferably a promoter functional in a plant), wherein the polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 21, 23, 25, 27, 29, 31, or 34, or (b) regenerating a transgenic plant from the regenerable plant cell after step (a), wherein the transgenic plant comprises in its genome the recombinant DNA construct; and (c) evaluating root architecture of the transgenic plant compared to a control plant not comprising the recombinant DNA construct. The method may further comprise (d) obtaining a progeny plant derived from the transgenic plant, wherein the progeny plant comprises in its genome the recombinant DNA construct; and (e) evaluating root architecture of the progeny plant compared to a control plant not comprising the recombinant DNA construct.

A method of evaluating altered root architecture in a plant, comprising (a) introducing into a regenerable plant cell a suppression DNA construct comprising at least one regulatory sequence (preferably a promoter functional in a plant) operably linked to:

(i) all or part of: (A) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 21, 23, 25, 27, 29, 31, or 34, or (B) a full complement of the nucleic acid sequence of (a)(i)(A); or (ii) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a EXST or EXST-like polypeptide; and (b) regenerating a transgenic plant from the regenerable plant cell after step (a), wherein the transgenic plant comprises in its genome the suppression DNA construct; and (c) evaluating the transgenic plant for altered root architecture compared to a control plant not comprising the suppression DNA construct. The method may further comprise (d) obtaining a progeny plant derived from the transgenic plant, wherein the progeny plant comprises in its genome the suppression DNA construct; and (e) evaluating the progeny plant for altered root architecture compared to a control plant not comprising the suppression DNA construct.

A method of evaluating altered root architecture in a plant, comprising (a) introducing into a regenerable plant cell a recombinant DNA construct comprising a polynucleotide operably linked to at least one regulatory sequence (preferably a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 21, 23, 25, 27, 29, 31, or 34 (b) regenerating a transgenic plant from the regenerable plant cell after step (a), wherein the transgenic plant comprises in its genome the recombinant DNA construct; (c) obtaining a progeny plant derived from said transgenic plant, wherein the progeny plant comprises in its genome the recombinant DNA construct; and (d) evaluating the progeny plant for altered root architecture compared to a control plant not comprising the recombinant DNA construct.

A method of evaluating root architecture in a plant, comprising:

(a) introducing into a regenerable plant cell a suppression DNA construct comprising at least one regulatory element operably linked to: (i) all or part of: (A) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 21, 23, 25, 27, 29, 31, or 34, or (B) a full complement of the nucleic acid sequence of (a)(i)(A); or (ii) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a EXST or EXST-like polypeptide; (b) regenerating a transgenic plant from the regenerable plant cell after step (a), wherein the transgenic plant comprises in its genome the suppression DNA construct; (c) obtaining a progeny plant derived from the transgenic plant, wherein the progeny plant comprises in its genome the suppression DNA construct; and (d) evaluating root architecture of the progeny plant compared to a control plant not comprising the suppression DNA construct.

A method of determining an alteration of an agronomic characteristic in a plant, comprising (a) introducing into a regenerable plant cell a recombinant DNA construct comprising a polynucleotide operably linked to at least on regulatory sequence (preferably a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 21, 23, 25, 27, 29, 31, or 34 (b) regenerating a transgenic plant from the regenerable plant cell after step (a), wherein the transgenic plant comprises in its genome said recombinant DNA construct; and (c) determining whether the transgenic plant exhibits an alteration of at least one agronomic characteristic when compared to a control plant not comprising the recombinant DNA construct. The method may further comprise (d) obtaining a progeny plant derived from the transgenic plant, wherein the progeny plant comprises in its genome the recombinant DNA construct; and (e) determining whether the progeny plant exhibits an alteration of at least one agronomic characteristic when compared to a control plant not comprising the recombinant DNA construct.

A method of determining an alteration of an agronomic characteristic in a plant, comprising (a) introducing into a regenerable plant cell a suppression DNA construct comprising at least one regulatory sequence (preferably a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 21, 23, 25, 27, 29, 31, or 34, or (ii) a full complement of the nucleic acid sequence of (i); (b) regenerating a transgenic plant from the regenerable plant cell after step (a), wherein the transgenic plant comprises in its genome the suppression DNA construct; and (c) determining whether the transgenic plant exhibits an alteration in at least one agronomic characteristic when compared to a control plant not comprising the suppression DNA construct. The method may further comprise (d) obtaining a progeny plant derived from the transgenic plant, wherein the progeny plant comprises in its genome the suppression DNA construct; and (e) determining whether the progeny plant exhibits an alteration in at least one agronomic characteristic when compared to a control plant not comprising the suppression DNA construct.

A method of determining an alteration of an agronomic characteristic in a plant, comprising (a) introducing into a regenerable plant cell a recombinant DNA construct comprising a polynucleotide operably linked to at least one regulatory sequence (preferably a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 21, 23, 25, 27, 29, 31, or 34 (b) regenerating a transgenic plant from the regenerable plant cell after step (a), wherein the transgenic plant comprises in its genome said recombinant DNA construct; (c) obtaining a progeny plant derived from said transgenic plant, wherein the progeny plant comprises in its genome the recombinant DNA construct; and (d) determining whether the progeny plant exhibits an alteration of at least one agronomic characteristic when compared to a control plant not comprising the recombinant DNA construct. The method of determining an alteration of an agronomic characteristic in a plant may further comprise determining whether the transgenic plant exhibits an alteration of at least one agronomic characteristic when compared, under varying environmental conditions, to a control plant not comprising the recombinant DNA construct.

A method of determining an alteration of an agronomic characteristic in a plant, comprising (a) introducing into a regenerable plant cell a suppression DNA construct comprising at least one regulatory sequence (preferably a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 21, 23, 25, 27, 29, 31, or 34, or (ii) a full complement of the nucleic acid sequence of (i);

(b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) determining whether the progeny plant exhibits an alteration in at least one agronomic characteristic when compared to a control plant not comprising the recombinant DNA construct.

A method of determining an alteration of an agronomic characteristic in a plant, comprising: (a) introducing into a regenerable plant cell a suppression DNA construct comprising at least one regulatory element operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a EXST or EXST-like polypeptide; (b) regenerating a transgenic plant from the regenerable plant cell after step (a), wherein the transgenic plant comprises in its genome the suppression DNA construct; and (c) determining whether the transgenic plant exhibits an alteration of at least one agronomic characteristic when compared to a control plant not comprising the suppression DNA construct. The method may further comprise: (d) obtaining a progeny plant derived from the transgenic plant, wherein the progeny plant comprises in its genome the suppression DNA construct; and (e) determining whether the progeny plant exhibits an alteration of at least one agronomic characteristic when compared to a control plant not comprising the suppression DNA construct.

A method of determining an alteration of an agronomic characteristic in a plant, comprising: (a) introducing into a regenerable plant cell a suppression DNA construct comprising at least one regulatory element operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a EXST or EXST-like polypeptide; (b) regenerating a transgenic plant from the regenerable plant cell after step (a), wherein the transgenic plant comprises in its genome the suppression DNA construct; (c) obtaining a progeny plant derived from the transgenic plant, wherein the progeny plant comprises in its genome the suppression DNA construct; and (d) determining whether the progeny plant exhibits an alteration of at least one agronomic characteristic when compared to a control plant not comprising the suppression DNA construct.

A method of producing seed (preferably seed that can be sold as a product offering with altered root architecture) comprising any of the preceding preferred methods, and further comprising obtaining seeds from said progeny plant, wherein said seeds comprise in their genome said recombinant DNA construct (or suppression DNA construct).

In any of the foregoing preferred methods or any other embodiments of methods of the present invention, the step of determining an alteration of an agronomic characteristic in a transgenic plant, if applicable, may preferably comprise determining whether the transgenic plant exhibits an alteration of at least one agronomic characteristic when compared, under varying environmental conditions, to a control plant not comprising the recombinant DNA construct.

In any of the foregoing preferred methods or any other embodiments of methods of the present invention, the step of determining an alteration of an agronomic characteristic in a progeny plant, if applicable, may preferably comprise determining whether the progeny plant exhibits an alteration of at least one agronomic characteristic when compared, under varying environmental conditions, to a control plant not comprising the recombinant DNA construct.

In any of the preceding preferred methods or any other embodiments of methods of the present invention, in said introducing step said regenerable plant cell preferably comprises a callus cell (preferably embryogenic), a gametic cell, a meristematic cell, or a cell of an immature embryo. The regenerable plant cells are preferably from an inbred maize plant.

In any of the preceding preferred methods or any other embodiments of methods of the present invention, said regenerating step preferably comprises: (i) culturing said transformed plant cells in a media comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding preferred methods or any other embodiments of methods of the present invention, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, preferably as part of a transposable element), and then screen for an event in which the regulatory sequence is operably linked to an endogenous gene encoding a polypeptide of the instant invention.

The introduction of recombinant DNA constructs of the present invention into plants may be carried out by any suitable technique, including but not limited to direct DNA uptake, chemical treatment, electroporation, microinjection, cell fusion, infection, vector mediated DNA transfer, bombardment, or *Agrobacterium* mediated transformation.

In any of the preceding preferred methods or any other embodiments of methods of the present invention, the at least one agronomic characteristic is preferably selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, stalk lodging, plant height, ear length, stalk lodging and harvest index. Yield, greenness, biomass and root lodging are particularly preferred agronomic characteristics for alteration (preferably an increase).

In any of the preceding preferred methods or any other embodiments of methods of the present invention, the plant preferably exhibits the alteration of at least one agronomic characteristic irrespective of the environmental conditions when compared to a control.

The introduction of recombinant DNA constructs of the present invention into plants may be carried out by any suitable technique, including but not limited to direct DNA uptake, chemical treatment, electroporation, microinjection, cell fusion, infection, vector mediated DNA transfer, bombardment, or *Agrobacterium* mediated transformation.

Preferred techniques are set forth below in the Examples below for transformation of maize plant cells and soybean plant cells.

Other preferred methods for transforming dicots, primarily by use of *Agrobacterium tumefaciens*, and obtaining transgenic plants include those published for cotton (U.S. Pat. No.

5,004,863, U.S. Pat. No. 5,159,135, U.S. Pat. No. 5,518,908); soybean (U.S. Pat. No. 5,569,834, U.S. Pat. No. 5,416,011, McCabe et. al., *Bio/Technology* 6:923 (1988), Christou et al., *Plant Physiol.* 87:671 674 (1988)); *Brassica* (U.S. Pat. No. 5,463,174); peanut (Cheng et al., *Plant Cell Rep.* 15:653 657 (1996), McKently et al., *Plant Cell Rep.* 14:699 703 (1995)); papaya; and pea (Grant et al., *Plant Cell Rep.* 15:254 258, (1995)).

Transformation of monocotyledons using electroporation, particle bombardment, and *Agrobacterium* have also been reported and are included as preferred methods, for example, transformation and plant regeneration as achieved in asparagus (Bytebier et al., *Proc. Natl. Acad. Sci. U.S.A.* 84:5354, (1987)); barley (Wan and Lemaux, *Plant Physiol.* 104:37 (1994)); *Zea mays* (Rhodes et al., *Science* 240:204 (1988), Gordon-Kamm et al., *Plant Cell* 2:603 618 (1990), Fromm et al., *Bio/Technology* 8:833 (1990), Koziel et al., *Bio/Technology* 11:194, (1993), Armstrong et al., *Crop Science* 35:550-557 (1995)); oat (Somers et al., *Bio/Technology* 10:1589 (1992)); orchard grass (Horn et al., *Plant Cell Rep.* 7:469 (1988)); rice (Toriyama et al., *Theor. Appl. Genet.* 205:34, (1986); Part et al., *Plant Mol. Biol.* 32:1135 1148, (1996); Abedinia et al., *Aust. J. Plant Physiol.* 24:133 141 (1997); Zhang and Wu, *Theor. Appl. Genet.* 76:835 (1988); Zhang et al., *Plant Cell Rep.* 7:379, (1988); Battraw and Hall, *Plant Sci.* 86:191 202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al., *Bio/Technology* 10:691 (1992)), and wheat (Vasil et al., *Bio/Technology* 10:667 (1992); U.S. Pat. No. 5,631,152).

There are a variety of methods for the regeneration of plants from plant tissue. The particular method of regeneration will depend on the starting plant tissue and the particular plant species to be regenerated.

The regeneration, development, and cultivation of plants from single plant protoplast transformants or from various transformed explants is well known in the art (Weissbach and Weissbach, In: Methods for Plant Molecular Biology, (Eds.), Academic Press, Inc. San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous isolated nucleic acid fragment that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In another aspect, this invention also concerns a method of mapping genetic variations related to altering root architecture and/or altering at least one agronomic characteristic in plants comprising:

(a) crossing two plant varieties; and
(c) evaluating genetic variations with respect to:
(i) a nucleic acid sequence selected from the group consisting of SEQ ID NO: 14, 16, 18, 20, 22, 24, 26, 28, 30 or 33; or
(iii) a nucleic acid sequence encoding a polypeptide selected from the group consisting of SEQ ID NO: 15; 17, 19, 21, 23, 25, 27, 29, 31 or 34
in progeny plants resulting from the cross of step (a) wherein the evaluation is made using a method selected from the group consisting of: RFLP analysis, SNP analysis, and PCR-based analysis.

In another embodiment, this invention concerns a method of molecular breeding to obtain an altered root architecture and/or at least one altered agronomic characteristic in plants comprising:

(a) crossing two plant varieties; and
(b) evaluating genetic variations with respect to:
(i) a nucleic acid sequence selected from the group consisting of SEQ ID NO: 14, 16, 18, 20, 22, 24, 26, 28, 30 or 33; or
(iii) a nucleic acid sequence encoding a polypeptide selected from the group consisting of SEQ ID NO: 15; 17, 19, 21, 23, 25, 27, 29, 31 or 34;
in progeny plants resulting from the cross of step (a) wherein the evaluation is made using a method selected from the group consisting of: RFLP analysis, SNP analysis, and PCR-based analysis.

The terms "mapping genetic variation" or "mapping genetic variability" are used interchangeably and define the process of identifying changes in DNA sequence, whether from natural or induced causes, within a genetic region that differentiates between different plant lines, cultivars, varieties, families, or species. The genetic variability at a particular locus (gene) due to even minor base changes can alter the pattern of restriction enzyme digestion fragments that can be generated. Pathogenic alterations to the genotype can be due to deletions or insertions within the gene being analyzed or even single nucleotide substitutions that can create or delete a restriction enzyme recognition site. RFLP analysis takes advantage of this and utilizes Southern blotting with a probe corresponding to the isolated nucleic acid fragment of interest.

Thus, if a polymorphism (i.e., a commonly occurring variation in a gene or segment of DNA; also, the existence of several forms of a gene (alleles) in the same species) creates or destroys a restriction endonuclease cleavage site, or if it results in the loss or insertion of DNA (e.g., a variable nucleotide tandem repeat (VNTR) polymorphism), it will alter the size or profile of the DNA fragments that are generated by digestion with that restriction endonuclease. As such, individuals that possess a variant sequence can be distinguished from those having the original sequence by restriction fragment analysis. Polymorphisms that can be identified in this manner are termed "restriction fragment length polymorphisms: ("RFLPs"). RFLPs have been widely used in human and plant genetic analyses (Glassberg, UK Patent Application 2135774; Skolnick et al, Cytogen. *Cell Genet.* 32:58-67 (1982); Botstein et al, *Ann. J. Hum. Genet.* 32:314-331 (1980); Fischer et al (PCT Application WO 90/13668; Uhlen, PCT Application WO 90/11369).

A central attribute of "single nucleotide polymorphisms" or "SNPs" is that the site of the polymorphism is at a single nucleotide. SNPs have certain reported advantages over RFLPs or VNTRs. First, SNPs are more stable than other classes of polymorphisms. Their spontaneous mutation rate is approximately $10^{-9}$ (Kornberg, DNA Replication, W.H. Freeman & Co., San Francisco, 1980), approximately, 1,000 times less frequent than VNTRs (U.S. Pat. No. 5,679,524). Second, SNPs occur at greater frequency, and with greater uniformity than RFLPs and VNTRs. As SNPs result from sequence variation, new polymorphisms can be identified by sequencing random genomic or cDNA molecules. SNPs can also result from deletions, point mutations and insertions. Any single base alteration, whatever the cause, can be a SNP. The greater frequency of SNPs means that they can be more readily identified than the other classes of polymorphisms.

SNPs can be characterized using any of a variety of methods. Such methods include the direct or indirect sequencing of the site, the use of restriction enzymes where the respective alleles of the site create or destroy a restriction site, the use of allele-specific hybridization probes, the use of antibodies that are specific for the proteins encoded by the different alleles of the polymorphism or by other biochemical interpretation. SNPs can be sequenced by a number of methods. Two basic methods may be used for DNA sequencing, the chain termination method of Sanger et al, *Proc. Natl. Acad. Sci.* (U.S.A.) 74:5463-5467 (1977), and the chemical degradation method of Maxam and Gilbert, *Proc. Natl. Acad. Sci.* (U.S.A.) 74: 560-564 (1977).

Furthermore, single point mutations can be detected by modified PCR techniques such as the ligase chain reaction ("LCR") and PCR-single strand conformational polymorphisms ("PCR-SSCP") analysis. The PCR technique can also be used to identify the level of expression of genes in extremely small samples of material, e.g., tissues or cells from a body. The technique is termed reverse transcription-PCR ("RT-PCR").

The term "molecular breeding" defines the process of tracking molecular markers during the breeding process. It is common for the molecular markers to be linked to phenotypic traits that are desirable. By following the segregation of the molecular marker or genetic trait, instead of scoring for a phenotype, the breeding process can be accelerated by growing fewer plants and eliminating assaying or visual inspection for phenotypic variation. The molecular markers useful in this process include, but are not limited to, any marker useful in identifying mapable genetic variations previously mentioned, as well as any closely linked genes that display synteny across plant species. The term "synteny" refers to the conservation of gene placement/order on chromosomes between different organisms. This means that two or more genetic loci, that may or may not be closely linked, are found on the same chromosome among different species. Another term for synteny is "genome colinearity".

The goal of gene mapping is to identify genes which contribute to phenotypes of interest. The first stage of mapping is usually to locate a general region of a chromosome which is associated with transmission of the phenotypes of interest. Next, the gene and ultimately, particular alleles, are identified as having a causative role.

Association mapping generally falls into two broad categories: 1) candidate-gene association mapping, which relates polymorphisms in selected candidate genes that have purported roles in controlling phenotypic variation for specific traits; and 2) genome-wide association mapping, or genome scan, which surveys genetic variation in the whole genome to find signals of association for various complex traits.

In candidate-gene association mapping, candidate genes are selected based on prior knowledge from mutational analysis, biochemical pathway, or linkage analysis of the trait of interest. An independent set of random markers need to be scored to infer genetic relationships.

Genome-wide association mapping is a comprehensive approach to systematically search the genome for causal genetic variation. A large number of markers are tested for association with various complex traits, and prior information regarding candidate genes is not required. (Zhu et al. (2008) The Plant Genome, 1: 5-20).

EXAMPLES

The present invention is further illustrated in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Creation of an *Arabidopsis* Population with Activation-Tagged Genes

Figure 1:
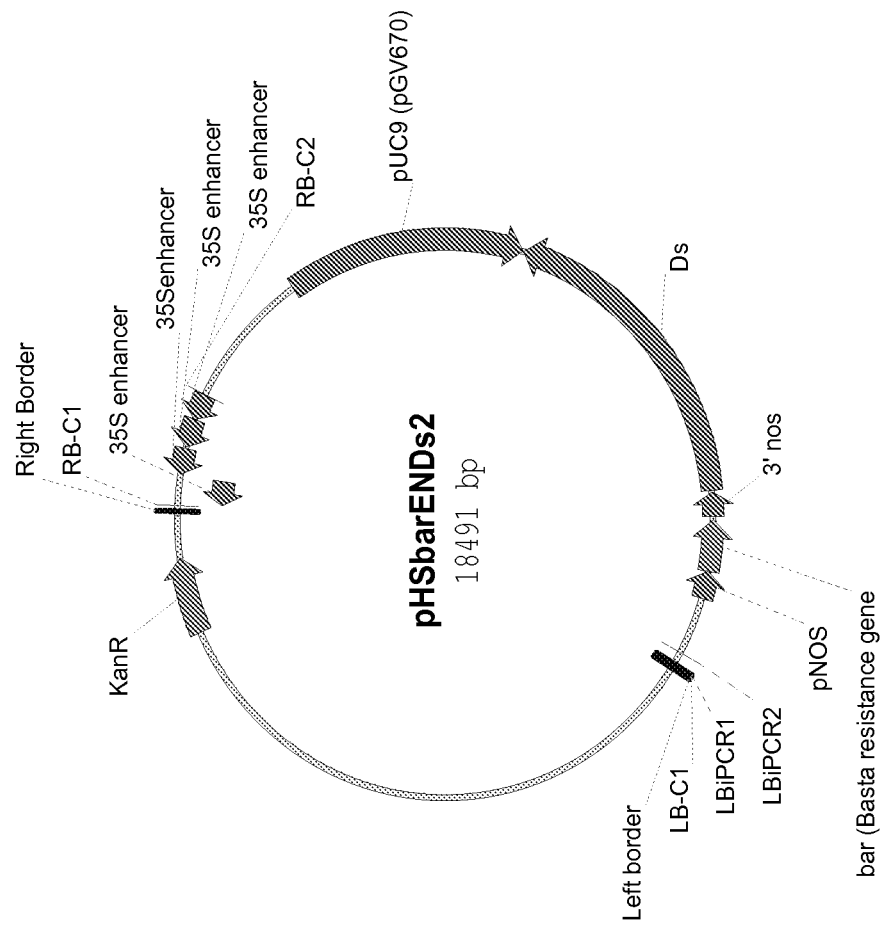
FIG. 1 shows a map of the pHSbarENDs2 activation tagging construct (SEQ ID NO:1) used to make the *Arabidopsis* populations.

A 18.5 kb T-DNA based binary construct was created, pHSbarENDs2 (FIG. 1; SEQ ID NO:1;) containing four multimerized enhancer elements derived from the Cauliflower Mosaic Virus 35S promoter, corresponding to sequences −341 to −64, as defined by Odell et al. (1985) *Nature* 313: 810-812. The construct also contains vector sequences (pUC9) to allow plasmid rescue, transposon sequences (Ds) to remobilize the T-DNA, and the bar gene to allow for glufosinate selection of transgenic plants. Only the 10.8 kb segment from the right border (RB) to left border (LB) inclusive will be transferred into the host plant genome. Since the enhancer elements are located near the RB, they can induce cis-activation of genomic loci following T-DNA integration.

The pHSbarENDs2 construct was transformed into *Agrobacterium tumefaciens* strain C58, grown in LB at 25° C. to OD600 ~1.0. Cells were then pelleted by centrifugation and resuspended in an equal volume of 5% sucrose/0.05% Silwet L-77 (OSI Specialties, Inc). At early bolting, soil grown *Arabidopsis thaliana* ecotype Col-0 were top watered with the *Agrobacterium* suspension. A week later, the same plants were top watered again with the same *Agrobacterium* strain in sucrose/Silwet. The plants were then allowed to set seed as normal. The resulting $T_1$ seed were sown on soil, and transgenic seedlings were selected by spraying with glufosinate (Finale®; AgrEvo; Bayer Environmental Science). $T_2$ seed was collected from approximately 35,000 individual glufosinate resistant $T_1$ plants. $T_2$ plants were grown and equal volumes of $T_3$ seed from 96 separate $T_2$ lines were pooled. This constituted 360 sub-populations.

A total of 100,000 glufosinate resistant $T_1$ seedlings were selected. $T_2$ seeds from each line were kept separate.

Example 2A

Screens to Identify Lines with Altered Root Architecture

Non-Limiting Nitrogen Conditions

Activation-tagged *Arabidopsis* seedlings, grown under non-limiting nitrogen conditions, can be analyzed for altered root system architecture when compared to control seedlings during early development from the population described in Example 1.

From each of 96,000 separate T1 activation-tagged lines, ten T2 seeds can be sterilized with chlorine gas and planted on petri plates containing the following medium: 0.5×N-Free Hoagland's, 60 mM $KNO_3$, 0.1% sucrose, 1 mM MES and 1% Phytagel™. Typically 10 plates are placed in a rack. Plates are kept for three days at 4° C. to stratify seeds and then held vertically for 11 days at 22° C. light and 20° C. dark. Photoperiod is 16 h; 8 h dark, average light intensity was ~180 µmol/m²/s. Racks (typically holding 10 plates each) are rotated daily within each shelf. At day 14, plates are evaluated for seedling status, whole plate digital images were taken, and analyzed for root area. Plates are arbitrarily divided in 10 horizontal areas. The root area in each of 10 horizontal zones on the plate is expressed as a percentage of the total area. Only areas in zones 3 to 9 are used to calculate the total root area of the line. Rootbot image analysis tool (proprietary) developed by ICORIA can be used to assess root area. Total root area is expressed in $mm^2$.

Lines with enhanced root growth characteristics are expected to lie at the upper extreme of the root area distributions. A sliding window approach can be used to estimate the variance in root area for a given rack with the assumption that there could be up to two outliers in the rack. Environmental variations in various factors including growth media, temperature, and humidity can cause significant variation in root growth, especially between sow dates. Therefore the lines are grouped by sow date and shelf for the data analysis. The racks in a particular sow date/shelf group are then sorted by mean root area. Root area distributions for sliding windows is performed by combining data for a rack, $r_i$, with data from the rack with the next lowest, ($r_{i-1}$, and the next highest mean root area, $r_{i+1}$. The variance of the combined distribution is then analyzed to identify outliers in $r_i$ using a Grubbs-type approach (Barnett et al., Outliers in Statistical Data, John Wiley & Sons, $3^{rd}$ edition (1994).

Lines with significant enhanced root growth as determined by the method outlined above, are designated as Phase 1 hits. Phase 1 hits are re-screened in duplicate under the same assay conditions. When either or both of the Phase 2 replicates shows a significant difference from the mean, the line is then considered a validated root architecture line.

Those lines that are again found to be outliers in at least one plate in Phase 2 are subjected to a Phase 3 screening performed in house, to validate the results obtained in Phase 1 and Phase 2. The results are validated in Phase 3 using both the Rootboot image analysis (as described above) and WinRHIZO® as described below. The confirmation is performed in the same fashion as in the first round of screening. T2 seeds are sterilized using 50% household bleach 0.01% triton X-100 solution and plated onto the same plate medium as described in the first round of screening at a density of 10 seeds/plate. Plates are kept for three days at 4° C. to stratify seeds, and grown in the same temperature and photoperiod as the first experiment with the light intensity ~160 µmol/m²/s. Plates are placed vertically into the eight center positions of a 10 plate rack with the first and last position holding blank plates. The racks and the plates within a rack are rotated every other day. Two sets of pictures are taken for each plate. The first set taking place at day 14-16 when the primary roots for most lines have reached the bottom of the plate, the second set of pictures two days later after more lateral roots have developed. The latter set of picture is usually used for data analysis. These seedlings grown on vertical plates are analyzed for root growth with the software WinRHIZO® (Regent Instruments Inc), an image analysis system specifically designed for root measurement. WinRHIZO® uses the contrast in pixels to distinguish the light root from the darker background. To identify the maximum amount of roots without picking up background, the pixel classification is 150-170 and the filter feature is used to remove objects that have a length/width ratio less then 10.0. The area on the plates analyzed is from the edge of the plant's leaves to about 1 cm from the bottom of the plate. The exact same WinRHIZO® settings and area of analysis are used to analyze all plates within a batch. The total root length score given by WinRHIZO® for a plate is divided by the number of plants that has germinated and has grown halfway down the plate. Three plates for every line are grown and their scores are averaged. This average is then compared to the average of three plates containing wild type seeds that are grown at the same time.

*Arabidopsis* activation tagged lines re-confirmed by having a higher value of root growth compared to wild type are then used for the molecular identification of the DNA flanking the T-DNA insertion.

Example 2B

Identification of Mutant Lines with an Altered Root Phenotype in a Mutant Population Limiting Nitrogen Conditions A Two-Step Screening Procedure can be Used, Comprising:
(1) Identification of an altered root growth phenotype in a vertical plate assay;
(2) Confirm herbicide resistance and root phenotype in rescued mutant lines; The primary screen is based on vertical plates containing Nitrogen-free Hoagland salts, 0.3% sucrose and 1 mM $KNO_3$. The media also contains 0.8%-1.0% Phyta-Gel as a gelling agent. Media with Phytagel at 1.0% is sometimes difficult to pour as it solidifies quickly, however, at below 0.8% the media will slide off plates when placed vertically. Mutants from an activation-tagged population where pools of 100 lines each are available for a total of 36000 lines are being screened. On each plate, 12 mutant and 2 wild type Columbia seeds are seeded. Plates are placed in a growth room with a constant temperature of 26° C., 16 hr-day cycle with an average of 110 µE/m²s light intensity at the top of the plates. These plates are photographed 3-4 times in a 2.5 week time frame. Individual seedlings are rescued when a clear root phenotype is observed. Rescued seedlings are grown to maturity in a growth chamber (24° c., 16 hr day, 250-300 µE/m²s) for seed collection.

For the secondary screening, seeds from putative hits identified in the primary screen are sowed on plates containing the same media as above plus 6 mg/L bialaphos. Wild type Columbia seeds are sown at the same time on the same media but without bialaphos. Each plate has 10 seeds. There are 3 plates for each mutant line, and 2 plates for wild type Columbia, as replication. These plates are placed under the same growth conditions as described above in a growth room. Those lines that do not have herbicide resistance or no obvious root phenotype are discarded as false positives. Lines validated by the second screen are saved for further study.

Example 3

Identification of Activation-Tagged Genes

Genes flanking the T-DNA insert in lines with altered root architecture are identified using one, or both, of the following two standard procedures: (1) thermal asymmetric interlaced (TAIL) PCR (Liu et al., (1995), *Plant J.* 8:457-63); and (2) SAIFF PCR (Siebert et al., (1995) *Nucleic Acids Res.*

23:1087-1088). In lines with complex multimerized T-DNA inserts, TAIL PCR and SAIFF PCR may both prove insufficient to identify candidate genes. In these cases, other procedures, including inverse PCR, plasmid rescue and/or genomic library construction, can be employed.

A successful result is one where a single TAIL or SAIFF PCR fragment contains a T-DNA border sequence and *Arabidopsis* genomic sequence.

Once a tag of genomic sequence flanking a T-DNA insert is obtained, candidate genes are identified by alignment to publicly available *Arabidopsis* genome sequence.

Specifically, the annotated gene nearest the 35S enhancer elements/T-DNA RB are candidates for genes that are activated.

To verify that an identified gene is truly near a T-DNA and to rule out the possibility that the TAIL/SAIFF fragment is a chimeric cloning artifact, a diagnostic PCR on genomic DNA is done with one oligo in the T-DNA and one oligo specific for the candidate gene. Genomic DNA samples that give a PCR product are interpreted as representing a T-DNA insertion. This analysis also verifies a situation in which more than one insertion event occurs in the same line, e.g., if multiple differing genomic fragments are identified in TAIL and/or SAIFF PCR analyses.

Example 4

Identification of Activation-Tagged exst Gene

The exst gene was obtained by the screening procedure as described in Example 2A. Identification of the activation-tagged gene was performed as described in Example 3.

One line (112299) displaying altered root architecture was further analyzed. DNA from the line was extracted and the T-DNA insertion was found by ligation mediated PCR (Siebert et al., (1995) *Nucleic Acids Res.* 23:1087-1088) using primers within the LeftBorder of the T-DNA. Once a tag of genomic sequence flanking a T-DNA insert was obtained, the candidate gene was identified by sequence alignment to the completed *Arabidopsis* genome. One of the insertion sites identified was identified as a chimeric insertion; Left Border T-DNA sequence was determined to be at both ends of the T-DNA insertion. It is still possible that the enhancer elements located near the Right Border of the T-DNA are close enough to have an effect on the nearby candidate gene. In this case the location of the Right Border was assumed to be present at the insertion site, and the two genes that flank the insertion site were chosen as candidates. One of the genes nearest the 35S enhancers of the chimeric insertion was AT3G03650 (nucleotides 245-1744 corresponding to the ORF (SEQ ID NO:33), encoding the EXST protein (SEQ ID NO:34), referred herein as EXOSTOSIN FAMILY or EXST.

Example 5A

Validation of a Candidate *Arabidopsis* Gene (AT3G03650) for its Ability to Enhance Root Architecture in Plants Via Transformation into *Arabidopsis*

Candidate genes can be transformed into *Arabidopsis* and overexpressed under the 35S promoter. If the same or similar phenotype is observed in the transgenic line as in the parent activation-tagged line, then the candidate gene is considered to be a validated "lead gene" in *Arabidopsis*.

The *Arabidopsis* AT3G03650 Gene can be directly tested for its ability to enhance Root Architecture in *Arabidopsis*.

The *Arabidopsis* AT3G03650 cDNA was PCR amplified with oligos that introduce the attB1 (SEQ ID NO:39) sequence, a consensus start sequence (CAACA) upstream of the ATG start codon and the first 25 nucleotides of the protein coding-region of the AT3G03650 DNA (SEQ ID NO:57) and the attB2 (SEQ ID NO:40) sequence and the last 25 nucleotides of the protein-coding region including the stop codon of said cDNA. Using Invitrogen™ Gateway® technology a MultiSite Gateway® BP Recombination Reaction was performed with pDONR™/Zeo (Invitrogen™, FIG. 2; SEQ ID NO:2). This process removes the bacteria lethal ccdB gene, as well as the chloramphenicol resistance gene (CAM) from pDONR™/Zeo and directionally clones the PCR product with flanking attB1 (SEQ ID NO:39) and attB2 (SEQ ID NO:40) sites creating entry clone PHP28732.

Figure 4:
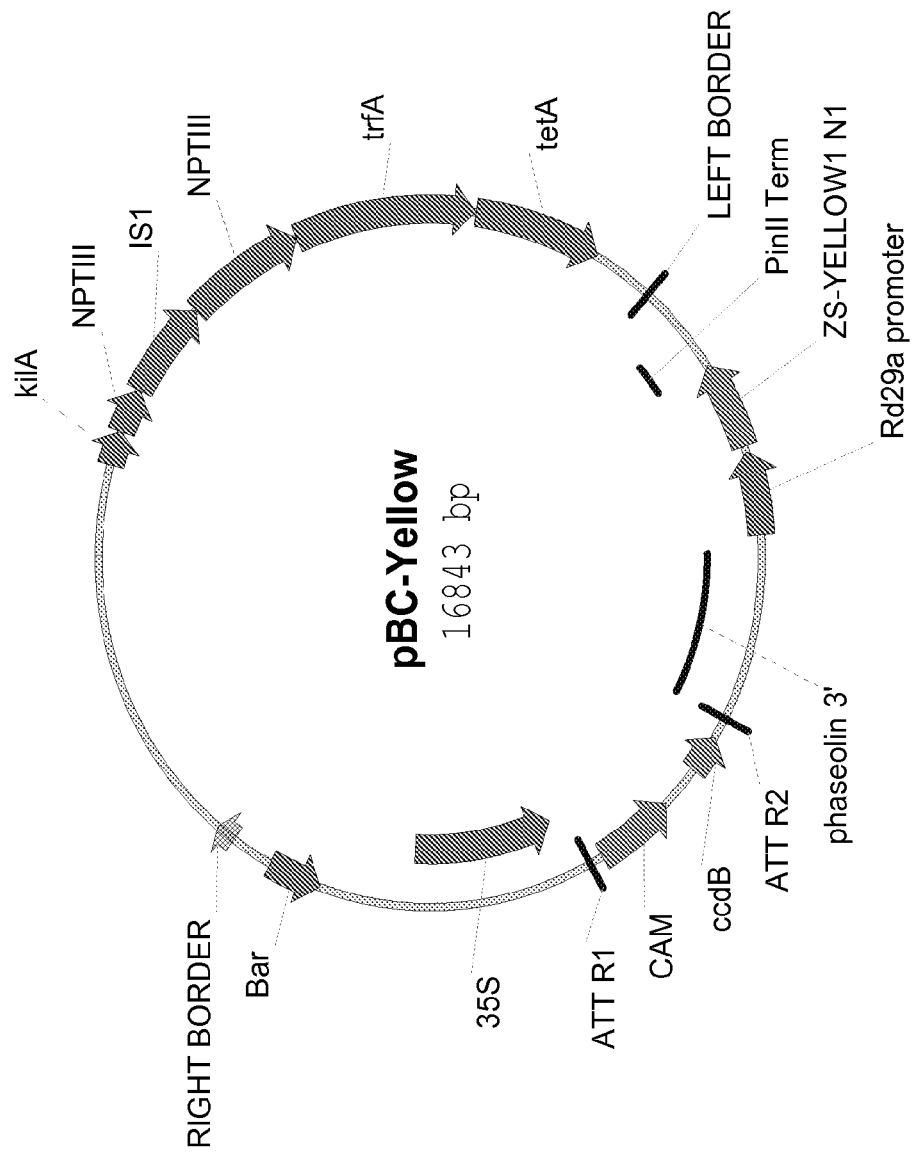
FIG. 4 shows a map of the vector pBC-yellow (SEQ ID NO:4), a destination vector for use in construction of expression vectors for *Arabidopsis*. The attR1 site is at nucleotides 11276-11399 (complementary strand); the attR2 site is at nucleotides 9695-9819 (complementary strand).

A 16.8-kb T-DNA based binary vector, called pBC-yellow (FIG. 4, SEQ ID NO:4), was constructed with the 1.3-kb 35S promoter immediately upstream of the Invitrogen™ Gateway® C1 conversion insert containing the ccdB gene and the chloramphenicol resistance gene (CAM) flanked by attR1 and attR2 sequences. The vector also contains a YFP marker under the control of the Rd29a promoter for the selection of transformed seeds.

Using Invitrogen™ Gateway® technology a MultiSite Gateway® LR Recombination Reaction was performed on the entry clone containing the directionally cloned PCR product and pBC-yellow. This allowed rapid and directional cloning of the AT3G03650 gene behind the 35S promoter in pBC-yellow.

The 35S-AT3G03650 gene construct was introduced into wild-type *Arabidopsis* ecotype Col-0, using the same *Agrobacterium*-mediated transformation procedure described in Example 1.

Transgenic T1 seeds were selected by the presence of the fluorescent YFP marker. Fluorescent seeds were subjected to the Root Architecture Assay following the procedure described in Example 2A. Transgenic T1 seeds were re-screened using 6 plates per construct. Two plates per rack containing non-transformed Columbia seed discarded from fluorescent seed sorting served as a control.

Six plates per construct were analyzed statistically and a trend was detected between the number of plants growing on a plate and their average WinRHIZO® score. WinRHIZO® scores were normalized for this trend and the root score corresponding to the construct was divided by the wild-type root score.

Example 5B

Screen of Candidate Genes Under Nitrogen Limiting Conditions

Transgenic T1 seed selected by the presence of the fluorescent marker YFP as described above in Example 5A can also be screened for their tolerance to grow under nitrogen limiting conditions. For this purpose 32 transgenic individuals can be grown next to 32 wild-type individuals on one plate with either 0.4 mM $KNO_3$ or 60 mM $KNO_3$. If a line shows a statistically significant difference from the controls, the line is considered a validated nitrogen-deficiency tolerant line. After masking the plate image to remove background color, two different measurements are collected for each individual: total rosetta area, and the percentage of color that falls into a green color bin. Using hue, saturation and intensity data (HIS), the green color bin consists of hues 50-66. Total rosetta area is used as a measure of plant biomass, whereas the green color bin has been shown by dose-response studies to be an indicator of nitrogen assimilation.

Example 5C

Validation of a Candidate *Arabidopsis* Gene (At3G03650) for its Ability to Improve Nitrogen Utilization in Plants Via Transformation into *Arabidopsis*

Transgenic seeds were screened for their ability to grow under nitrogen limiting conditions as described in Example 5B.

Plants were evaluated at 10, 11, 12 and 13 days. Transgenic individuals expressing the *Arabidopsis* Candidate gene (AT3G03650) did not validate as nitrogen-deficient tolerant compared to the wild type plants, when grown on media containing limiting concentrations of nitrogen (0.4 mM $KNO_3$).

Example 5D

Screen to Identify Lines with Improved Nitrate Uptake

For each overexpressor line, twelve T2 plants are sown on 96 well micro titer plates containing 2 mM $MgSO_4$, 0.5 mM $KH_2PO_4$, 1 mM $CaCl_2$, 2.5 mM KCl, 0.15 mM Sprint 330, 0.06 mM $FeSO_4$, 1 µM $MnCl_2.4H_2O$, 1 µM $ZnSO_4.7H_2O$, 3 µM $H_3BO_3$, 0.1 µM $NaMoO_4$, 0.1 µM $CuSO_4.5H_2O$, 0.8 mM potassium nitrate, 0.1% sucrose, 1 mM MES, 200 µM bromophenol red and 0.40% Phytagel™ (pH assay medium). The pH of the medium is so that the color of bromophenol is red, the pH indicator dye, is yellow.

Four lines are plated per plate, and the inclusion of 12 wild-type individuals and 12 individuals from a line that has shown an improvement in nitrate uptake (positive control) on each plate makes for a total of 72 individuals on each 96 well micro titer plate A web-based random sequence generator can be used to determine the order of the lines on each plate. Seeds are not plated in Row A or Row H on the 96 well micro titer plate. Four plates are plated for each experiment, resulting in a maximum of 48 plants per line analyzed. Plates are kept for three days in the dark at 4° C. to stratify seeds, and then placed horizontally for six days at 22° C. light and dark. Photoperiod is sixteen hours light; eight hours dark, with an average light intensity of ~200 mmol/m²/s. Plates are rotated and shuffled within each shelf. At day eight or nine (five or six days of growth), seedling status is evaluated by recording the color of the medium as pink, peach, yellow or no germination. Then the plants and/or seeds are removed from each well. Each medium plug is transferred to 1.2 ml micro titer tubes and placed in the corresponding well in a 96 well deep micro titer plate. An equal volume of water containing 2 µM flourescein is added to each 1.2 ml micro titer tube. The plate is covered with foil and autoclaved on liquid cycle. Each tube is mixed well, and an aliquot is removed from each tube and analyzed for amount of nitrate remaining in the medium. If t-test shows that a line is significantly different (p<0.05) from wild-type control, the line is then considered a validated improved nitrate uptake line.

Example 5E

Validation of Increased Nitrate Uptake by Transgenic Lines Containing the Candidate *Arabidopsis* Gene (AT3G03650)

Transgenic seeds were screened for increased nitrate uptake as described in Example 5D.

Transgenic individuals overexpressing the *Arabidopsis* Candidate gene (AT3G03650) did not validate as an improved nitrate uptake line compared to wild type plants not overexpressing the *Arabidopsis* candidate gene.

Example 6

Composition of cDNA Libraries

Isolation and Sequencing of cDNA Clones cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred and Phrap (Ewing et al. (1998) *Genome Res.* 8:175-185; Ewing and Green (1998) *Genome*

Res. 8:186-194). Phred is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (Gordon et al. (1998) *Genome Res.* 8:195-202).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen™ (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 7

Identification of cDNA Clones cDNA clones encoding EXST-like polypeptides can be identified by conducting BLAST (Basic Local Alignment Search Tool; Altschul et al. (1993) *J. Mol. Biol.* 215:403-410; see also the explanation of the BLAST algorithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained as described in Example 6 can be analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the Genbank database as described above. ESTs that contain sequences more 5- or 3-prime can be found by using the BLASTn algorithm (Altschul et al (1997) *Nucleic Acids Res.* 25:3389-3402) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 6. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 8

Preparation of cDNA Libraries and Characterization of cDNA Clones Encoding EXST-Like Polypeptides cDNA libraries representing mRNAs from various tissues of Maize, Soybean, Rice, Sunflower, Guar, Wheat, Florida bitterbush, Oat, Cotton, Amaranth and Canola were prepared as described in Example 6 of the libraries are described below. The characteristics of the libraries are described below.

TABLE 2 cDNA Libraries from Maize, Soybean, Rice, Sunflower, Guar, Wheat, Florida bitterbush, Oat, Cotton, *Amaranth* and Canola

| Library | Tissue | Clone |
|---------|--------|-------|
| cfp5n | Maize Kernel, pooled stages, Full-length enriched, normalized | cfp5n.pk007.k11 |
| p0127 | Nucellus tissue, 5 days after silking, screened 1. | p0127.cntdd86ra |
| cfp6n | Maize Leaf and Seed pooled, Full-length enriched normalized | cfp6n.pk002.a5<br>cfp6n.pk002.a5:fis |
| Ctn1c | Corn (*Zea mays* L., B73) night harvested tassel (v12 stage). | ctn1c.pk002.p16 |

TABLE 2-continued cDNA Libraries from Maize, Soybean, Rice, Sunflower, Guar, Wheat, Florida bitterbush, Oat, Cotton, *Amaranth* and Canola

| Library | Tissue | Clone |
|---|---|---|
| rls24 | Rice Leaf 15 Days After Germination, 24 Hours After Infection of Strain *Magnaporthe grisea* 4360-R-67 (AVR2-YAMO); Susceptible | rls24.pk0026.h11<br>rls24.pk0026.h11:fis |
| esl1c | rye leaves, chilled, to induce cold-responsive gene sequences that can be used to transform corn for tolerance to cold or dehydration stress.. | esl1c.pk006.l19<br>esl1c.pk006.l19:fis |
| cfp1n | Maize Tassel V7 to V12 pooled, Full-length enriched normalized | cfp1n.pk002.o16.f:fis |
| ebb2c | Immature buds of Canola Rf gene knock out mutant line, 02SM5. | ebb2c.pk005.f9<br>ebb2c.pk005.f9:fis |
| lds1c | Guar (*Cyamopsis tetragonoloba*) seeds harvested at 15 DAF | lds1c.pk008.m15<br>lds1c.pk008.m15:fis |
| eas1c | *Amaranthus retroflexus* young seeds | eas1c.pk002.p14<br>eas1c.pk002.p14:fis |
| egh1c | Upland Cotton (*Gossypium hirsutum*) germinating seeds. | egh1c.pk005.b21<br>egh1c.pk005.b21:fis |
| ort1f | Oat (*Avena strigosa*) full length oat root tip | ort1f.pk014.e9<br>ort1f.pk014.e9:fis |
| pps | Developing Seeds of *Picramnia pentandra* (Florida bitterbush) | pps.pk0007.b3<br>pps.pk0007.b3:fis |
| hso1c | Oxalate oxidase-transgenic sunflower plants | hso1c.pk001.n10<br>hso1c.pk001.n10:fis |
| sgs1c | Soybean Seeds 4 Hours After Germination | sgs1c.pk004.m16<br>sgs1c.pk004.m14 |
| scn1c | Soybean (*Glycine max* L., 6705) Embryogenic suspension culture 10 months old (necrotic tissue). | scn1c.pk001.m7<br>scn1c.pk001.m7:fis |
| wpa1c | Wheat (*Triticum aestivum*)pre-meiotic anthers JIC | wpa1c.pk011.n19<br>wpa1c.pk011.n19:fis |
| rdi2c | Rice (*Oryza sativa*, Nipponbare) developing inflorescence at rachis branch-floral organ primordia formation | rdi2c.pk011.p5<br>rdi2c.pk011.p5:fis |
| smj1c | Characterization of IPT transcripts from transgenic soybean. The lead Yield Enhancement (Soy YE2.1) construct is expressing Agrobacterium isopentenyl transferase gene. | smj1c.pk006.c12.f<br>smj1c.pk006.c12.f:fis |

The BLASTX search using the EST sequences from clones listed in Table 1 revealed similarity of the polypeptides to EXST-like polypeptides from rice (GI No. 115476598, 115487106, 115452759 and 115441893 corresponding to SEQ ID NO's:35, 36, 37, and 38, respectively. Shown in Table 3 are the BLASTP results for the sequences of the entire cDNA inserts ("Full-insert Sequence" or "FIS") of the clones listed in Table 2. Each cDNA insert encodes an entire or functional protein ("Complete Gene Sequence" or "CGS"). Also shown in Tables 3 and 4 are the percent sequence identity values for each pair of amino acid sequences using the Clustal V method of alignment with default parameters:

TABLE 3

BLASTP Results and Percent Identity for Sequences Encoding Polypeptides Homologous to EXST-like Polypeptides

| Sequence | Status | NCBI GI No. | BLAST pLog Score | % identity |
|---|---|---|---|---|
| Contig of:<br>cfp5n.pk007.k11<br>cfp5n.pk007.k11.f<br>cfp6n.pk005.i1<br>SEQ ID NO: 14 | Contig | 115487106<br>(*Oryza sativa*)<br>SEQ ID NO: 36 | >180 | 77.5 |
| Contig of:<br>cfp3n.pk069.l15<br>cfp3n.pk069.l15.f<br>p0127.cntdd86ra<br>p0127.cntdd86ra.f<br>SEQ ID NO: 16 | Contig | 115452759<br>(*Oryza sativa*)<br>SEQ ID NO: 37 | 176 | 70.0 |

TABLE 3-continued

BLASTP Results and Percent Identity for Sequences Encoding Polypeptides Homologous to EXST-like Polypeptides

| Sequence | Status | NCBI GI No. | BLAST pLog Score | % identity |
|---|---|---|---|---|
| my.ceb1.pk0010.e5<br>SEQ ID NO: 18 | FIS | 115441893<br>(*Oryza sativa*)<br>SEQ ID NO: 38 | 160 | 90.1 |
| cfp6n.pk002.a5:fis<br>SEQ ID NO: 20 | CGS | 115452759<br>(*Oryza sativa*)<br>SEQ ID NO: 37 | >180 | 82.4 |
| rls24.pk0026.h11:fis<br>SEQ ID NO: 22 | CGS | 115476598<br>(*Oryza sativa*)<br>SEQ ID NO: 35 | >180 | 99.8 |
| p0127.cntdd86ra:fis<br>SEQ ID NO: 24 | CGS | 11542759<br>(*Oryza sativa*)<br>SEQ ID NO: 37 | >180 | 80.8 |
| cfp5n.pk007.k11:fis<br>SEQ ID NO: 26 | FIS | 115487106<br>(*Oryza sativa*)<br>SEQ ID NO: 36 | 85 | 36.2 |
| esl1c.pk006.l19:fis<br>SEQ ID NO: 28 | CGS | 115487106<br>(*Oryza sativa*)<br>SEQ ID NO: 36 | >180 | 78.9 |
| cfp1n.pk002.o16.f:fis<br>SEQ ID NO: 30 | CGS | 115476598<br>(*Oryza sativa*)<br>SEQ ID NO: 35 | >180 | 63.5 |

FIGS. 15A-15I show the multiple alignment of the full length amino acid sequences of SEQ ID NOs: 15, 17, 19, 21, 23, 25, 27, 29, 31, 34, and SEQ ID NOs:35, 36, 37, and 38.
FIG. 16 presents the percent sequence identities and divergence values for each sequence pair presented in FIGS. 15A-15I.

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Sequence alignments and BLAST scores and probabilities indicate that the nucleic acid fragments comprising the instant cDNA clones encode EXST-like polypeptides.

TABLE 4

BLASTP Results for Sequences Encoding Polypeptides Homologous to EXST and EXST-like polypeptides

| Sequence | Status | Reference | BLAST pLog Score | % identity |
|---|---|---|---|---|
| Contig of:<br>cfp5n.pk007.k11<br>cfp5n.pk007.k11.f<br>cfp6n.pk005.i1<br>SEQ ID NO: 14 | CGS | SEQ ID 49101 in JP2005185101 | >180 | 77.5 |
| Contig of:<br>cfp3n.pk069.l15<br>cfp3n.pk069.l15.f<br>p0127.cntdd86ra<br>p0127.cntdd86ra.f<br>SEQ ID NO: 16 | EST | SEQ ID 345741 in US2004214272 | >180 | 80.1 |
| my.ceb1.pk0010.e5<br>SEQ ID NO: 18 | CGS | SEQ ID 7611 in US2004216190 | 175 | 99.6 |
| cfp6n.pk002.a5:fis<br>SEQ ID NO: 20 | CGS | SEQ ID 345741 in US2004214272 | >180 | 98.9 |
| rls24.pk0026.h11:fis<br>SEQ ID NO: 22 | CGS | SEQ ID NO 54370 in JP2005185101 | >180 | 99.8 |
| p0127.cntdd86ra:fis<br>SEQ ID NO: 24 | CGS | SEQ ID 345741 in US20042 | >180 | 91.4 |
| cfp5n.pk007.k11:fis<br>SEQ ID NO: 26 | CGS | SEQ ID 361954 in US2004214272 | 94 | 75.1 |
| esl1c.pk006.l19:fis<br>SEQ ID NO: 28 | CGS | SEQ ID 10067 in US2004216190-A1 | >180 | 98.3 |
| cfp1n.pk002.o16.f:fis<br>SEQ ID NO: 30 | CGS | SEQ ID 54370 in JP2005185101 | >180 | 63.5 |

Example 9

Preparation of a Plant Expression Vector Containing a Homolog of the *Arabidopsis* Lead Gene (AT3G03650)

Sequences homologous to the lead EXST gene can be identified using sequence comparison algorithms such as BLAST (Basic Local Alignment Search Tool; Altschul et al., J. Mol. Biol. 215:403-410 (1993); see also the explanation of the BLAST algorithm on the world wide web site for the National Center for Biotechnology Information at the National Library of Medicine of the National Institutes of Health). Homologous EXST-like sequences, such as the ones described in Example 8, can be PCR-amplified by either of the following methods.

Method 1 (RNA-based): If the 5' and 3' sequence information for the protein-coding region of a EXST homolog is available, gene-specific primers can be designed as outlined in Example 5A. RT-PCR can be used with plant RNA to obtain a nucleic acid fragment containing the EXST protein-coding region flanked by attB1 (SEQ ID NO:39) and attB2 (SEQ ID NO:40) sequences. The primer may contain a consensus Kozak sequence (CAACA) upstream of the start codon.

Method 2 (DNA-based): Alternatively, if a cDNA clone is available for a gene encoding an EXST polypeptide homolog, the entire cDNA insert (containing 5' and 3' non-coding regions) can be PCR amplified. Forward and reverse primers can be designed that contain either the attB1 sequence and vector-specific sequence that precedes the cDNA insert or the attB2 sequence and vector-specific sequence that follows the cDNA insert, respectively. For a cDNA insert cloned into the vector pBluescript SK+, the forward primer VC062 (SEQ ID NO:41) and the reverse primer VC063 (SEQ ID NO:42) can be used.

Methods 1 and 2 can be modified according to procedures known by one skilled in the art. For example, the primers of method 1 may contain restriction sites instead of attB1 and attB2 sites, for subsequent cloning of the PCR product into a vector containing attB1 and attB2 sites. Additionally, method 2 can involve amplification from a cDNA clone, a lambda clone, a BAC clone or genomic DNA.

Figure 2:
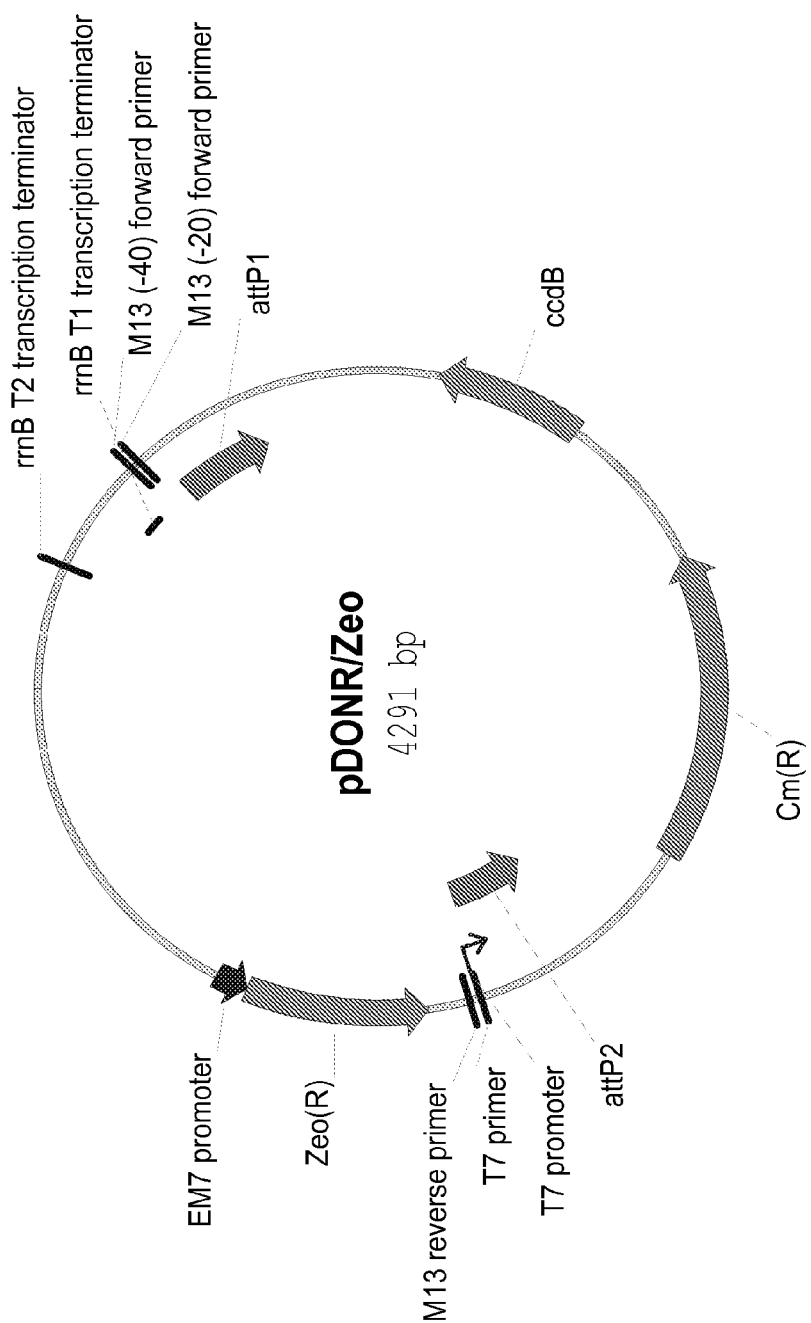
FIG. 2 shows a map of the vector pDONR™/Zeo (SEQ ID NO:2). The attP1 site is at nucleotides 570-801; the attP2 site is at nucleotides 2754-2985 (complementary strand).
Figure 3:
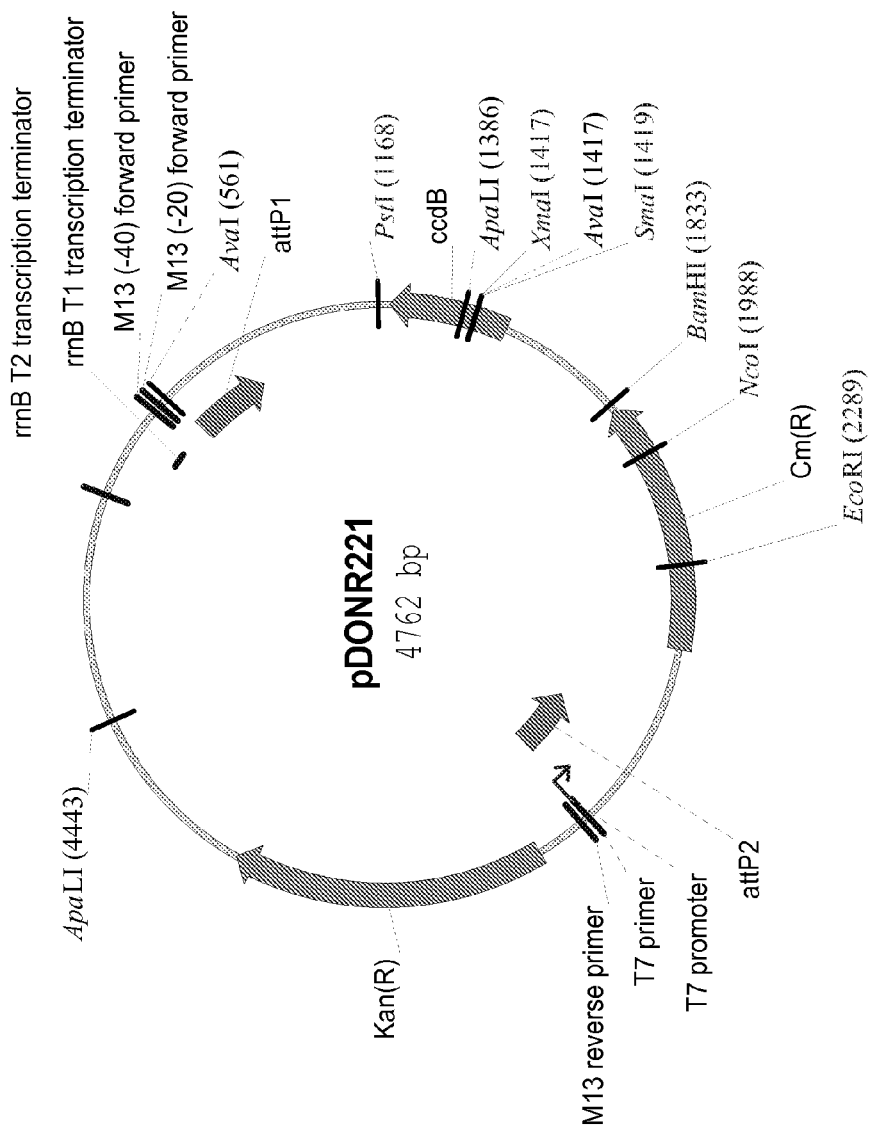
FIG. 3 shows a map of the vector pDONR™221 (SEQ ID NO:3). The attP1 site is at nucleotides 570-801; the attP2 site is at nucleotides 2754-2985 (complementary strand).
Figure 5:
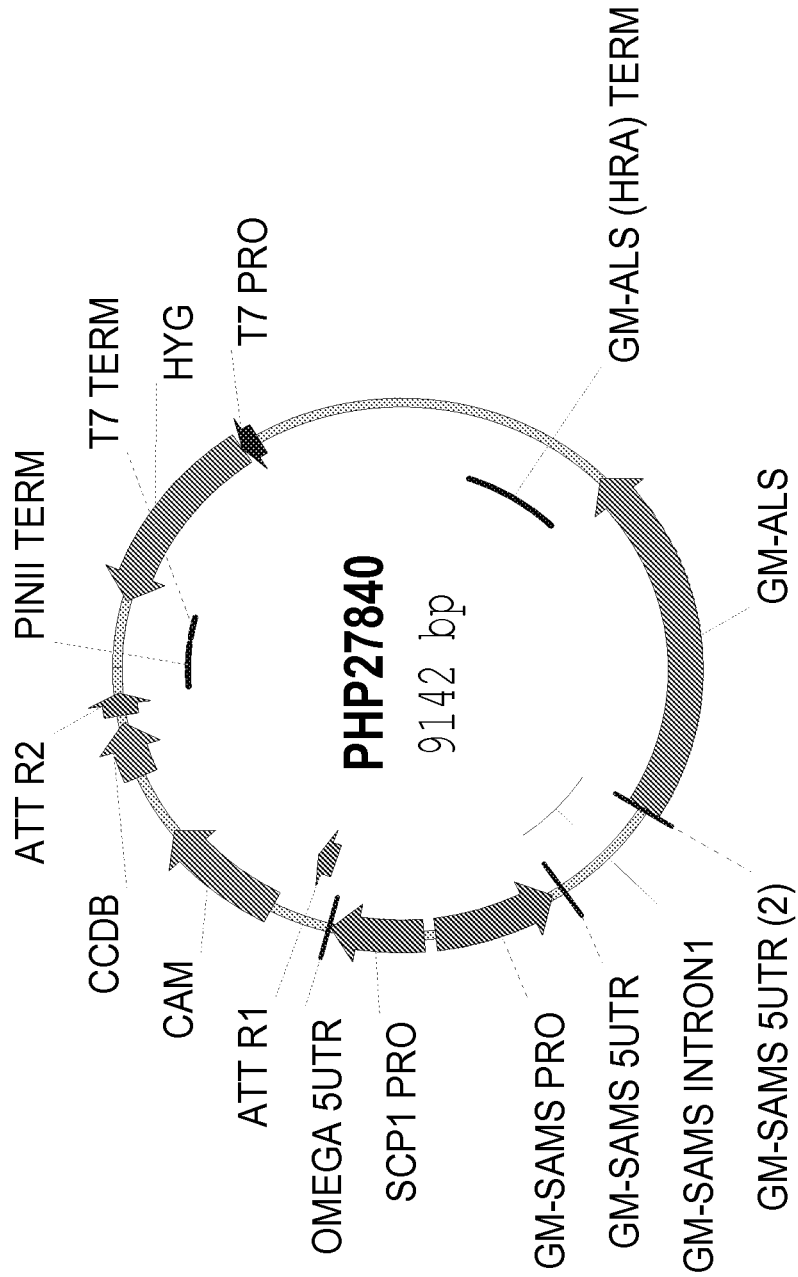
FIG. 5 shows a map of PHP27840 (SEQ ID NO:5), a destination vector for use in construction of expression vectors for soybean. The attR1 site is at nucleotides 7310-7434; the attR2 site is at nucleotides 8890-9014.
Figure 6:
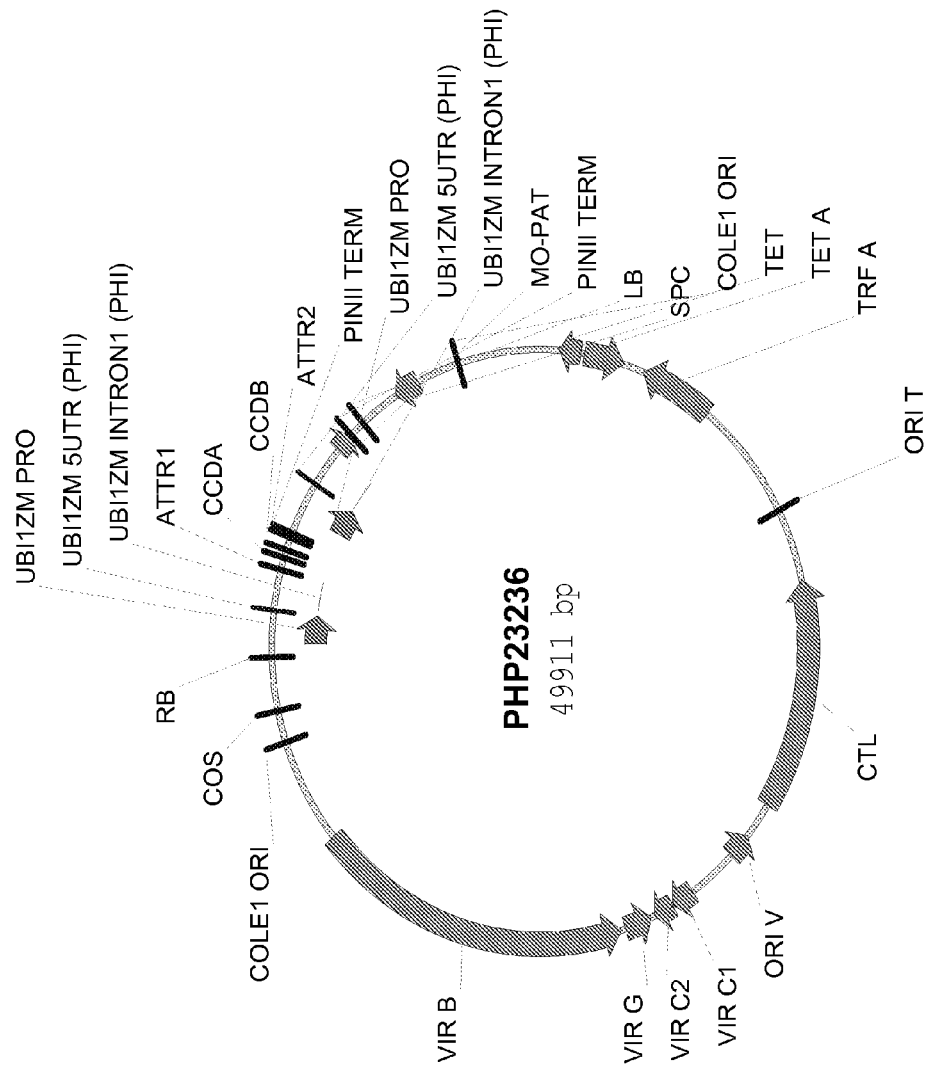
FIG. 6 shows a map of PHP23236 (SEQ ID NO:6), a destination vector for use in construction of expression vectors for Gaspe Flint derived maize lines. The attR1 site is at nucleotides 2006-2130; the attR2 site is at nucleotides 2899-3023.

A PCR product obtained by either method above can be combined with the Gateway® donor vector, such as pDONR™/Zeo (Invitrogen™, FIG. 2; SEQ ID NO:2) or pDONR™221 (Invitrogen™, FIG. 3; SEQ ID NO:3) using a BP Recombination Reaction. This process removes the bacteria lethal ccdB gene, as well as the chloramphenicol resistance gene (CAM) from pDONR™221 and directionally clones the PCR product with flanking attB1 and attB2 sites to create an entry clone. Using the Invitrogen™ Gateway® Clonase™ technology, the homologous EXST-like gene from the entry clone can then be transferred to a suitable destination vector to obtain a plant expression vector for use with *Arabidopsis*, corn and soy, such as pBC-Yellow (FIG. 4; SEQ ID NO:4), PHP27840 (FIG. 5; SEQ ID NO:5) or PHP23236 (FIG. 6; SEQ ID NO:6), to obtain a plant expression vector for use with *Arabidopsis*, soybean and corn, respectively.

Alternatively a MultiSite Gateway® LR recombination reaction between multiple entry clones and a suitable destination vector can be performed to create an expression vector. An Example of this procedure is outlined in Example 14A, describing the construction of maize expression vectors for transformation of maize lines.

Example 10

Preparation of Soybean Expression Vectors and Transformation of Soybean with Validated *Arabidopsis* Lead Genes and Homologs Thereof Soybean plants can be transformed to overexpress the validated *Arabidopsis* gene (AT3G03650) and the corresponding homologs from various species in order to examine the resulting phenotype.

The entry clones described in Example 5A and 9 can be used to directionally clone each gene into PHP27840 vector (FIG. 5, SEQ ID NO:5) such that expression of the gene is under control of the SCP1 promoter.

Soybean embryos may then be transformed with the expression vector comprising sequences encoding the instant polypeptides.

To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos, which produce secondary embryos, are then excised and placed into a suitable liquid medium. After repeated selection for clusters of somatic embryos which multiply as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium. Soybean embryogenic suspension cultures may then be transformed by the method of particle gun bombardment (Klein et al. (1987) *Nature* (London) 327:70-73, U.S. Pat. No. 4,945, 050). A DuPont Biolistic™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. Another selectable marker gene which can be used to facilitate soybean transformation is an herbicide-resistant acetolactate synthase (ALS) gene from soybean or *Arabidopsis*. ALS is the first common enzyme in the biosynthesis of the branched-chain amino acids valine, leucine and isoleucine. Mutations in ALS have been identified that convey resistance to some or all of three classes of inhibitors of ALS (U.S. Pat. No. 5,013,659; the entire contents of which are herein incorporated by reference). Expression of the herbicide-resistant ALS gene can be under the control of a SAM synthetase promoter (U.S. Patent Application No. US-2003-0226166-A1; the entire contents of which are herein incorporated by reference).

To 50 μL of a 60 mg/mL 1 μm gold particle suspension is added (in order): 5 μL DNA (1 μg/μL), 20 μL spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Enhanced root architecture can be measured in soybean by growing the plants in soil and wash the roots before analysis of the total root mass with WinRHIZO®.

Soybean plants transformed with validated genes can then be assayed to study agronomic characteristics relative to control or reference plants. For example, nitrogen utilization efficacy, yield enhancement and/or stability under various environmental conditions (e.g. nitrogen limiting conditions, drought etc.).

Example 11

Transformation of Maize with Validated *Arabidopsis* Lead Genes Using Particle Bombardment Maize plants can be transformed to overexpress a validated *Arabidopsis* lead gene or the corresponding homologs from various species in order to examine the resulting phenotype.

The Gateway® entry clones described in Example 5A can be used to directionally clone each gene into a maize transformation vector. Expression of the gene in maize can be under control of a constitutive promoter such as the maize ubiquitin promoter (Christensen et al., *Plant Mol. Biol.* 12:619-632 (1989) and Christensen et al., *Plant Mol. Biol.* 18:675-689 (1992))

The recombinant DNA construct described above can then be introduced into maize cells by the following procedure. Immature maize embryos can be dissected from developing caryopses derived from crosses of the inbred maize lines H99 and LH132. The embryos are isolated ten to eleven days after pollination when they are 1.0 to 1.5 mm long. The embryos are then placed with the axis-side facing down and in contact with agarose-solidified N6 medium (Chu et al., *Sci. Sin. Peking* 18:659-668 (1975)). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every two to three weeks.

The plasmid, p35S/Ac (obtained from Dr. Peter Eckes, Hoechst Ag, Frankfurt, Germany) may be used in transformation experiments in order to provide for a selectable marker. This plasmid contains the pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al., *Nature* 313:810-812 (1985)) and the 3' region of the nopaline synthase gene from the T-DNA of the Ti plasmid of *Agrobacterium tumefaciens*.

The particle bombardment method (Klein et al., *Nature* 327:70-73 (1987)) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After ten minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the maize tissue with a Biolistic® PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialaphos (5 mg per liter) and lacks casein or proline. The tissue continues to grow slowly on this medium. After an additional two weeks the tissue can be transferred to fresh N6 medium containing bialaphos. After six weeks, areas of about 1 cm in diameter of actively growing callus can be identified on some of the plates containing the bialaphos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., *Bio/Technology* 8:833-839 (1990)).

Transgenic T0 plants can be regenerated and their phenotype determined following HTP procedures. T1 seed can be collected.

T1 plants can be grown and analyzed for phenotypic changes. The following parameters can be quantified using image analysis: plant area, volume, growth rate and color analysis can be collected and quantified. Expression constructs that result in an alteration of root architecture or any one of the agronomic characteristics listed above compared to suitable control plants, can be considered evidence that the *Arabidopsis* lead gene functions in maize to alter root architecture or plant architecture.

Furthermore, a recombinant DNA construct containing a validated *Arabidopsis* gene can be introduced into a maize line either by direct transformation or introgression from a separately transformed line.

Transgenic plants, either inbred or hybrid, can undergo more vigorous field-based experiments to study root or plant architecture, yield enhancement and/or resistance to root lodging under various environmental conditions (e.g. variations in nutrient and water availability).

Subsequent yield analysis can also be done to determine whether plants that contain the validated *Arabidopsis* lead gene have an improvement in yield performance, when compared to the control (or reference) plants that do not contain the validated *Arabidopsis* lead gene. Plants containing the validated *Arabidopsis* lead gene would improved yield relative to the control plants, preferably 50% less yield loss under adverse environmental conditions or would have increased yield relative to the control plants under varying environmental conditions (e.g. increased yield under non limiting nitrogen conditions compared to control.

Example 12

Electroporation of *Agrobacterium tumefaciens* LBA4404

Electroporation competent cells (40 μl), such as *Agrobacterium tumefaciens* LBA4404 (containing PHP10523), are thawn on ice (20-30 min). PHP10523 contains VIR genes for T-DNA transfer, an *Agrobacterium* low copy number plasmid origin of replication, a tetracycline resistance gene, and a cos site for in vivo DNA biomolecular recombination. Meanwhile the electroporation cuvette is chilled on ice. The electroporator settings are adjusted to 2.1 kV.

A DNA aliquot (0.5 μL JT (U.S. Pat. No. 7,087,812) parental DNA at a concentration of 0.2 μg-1.0 μg in low salt buffer or twice distilled $H_2O$) is mixed with the thawn *Agrobacterium* cells while still on ice. The mix is transferred to the bottom of electroporation cuvette and kept at rest on ice for 1-2 min. The cells are electroporated (Eppendorf electroporator 2510) by pushing "Pulse" button twice (ideally achieving a 4.0 msec pulse). Subsequently 0.5 ml 2×YT medium (or SOCmedium) are added to cuvette and transferred to a 15 ml Falcon tube. The cells are incubated at 28-30° C., 200-250 rpm for 3 h.

Aliquots of 250 μl are spread onto #30B (YM+50 μg/mL Spectinomycin) plates and incubated 3 days at 28-30° C. To increase the number of transformants one of two optional steps can be performed:

Option 1: overlay plates with 30 μl of 15 mg/ml Rifampicin. LBA4404 has a chromosomal resistance gene for Rifampicin. This additional selection eliminates some contaminating colonies observed when using poorer preparations of LBA4404 competent cells.

Option 2: Perform two replicates of the electroporation to compensate for poorer electrocompetent cells.

Identification of Transformants:

Four independent colonies are picked and streaked on AB minimal medium plus 50 mg/mL Spectinomycin plates (#12S medium) for isolation of single colonies. The plated are incubate at 28° C. for 2-3 days.

A single colony for each putative co-integrate is picked and inoculated with 4 ml #60A with 50 mg/l Spectinomycin. The mix is incubated for 24 h at 28° C. with shaking. Plasmid DNA from 4 ml of culture is isolated using Qiagen Miniprep+ optional PB wash. The DNA is eluted in 30 μl. Aliquots of 2 μl are used to electroporate 20 μl of DH10b+20 μl of dd$H_2O$ as per above.

Optionally a 15 μl aliquot can be used to transform 75-100 μl of Invitrogen™-Library Efficiency DH5α. The cells are spread on LB medium plus 50 mg/mL Spectinomycin plates (#34T medium) and incubated at 37° C. overnight.

Three to four independent colonies are picked for each putative co-integrate and inoculated 4 ml of 2×YT (#60A) with 50 μg/ml Spectinomycin. The cells are incubated at 37° C. overnight with shaking.

The plasmid DNA is isolated from 4 ml of culture using QIAprep® Miniprep with optional PB wash (elute in 50 μl) and 8 μl are used for digestion with SalI (using JT parent and PHP10523 as controls).

Three more digestions using restriction enzymes BamHI, EcoRI, and HindIII are performed for 4 plasmids that represent 2 putative co-integrates with correct SalI digestion pattern (using parental DNA and PHP10523 as controls). Electronic gels are recommended for comparison.

Alternatively, for high throughput applications, such as described for Gaspe Flint Derived Maize Lines (Examples 15-17), instead of evaluating the resulting co-integrate vectors by restriction analysis, three colonies can be simultaneously used for the infection step as described in Example 13.

Example 13

Agrobacterium Mediated Transformation into Maize

Maize plants can be transformed to overexpress a validated *Arabidopsis* lead gene or the corresponding homologs from various species in order to examine the resulting phenotype.

*Agrobacterium*-mediated transformation of maize is performed essentially as described by Zhao et al., in *Meth. Mol. Biol.* 318:315-323 (2006) (see also Zhao et al., *Mol. Breed.* 8:323-333 (2001) and U.S. Pat. No. 5,981,840 issued Nov. 9, 1999, incorporated herein by reference). The transformation process involves bacterium innoculation, co-cultivation, resting, selection and plant regeneration.

1. Immature Embryo Preparation

Immature embryos are dissected from caryopses and placed in a 2 mL microtube containing 2 mL PHI-A medium.

2. *Agrobacterium* Infection and Co-Cultivation of Embryos 2.1 Infection Step

PHI-A medium is removed with 1 mL micropipettor and 1 mL *Agrobacterium* suspension is added. Tube is gently inverted to mix. The mixture is incubated for 5 min at room temperature.

2.2 Co-Culture Step

The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for 3 days. L-Cysteine can be used in the co-cultivation phase. With the standard binary vector, the co-cultivation medium supplied with 100-400 mg/L L-cysteine is critical for recovering stable transgenic events.

3. Selection of Putative Transgenic Events

To each plate of PHI-D medium in a 100×15 mm Petri dish, 10 embryos are transferred, maintaining orientation and the dishes are sealed with Parafilm. The plates are incubated in darkness at 28° C. Actively growing putative events, as pale yellow embryonic tissue are expected to be visible in 6-8 weeks. Embryos that produce no events may be brown and necrotic, and little friable tissue growth is evident. Putative transgenic embryonic tissue is subcultured to fresh PHI-D plates at 2-3 week intervals, depending on growth rate. The events are recorded.

4. Regeneration of T0 Plants

Embryonic tissue propagated on PHI-D medium is subcultured to PHI-E medium (somatic embryo maturation medium); in 100×25 mm Petri dishes and incubated at 28° C., in darkness, until somatic embryos mature, for about 10-18 days. Individual, matured somatic embryos with well-defined scutellum and coleoptile are transferred to PHI-F embryo germination medium and incubated at 28° C. in the light (about 80 µE from cool white or equivalent fluorescent lamps). In 7-10 days, regenerated plants, about 10 cm tall, are potted in horticultural mix and hardened-off using standard horticultural methods.

Media for Plant Transformation

1. PHI-A: 4 g/L CHU basal salts, 1.0 mL/L 1000×Eriksson's vitamin mix, 0.5 mg/L thiamin HCL, 1.5 mg/L 2,4-D, 0.69 g/L L-proline, 68.5 g/L sucrose, 36 g/L glucose, pH 5.2. Add 100 µM acetosyringone, filter-sterilized before using.
2. PHI-B: PHI-A without glucose, increased 2,4-D to 2 mg/L, reduced sucrose to 30 g/L and supplemented with 0.85 mg/L silver nitrate (filter-sterilized), 3.0 g/L gelrite, 100 µM acetosyringone (filter-sterilized), 5.8.
3. PHI-C: PHI-B without gelrite and acetosyringonee, reduced 2,4-D to 1.5 mg/L and supplemented with 8.0 g/L agar, 0.5 g/L Ms-morpholino ethane sulfonic acid (MES) buffer, 100 mg/L carbenicillin (filter-sterilized).
4. PHI-D: PHI-C supplemented with 3 mg/L bialaphos (filter-sterilized).
5. PHI-E: 4.3 g/L of Murashige and Skoog (MS) salts, (Gibco, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, cat. no. Z-0164), 1 mg/L indole acetic acid (IAA), 26.4 µg/L abscisic acid (ABA), 60 g/L sucrose, 3 mg/L bialaphos (filter-sterilized), 100 mg/L carbenicillin (filtered-sterilized), 8 g/L agar, pH 5.6.
6. PHI-F: PHI-E without zeatin, IAA, ABA; sucrose reduced to 40 g/L; replacing agar with 1.5 g/L gelrite; pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Phenotypic analysis of transgenic T0 plants and T1 plants can be performed.

T1 plants can be analyzed for phenotypic changes. Using image analysis T1 plants can be analyzed for phenotypical changes in plant area, volume, growth rate and color analysis can be taken at multiple times during growth of the plants. Alteration in root architecture can be assayed as described in Example 20.

Subsequent analysis of alterations in agronomic characteristics can be done to determine whether plants containing the validated *Arabidopsis* lead gene have an improvement of at least one agronomic characteristic, when compared to the control (or reference) plants that do not contain the validated *Arabidopsis* lead gene. The alterations may also be studied under various environmental conditions.

Expression constructs that result in a significant alteration in root architecture will be considered evidence that the *Arabidopsis* gene functions in maize to alter root architecture.

Example 14A

Construction of Maize Expression Vectors with the *Arabidopsis* Lead Gene (AT3G03650) Using *Agrobacterium* Mediated Transformation Maize expression vectors were prepared with the *Arabidopsis* EXST gene (AT3G03650) under the control of the NAS2 (SEQ ID NO:44) and GOS2 (SEQ ID NO:45) promoter. PINII was the terminator (SEQ ID NO:48)

Figure 9:
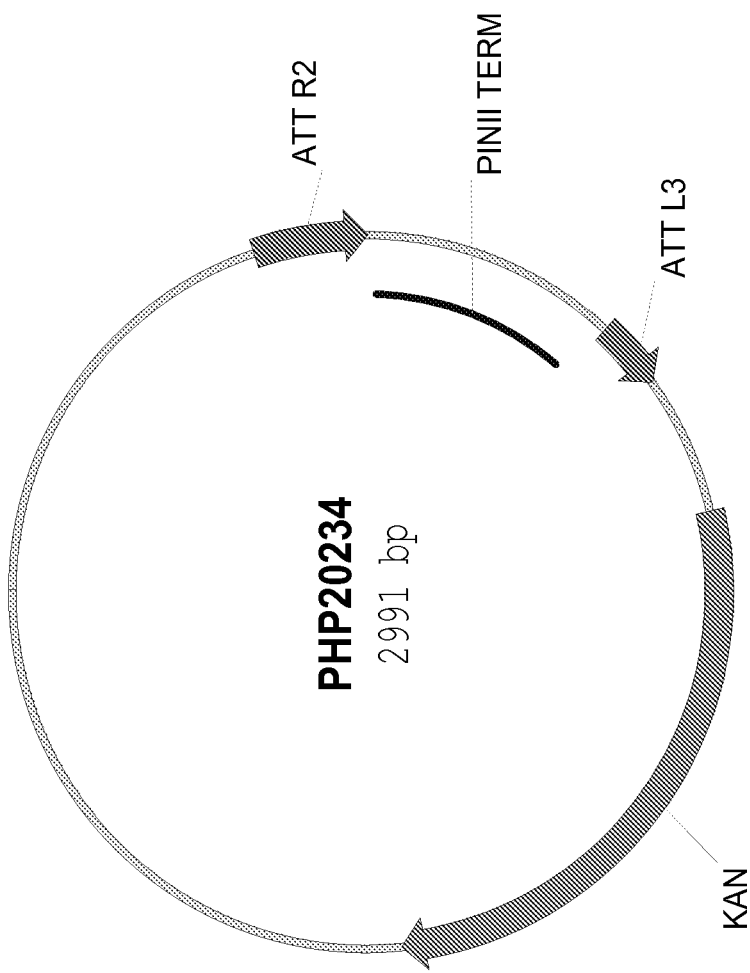
FIG. 9 shows a map of the entry clone PHP20234 (SEQ ID NO:9), a vector carrying the PINII terminator. The attR2 site is at nucleotides 591-747; the attL3 site is at nucleotides 1100-1195.
Figure 10:
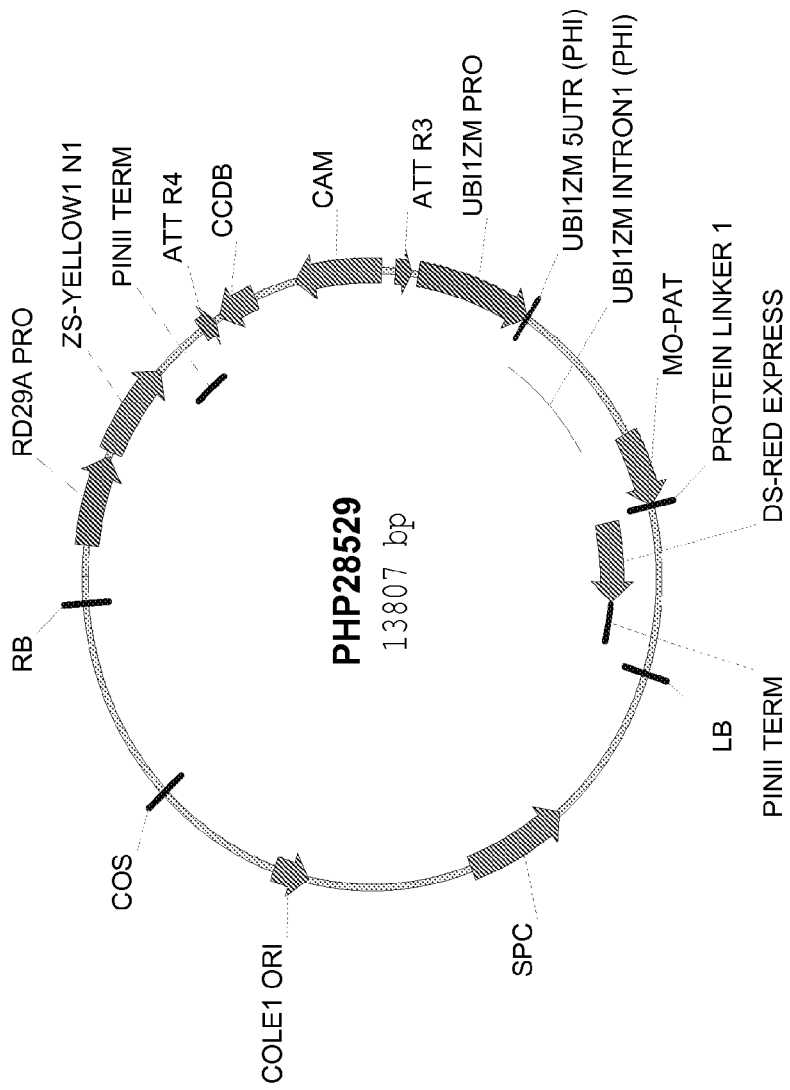
FIG. 10 shows a map of PHP28529 (SEQ ID NO:10), a destination vector for use in construction of expression vectors for maize lines. The attR3 site is at nucleotides 3613-3737; the attR4 site is at nucleotides 2035-2159.
Figure 11:
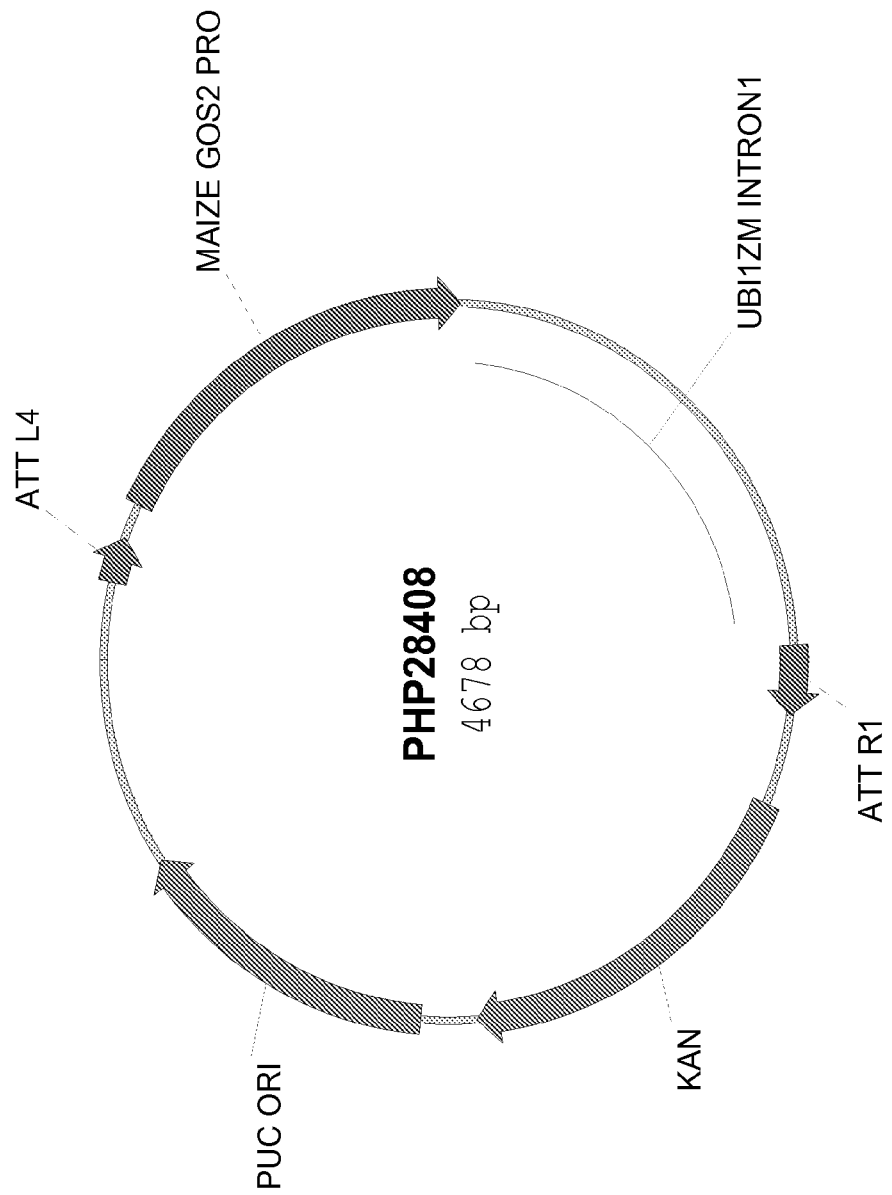
FIG. 11 shows a map of the entry clone PHP28408 (SEQ ID NO:11), a vector carrying the constitutive maize GOS2 promoter. The attL4 site is at nucleotides 160-255; the attR1 site is at nucleotides 2301-2447.

Using Invitrogen™ Gateway® technology the entry clone, created as described in Example 5A, PHP 28739, containing the *Arabidopsis* EXST gene (AT3G03650) was used in separate Gateway® LR reactions with:

1) the constitutive maize GOS2 promoter entry clone (PHP28408, FIG. 11, SEQ ID NO:11) and the PinII Terminator entry clone (PHP20234, FIG. 9, SEQ ID NO:9) into the destination vector PHP28529 (FIG. 10, SEQ ID NO:10). The resulting vector was named PHP28976.

Figure 12:
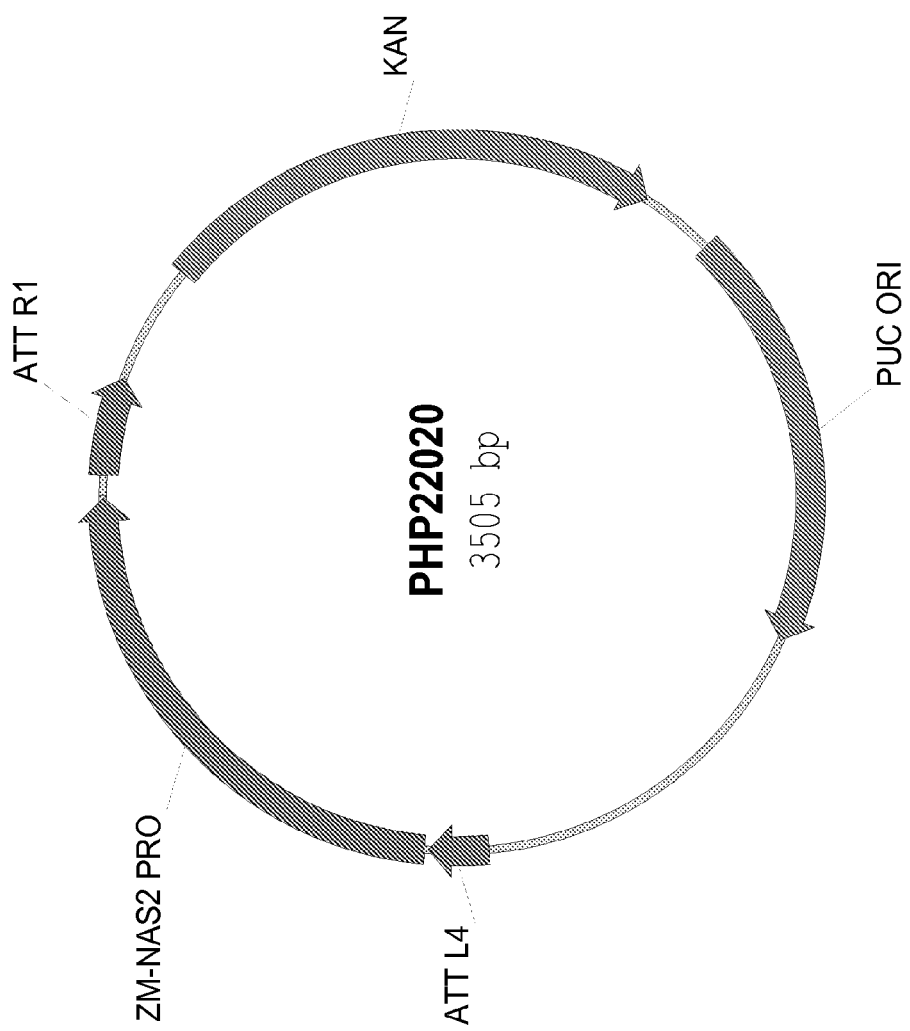
FIG. 12 shows a map of the entry clone PHP22020 (SEQ ID NO:12), a vector carrying the root maize NAS2 promoter. The attR1 site is at nucleotides 31-187; the attL4 site is at nucleotides 2578-2673.

2) the root maize NAS2 promoter entry clone (PHP22020, FIG. 12, SEQ ID NO:12) and the PinII Terminator entry clone (PHP20234, FIG. 9, SEQ ID NO:9) into the destination vector PHP28529 (FIG. 10, SEQ ID NO:10). The resulting vector was named PHP28913.

The destination vector PHP28529 added to each of the final vectors (PHP28983 and PHP28984) also an:
1) RD29A promoter::yellow fluorescent protein::PinII terminator cassette for *Arabidopsis* seed sorting
2) a Ubiquitin promoter::moPAT/red fluorescent protein fusion::PinII terminator cassette for transformation selection and *Z. mays* seed sorting.

Example 14B

Preparation of Maize Expression Constructs Containing the *Arabidopsis* EXST Gene and Homologs Thereof The *Arabidopsis* EXST gene and the corresponding homologs from maize and other species (Table 1) can be transformed into maize lines using the procedures outlined in Examples 5A and 14A. Maize expression vectors with *Arabidopsis* EXST gene and the corresponding homologs from maize and other species (Table 1) can be prepared as outlined in Examples 5A and 14A. In addition to the GOS2 or NAS2 promoter, other promoters such as, but not limited to the ubiquitin promoter, the S2A and S2B promoter, the maize ROOTMET2 promoter, the maize Cyclo, the CR1BIO, the CRWAQ81 and the maize ZRP2.4447 are useful for directing expression of EXST and EXST-like genes in maize. Furthermore, a variety of terminators, such as, but not limited to the PINII terminator, could be used to achieve expression of the gene of interest in maize.

Example 14C

Figure 7:
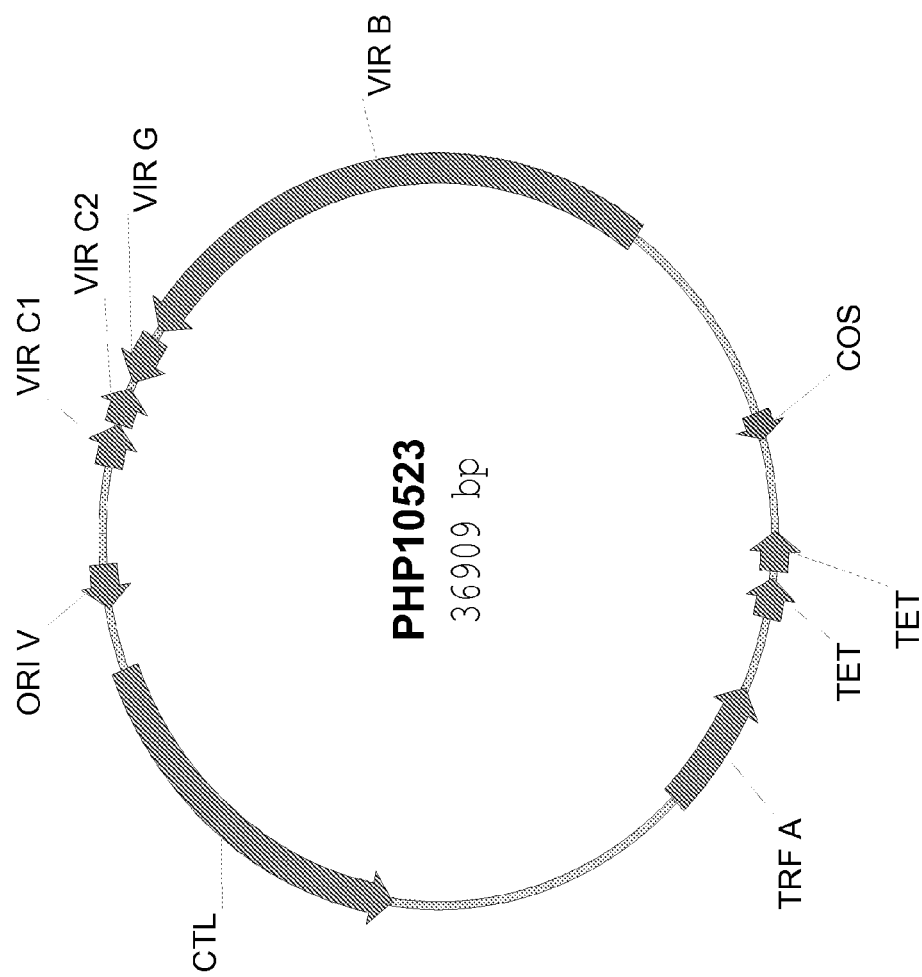
FIG. 7 shows a map of PHP10523 (SEQ ID NO:7), a plasmid DNA present in *Agrobacterium* strain LBA4404.

Transformation of Maize Lines with the *Arabidopsis* Lead Gene (AT3G03650) and Corresponding Homologs from Other Species Using *Agrobacterium* Mediated Transformation The final vectors (vectors for expression in Maize, Example 14A and B) can be then electroporated separately into LBA4404 *Agrobacterium* containing PHP10523 (FIG. 7; SEQ ID NO:7, Komari et al. Plant J 10:165-174 (1996), NCBI GI: 59797027) to create the co-integrate vectors for maize transformation. The co-integrate vectors are formed by recombination of the final vectors (maize expression vectors) with PHP10523, through the COS recombination sites contained on each vector. The co-integrate vectors contain in addition to the expression cassettes described in Examples 14A-B, also genes needed for the *Agrobacterium* strain and the *Agrobacterium* mediated transformation, (TET, TET, TRFA, ORI terminator, CTL, ORI V, VIR C1, VIR C2, VIR G, VIR B). Transformation into a maize line can be performed as described in Example 13.

Example 15

Figure 8:
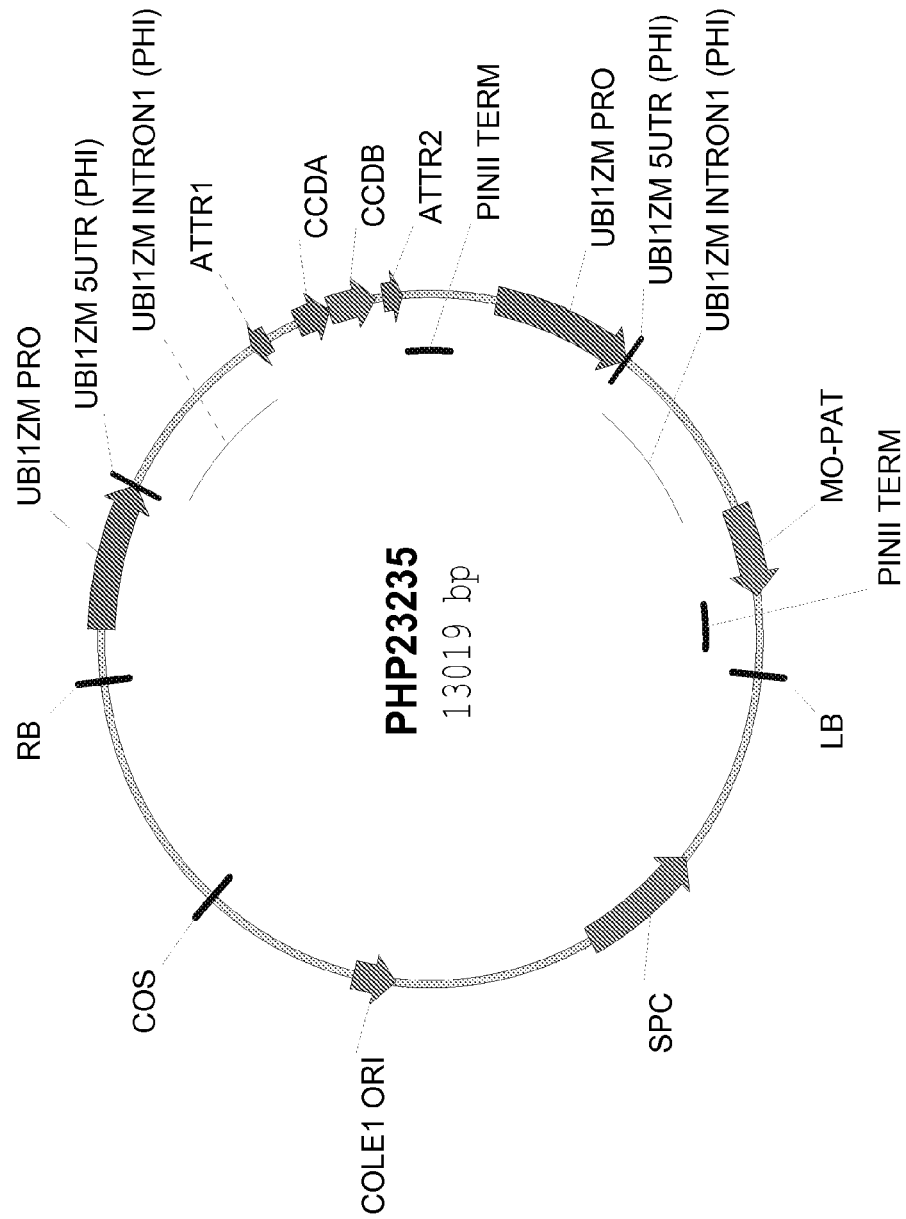
FIG. 8 shows a map of PHP23235 (SEQ ID NO:8), a vector used to construct the destination vector PHP23236.

Preparation of the Destination Vectors PHP23236 and PHP29635 for Transformation of Gaspe Flint Derived Maize Lines Destination vector PHP23236 (FIG. 6, SEQ ID NO:6) was obtained by transformation of *Agrobacterium* strain LBA4404 containing plasmid PHP10523 (FIG. 7, SEQ ID NO:7) with plasmid PHP23235 (FIG. 8, SEQ ID NO:8) and isolation of the resulting co-integration product. Destination vector PHP23236, can be used in a recombination reaction with an entry clone as described in Example 16 to create a maize expression vector for transformation of Gaspe Flint derived maize lines. Expression of the gene of interest is under control of the ubiquitin promoter (SEQ ID NO:46).

Figure 13:
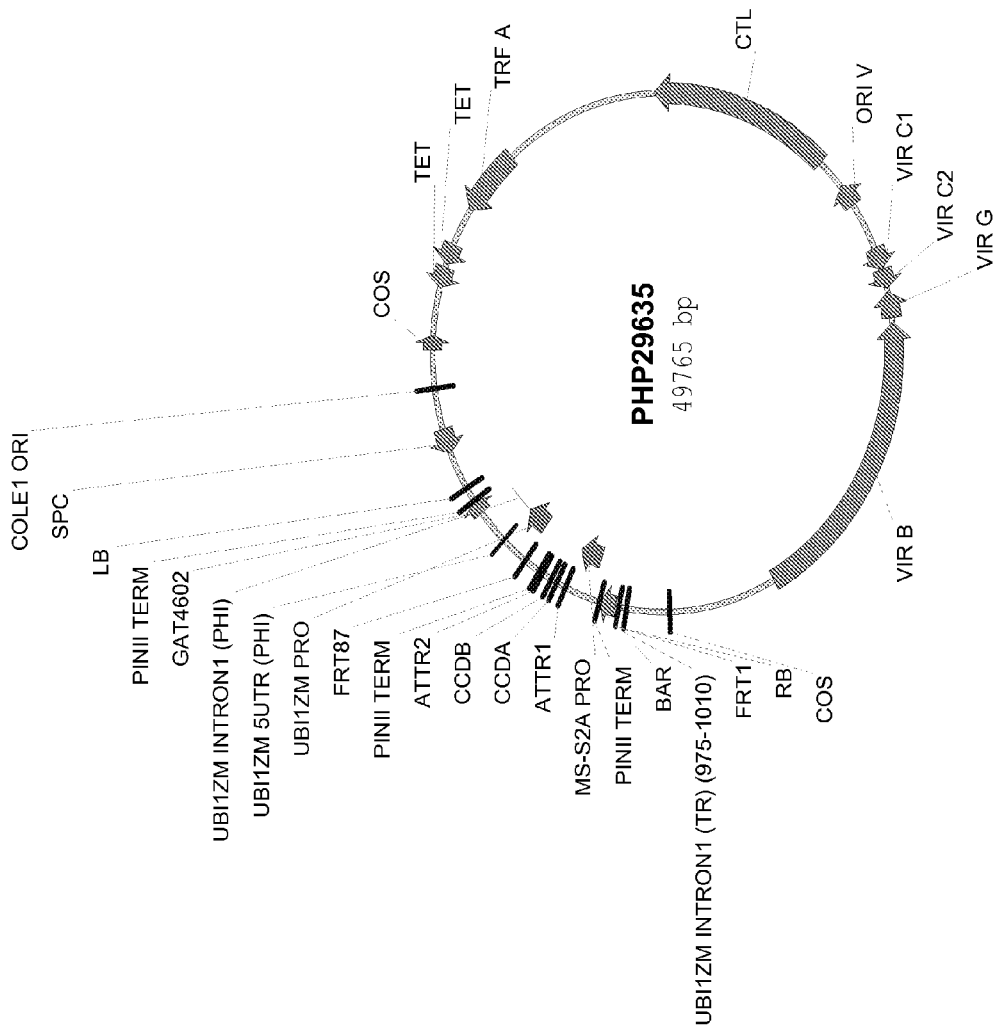
FIG. 13 shows a map of PHP29635 (SEQ ID NO:13), a destination vector for use in construction of expression vectors for Gaspe Flint derived maize lines. The attR1 site is at nucleotides 40786-40910; the attR2 site is at nucleotides 41679-41803.
Figure 14:
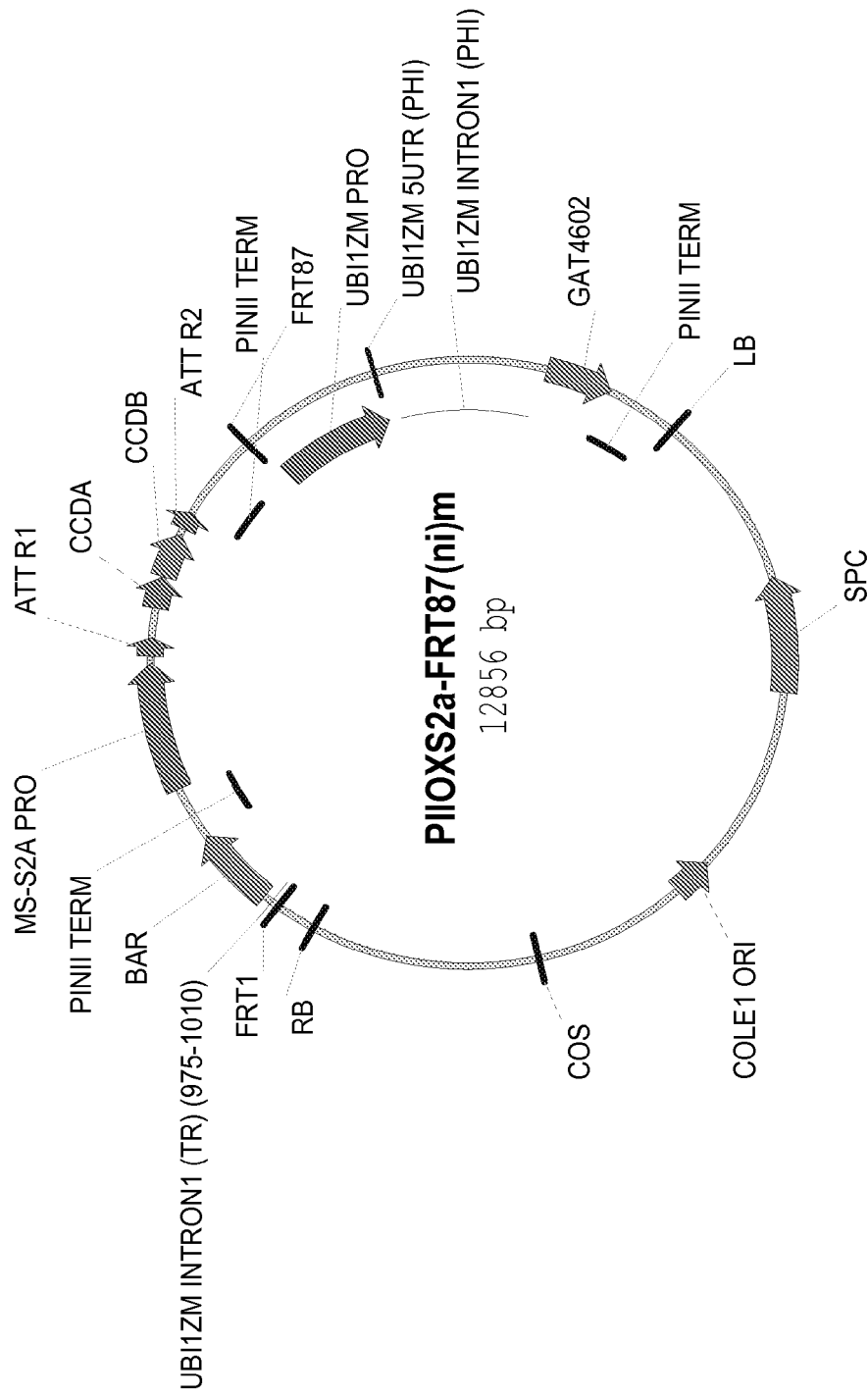
FIG. 14 shows a map of PHOXS2a-FRT87(ni)m (SEQ ID NO:43), a vector used to construct the destination vector PHP29635.

PHP29635 (FIG. 13, SEQ ID NO:13) was obtained by transformation of *Agrobacterium* strain LBA4404 containing plasmid PHP10523 with plasmid PIIOXS2a-FRT87(ni)m (FIG. 14, SEQ ID NO:43) and isolation of the resulting co-integration product. Destination vector PHP29635 can be used in a recombination reaction with an entry clone as described in Example 16 to create a maize expression vector for transformation of Gaspe Flint derived maize lines. Expression of the gene of interest is under control of the S2A promoter (SEQ ID NO:47).

Example 16

Preparation of Plasmids for Transformation of Gaspe Flint Derived Maize Lines

Using Invitrogen™ Gateway® Recombination technology, entry clones containing the *Arabidopsis* EXST gene (AT3G03650) or a maize EXST-like homolog can be created, as described in Examples 5A and 9 and used to directionally clone each gene into destination vector PHP23236 (Example 15) for expression under the ubiquitin promoter or into destination vector PHP29635 (Example 15) for expression under the S2A promoter. Each of the expression vectors are T-DNA binary vectors for *Agrobacterium*-mediated transformation into corn.

Gaspe Flint Derived Maize Lines can be transformed with the expression constructs as described in Example 17.

Example 17

Transformation of Gaspe Flint Derived Maize Lines with Validated *Arabidopsis* Lead Genes and Corresponding Homologs from Other Species Maize plants can be transformed as described in Example 16 to overexpress the *Arabidopsis* AT3G03650 gene and the corresponding homologs from other species, such as the ones listed in Table 1, in order to examine the resulting phenotype. In addition to the promoters described in Example 16 other promoters such the S2B promoter, the maize ROOTMET2 promoter, the maize Cyclo, the CR1BIO, the CRWAQ81 and the maize ZRP2.4447 are useful for directing expression of exst and exst-like genes in maize. Furthermore, a variety of terminators, such as, but not limited to the PINII terminator, can be used to achieve expression of the gene of interest in Gaspe Flint Derived Maize Lines.

Recipient Plants

Recipient plant cells can be from a uniform maize line having a short life cycle ("fast cycling"), a reduced size, and high transformation potential. Typical of these plant cells for maize are plant cells from any of the publicly available Gaspe Flint (GF) line varieties. One possible candidate plant line variety is the F1 hybrid of GF×QTM (Quick Turnaround Maize, a publicly available form of Gaspe Flint selected for growth under greenhouse conditions) disclosed in Tomes et al. U.S. Patent Application Publication No. 2003/0221212. Transgenic plants obtained from this line are of such a reduced size that they can be grown in four inch pots (¼ the space needed for a normal sized maize plant) and mature in less than 2.5 months. (Traditionally 3.5 months is required to obtain transgenic T0 seed once the transgenic plants are acclimated to the greenhouse.) Another suitable line is a double haploid line of GS3 (a highly transformable line) X Gaspe Flint. Yet another suitable line is a transformable elite inbred line carrying a transgene which causes early flowering, reduced stature, or both.

Transformation Protocol

Any suitable method may be used to introduce the transgenes into the maize cells, including but not limited to inoculation type procedures using *Agrobacterium* based vectors as described in Example 9. Transformation may be performed on immature embryos of the recipient (target) plant.

Precision Growth and Plant Tracking

The event population of transgenic (T0) plants resulting from the transformed maize embryos is grown in a controlled greenhouse environment using a modified randomized block design to reduce or eliminate environmental error. A randomized block design is a plant layout in which the experimental plants are divided into groups (e.g., thirty plants per group), referred to as blocks, and each plant is randomly assigned a location with the block.

For a group of thirty plants, twenty-four transformed, experimental plants and six control plants (plants with a set phenotype) (collectively, a "replicate group") are placed in pots which are arranged in an array (a.k.a. a replicate group or block) on a table located inside a greenhouse. Each plant, control or experimental, is randomly assigned to a location with the block which is mapped to a unique, physical greenhouse location as well as to the replicate group. Multiple replicate groups of thirty plants each may be grown in the same greenhouse in a single experiment. The layout (arrangement) of the replicate groups should be determined to minimize space requirements as well as environmental effects within the greenhouse. Such a layout may be referred to as a compressed greenhouse layout.

An alternative to the addition of a specific control group is to identify those transgenic plants that do not express the gene of interest. A variety of techniques such as RT-PCR can be applied to quantitatively assess the expression level of the introduced gene. T0 plants that do not express the transgene can be compared to those which do.

Each plant in the event population is identified and tracked throughout the evaluation process, and the data gathered from that plant is automatically associated with that plant so that the gathered data can be associated with the transgene carried by the plant. For example, each plant container can have a machine readable label (such as a Universal Product Code (UPC) bar code) which includes information about the plant identity, which in turn is correlated to a greenhouse location so that data obtained from the plant can be automatically associated with that plant.

Alternatively any efficient, machine readable, plant identification system can be used, such as two-dimensional matrix codes or even radio frequency identification tags (RFID) in which the data is received and interpreted by a radio frequency receiver/processor. See U.S. Published Patent Application No. 2004/0122592, incorporated herein by reference.

Phenotypic Analysis Using Three-Dimensional Imaging

Each greenhouse plant in the T0 event population, including any control plants, is analyzed for agronomic characteristics of interest, and the agronomic data for each plant is recorded or stored in a manner so that it is associated with the identifying data (see above) for that plant. Confirmation of a phenotype (gene effect) can be accomplished in the T1 generation with a similar experimental design to that described above.

The T0 plants are analyzed at the phenotypic level using quantitative, non-destructive imaging technology throughout the plant's entire greenhouse life cycle to assess the traits of interest. Preferably, a digital imaging analyzer is used for automatic multi-dimensional analyzing of total plants. The imaging may be done inside the greenhouse. Two camera systems, located at the top and side, and an apparatus to rotate the plant, are used to view and image plants from all sides. Images are acquired from the top, front and side of each plant. All three images together provide sufficient information to evaluate the biomass, size and morphology of each plant.

Due to the change in size of the plants from the time the first leaf appears from the soil to the time the plants are at the end of their development, the early stages of plant development are best documented with a higher magnification from the top. This may be accomplished by using a motorized zoom lens system that is fully controlled by the imaging software.

In a single imaging analysis operation, the following events occur: (1) the plant is conveyed inside the analyzer area, rotated 360 degrees so its machine readable label can be read, and left at rest until its leaves stop moving; (2) the side image is taken and entered into a database; (3) the plant is rotated 90 degrees and again left at rest until its leaves stop moving, and (4) the plant is transported out of the analyzer.

Plants are allowed at least six hours of darkness per twenty four hour period in order to have a normal day/night cycle.

Imaging Instrumentation

Any suitable imaging instrumentation may be used, including but not limited to light spectrum digital imaging instrumentation commercially available from LemnaTec GmbH of Wurselen, Germany. The images are taken and analyzed with a LemnaTec Scanalyzer HTS LT-0001-2 having a ½" IT Progressive Scan IEE CCD imaging device. The imaging cameras may be equipped with a motor zoom, motor aperture and motor focus. All camera settings may be made using LemnaTec software. Preferably, the instrumental variance of the imaging analyzer is less than about 5% for major components and less than about 10% for minor components.

Software

The imaging analysis system comprises a LemnaTec HTS Bonit software program for color and architecture analysis and a server database for storing data from about 500,000 analyses, including the analysis dates. The original images and the analyzed images are stored together to allow the user to do as much reanalyzing as desired. The database can be connected to the imaging hardware for automatic data collection and storage. A variety of commercially available software systems (e.g. Matlab, others) can be used for quantitative interpretation of the imaging data, and any of these software systems can be applied to the image data set.

Conveyor System

A conveyor system with a plant rotating device may be used to transport the plants to the imaging area and rotate them during imaging. For example, up to four plants, each with a maximum height of 1.5 m, are loaded onto cars that travel over the circulating conveyor system and through the imaging measurement area. In this case the total footprint of the unit (imaging analyzer and conveyor loop) is about 5 m×5 m.

The conveyor system can be enlarged to accommodate more plants at a time. The plants are transported along the conveyor loop to the imaging area and are analyzed for up to 50 seconds per plant. Three views of the plant are taken. The conveyor system, as well as the imaging equipment, should be capable of being used in greenhouse environmental conditions.

Illumination

Any suitable mode of illumination may be used for the image acquisition. For example, a top light above a black background can be used. Alternatively, a combination of top- and backlight using a white background can be used. The illuminated area should be housed to ensure constant illumination conditions. The housing should be longer than the measurement area so that constant light conditions prevail without requiring the opening and closing or doors. Alternatively, the illumination can be varied to cause excitation of either transgene (e.g., green fluorescent protein (GFP), red fluorescent protein (RFP)) or endogenous (e.g. Chlorophyll) fluorophores.

Biomass Estimation Based on Three-Dimensional Imaging

For best estimation of biomass the plant images should be taken from at least three axes, preferably the top and two side (sides 1 and 2) views. These images are then analyzed to separate the plant from the background, pot and pollen control bag (if applicable). The volume of the plant can be estimated by the calculation:

$$\text{Volume(voxels)} = \sqrt{\text{TopArea(pixels)}} \times \sqrt{\text{Side1Area(pixels)}} \times \sqrt{\text{Side2Area(pixels)}}$$

In the equation above the units of volume and area are "arbitrary units". Arbitrary units are entirely sufficient to detect gene effects on plant size and growth in this system because what is desired is to detect differences (both positive-larger and negative-smaller) from the experimental mean, or control mean. The arbitrary units of size (e.g. area) may be trivially converted to physical measurements by the addition of a physical reference to the imaging process. For instance, a physical reference of known area can be included in both top and side imaging processes. Based on the area of these physical references a conversion factor can be determined to allow conversion from pixels to a unit of area such as square centimeters ($cm^2$). The physical reference may or may not be an independent sample. For instance, the pot, with a known diameter and height, could serve as an adequate physical reference.

Color Classification

The imaging technology may also be used to determine plant color and to assign plant colors to various color classes. The assignment of image colors to color classes is an inherent feature of the LemnaTec software. With other image analysis software systems color classification may be determined by a variety of computational approaches.

For the determination of plant size and growth parameters, a useful classification scheme is to define a simple color scheme including two or three shades of green and, in addition, a color class for chlorosis, necrosis and bleaching, should these conditions occur. A background color class which includes non plant colors in the image (for example pot and soil colors) is also used and these pixels are specifically excluded from the determination of size. The plants are analyzed under controlled constant illumination so that any change within one plant over time, or between plants or different batches of plants (e.g. seasonal differences) can be quantified.

In addition to its usefulness in determining plant size growth, color classification can be used to assess other yield component traits. For these other yield component traits additional color classification schemes may be used. For instance, the trait known as "staygreen", which has been associated with improvements in yield, may be assessed by a color classification that separates shades of green from shades of yellow and brown (which are indicative of senescing tissues). By applying this color classification to images taken toward the end of the T0 or T1 plants' life cycle, plants that have increased amounts of green colors relative to yellow and brown colors (expressed, for instance, as Green/Yellow Ratio) may be identified. Plants with a significant difference in this Green/Yellow ratio can be identified as carrying transgenes which impact this important agronomic trait.

The skilled plant biologist will recognize that other plant colors arise which can indicate plant health or stress response (for instance anthocyanins), and that other color classification schemes can provide further measures of gene action in traits related to these responses.

Plant Architecture Analysis

Transgenes which modify plant architecture parameters may also be identified using the present invention, including such parameters as maximum height and width, internodal distances, angle between leaves and stem, number of leaves starting at nodes and leaf length. The LemnaTec system software may be used to determine plant architecture as follows. The plant is reduced to its main geometric architecture in a first imaging step and then, based on this image, parameterized identification of the different architecture parameters can be performed. Transgenes that modify any of these architecture parameters either singly or in combination can be identified by applying the statistical approaches previously described.

Pollen Shed Date

Pollen shed date is an important parameter to be analyzed in a transformed plant, and may be determined by the first appearance on the plant of an active male flower. To find the male flower object, the upper end of the stem is classified by color to detect yellow or violet anthers. This color classification analysis is then used to define an active flower, which in turn can be used to calculate pollen shed date.

Alternatively, pollen shed date and other easily visually detected plant attributes (e.g. pollination date, first silk date) can be recorded by the personnel responsible for performing plant care. To maximize data integrity and process efficiency this data is tracked by utilizing the same barcodes utilized by the LemnaTec light spectrum digital analyzing device. A computer with a barcode reader, a palm device, or a notebook PC may be used for ease of data capture recording time of observation, plant identifier, and the operator who captured the data.

Orientation of the Plants

Mature maize plants grown at densities approximating commercial planting often have a planar architecture. That is, the plant has a clearly discernable broad side, and a narrow side. The image of the plant from the broadside is determined. To each plant a well defined basic orientation is assigned to obtain the maximum difference between the broadside and edgewise images. The top image is used to determine the main axis of the plant, and an additional rotating device is used to turn the plant to the appropriate orientation prior to starting the main image acquisition.

Example 18

Screening of Gaspe Flint Derived Maize Lines Under Nitrogen Limiting Conditions

Transgenic plants will contain two or three doses of Gaspe Flint-3 with one dose of GS3 (GS3/(Gaspe-3)2× or GS3/(Gaspe-3)3×) and will segregate 1:1 for a dominant transgene. Plants will be planted in Turface, a commercial potting medium, and watered four times each day with 1 mM $KNO_3$ growth medium and with 2 mM $KNO_3$, or higher, growth medium (see FIG. 23). Control plants grown in 1 mM $KNO_3$ medium will be less green, produce less biomass and have a smaller ear at anthesis (see FIG. 24 for an illustration of sample data).

Statistics are used to decide if differences seen between treatments are really different. FIG. 18 illustrates one method which places letters after the values. Those values in the same column that have the same letter (not group of letters) following them are not significantly different. Using this method, if there are no letters following the values in a column, then there are no significant differences between any of the values in that column or, in other words, all the values in that column are equal.

Expression of a transgene will result in plants with improved plant growth in 1 mM $KNO_3$ when compared to a transgenic null. Thus biomass and greenness (as described in Example 17) will be monitored during growth and compared to a transgenic null. Improvements in growth, greenness and ear size at anthesis will be indications of increased nitrogen tolerance.

Example 19

Yield Analysis of Maize Lines with Validated *Arabidopsis* Lead Gene (AT3G03650)

A recombinant DNA construct containing a validated *Arabidopsis* gene can be introduced into a maize line either by direct transformation or introgression from a separately transformed line.

Transgenic plants, either inbred or hybrid, can undergo more vigorous field-based experiments to study yield enhancement and/or stability under various environmental conditions, such as variations in water and nutrient availability.

Subsequent yield analysis can be done to determine whether plants that contain the validated *Arabidopsis* lead gene have an improvement in yield performance under various environmental conditions, when compared to the control plants that do not contain the validated *Arabidopsis* lead gene. Reduction in yield can be measured for both. Plants containing the validated *Arabidopsis* lead gene have less yield loss relative to the control plants, preferably 50% less yield loss.

Example 20

Assays to Determine Alterations of Root Architecture in Maize

Transgenic maize plants are assayed for changes in root architecture at seedling stage, flowering time or maturity. Assays to measure alterations of root architecture of maize plants include, but are not limited to the methods outlined below. To facilitate manual or automated assays of root architecture alterations, corn plants can be grown in clear pots.
1) Root mass (dry weights). Plants are grown in Turface, a growth media that allows easy separation of roots. Oven-dried shoot and root tissues are weighed and a root/shoot ratio calculated.
2) Levels of lateral root branching. The extent of lateral root branching (e.g. lateral root number, lateral root length) is determined by sub-sampling a complete root system, imaging with a flat-bed scanner or a digital camera and analyzing with WinRHIZO™ software (Regent Instruments Inc.).
3) Root band width measurements. The root band is the band or mass of roots that forms at the bottom of greenhouse pots as the plants mature. The thickness of the root band is measured in mm at maturity as a rough estimate of root mass.
4) Nodal root count. The number of crown roots coming off the upper nodes can be determined after separating the root from the support medium (e.g. potting mix). In addition the angle of crown roots and/or brace roots can be measured. Digital analysis of the nodal roots and amount of branching of nodal roots form another extension to the aforementioned manual method.

All data taken on root phenotype are subjected to statistical analysis, normally a t-test to compare the transgenic roots with that of non-transgenic sibling plants. One-way ANOVA may also be used in cases where multiple events and/or constructs are involved in the analysis.

Example 21

Nitrogen Utilization Efficiency Seedling Assay

Seed of transgenic events are separated into transgene (heterozygous) and null seed using a seed color marker. Two different random assignments of treatments are made to each block of 54 pots arranged 6 rows by 9 columns using 9 replicates of all treatments.

Two seed of each treatment are planted in 4 inch, square pots containing Turface on 8 inch, staggered centers and watered four times each day with a solution containing the following nutrients:

| | | | |
|---|---|---|---|
| 1 mM $CaCl_2$ | 2 mM $MgSO_4$ | 0.5 mM $KH_2PO_4$ | 83 ppm Sprint330 |
| 3 mM KCl | 1 mM $KNO_3$ | 1 µM $ZnSO_4$ | 1 µM $MnCl_2$ |
| 3 µM $H_3BO_4$ | 1 µM $MnCl_2$ | 0.1 µM $CuSO_4$ | 0.1 µM $NaMoO_4$ |

After emergence the plants are thinned to one seed per pot. At harvest, plants are removed from the pots and the Turface is washed from the roots. The roots are separated from the shoot, placed in a paper bag and dried at 70° C. for 70 hr. The dried plant parts (roots and shoots) are weighed and placed in a 50 ml conical tube with approximately 20 5/32 inch steel balls and ground by shaking in a paint shaker. Approximately, 30 mg of the ground tissue (weight recorded for later adjustment) is hydrolyzed in 2 ml of 20% $H_2O_2$ and 6M $H_2SO_4$ for 30 min at 170° C. After cooling, water is added to 20 ml, mixed thoroughly, and a 50 µl aliquot is removed and added to 950 µl 1M $Na_2CO_3$. The ammonia in this solution is used to estimate total reduced plant nitrogen by placing 100 µl of this solution into individual wells of a 96 well plate followed by adding 50 µl of OPA solution. Fluorescence, excitation=360 nM/emission=530 nM, is determined and compared to $NH_4Cl$ standards dissolved in a similar solution and treated with OPA solution.

OPA solution—5 µl Mercaptoethanol+1 ml OPA stock solution

OPA stock—50 mg o-phthadialdehyde (OPA—Sigma #P0657) dissolved in 1.5 ml methanol+4.4 ml 1M Borate buffer pH9.5 (3.09 g $H_3BO_4$+1 g NaOH in 50 ml water)+0.55 ml 20% SDS Using these data the following parameters are measured and means compared to null mean parameters using a Student's t test:

Total Plant Biomass
Root Biomass
Shoot Biomass
Root/Shoot Ratio
Plant N concentration
Total Plant N Variance is calculated within each block using a nearest neighbor calculation as well as by Analysis of Variance (ANOVA) using a completely random design (CRD) model. An overall treatment effect for each block is calculated using an F statistic by dividing overall block treatment mean square by the overall block error mean square. The probability of a greater Student's t test is calculated for each transgenic mean compared to the appropriate null (either construct bulked or individual event null mean) mean. A minimum (P<t) of 0.1 is used as a cut off.

Example 22

Analysis of Roots of Maize Seedlings Containing the *Arabidopsis* Exostosin Gene Compared to Roots from Seedlings not Containing the Exostosin Gene A maize expression vector, containing the maize NAS2 promoter (SEQ ID NO:44) and the *Arabidopsis* exostosin gene (SEQ ID NO:33) was prepared as described in Example 14A.

Transformation of maize was achieved via *Agrobacterium* mediated transformation as described in Example 14C by creating a cointegrate vector (PHP29009) and roots were assayed as described in Example 20 using a seedling assay.

All 10 events from construct PHP29009 (ZM-NAS2::AT-EXST) were assayed in a greenhouse experiment, where 9 plants per each event were grown in Turface media to V4 stage. Seeds were from T1 generation (from ears collected off T0 plants). The control experiment included 15 plants of bulked nulls (non-transgenic segregates) grown to the same stage. Seeds were planted using a complete random block design. Plants were harvested 18 days after planting, when they reached V4 stage. Roots were washed and collected separately from shoots. All samples were oven-dried before dry weights were taken on an analytical balance.

A total of 4 events were found to have significant changes in root dry weights, 5 events in shoot dry weights, and 7 events in root to shoot ratios, when compared to the bulked null control, at a P-value less than 0.1. Six events, #4, #5, #6. #7, #9, and #10, had significant increases in Root/Shoot ratios, and 1 event, #1, had a significant decrease.

T-test analysis was performed to show significant differences between each transgenic event and the control. The p-values are shown for each trait: root dry weights, shoot dry weights, and root-to-shoot ratios. Bold face fonts indicate the transgenic had a higher value that the control. Those that had a p-value of less than 0.1 are indicated with an asterix (*).

TABLE 5

Comparison of transgenic and control seedlings

| EVENT | Root Dry Weight | Shoot Dry Weight | Root/Shoot Ratio |
|---|---|---|---|
| 1 | 0.407 | 1.000 | 0.057* |
| 2 | 0.737 | 0.909 | 0.501 |
| 3 | 0.931 | 0.893 | 0.576 |
| 4 | 0.012* | 0.093* | 0.000* |
| 5 | 0.000* | 0.431 | 0.000* |
| 6 | 0.022* | 0.859 | 0.005* |
| 7 | 0.431 | 0.001* | 0.061* |
| 8 | 0.949 | 0.017* | 0.163 |
| 9 | 0.003* | 0.001* | 0.000* |
| 10 | 0.404 | 0.000* | 0.027* |

Example 23

Yield Testing of Transgenic Hybrids Under Normal and Under Nitrogen Depleted Conditions in the Field A field experiment was carried out on a farm in Johnston, Iowa for the 2007 season.

Seven (7) transgenic events expressing the exostosin gene driven by the maize NAS2 promoter, and two controls were included in the experiment. One control was a non-transgenic null with nulls bulked across 7 events. The other control was the wild type used for transformation. All the events were hybrids generated from a common inbred tester.

Two treatments were applied, consisting of conditions wherein the plants were either grown under "normal" nitrogen or under nitrogen "depleted" (stress) conditions. The "normal" treatment included application of a nitrogen fertilizer at a rate of 250 lb per acre. Nitrogen "depleted" conditions were achieved by growing the transgenic and non-transgenic control maize lines in a field wherein soil nitrogen levels had been withdrawn by crops grown in previous years in the absence of fertilizer.

Nitrogen depletion was controlled at the level that caused 30% yield reduction, compared to the normal nitrogen treatment, and required a 100 lb per acre nitrogen fertilization rate. The experiments were set up as 2-row plots with a density of 32000 plants per acre. Four (4) and six (6) replications were included in the normal and the depleted nitrogen treatment, respectively. Plants were planted May 21, 2007 and combine harvested on Sep. 26 and 27, 2007. Yield was measured as bushels per acre.

The combine yield data in bushels per acre from the experiments are summarized as percent increases over the null controls, in Table 6. Event #7 was not tested under normal nitrogen due to seed shortage. Overall, there were 3 events under low nitrogen and 4 events under normal nitrogen that had significant increase in yield over the bulked null control. All events tested showed a positive trend in yield increase over nulls.

TABLE 6

Yield Tests of Transgenic versus Control Plants under Low and Normal Nitrogen Conditions

| Event | Yield increase over null | Significance | Treatment |
|---|---|---|---|
| 1 | 16.15% | P = 0.1 | Low nitrogen |
| 2 | 6.15% | 1 stand error | Low nitrogen |
| 3 | 6.15% | 1 stand error | Low nitrogen |
| 4 | 3.08% | | Low nitrogen |
| 5 | 7.69% | P = 0.1 | Low nitrogen |
| 6 | 2.31% | | Low nitrogen |
| 7 | 7.69% | P = 0.1 | Low nitrogen |
| 1 | 7.53% | P = 0.1 | Normal nitrogen |
| 2 | 7.65% | P = 0.1 | Normal nitrogen |
| 3 | 8.82% | P = 0.1 | Normal nitrogen |
| 4 | 12.35% | P = 0.1 | Normal nitrogen |
| 5 | 4.71% | | Normal nitrogen |
| 6 | 7.53% | 1 stand error | Normal nitrogen |

Example 24

Genome-Wide Association Mapping Analysis

An association mapping strategy can be undertaken to identify markers associated with alterations in root architecture in maize. In this association analysis, a collection of maize lines can be analyzed by DNA sequencing at several thousand genes (genetic loci). The lines can encompass elite germplasm, commercially released cultivars, and other public varieties.

Phenotypic scores for an alteration in root architecture or in at least one agronomic characteristic will be obtained. Lines with extreme phenotypes will be tested against genotypes in a whole genome association test (using 2×2 contingency tables with Fisher's exact test). A structure-based association analysis will be used, where the population structure is controlled using marker data. The model-based cluster analysis software, Structure, developed by Pritchard et al., (*Genetics* 155:945-959 (2000)) will be used with haplotype data for hundreds of elite maize inbreds at several hundred markers to estimate admixture coefficients and assign the inbreds to a number of subpopulations. This reduces the occurrence of false positives that can arise due to the effect of population structure on association mapping statistics. Kuiper's statistic for testing whether two distributions are the same was used to test a given marker for association between haplotype and phenotype in a given subpopulation (Press et al., Numerical Recipes in C, second edition, Cambridge University Press, NY (2002)).

At least one strong peak in at least one subpopulation is indicative of significant marker-trait associations (e.g. p<0.001). Marker positions are given in cM, with position zero being the first (most distal from the centromere) marker known at the beginning of a chromosome. These map positions are not absolute, and represent an estimate of map position based on the internally derived genetic map.

Example 25

Candidate Gene Association Mapping

Primers are designed to amplify a portion of the candidate gene locus from individual inbred lines. Genotypes are obtained for each of the inbred lines at this locus and the polymorphic loci are tested for statistically significant associations with altered root architecture or at least one alteration in one agronomic characteristic.

What is claimed is:

1. A plant comprising in its genome a recombinant DNA construct comprising a polynucleotide operably linked to at least one heterologous regulatory element, wherein said polynucleotide encodes a polypeptide having an amino acid sequence of at least 95% sequence identity, based on the Clustal V method of alignment, when compared to SEQ ID NO: 34 and wherein said plant exhibits increased root biomass when compared to a control plant not comprising said recombinant DNA construct.

2. The plant of claim 1, wherein the plant is a maize plant or a soybean plant.

3. A plant comprising in its genome a recombinant DNA construct comprising a polynucleotide operably linked to at least one heterologous regulatory element, wherein said polynucleotide encodes a polypeptide having an amino acid sequence of at least 95% sequence identity, based on the Clustal V method of alignment, when compared to SEQ ID NO: 34, and wherein said plant exhibits an increase of at least one agronomic characteristic selected from the group consisting of: yield, biomass, fresh weight at maturation and dry weight at maturation, when compared to a control plant not comprising said recombinant DNA construct.

4. The plant of claim 3, wherein the plant is a maize plant or a soybean plant.

5. The plant of claim 3, wherein said plant exhibits said increase of said at least one agronomic characteristic when compared, under limiting nitrogen conditions, to said control plant not comprising said recombinant DNA construct.

6. The plant of claim 5, wherein the plant is a maize plant or a soybean plant.

7. A method of increasing root biomass in a plant, comprising:
(a) introducing into a regenerable plant cell a recombinant DNA construct comprising a polynucleotide operably linked to at least one heterologous regulatory sequence, wherein the polynucleotide encodes a polypeptide having an amino acid sequence of at least 95% sequence identity, based on the Clustal V method of alignment, when compared to SEQ ID NO: 34; and
(b) regenerating a transgenic plant from the regenerable plant cell after step (a), wherein the transgenic plant comprises in its genome the recombinant DNA construct and exhibits increased root biomass when compared to a control plant not comprising the recombinant DNA construct.

8. The method of claim 7, further comprising:
(c) obtaining a progeny plant derived from the transgenic plant, wherein said progeny plant comprises in its genome the recombinant DNA construct and exhibits increased root biomass when compared to a control plant not comprising the recombinant DNA construct.

9. A method of increasing an agronomic characteristic in a plant, comprising:
(a) introducing into a regenerable plant cell a recombinant DNA construct comprising a polynucleotide operably linked to at least one heterologous regulatory sequence, wherein the polynucleotide encodes a polypeptide having an amino acid sequence of at least 95% sequence identity, based on the Clustal V method of alignment, when compared to SEQ ID NO: 34;
(b) regenerating a transgenic plant from the regenerable plant cell after step (a), wherein the transgenic plant comprises in its genome the recombinant DNA construct; and
(c) selecting a transgenic plant of step (b) that exhibits an increase of at least one agronomic characteristic selected from the group consisting of: yield, biomass, fresh weight at maturation and dry weight at maturation, when compared to a control plant not comprising the recombinant DNA construct.

10. The method of claim 9, further comprising:
(d) obtaining a progeny plant derived from the transgenic plant, wherein the progeny plant comprises in its genome the recombinant DNA construct; and
(e) selecting a progeny plant of step (d) that exhibits an increase of at least one agronomic characteristic selected from the group consisting of: yield, biomass, fresh weight at maturation and dry weight at maturation, when compared to a control plant not comprising the recombinant DNA construct.

11. The method of claim 9, wherein the transgenic plant of step (c) exhibits an increase of at least one agronomic characteristic when compared, under limiting nitrogen conditions, to a control plant not comprising the recombinant DNA construct.

12. The method of claim 10, wherein the progeny plant of step (e) exhibits an increase of at least one agronomic characteristic when compared, under limiting nitrogen conditions, to a control plant not comprising the recombinant DNA construct.

13. A method of increasing an agronomic characteristic in a plant, comprising:
(a) introducing into a regenerable plant cell a recombinant DNA construct comprising a polynucleotide operably linked to at least one heterologous regulatory sequence, wherein the polynucleotide encodes a polypeptide having an amino acid sequence of at least 95% sequence identity, based on the Clustal V method of alignment, when compared to SEQ ID NO: 34;
(b) regenerating a transgenic plant from the regenerable plant cell after step (a), wherein the transgenic plant comprises in its genome the recombinant DNA construct;
(c) obtaining a progeny plant derived from the transgenic plant, wherein the progeny plant comprises in its genome the recombinant DNA construct; and
(d) selecting a progeny plant of step (c) that exhibits an increase of at least one agronomic characteristic selected from the group consisting of: yield, biomass, fresh weight at maturation and dry weight at maturation, when compared to a control plant not comprising the recombinant DNA construct.

14. The method of claim 13, wherein said progeny plant of step (d) exhibits an increase of at least one agronomic characteristic when compared, under limiting nitrogen conditions, to a control plant not comprising the recombinant DNA construct.

* * * * *

SEQUENCE LISTING

<160> NUMBER OF SEQ ID NOS: 49

<210> SEQ ID NO 1
<211> LENGTH: 18491
<212> TYPE: DNA
<213> ORGANISM: artificial sequence
<220> FEATURE:
<223> OTHER INFORMATION: vector

<400> SEQUENCE: 1

```
catgaatcaa acaaacatac acagcgactt attcacacga gctcaaatta caacggtata      60
tatcctgccg tcgacaacca tggtctagac aggatccccg ggtaccgagc tcgaatttgc     120
aggtcgactg cgtcatccct tacgtcagtg gagatatcac atcaatccac ttgctttgaa     180
gacgtggttg gaacgtcttc tttttccacg atgctcctcg tgggtggggg tccatctttg     240
ggaccactgt cggcagaggc atcttgaacg atagcctttc ctttatcgca atgatggcat     300
ttgtaggtgc caccttcctt ttctactgtc cttttgatga agtgacagat agctgggcaa     360
tggaatccga ggaggtttcc cgatattacc ctttgttgaa aagtctcaat tgcccttttgg    420 tcttctgaga ctgttgcgtc atcccttacg tcagtggaga tatcacatca atccacttgc     480
tttgaagacg tggttggaac gtcttctttt tccacgatgc tcctcgtggg tggggtcca     540 tctttgggac cactgtcggc agaggcatct tgaacgatag cctttccttt atcgcaatga     600
tggcatttgt aggtgccacc ttccttttct actgtccttt tgatgaagtg acagatagct     660
gggcaatgga atccgaggag gtttcccgat attaccctt gttgaaaagt ctcagttaac     720
ccgcgatcct gcgtcatccc ttacgtcagt ggagatatca catcaatcca cttgctttga     780
agacgtggtt ggaacgtctt cttttttccac gatgctcctc gtgggtgggg gtccatcttt    840
gggaccactg tcggcagagg catcttgaac gatagccttt cctttatcgc aatgatggca     900
tttgtaggtg ccaccttcct tttctactgt cttttgatg aagtgacaga tagctgggca     960
atggaatccg aggaggtttc ccgatattac cctttgttga aaagtctcaa ttgcccttttg   1020 gtcttctgag actgttgcgt catccttac gtcagtggag atatcacatc aatccacttg    1080
ctttgaagac gtggttggaa cgtcttcttt tccacgatg ctcctcgtgg gtgggggtcc     1140
atctttggga ccactgtcgg cagaggcatc ttgaacgata gcctttcctt tatcgcaatg    1200
atggcatttg taggtgccac cttcctttc tactgtcctt tgatgaagt gacagatagc     1260
```

```
tgggcaatgg aatccgagga ggtttcccga tattacccct tgttgaaaag tctcagttaa    1320
cccgcaattc actggccgtc gttttacaac gtcgtgactg ggaaaaccct ggcgttaccc    1380
aacttaatcg ccttgcagca catccccctt tcgccagctg gcgtaatagc gaagaggccc    1440
gcaccgatcg cccttcccaa cagttgcgca gcctgaatgg cgaatggatc gatccgtcga    1500
tcgaccaaag cggccatcgt gcctccccac tcctgcagtt cggggggcatg gatgcgcgga    1560 tagccgctgc tggtttcctg gatgccgacg gatttgcact gccggtagaa ctccgcgagg    1620
tcgtccagcc tcaggcagca gctgaaccaa ctcgcgaggg gatcgagccc ctgctgagcc    1680
tcgacatgtt gtcgcaaaat tcgccctgga cccgcccaac gatttgtcgt cactgtcaag    1740
gtttgacctg cacttcattt ggggcccaca taccaaaaa aaatgctgca taattctcgg    1800
ggcagcaagt cggttacccg gccgccgtgc tggaccgggt tgaatggtgc ccgtaacttt    1860
cggtagagcg gacggccaat actcaacttc aaggaatctc acccatgcgc gccggcgggg    1920
aaccggagtt cccttcagtg aacgttatta gttcgccgct cggtgtgtcg tagatactag    1980
cccctggggc cttttgaaat ttgaataaga tttatgtaat cagtcttta ggtttgaccg    2040 gttctgccgc ttttttaaa attggatttg taataataaa acgcaattgt ttgttattgt    2100
ggcgctctat catagatgtc gctataaacc tattcagcac aatatattgt tttcatttta    2160
atattgtaca tataagtagt agggtacaat cagtaaattg aacggagaat attattcata    2220
aaaatacgat agtaacgggt gatatattca ttagaatgaa ccgaaaccgg cggtaaggat    2280
ctgagctaca catgctcagg tttttacaa cgtgcacaac agaattgaaa gcaaatatca    2340
tgcgatcata ggcgtctcgc atatctcatt aaagcagggg gtgggcgaag aactccagca    2400
tgagatcccc gcgctggagg atcatccagc cggcgtcccg gaaaacgatt ccgaagccca    2460
acctttcata gaaggcggcg gtggaatcga atctcgtga tggcaggttg ggcgtcgctt    2520
ggtcggtcat ttcgaacccc agagtcccgc tcagaagaac tcgtcaagaa ggcgatagaa    2580
ggcgatgcgc tgcgaatcgg gagcggcgat accgtaaagc acgaggaagc ggtcagccca    2640
ttcgccgcca agctcttcag caatatcacg ggtagccaac gctatgtcct gatagcggtc    2700
cgccacaccc agccggccac agtcgatgaa tccagaaaag cggccatttt ccaccatgat    2760
attcggcaag caggcatcgc catgggtcac gacgagatcc tcgccgtcgg gcatgccccc    2820
caattcactg gccgtcgttt tacaacgtcg tgactgggaa aacctggcg ttacccaact    2880 taatcgcctt gcagcacatc cccctttcgc cagctggcgt aatagcgaag aggcccgcac    2940
cgatcgccct tcccaacagt tgcgcagcct gaatggcgaa tggcgcctga tcggtattt    3000 tctccttacg catctgtgcg gtatttcaca ccgcatatgg tgcactctca gtacaatctg    3060
ctctgatgcc gcatagttaa gccagccccg acacccgcca acaccgctg acgcgccctg    3120 acgggcttgt ctgctcccgg catccgctta cagacaagct gtgaccgtct ccgggagctg    3180
catgtgtcag aggttttcac cgtcatcacc gaaacgcgcg agacgaaagg gcctcgtgat    3240
acgcctattt ttataggtta atgtcatgat aataatggtt tcttagacgt caggtggcac    3300
ttttcgggga atgtgcgcg gaaccccat ttgtttattt ttctaaatac attcaaatat    3360
gtatccgctc atgagacaat aaccctgata aatgcttcaa taatattgaa aaggaagag    3420 tatgagtatt caacatttcc gtgtcgccct tattcccttt tttgcggcat tttgccttcc    3480 tgttttgct cacccagaaa cgctggtgaa agtaaaagat gctgaagatc agttgggtgc    3540
acgagtgggt tacatcgaac tggatctcaa cagcggtaag atccttgaga gttttcgccc    3600
```

```
cgaagaacgt tttccaatga tgagcacttt taaagttctg ctatgtggcg cggtattatc    3660
ccgtattgac gccgggcaag agcaactcgg tcgccgcata cactattctc agaatgactt    3720
ggttgagtac tcaccagtca cagaaaagca tcttacggat ggcatgacag taagagaatt    3780
atgcagtgct gccataacca tgagtgataa cactgcggcc aacttacttc tgacaacgat    3840
cggaggaccg aaggagctaa ccgcttttt gcacaacatg ggggatcatg taactcgcct     3900
tgatcgttgg gaaccggagc tgaatgaagc cataccaaac gacgagcgtg acaccacgat    3960
gcctgtagca atggcaacaa cgttgcgcaa actattaact ggcgaactac ttactctagc    4020
ttcccggcaa caattaatag actggatgga ggcggataaa gttgcaggac cacttctgcg    4080
ctcggccctt ccggctggct ggtttattgc tgataaatct ggagccggtg agcgtgggtc    4140
tcgcggtatc attgcagcac tggggccaga tggtaagccc tcccgtatcg tagttatcta    4200
cacgacgggg agtcaggcaa ctatggatga acgaaataga cagatcgctg agataggtgc    4260
ctcactgatt aagcattggt aactgtcaga ccaagtttac tcatatatac tttagattga    4320
tttaaaactt catttttaat ttaaaaggat ctaggtgaag atcctttttg ataatctcat    4380
gaccaaaatc ccttaacgtg agttttcgtt ccactgagcg tcagacccg tagaaaagat     4440 caaaggatct cttgagatc ctttttttct gcgcgtaatc tgctgcttgc aaacaaaaaa     4500
accaccgcta ccagcggtgg tttgtttgcc ggatcaagag ctaccaactc tttttccgaa    4560
ggtaactggc ttcagcagag cgcagatacc aaatactgtc cttctagtgt agccgtagtt    4620
aggccaccac ttcaagaact ctgtagcacc gcctacatac ctcgctctgc taatcctgtt    4680
accagtggct gctgccagtg gcgataagtc gtgtcttacc gggttggact caagacgata    4740
gttaccggat aaggcgcagc ggtcgggctg aacggggggt tcgtgcacac agcccagctt    4800
ggagcgaacg acctacaccg aactgagata cctacagcgt gagcattgag aaagcgccac    4860
gcttcccgaa gggagaaagg cggacaggta tccggtaagc ggcagggtcg gaacaggaga    4920
gcgcacgagg gagcttccag ggggaaacgc ctggtatctt tatagtcctg tcgggtttcg    4980
ccacctctga cttgagcgtc gatttttgtg atgctcgtca ggggggcgga gcctatggaa    5040
aaacgccagc aacgcggcct ttttacggtt cctggccttt tgctggcctt ttgctcacat    5100
gttctttcct gcgttatccc ctgattctgt ggataaccgt attaccgcct ttgagtgagc    5160
tgataccgct cgccgcagcc gaacgaccga gcgcagcgag tcagtgagcg aggaagcgga    5220
agagcgccca atacgcaaac cgcctctccc cgcgcgttgg ccgattcatt aatgcagctg    5280
gcacgacagg tttcccgact ggaaagcggg cagtgagcgc aacgcaatta atgtgagtta    5340
gctcactcat taggcacccc aggctttaca ctttatgctt ccggctcgta tgttgtgtgg    5400
aattgtgagc ggataacaat ttcacacagg aaacagctat gaccatgatt acgccaagct    5460
ttctaggggg ggggtaccga tctgagatcg gtaacgaaaa cgaacgggta gggatgaaaa    5520
cggtcggtaa cggtcggtaa aatacctcta ccgttttcat tttcatattt aacttgcggg    5580
acggaaacga aaacgggata taccggtaac gaaaacgaac gggataaaata cggtaatcga    5640 aaaccgatac gatccggtcg ggttaaagtc gaaatcggac gggaaccggt attttgttc     5700 ggtaaaatca cacatgaaaa catatattca aaacttaaaa acaaatataa aaaattgtaa    5760
acacaagtct taatgatcac tagtggcgcg cctaggagat ctcgagtagg gataacaggg    5820
taatacatag ataaaatcca tataaatctg gagcacacat agtttaatgt agcacataag    5880
tgataagtct tgggctcttg gctaaactaa gaagccatat aagtctacta gcacacatga    5940
cacaatataa agtttaaaac acatattcat aatcacttgc tcacatctgg atcacttagc    6000
```

```
atgctacagc tagtgcaata ttagacactt tccaatattt ctcaaacttt tcactcattg    6060
caacggccat tctcctaatg acaaattttt catgaacaca ccattggtca atcaaatcct    6120
ttatctcaca gaaacctttg taaaataaat ttgcagtgga atattgagta ccagatagga    6180
gttcagtgag atcaaaaaac ttcttcaaac acttaaaaag agttaatgcc atcttccact    6240
cctcggcttt aggacaaatt gcatcgtacc tacaataatt gacatttgat taattgagaa    6300
tttataatga tgacatgtac aacaattgag acaaacatac ctgcgaggat cacttgtttt    6360
aagccgtgtt agtgcaggct tataatataa ggcatccctc aacatcaaat aggttgaatt    6420
ccatctagtt gagacatcat atgagatccc tttagattta tccaagtcac attcactagc    6480
acacttcatt agttcttccc actgcaaagg agaagatttt acagcaagaa caatcgcttt    6540
gattttctca attgttcctg caattacagc caagccatcc tttgcaacca agttcagtat    6600
gtgacaagca cacctcacat gaaagaaagc accatcacaa actagatttg aatcagtgtc    6660
ctgcaaatcc tcaattatat cgtgcacagc tacttcattt gcactagcat tatccaaaga    6720
caaggcaaac aattttttct caatgttcca cttaaccatg attgcagtga aggtttgtga    6780
taacctttgg ccagtgtggc gcccttcaac atgaaaaaag ccaacaattc ttttttggag    6840
acaccaatca tcatcaatcc aatggatggt gacacacatg tatgacttat tttgacaaga    6900
tgtccacata tccatagttg tactgaagcg agactgaaca tcttttagtt ttccatacaa    6960
cttttctttt tcttccaaat acaaatccat gatatatttt ctagcagtga cacgggactt    7020
tattggaaag tgagggcgca gagacttaac aaactcaaca aagtactcat gttctacaat    7080
attgaaagga tattcatgca tgattattgc caaatgaagc ttctttaggc taaccacttc    7140
atcgtactta taaggctcaa tgagatttat gtctttgcca tgatcctttt cactttttag    7200
acacaactga cctttaacta aactatgtga tgttctcaag tgatttcgaa atccgcttgt    7260
tccatgatga ccctcagccc tatacttagc cttgcaatta ggaaagttgc aatgtcccca    7320
tacctgaacg tatttctttc catcgacctc cacttcaatt tccttcttgg tgaaatgctg    7380
ccatacatcc gatgtgcact tctttgccct cttctgtggt gcttcttctt cgggttcagg    7440
ttgtggctgt ggttgtggtt ctggttgtgg ttgtggttgt ggttgtggtt catgaacaat    7500
agccatatca tcttgactcg gatctgtagc tgtaccatt tgcattactac tgcttacact    7560 ctgaataaaa tgcctctcgg cctcagctgt tgatgatgat ggtgatgtgc ggccacatcc    7620
atgcccacgc gcacgtgcac gtacattctg aatccgacta aagaggctt cagcttttct    7680 tttcaaccct gttataaaca gattttttcgt attattctac agtcaatatg atgcttccca    7740
atctacaacc aattagtaat gctaatgcta ttgctactgt ttttctaata tataccttga    7800
gcatatgcag agaatacgga atttgttttg cgagtagaag gcgctcttgt ggtagacatc    7860
aacttggcca atcttatggc tgagcctgag ggaggattat ttccaaccgg aggcgtcatc    7920
tgaggaatgg agtcgtagcc ggctagccga agtggagagc agagccctgg acagcaggtg    7980
ttcagcaatc agcttggtgc tgtactgctg tgacttgtga gcacctggac ggctggacag    8040
caatcagcag gtgttgcaga gccccctggac agcacacaaa tgacacaaca gcttggtgca    8100
atggtgctga cgtgctgtac tgctaagtgc tgtgagcctg tgagcagccg tggagacagg    8160
gagaccgcgg atggccggat gggcgagcgc cgagcagtgg aggtctggag gaccgctgac    8220
cgcagatggc ggatggcgga tgggcggacc gcggatgggc gagcagtgga gtggaggtct    8280
gggcggatgg gcggaccgcg gcgcggatgg gcgagtcgcg agcagtggag tggagggcgg    8340
```

```
accgtggatg gcggcgtctg cgtccggcgt gccgcgtcac ggccgtcacc gcgtgtggtg      8400
cctggtgcag cccagcggcc ggccggctgg gagacaggga gagtcggaga gagcaggcga      8460
gagcgagacg cgtcgccggc gtcggcgtgc ggctggcggc gtccggactc cggcgtgggc      8520
gcgtggcggc gtgtgaatgt gtgatgctgt tactcgtgtg gtgcctggcc gcctgggaga      8580
gaggcagagc agcgttcgct aggtatttct tacatgggct gggcctcagt ggttatggat      8640
gggagttgga gctggccata ttgcagtcat cccgaattag aaaatacggt aacgaaacgg      8700
gatcatcccg attaaaaacg ggatcccggt gaaacggtcg ggaaactagc tctaccgttt      8760
ccgtttccgt ttaccgtttt gtatatcccg tttccgttcc gttttcgttt tttacctcgg      8820
gttcgaaatc gatcgggata aaactaacaa atcggttat acgataacgg tcggtacggg       8880
attttcccat cctactttca tccctgagat tattgtcgtt tctttcgcag atcggtaccc      8940 ccccctaga gtcgacatcg atctagtaac atagatgaca ccgcgcgcga taatttatcc      9000
tagtttgcgc gctatatttt gttttctatc gcgtattaaa tgtataattg cgggactcta      9060
atcataaaaa cccatctcat aaataacgtc atgcattaca tgttaattat tacatgctta      9120
acgtaattca acagaaatta tatgataatc atcgcaagac cggcaacagg attcaatctt      9180
aagaaacttt attgccaaat gttgaacga tctgcttcga cgcactcctt ctttaggtac        9240
ggactagatc tcggtgacgg gcaggaccgg acggggcggt accggcaggc tgaagtccag      9300
ctgccagaaa cccacgtcat gccagttccc gtgcttgaag ccggccgccc gcagcatgcc      9360 gcgggggca tatccgagcg cctcgtgcat gcgcacgctc gggtcgttgg gcagcccgat        9420
gacagcgacc acgctcttga agccctgtgc ctccaggaca ttcagcaggt gggtgtagag      9480
cgtggagccc agtcccgtcc gctggtggcg gggggagacg tacacggtcg actcggccgt      9540
ccagtcgtag gcgttgcgtg ccttccaggg gcccgcgtag gcgatgccgg cgacctcgcc      9600
gtccacctcg gcgacgagcc agggatagcg ctcccgcaga cggacgaggt cgtccgtcca      9660
ctcctgcggt tcctgcggct cggtacggaa gttgaccgtg cttgtctcga tgtagtggtt      9720
gacgatggtg cagaccgccg gcatgtccgc ctcggtggca cggcggatgt cggccgggcg      9780
tcgttctggg ctcatggatc tggattgaga gtgaatatga gactctaatt ggataccgag      9840
gggaatttat ggaacgtcag tggagcattt ttgacaagaa atatttgcta gctgatagtg      9900
accttaggcg actttttgaac gcgcaataat ggtttctgac gtatgtgctt agctcattaa     9960
actccagaaa cccgcggctg agtggctcct tcaatcgttg cggttctgtc agttccaaac    10020
gtaaaacggc ttgtcccgcg tcatcggcgg gggtcataac gtgactccct taattctccg    10080
ctcatgatcc ccgggtaccg agctcgaatt gcggctgagt ggctccttca atcgttgcgg    10140
ttctgtcagt tccaaacgta aaacggcttg tcccgcgtca tcggcggggg tcataacgtg    10200
actcccttaa ttctccgctc atgatcttga tcccctgcgc catcagatcc ttggcggcaa    10260
gaaagccatc cagtttactt tgcagggctt cccaaccta ccagagggcg ccccagctgg      10320
caattccggt tcgcttgctg tatcgatatg gtggatttat cacaaatggg acccgccgcc    10380
gacagaggtg tgatgttagg ccaggacttt gaaaatttgc gcaactatcg tatagtggcc    10440
gacaaattga cgccgagttg acagactgcc tagcatttga gtgaattatg tgaggtaatg    10500
ggctacactg aattggtagc tcaaactgtc agtatttatg tatatgagtg tatattttcg    10560
cataatctca gaccaatctg aagatgaaat gggtatctgg gaatggcgaa atcaaggcat    10620
cgatcgtgaa gtttctcatc taagcccca tttggacgtg aatgtagaca cgtcgaaata      10680
aagatttccg aattagaata atttgtttat tgctttcgcc tataaatacg acggatcgta    10740
```

```
atttgtcgtt ttatcaaaat gtactttcat tttataataa cgctgcggac atctacattt    10800
ttgaattgaa aaaaaattgg taattactct ttcttttcct ccatattgac catcatactc    10860
attgctgatc catgtagatt tcccggacat gaagccattt acaattgaat atatcctgcc    10920
gccgctgccg ctttgcaccc ggtggagctt gcatgttggt ttctacgcag aactgagccg    10980
gttaggcaga taatttccat tgagaactga gccatgtgca ccttcccccc aacacggtga    11040
gcgacggggc aacggagtga tccacatggg acttttaaac atcatccgtc ggatggcgtt    11100
gcgagagaag cagtcgatcc gtgagatcag ccgacgcacc gggcaggcgc gcaacacgat    11160
cgcaaagtat ttgaacgcag gtacaatcga gccgacgttc accgtcaccc tggatgctgt    11220
aggcataggc ttggttatgc cggtactgcc gggcctcttg cgggatatcg tccattccga    11280
cagcatcgcc agtcactatg gcgtgctgct agcgctatat gcgttgatgc aatttctatg    11340
cgcacccgtt ctcggagcac tgtccgaccg ctttggccgc cgcccagtcc tgctcgcttc    11400
gctacttgga gccactatcg actacgcgat catggcgacc acacccgtcc tgtggtccaa    11460
cccctccgct gctatagtgc agtcggcttc tgacgttcag tgcagccgtc ttctgaaaac    11520
gacatgtcgc acaagtccta agttacgcga caggctgccg ccctgccctt ttcctggcgt    11580
tttcttgtcg cgtgttttag tcgcataaag tagaatactt gcgactagaa ccggagacat    11640
tacgccatga acaagagcgc cgccgctggc ctgctgggct atgcccgcgt cagcaccgac    11700
gaccaggact tgaccaacca acgggccgaa ctgcacgcgg ccgctgcac caagctgttt    11760 tccgagaaga tcaccggcac caggcgcgac cgcccggagc tggccaggat gcttgaccac    11820
ctacgccctg gcgacgttgt gacagtgacc aggctagacc gcctggcccg cagcacccgc    11880
gacctactgg acattgccga gcgcatccag gaggccggcg cgggcctgcg tagcctggca    11940
gagccgtggg ccgacaccac cacgccggcc ggccgcatgg tgttgaccgt gttcgccggc    12000
attgccgagt tcgagcgttc cctaatcatc gaccgcaccc ggagcgggcg cgaggccgcc    12060
aaggcccgag gcgtgaagtt tggcccccgc cctaccctca ccccggcaca gatcgcgcac    12120
gcccgcgagc tgatcgacca ggaaggccgc accgtgaaag aggcggctgc actgcttggc    12180
gtgcatcgct cgaccctgta ccgcgcactt gagcgcagcg aggaagtgac gcccaccgag    12240
gccaggcggc gcggtgcctt ccgtgaggac gcattgaccg aggccgacgc cctggcggcc    12300
gccgagaatg aacgccaaga ggaacaagca tgaaaccgca ccaggacggc caggacgaac    12360
cgtttttcat taccgaagag atcgaggcgg agatgatcgc ggccgggtac gtgttcgagc    12420
cgcccgcgca cgtctcaacc gtgcggctgc atgaaatcct ggccggtttg tctgatgcca    12480
agctggcggc ctggccggcc agcttggccg ctgaagaaac cgagcgccgc cgtctaaaaa    12540
ggtgatgtgt atttgagtaa aacagcttgc gtcatgcggt cgctgcgtat atgatgcgat    12600
gagtaaataa acaaatacgc aagggaacgc atgaagttat cgctgtactt aaccagaaag    12660
gcgggtcagg caagacgacc atcgcaaccc atctagcccg cgccctgcaa ctcgccgggg    12720
ccgatgttct gttagtcgat tccgatcccc agggcagtgc ccgcgattgg cggccgtgc    12780 gggaagatca accgctaacc gttgtcggca tcgaccgccc gacgattgac cgcgacgtga    12840
aggccatcgg ccgcgcgac ttcgtagtga tcgacggagc gccccaggcg gcggacttgg    12900
ctgtgtccgc gatcaaggca gccgacttcg tgctgattcc ggtgcagcca gcccttacg    12960 acatatgggc caccgccgac ctggtggagc tggttaagca gcgcattgag gtcacggatg    13020
gaaggctaca gcggcctttt gtcgtgtcgc gggcgatcaa aggcacgcgc atcggcggtg    13080
```

```
aggttgccga ggcgctggcc gggtacgagc tgcccattct tgagtcccgt atcacgcagc   13140
gcgtgagcta cccaggcact gccgccgccg gcacaaccgt tcttgaatca gaacccgagg   13200
gcgacgctgc ccgcgaggtc caggcgctgg ccgctgaaat taaatcaaaa ctcatttgag   13260
ttaatgaggt aaagagaaaa tgagcaaaag cacaaacacg ctaagtgccg gccgtccgag   13320
cgcacgcagc agcaaggctg caacgttggc cagcctggca gacacgccag ccatgaagcg   13380
ggtcaacttt cagttgccgg cggaggatca caccaagctg aagatgtacg cggtacgcca   13440
aggcaagacc attaccgagc tgctatctga atacatcgcg cagctaccag agtaaatgag   13500
caaatgaata aatgagtaga tgaattttag cggctaaagg aggcggcatg gaaaatcaag   13560
aacaaccagg caccgacgcc gtggaatgcc ccatgtgtgg aggaacgggc ggttggccag   13620
gcgtaagcgg ctgggttgtc tgccggccct gcaatggcac tggaaccccc aagcccgagg   13680
aatcggcgtg agcggtcgca aaccatccgg cccggtacaa atcggcgcgg cgctgggtga   13740
tgacctggtg gagaagttga aggccgcgca ggccgcccag cggcaacgca tcgaggcaga   13800
agcacgcccc ggtgaatcgt ggcaagcggc cgctgatcga atccgcaaag aatcccggca   13860
accgccggca gccggtgcgc cgtcgattag gaagccgccc aagggcgacg agcaaccaga   13920
ttttttcgtt ccgatgctct atgacgtggg caccccgcgat agtcgcagca tcatggacgt   13980
ggccgttttc cgtctgtcga agcgtgaccg acgagctggc gaggtgatcc gctacgagct   14040
tccagacggg cacgtagagg tttccgcagg gccggccggc atggccagtg tgtgggatta   14100
cgacctggta ctgatggcgg tttcccatct aaccgaatcc atgaaccgat accgggaagg   14160
gaagggagac aagcccggcc gcgtgttccg tccacacgtt gcggacgtac tcaagttctg   14220
ccggcgagcc gatggcggaa agcagaaaga cgacctggta gaaacctgca ttcggttaaa   14280
caccacgcac gttgccatgc agcgtacgaa gaaggccaag aacggccgcc tggtgacggt   14340
atccgagggt gaagccttga ttagccgcta caagatcgta aagagcgaaa ccgggcggcc   14400
ggagtacatc gagatcgagc tagctgattg gatgtaccgc gagatcacag aaggcaagaa   14460
cccggacgtg ctgacggttc accccgatta ctttttgatc gatcccggca tcggccgttt   14520
tctctaccgc ctggcacgcc gcgccgcagg caaggcagaa gccagatggt tgttcaagac   14580
gatctacgaa cgcagtggca gcgccggaga gttcaagaag ttctgtttca ccgtgcgcaa   14640
gctgatcggg tcaaatgacc tgccggagta cgatttgaag gaggaggcgg ggcaggctgg   14700
cccgatccta gtcatgcgct accgcaacct gatcgagggc gaagcatccg ccggttccta   14760
atgtacggag cagatgctag gcaaattgcc cctagcaggg gaaaaaggtc gaaaaggtct   14820 cttttcctgtg gatagcacgt acattgggaa cccaaagccg tacattggga accggaaccc   14880
gtacattggg aacccaaagc cgtacattgg gaaccggtca cacatgtaag tgactgatat   14940
aaaagagaaa aaggcgattt ttccgcccta aaactcttta aaacttatta aaactcttaa   15000
aacccgcctg gcctgtgcat aactgtctgg ccagcgcaca gccgaagagc tgcaaaaagc   15060 gcctacccctt cggtcgctgc gctccctacg ccccgccgct tcgcgtcggc ctatcgcggc   15120
cgctggccgc tcaaaaatgg ctggcctacg gccaggcaat ctaccagggc gcggacaagc   15180
cgcgccgtcg ccactcgacc gccggcgccc acatcaaggc accctgcctc gcgcgtttcg   15240
gtgatgacgg tgaaaacctc tgacacatgc agctcccgga cggtcaca gcttgtctgt   15300 aagcggatgc cgggagcaga caagcccgtc agggcgcgtc agcgggtgtt ggcgggtgtc   15360
ggggcgcagc catgacccag tcacgtagcg atagcggagt gtatactggc ttaactatgc   15420
ggcatcagag cagattgtac tgagagtgca ccatatgcgg tgtgaaatac cgcacagatg   15480
```

```
cgtaaggaga aaataccgca tcaggcgctc ttccgcttcc tcgctcactg actcgctgcg   15540
ctcggtcgtt cggctgcggc gagcggtatc agctcactca aaggcggtaa tacggttatc   15600
cacagaatca ggggataacg caggaaagaa catgtgagca aaaggccagc aaaaggccag   15660
gaaccgtaaa aaggccgcgt tgctggcgtt tttccatagg ctccgccccc ctgacgagca   15720
tcacaaaaat cgacgctcaa gtcagaggtg gcgaaacccg acaggactat aaagatacca   15780
ggcgtttccc cctggaagct ccctcgtgcg ctctcctgtt ccgaccctgc cgcttaccgg   15840
atacctgtcc gcctttctcc cttcgggaag cgtggcgctt tctcatagct cacgctgtag   15900
gtatctcagt tcggtgtagg tcgttcgctc caagctgggc tgtgtgcacg aaccccccgt   15960
tcagcccgac cgctgcgcct tatccggtaa ctatcgtctt gagtccaacc cggtaagaca   16020
cgacttatcg ccactggcag cagccactgg taacaggatt agcagagcga ggtatgtagg   16080
cggtgctaca gagttcttga agtggtggcc taactacggc tacactagaa ggacagtatt   16140
tggtatctgc gctctgctga agccagttac cttcggaaaa agagttggta gctcttgatc   16200
cggcaaacaa accaccgctg gtagcggtgg tttttttgtt tgcaagcagc agattacgcg   16260
cagaaaaaaa ggatctcaag aagatccttt gatcttttct acggggtctg acgctcagtg   16320
gaacgaaaac tcacgttaag ggattttggt catgagatta tcaaaaagga tcttcaccta   16380
gatcctttta aattaaaaat gaagttttaa atcaatctaa agtatatatg agtaaacttg   16440
gtctgacagt taccaatgct taatcagtga ggcacctatc tcagcgatct gtctatttcg   16500
ttcatccata gttgcctgac tccccgtcgt gtagataact acgatacggg agggcttacc   16560
atctggcccc agtgctgcaa tgataccgcg agacccacgc tcaccggctc cagatttatc   16620
agcaataaac cagccagccg gaagggccga gcgcagaagt ggtcctgcaa ctttatccgc   16680
ctccatccag tctattaatt gttgccggga agctagagta agtagttcgc cagttaatag   16740
tttgcgcaac gttgttgcca ttgctacagg catcgtggtg tcacgctcgt cgtttggtat   16800
ggcttcattc agctccggtt cccaacgatc aaggcgagtt acatgatccc ccatgttgtg   16860
caaaaaagcg gttagctcct tcggtcctcc gatcgttgtc agaagtaagt tggccgcagt   16920
gttatcactc atggttatgg cagcactgca taattctctt actgtcatgc catccgtaag   16980
atgcttttct gtgactggtg agtactcaac caagtcattc tgagaatagt gtatgcggcg   17040
accgagttgc tcttgcccgg cgtcaacacg ggataatacc gcgccacata gcagaacttt   17100
aaaagtgctc atcattggaa aagacctgca ggggggggg ggaaagccac gttgtgtctc   17160
aaaatctctg atgttacatt gcacaagata aaaatatatc atcatgaaca ataaaactgt   17220
ctgcttacat aaacagtaat acaaggggtg ttatgagcca tattcaacgg gaaacgtctt   17280
gctcgaggcc gcgattaaat tccaacatgg atgctgattt atatgggtat aaatgggctc   17340
gcgataatgt cgggcaatca ggtgcgacaa tctatcgatt gtatgggaag cccgatgcgc   17400
cagagttgtt tctgaaacat ggcaaaggta gcgttgccaa tgatgttaca gatgagatgg   17460
tcagactaaa ctggctgacg gaatttatgc ctcttccgac catcaagcat tttatccgta   17520
ctcctgatga tgcatggtta ctcaccactg cgatccccgg aaaacagca ttccaggtat   17580 tagaagaata tcctgattca ggtgaaaata ttgttgatgc gctggcagtg ttcctgcgcc   17640
ggttgcattc gattcctgtt tgtaattgtc cttttaacag cgatcgcgta tttcgtctcg   17700
ctcaggcgca atcacgaatg aataacggtt tggttgatgc gagtgatttt gatgacgagc   17760
gtaatggctg gcctgttgaa caagtctgga agaaatgca taagcttttg ccattctcac   17820
```

```
cggattcagt cgtcactcat ggtgatttct cacttgataa ccttatttt gacgagggga    17880 aattaatagg ttgtattgat gttggacgag tcggaatcgc agaccgatac caggatcttg    17940
ccatcctatg gaactgcctc ggtgagtttt ctccttcatt acagaaacgg cttttcaaa    18000 aatatggtat tgataatcct gatatgaata aattgcagtt tcatttgatg ctcgatgagt    18060
ttttctaatc agaattggtt aattggttgt aacactggca gagcattacg ctgacttgac    18120
gggacggcgg ctttgttgaa taaatcgaac ttttgctgag ttgaaggatc agatcacgca    18180
tcttcccgac aacgcagacc gttccgtggc aaagcaaaag ttcaaaatca ccaactggtc    18240
cacctacaac aaagctctca tcaaccgtgg ctccctcact ttctggctgg atgatggggc    18300
gattcaggcc tggtatgagt cagcaacacc ttcttcacga ggcagacctc agcgcccccc    18360
cccccctgca ggtcaattcg gtcgatatgg ctattacgaa gaaggctcgt gcgcggagtc    18420
ccgtgaactt cccacgcaa caagtgaacc gcaccgggtt tgccggaggc catttcgtta    18480
aaatgcgcag c                                                        18491

<210> SEQ ID NO 2
<211> LENGTH: 4291
<212> TYPE: DNA
<213> ORGANISM: artificial sequence
<220> FEATURE:
<223> OTHER INFORMATION: vector

<400> SEQUENCE: 2
ctttcctgcg ttatcccctg attctgtgga taaccgtatt accgcctttg agtgagctga    60
taccgctcgc cgcagccgaa cgaccgagcg cagcgagtca gtgagcgagg aagcggaaga   120
gcgcccaata cgcaaaccgc ctctccccgc gcgttggccg attcattaat gcagctggca   180
cgacaggttt cccgactgga aagcgggcag tgagcgcaac gcaattaata cgcgtaccgc   240
tagccaggaa gagtttgtag aaacgcaaaa aggccatccg tcaggatggc cttctgctta   300
gtttgatgcc tggcagttta tggcgggcgt cctgcccgcc accctccggg ccgttgcttc   360
acaacgttca aatccgctcc cggcggattt gtcctactca ggagagcgtt caccgacaaa   420
caacagataa aacgaaaggc ccagtcttcc gactgagcct ttcgttttat ttgatgcctg   480
gcagttccct actctcgcgt taacgctagc atggatgttt tcccagtcac gacgttgtaa   540
aacgacggcc agtcttaagc tcgggcccca ataatgatt ttattttgac tgatagtgac   600
ctgttcgttg caacacattg atgagcaatg cttttttata tgccaactt tgtacaaaaa    660 agctgaacga gaaacgtaaa atgatataaa tatcaatata ttaaattaga ttttgcataa   720
aaaacagact acataatact gtaaaacaca acatatccag tcactatgaa tcaactactt   780
agatggtatt agtgacctgt agtcgaccga cagccttcca aatgttcttc gggtgatgct   840
gccaacttag tcgaccgaca gccttccaaa tgttcttctc aaacggaatc gtcgtatcca   900
gcctactcgc tattgtcctc aatgccgtat taaatcataa aaagaaataa gaaaagagg    960 tgcgagcctc ttttttgtgt gacaaaataa aacatctac ctattcatat acgctagtgt   1020
catagtcctg aaaatcatct gcatcaagaa caatttcaca actcttatac ttttctctta   1080
caagtcgttc ggcttcatct ggattttcag cctctatact tactaaacgt gataaagttt   1140
ctgtaatttc tactgtatcg acctgcagac tggctgtgta agggagcc tgacatttat    1200 attccccaga acatcaggtt aatggcgttt ttgatgtcat tttcgcggtg gctgagatca   1260
gccacttctt ccccgataac ggagaccggc acactggcca tcggtggt catcatgcgc   1320 cagcttttcat ccccgatatg caccaccggg taaagttcac gggagacttt atctgacagc   1380
```

```
agacgtgcac tggccagggg gatcaccatc cgtcgcccgg gcgtgtcaat aatatcactc    1440
tgtacatcca caaacagacg ataacggctc tctcttttat aggtgtaaac cttaaactgc    1500
atttcaccag cccctgttct cgtcagcaaa agagccgttc atttcaataa accgggcgac    1560
ctcagccatc ccttcctgat tttccgcttt ccagcgttcg gcacgcagac gacgggcttc    1620
attctgcatg gttgtgctta ccagaccgga gatattgaca tcatatatgc cttgagcaac    1680
tgatagctgt cgctgtcaac tgtcactgta atacgctgct tcatagcata cctcttttg     1740 acatacttcg ggtatacata tcagtatata ttcttatacc gcaaaaatca gcgcgcaaat    1800
acgcatactg ttatctggct tttagtaagc cggatccacg cggcgtttac gccccgccct    1860
gccactcatc gcagtactgt tgtaattcat taagcattct gccgacatgg aagccatcac    1920
agacggcatg atgaacctga atcgccagcg gcatcagcac cttgtcgcct tgcgtataat    1980
atttgcccat ggtgaaaacg ggggcgaaga agttgtccat attggccacg tttaaatcaa    2040
aactggtgaa actcacccag ggattggctg agacgaaaaa catattctca ataaaccctt    2100
tagggaaata ggccaggttt tcaccgtaac acgccacatc ttgcgaatat atgtgtagaa    2160
actgccggaa atcgtcgtgg tattcactcc agagcgatga aaacgtttca gtttgctcat    2220
ggaaaacggt gtaacaaggg tgaacactat cccatatcac cagctcaccg tctttcattg    2280
ccatacggaa ttccggatga gcattcatca ggcgggcaag aatgtgaata aaggccggat    2340
aaaacttgtg cttattttc tttacggtct ttaaaaaggc cgtaatatcc agctgaacgg    2400 tctggtttata ggtacattga gcaactgact gaaatgcctc aaaatgttct ttacgatgcc    2460
attgggatat atcaacggtg gtatatccag tgatttttt ctccatttta gcttccttag    2520
ctcctgaaaa tctcgataac tcaaaaaata cgcccggtag tgatcttatt tcattatggt    2580
gaaagttgga acctcttacg tgccgatcaa cgtctcattt tcgccaaaag ttggcccagg    2640
gcttcccggt atcaacaggg acaccaggat ttatttattc tgcgaagtga tcttccgtca    2700
caggtattta ttcggcgcaa agtgcgtcgg gtgatgctgc caacttagtc gactacaggt    2760
cactaatacc atctaagtag ttgattcata gtgactggat atgttgtgtt ttacagtatt    2820
atgtagtctg ttttttatgc aaaatctaat ttaatatatt gatatttata tcatttacg    2880 tttctcgttc agcttcttg tacaaagttg gcattataag aaagcattgc ttatcaattt    2940
gttgcaacga acaggtcact atcagtcaaa ataaaatcat tatttgccat ccagctgata    3000
tcccctatag tgagtcgtat tacatggtca tagctgtttc ctggcagctc tggcccgtgt    3060
ctcaaaatct ctgatgttac attgcacaag ataaataat atcatcatga tcagtcctgc    3120
tcctcggcca cgaagtgcac gcagttgccg ccgggtcgc gcagggcgaa ctcccgcccc    3180
cacggctgct cgccgatctc ggtcatggcc ggcccgaggg cgtcccggaa gttcgtggac    3240
acgacctccg accactcggc gtacagctcg tccaggccgc gcacccacac ccaggccagg    3300
gtgttgtccg gcaccacctg gtcctggacc gcgctgatga acagggtcac gtcgtcccgg    3360
accacaccgg cgaagtcgtc ctccacgaag tcccgggaga acccgagccg tcggtccag    3420 aactcgaccg ctccggcgac gtcgcgcgcg gtgagcaccg gaacggcact ggtcaacttg    3480
gccatggttt agttcctcac cttgtcgtat tatactatgc cgatatacta tgccgatgat    3540
taattgtcaa cacgtgctga tcatgaccaa aatcccttaa cgtgagttac gcgtcgttcc    3600
actgagcgtc agacccgta gaaaagatca aaggatcttc ttgagatcct ttttttctgc    3660
gcgtaatctg ctgcttgcaa acaaaaaaac caccgctacc agcggtggtt tgtttgccgg    3720
```

```
atcaagagct accaactctt tttccgaagg taactggctt cagcagagcg cagataccaa    3780
atactgttct tctagtgtag ccgtagttag gccaccactt caagaactct gtagcaccgc    3840
ctacatacct cgctctgcta atcctgttac cagtggctgc tgccagtggc gataagtcgt    3900
gtcttaccgg gttggactca agacgatagt taccggataa ggcgcagcgg tcgggctgaa    3960
cggggggttc gtgcacacag cccagcttgg agcgaacgac ctacaccgaa ctgagatacc    4020
tacagcgtga gctatgagaa agcgccacgc ttcccgaagg gagaaaggcg gacaggtatc    4080
cggtaagcgg cagggtcgga acaggagagc gcacgaggga gcttccaggg ggaaacgcct    4140
ggtatcttta tagtcctgtc gggtttcgcc acctctgact tgagcgtcga ttttgtgat    4200 gctcgtcagg ggggcggagc ctatggaaaa acgccagcaa cgcggccttt ttacggttcc    4260
tggccttttg ctggccttt gctcacatgt t                                   4291
```

<210> SEQ ID NO 3
<211> LENGTH: 4762
<212> TYPE: DNA
<213> ORGANISM: artificial sequence
<220> FEATURE:
<223> OTHER INFORMATION: vector

<400> SEQUENCE: 3

```
ctttcctgcg ttatcccctg attctgtgga taaccgtatt accgcctttg agtgagctga     60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca atccgctcc cggcggattt gtcctactca ggagagcgtt caccgacaaa    420
caacagataa aacgaaaggc ccagtcttcc gactgagcct tcgttttat ttgatgcctg    480 gcagttccct actctcgcgt taacgctagc atggatgttt tcccagtcac gacgttgtaa    540
aacgacggcc agtcttaagc tcgggcccca aataatgatt ttattttgac tgatagtgac    600
ctgttcgttg caacacattg atgagcaatg cttttttata atgccaactt tgtacaaaaa    660
agctgaacga gaaacgtaaa atgatataaa tatcaatata ttaaattaga ttttgcataa    720
aaaacagact acataatact gtaaaacaca acatatccag tcactatgaa tcaactactt    780
agatggtatt agtgacctgt agtcgaccga cagccttcca atgttcttc gggtgatgct    840 gccaacttag tcgaccgaca gccttccaaa tgttcttctc aaacggaatc gtcgtatcca    900
gcctactcgc tattgtcctc aatgccgtat taaatcataa aagaaataa gaaaagagg     960 tgcgagcctc ttttttgtgt gacaaaataa aaacatctac ctattcatat acgctagtgt    1020
catagtcctg aaaatcatct gcatcaagaa caatttcaca actcttatac ttttctctta    1080
caagtcgttc ggcttcatct ggattttcag cctctatact tactaaacgt gataaagttt    1140
ctgtaatttc tactgtatcg acctgcagac tggctgtgta agggagcc tgacatttat    1200 attccccaga acatcaggtt aatggcgttt ttgatgtcat tttcgcggtg gctgagatca    1260
gccacttctt ccccgataac ggagaccggc acactggcca tatcggtggt catcatgcgc    1320 cagcttttcat ccccgatatg caccaccggg taaagttcac gggagacttt atctgacagc    1380
agacgtgcac tggccagggg gatcaccatc cgtcgcccgg gcgtgtcaat aatatcactc    1440
tgtacatcca caaacagacg ataacggctc tctcttttat aggtgtaaac cttaaactgc    1500
```

```
atttcaccag cccctgttct cgtcagcaaa agagccgttc atttcaataa accgggcgac   1560
ctcagccatc ccttcctgat tttccgcttt ccagcgttcg gcacgcagac gacgggcttc   1620
attctgcatg gttgtgctta ccagaccgga gatattgaca tcatatatgc cttgagcaac   1680
tgatagctgt cgctgtcaac tgtcactgta atacgctgct tcatagcata cctcttttg   1740 acatacttcg ggtatacata tcagtatata ttcttatacc gcaaaaatca gcgcgcaaat   1800
acgcatactg ttatctggct tttagtaagc cggatccacg cggcgtttac gccccgccct   1860
gccactcatc gcagtactgt tgtaattcat taagcattct gccgacatgg aagccatcac   1920
agacggcatg atgaacctga atcgccagcg gcatcagcac cttgtcgcct gcgtataat   1980 atttgcccat ggtgaaaacg ggggcgaaga agttgtccat attggccacg tttaaatcaa   2040
aactggtgaa actcacccag ggattggctg agacgaaaaa catattctca ataaaccctt   2100
tagggaaata ggccaggttt tcaccgtaac acgccacatc ttgcgaatat atgtgtagaa   2160
actgccggaa atcgtcgtgg tattcactcc agagcgatga aaacgtttca gtttgctcat   2220
ggaaaacggt gtaacaaggg tgaacactat cccatatcac cagctcaccg tctttcattg   2280 ccatacgaa ttccggatga gcattcatca ggcgggcaag aatgtgaata aaggccggat   2340
aaaacttgtg cttatttttc tttacggtct ttaaaaaggc cgtaatatcc agctgaacgg   2400
tctggttata ggtacattga gcaactgact gaaatgcctc aaaatgttct ttacgatgcc   2460
attgggatat atcaacggtg gtatatccag tgatttttt ctccatttta gcttccttag   2520
ctcctgaaaa tctcgataac tcaaaaaata cgcccggtag tgatcttatt tcattatggt   2580
gaaagttgga acctcttacg tgccgatcaa cgtctcattt tcgccaaaag ttggcccagg   2640
gcttcccggt atcaacaggg acaccaggat ttatttattc tgcgaagtga tcttccgtca   2700
caggtattta ttcggcgcaa agtgcgtcgg gtgatgctgc caacttagtc gactacaggt   2760
cactaatacc atctaagtag ttgattcata gtgactggat atgttgtgtt ttacagtatt   2820
atgtagtctg ttttttatgc aaaatctaat ttaatatatt gatatttata tcattttacg   2880
tttctcgttc agctttcttg tacaaagttg gcattataag aaagcattgc ttatcaattt   2940
gttgcaacga acaggtcact atcagtcaaa ataaaatcat tatttgccat ccagctgata   3000
tcccctatag tgagtcgtat tacatggtca tagctgtttc ctggcagctc tggcccgtgt   3060
ctcaaaatct ctgatgttac attgcacaag ataaataat atcatcatga acaataaaac   3120
tgtctgctta cataaacagt aatacaaggg gtgttatgag ccatattcaa cgggaaacgt   3180
cgaggccgcg attaaattcc aacatggatg ctgatttata tgggtataaa tgggctcgcg   3240
ataatgtcgg gcaatcaggt gcgacaatct atcgcttgta tgggaagccc gatgcgccag   3300
agttgtttct gaaacatggc aaaggtagcg ttgccaatga tgttacagat gagatggtca   3360
gactaaactg gctgacggaa tttatgcctc ttccgaccat caagcatttt atccgtactc   3420
ctgatgatgc atggttactc accactgcga tccccggaaa acagcattc caggtattag   3480 aagaatatcc tgattcaggt gaaaatattg ttgatgcgct ggcagtgttc ctgcgccggt   3540
tgcattcgat tcctgtttgt aattgtcctt ttaacagcga tcgcgtattt cgtctcgctc   3600
aggcgcaatc acgaatgaat aacggtttgg ttgatgcgag tgattttgat gacgagcgta   3660
atggctggcc tgttgaacaa gtctggaaag aaatgcataa acttttgcca ttctcaccgg   3720
attcagtcgt cactcatggt gatttctcac ttgataacct tattttgac gaggggaaat   3780 taataggttg tattgatgtt ggacgagtcg gaatcgcaga ccgataccag gatcttgcca   3840
```

-continued

| | |
|---|---|
| tcctatggaa ctgcctcggt gagttttctc cttcattaca gaaacggctt tttcaaaaat | 3900 |
| atggtattga taatcctgat atgaataaat tgcagtttca tttgatgctc gatgagtttt | 3960 |
| tctaatcaga attggttaat tggttgtaac actggcagag cattacgctg acttgacggg | 4020 |
| acggcgcaag ctcatgacca aaatccctta acgtgagtta cgcgtcgttc cactgagcgt | 4080 |
| cagacccgt agaaaagatc aaaggatctt cttgagatcc ttttttctg cgcgtaatct | 4140 |
| gctgcttgca acaaaaaaa ccaccgctac cagcggtggt ttgtttgccg gatcaagagc | 4200 |
| taccaactct ttttccgaag gtaactggct tcagcagagc gcagatacca aatactgttc | 4260 |
| ttctagtgta gccgtagtta ggccaccact tcaagaactc tgtagcaccg cctacatacc | 4320 |
| tcgctctgct aatcctgtta ccagtggctg ctgccagtgg cgataagtcg tgtcttaccg | 4380 |
| ggttggactc aagacgatag ttaccggata aggcgcagcg gtcgggctga acggggggtt | 4440 |
| cgtgcacaca gcccagcttg gagcgaacga cctacaccga actgagatac ctacagcgtg | 4500 |
| agctatgaga aagcgccacg cttcccgaag gagaaaggc ggacaggtat ccggtaagcg | 4560 |
| gcagggtcgg aacaggagag cgcacgaggg agcttccagg gggaaacgcc tggtatcttt | 4620 |
| atagtcctgt cgggtttcgc cacctctgac ttgagcgtcg attttttgtga tgctcgtcag | 4680 |
| gggggcggag cctatggaaa aacgccagca acgcggcctt tttacggttc ctggccttttt | 4740 |
| gctggccttt tgctcacatg tt | 4762 |

<210> SEQ ID NO 4
<211> LENGTH: 16843
<212> TYPE: DNA
<213> ORGANISM: artificial sequence
<220> FEATURE:
<223> OTHER INFORMATION: vector

<400> SEQUENCE: 4

| | |
|---|---|
| ccgggctggt tgccctcgcc gctgggctgg cggccgtcta tggccctgca aacgcgccag | 60 |
| aaacgccgtc gaagccgtgt gcgagacacc gcggccgccg gcgttgtgga tacctcgcgg | 120 |
| aaaacttggc cctcactgac agatgagggg cggacgttga cacttgaggg gccgactcac | 180 |
| ccggcgcggc gttgacagat gaggggcagg ctcgatttcg gccggcgacg tggagctggc | 240 |
| cagcctcgca aatcggcgaa aacgcctgat tttacgcgag tttcccacag atgatgtgga | 300 |
| caagcctggg gataagtgcc ctgcggtatt gacacttgag gggcgcgact actgacagat | 360 |
| gagggcgcg atccttgaca cttgaggggc agagtgctga cagatgaggg gcgcacctat | 420 |
| tgacatttga ggggctgtcc acaggcagaa aatccagcat ttgcaagggt ttccgcccgt | 480 |
| ttttcggcca ccgctaacct gtcttttaac ctgctttttaa accaatattt ataaaccttg | 540 |
| tttttaacca gggctgcgcc ctgtgcgcgt gaccgcgcac gccgaagggg ggtgccccc | 600 |
| cttctcgaac cctcccggcc cgctaacgcg ggcctcccat cccccaggg gctgcgcccc | 660 |
| tcggccgcga acggcctcac cccaaaaatg gcagcgctgg cagtccttgc cattgccggg | 720 |
| atcggggcag taacgggatg ggcgatcagc ccgagcgcga cgcccggaag cattgacgtg | 780 |
| ccgcaggtgc tggcatcgac attcagcgac caggtgccgg gcagtgaggg cggcggcctg | 840 |
| ggtggcggcc tgcccttcac ttcggccgtc ggggcattca cggacttcat ggcggggccg | 900 |
| gcaatttttta ccttgggcat tcttggcata gtggtcgcgg gtgccgtgct cgtgttcggg | 960 |
| ggtgcgataa acccagcgaa ccatttgagg tgataggtaa gattataccg aggtatgaaa | 1020 |
| acgagaattg gaccttttaca gaattactct atgaagcgcc atatttaaaa agctaccaag | 1080 |
| acgaagagga tgaagaggat gaggaggcag attgccttga atatattgac aatactgata | 1140 |

```
agataatata tcttttatat agaagatatc gccgtatgta aggatttcag ggggcaaggc    1200
ataggcagcg cgcttatcaa tatatctata gaatgggcaa agcataaaaa cttgcatgga    1260
ctaatgcttg aaacccagga cataaccctt atagcttgta aattctatca taattgggta    1320
atgactccaa cttattgata gtgttttatg ttcagataat gcccgatgac tttgtcatgc    1380
agctccaccg attttgagaa cgacagcgac ttccgtccca gccgtgccag gtgctgcctc    1440
agattcaggt tatgccgctc aattcgctgc gtatatcgct tgctgattac gtgcagcttt    1500
cccttcaggc gggattcata cagcggccag ccatccgtca tccatatcac cacgtcaaag    1560
ggtgacagca ggctcataag acgccccagc gtcgccatag tgcgttcacc gaatacgtgc    1620
gcaacaaccg tcttccggag actgtcatac gcgtaaaaca gccagcgctg gcgcgattta    1680 gcccccgacat agccccactg ttcgtccatt tccgcgcaga cgatgacgtc actgcccggc    1740
tgtatgcgcg aggttaccga ctgcggcctg agttttttaa gtgacgtaaa atcgtgttga    1800
ggccaacgcc cataatgcgg gctgttgccc ggcatccaac gccattcatg gccatatcaa    1860
tgattttctg gtgcgtaccg ggttgagaag cggtgtaagt gaactgcagt tgccatgttt    1920
tacggcagtg agagcagaga tagcgctgat gtccggcggt gcttttgccg ttacgcacca    1980
ccccgtcagt agctgaacag gagggacagc tgatagacac agaagccact ggagcacctc    2040
aaaaacacca tcatacacta aatcagtaag ttggcagcat cacccataat tgtggtttca    2100
aaatcggctc cgtcgatact atgttatacg ccaactttga aaacaacttt gaaaaagctg    2160
ttttctggta tttaaggttt tagaatgcaa ggaacagtga attggagttc gtcttgttat    2220
aattagcttc ttggggtatc tttaaatact gtagaaaaga ggaaggaaat aataaatggc    2280
taaaatgaga atatcaccgg aattgaaaaa actgatcgaa aaataccgct gcgtaaaaga    2340
tacggaagga atgtctcctg ctaaggtata taagctggtg ggagaaaatg aaaacctata    2400
tttaaaaatg acggacagcc ggtataaagg gaccacctat gatgtggaac gggaaaagga    2460
catgatgcta tggctggaag gaaagctgcc tgttccaaag gtcctgcact ttgaacggca    2520
tgatggctgg agcaatctgc tcatgagtga ggccgatggc gtcctttgct cggaagagta    2580
tgaagatgaa caaagccctg aaaagattat cgagctgtat gcggagtgca tcaggctctt    2640
tcactccatc gacatatcgg attgtcccta tacgaatagc ttagacagcc gcttagccga    2700
attggattac ttactgaata acgatctggc cgatgtggat tgcgaaaact gggaagaaga    2760
cactccattt aaagatccgc gcgagctgta tgatttttta aagacggaaa agcccgaaga    2820
ggaacttgtc ttttcccacg cgacctggg agacagcaac atctttgtga aagatggcaa    2880
agtaagtggc tttattgatc ttgggagaag cggcagggcg gacaagtggt atgacattgc    2940
cttctgcgtc cggtcgatca ggaggatat cggggaagaa cagtatgtcg agctatttt    3000 tgacttactg gggatcaagc ctgattggga gaaaataaaa tattatattt tactggatga    3060
attgttttag tacctagatg tggcgcaacg atgccggcga caagcaggag cgcaccgact    3120
tcttccgcat caagtgtttt ggctctcagg ccgaggccca cggcaagtat ttgggcaagg    3180
ggtcgctggt attcgtgcag ggcaagattc ggaataccaa gtacgagaag gacggccaga    3240
cggtctacgg gaccgacttc attgccgata aggtggatta tctggacacc aaggcaccag    3300
gcgggtcaaa tcaggaataa gggcacattg ccccggcgtg agtcggggca atcccgcaag    3360
gagggtgaat gaatcggacg tttgaccgga aggcatacag gcaagaactg atcgacgcgg    3420
ggttttccgc cgaggatgcc gaaaccatcg caagccgcac cgtcatgcgt gcgccccgcg    3480
```

```
aaaccttcca gtccgtcggc tcgatggtcc agcaagctac ggccaagatc gagcgcgaca    3540
gcgtgcaact ggctccccct gccctgcccg cgccatcggc cgccgtggag cgttcgcgtc    3600
gtctcgaaca ggaggcggca ggtttggcga agtcgatgac catcgacacg cgaggaacta    3660
tgacgaccaa gaagcgaaaa accgccggcg aggacctggc aaaacaggtc agcgaggcca    3720
agcaggccgc gttgctgaaa cacacgaagc agcagatcaa ggaaatgcag ctttccttgt    3780
tcgatattgc gccgtggccg gacacgatgc gagcgatgcc aaacgacacg gcccgctctg    3840
ccctgttcac cacgcgcaac aagaaaatcc cgcgcgaggc gctgcaaaac aaggtcattt    3900
tccacgtcaa caaggacgtg aagatcacct acaccggcgt cgagctgcgg gccgacgatg    3960
acgaactggt gtggcagcag gtgttggagt acgcgaagcg caccccctat cggcgagccga   4020
tcaccttcac gttctacgag ctttgccagg acctgggctg gtcgatcaat ggccggtatt    4080
acacgaaggc cgaggaatgc ctgtcgcgcc tacaggcgac ggcgatgggc ttcacgtccg    4140
accgcgttgg gcacctggaa tcggtgtcgc tgctgcaccg cttccgcgtc ctggaccgtg    4200
gcaagaaaac gtcccgttgc caggtcctga tcgacgagga atcgtcgtg ctgtttgctg     4260
gcgaccacta cacgaaattc atatgggaga agtaccgcaa gctgtcgccg acggcccgac    4320
ggatgttcga ctatttcagc tcgcaccggg agccgtaccc gctcaagctg gaaaccttcc    4380
gcctcatgtg cggatcggat tccacccgcg tgaagaagtg gcgcgagcag gtcggcgaag    4440
cctgcgaaga gttgcgaggc agcggcctgg tggaacacgc ctgggtcaat gatgacctgg    4500
tgcattgcaa acgctagggc cttgtggggt cagttccggc tgggggttca gcagccagcg    4560
ctttactggc atttcaggaa caagcgggca ctgctcgacg cacttgcttc gctcagtatc    4620
gctcgggacg cacggcgcgc tctacgaact gccgataaac agaggattaa aattgacaat    4680
tgtgattaag gctcagattc gacggcttgg agcggccgac gtgcaggatt ccgcgagat    4740
ccgattgtcg gccctgaaga aagctccaga gatgttcggg tccgtttacg agcacgagga    4800
gaaaaagccc atggaggcgt tcgctgaacg gttgcgagat gccgtggcat tcggcgccta    4860
catcgacggc gagatcattg ggctgtcggt cttcaaacag gaggacggcc ccaaggacgc    4920
tcacaaggcg catctgtccg gcgttttcgt ggagcccgaa cagcgaggcc gaggggtcgc    4980
cggtatgctg ctgcgggcgt tgccggcggg tttattgctc gtgatgatcg tccgacagat    5040
tccaacggga atctggtgga tgcgcatctt catcctcggc gcacttaata tttcgctatt    5100
ctggagcttg ttgtttattt cggtctaccg cctgccgggc ggggtcgcgg cgacggtagg    5160
cgctgtgcag ccgctgatgg tcgtgttcat ctctgccgct ctgctaggta gcccgatacg    5220
attgatggcg gtcctggggg ctatttgcgg aactgcgggc gtggcgctgt tggtgttgac    5280
accaaacgca cgctagatc ctgtcggcgt cgcagcgggc ctggcggggg cggtttccat     5340
ggcgttcgga accgtgctga cccgcaagtg gcaacctccc gtgcctctgc tcacctttac    5400
cgcctggcaa ctggcggccg gaggacttct gctcgttcca gtagctttag tgtttgatcc    5460
gccaatcccg atgcctacag gaaccaatgt tctcggcctg gcgtggctcg gcctgatcgg    5520
agcgggttta acctacttcc tttggttccg ggggatctcg cgactcgaac ctacagttgt    5580
ttccttactg ggctttctca gccccagatc tgggtcgat cagccgggga tgcatcaggc     5640
cgacagtcgg aacttcgggt ccccgacctg taccattcgg tgagcaatgg ataggggagt    5700
tgatatcgtc aacgttcact tctaaagaaa tagcgccact cagcttcctc agcggcttta    5760
tccagcgatt tcctattatg tcggcatagt tctcaagatc gacagcctgt cacggttaag    5820
cgagaaatga ataagaaggc tgataattcg gatctctgcg agggagatga tatttgatca    5880
```

```
caggcagcaa cgctctgtca tcgttacaat caacatgcta ccctccgcga gatcatccgt      5940
gtttcaaacc cggcagctta gttgccgttc ttccgaatag catcggtaac atgagcaaag      6000
tctgccgcct tacaacggct ctcccgctga cgccgtcccg gactgatggg ctgcctgtat      6060
cgagtggtga ttttgtgccg agctgccggt cggggagctg ttggctggct ggtggcagga      6120
tatattgtgg tgtaaacaaa ttgacgctta gacaacttaa taacacattg cggacgtttt      6180
taatgtactg gggtggtttt tcttttcacc agtgagacgg gcaacagctg attgcccttc      6240
accgcctggc cctgagagag ttgcagcaag cggtccacgc tggtttgccc cagcaggcga      6300
aaatcctgtt tgatggtggt tccgaaatcg gcaaatccc ttataaatca aagaatagc       6360
ccgagatagg gttgagtgtt gttccagttt ggaacaagag tccactatta agaacgtgg      6420
actccaacgt caaagggcga aaaccgtct atcagggcga tggcccacta cctgtatggc      6480
cgcattcgca aaacacacct agactagatt tgttttgcta acccaattga tattaattat      6540
atatgattaa tatttatatg tatatggatt tggttaatga aatgcatctg gttcatcaaa      6600
gaattataaa gacacgtgac attcatttag gataagaaat atggatgatc tctttctctt      6660
ttattcagat aactagtaat tacacataac acacaacttt gatgcccaca ttatagtgat      6720
tagcatgtca ctatgtgtgc atccttttat ttcatacatt aattaagttg gccaatccag      6780
aagatggaca agtctaggtt aaccatgtgg tacctacgcg ttcgaatatc catgggccgc      6840
ttcaggccag ggcgctgggg aaggcgatgg cgtgctcggt cagctgccac ttctggttct      6900
tggcgtcgct ccggtcctcc cgcagcagct tgtgctggat gaagtgccac tcgggcatct      6960
tgctgggcac gctcttggcc ttgtacacgg tgtcgaactg gcaccggtac cggccgccgt      7020
ccttcagcag caggtacatg ctcacgtcgc ccttcaggat gccctgctta ggcacgggca      7080
tgatcttctc gcagctggcc tcccagttgg tggtcatctt cttcatcacg gggccgtcgg      7140
cggggaagtt cacgccgttg aagatgctct tgtggtagat gcagttctcc ttcacgctca      7200
cggtgatgtc cacgttacag atgcacacgg cgccgtcctc gaacaggaag ctccggcccc      7260
aggtgtagcc ggcggggcag ctgttcttga agtagtccac gatgtcctgg gggtactcgg      7320
tgaagatccg gtcgccgtac ttgaagccgg cgctcaggat gtcctcgctg aagggcaggg      7380
ggccgccctc gatcacgcac aggttgatgg tctgcttgcc cttgaagggg tagccgatgc      7440
cctcgccggt gatcacgaac ttgtggccgt tcacgcagcc ctccatgtgg tacttcatgg      7500
tcatctcctc cttcaggccg tgcttgctgt gggccatggt ggcgaccggt gaattcgagc      7560
tcggtacccg gggatcctga gtaaaacaga ggagggtctc actaagttta tagagagact      7620
gagagagata aagggacacg tatgaagcgt ctgttttcgt ggtgtgacgt caaagtcatt      7680
ttgctctcta cgcgtgtctg tgtcggcttg atcttttttt ttgcttttg gaactcatgt      7740
cggtagtata tcttttattt attttttctt tttttccctt ttctttcaaa ctgatgtcgg      7800
tatgatattt attccatcct aaaatgtaac ttactattat tagtagtcgg tccatgtcta      7860
ttggcccatc atgtggtcat tttacgttta cgtcgtgtgg ctgtttatta taacaaacgg      7920
cacatccttc tcattcgaat tgtatttctc cttaatcgtt ctaataggta tgatcttta      7980
ttttatacgt aaaattaaaa ttgaatgatg tcaagaacga aaattaattt gtatttacaa      8040
aggagctaaa tattgtttat tcctctactg gtagaagata aagaagtag atgaaataat      8100
gatcttacta gagaatattc ctcatttaca ctagtcaaat ggaaatcttg taaacttta      8160
caataattta tcctgaaaat atgaaaaat agaagaaaat gtttacctcc tctctcctct      8220
```

```
taattcacct acgatcggtg cgggcctctt cgctattacg ccagctggcg aaaggggat    8280
gtgctgcaag gcgattaagt tgggtaacgc cagggttttc ccagtcacga cgttgtaaaa    8340
cgacggccag tgaattcgag ctcggtaccc ggggatcctc tagagtcgac ctgcaggcat    8400
gcaagcttgt tgaaacatcc ctgaagtgtc tcattttatt ttatttattc tttgctgata    8460
aaaaaataaa ataaaagaag ctaagcacac ggtcaaccat tgctctactg ctaaaagggt    8520
tatgtgtagt gttttactgc ataaattatg cagcaaacaa gacaactcaa attaaaaaat    8580
ttcctttgct tgttttttttg ttgtctctga cttgactttc ttgtggaagt tggttgtata    8640
aggattggga cacaccattg tccttcttaa tttaatttta tttctttgct gataaaaaaa    8700
aaaaatttca tatagtgtta ataataatt tgttaaataa ccaaaaagtc aaatatgttt    8760
actctcgttt aaataattga gagtcgtcca gcaaggctaa acgattgtat agatttatga    8820
caatatttac ttttttatag ataaatgtta tattataata aatttatata catatattat    8880
atgttattta ttatttatta ttattttaaa tccttcaata tttatcaaa ccaactcata    8940
atttttttt tatctgtaag aagcaataaa attaaataga cccactttaa ggatgatcca    9000
acctttatac agagtaagag agttcaaata gtacccttc atatacatat caactaaaat    9060
attagaaata tcatggatca aaccttataa agacattaaa taagtggata agtataatat    9120
ataaatgggt agtatataat atataaatgg atacaaactt ctctctttat aattgttatg    9180
tctccttaac atcctaatat aatacataag tgggtaatat ataatatata aatggagaca    9240
aacttcttcc attataattg ttatgtcttc ttaacactta tgtctcgttc acaatgctaa    9300
agttagaatt gtttagaaag tcttatagta cacatttgtt tttgtactat ttgaagcatt    9360
ccataagccg tcacgattca gatgatttat aataataaga ggaaatttat catagaacaa    9420
taaggtgcat agatagagtg ttaatatatc ataacatcct tgttttattc atagaagaag    9480
tgagatggag ctcagttatt atactgttac atggtcggat acaatattcc atgctctcca    9540
tgagctctta cacctacatg catttttagtt catacttcat gcacgtggcc atcacagcta    9600
gctgcagcta catatttaca ttttacaaca ccaggagaac tgccctgtta gtgcataaca    9660
atcagaagat ggccgtggct actcgagtta tcgaaccact ttgtacaaga aagctgaacg    9720
agaaacgtaa aatgatataa atatcaatat attaaattag attttgcata aaaaacagac    9780
tacataatac tgtaaaacac aacatatcca gtcactatgg tcgacctgca gactggctgt    9840
gtataaggga gcctgacatt tatattcccc agaacatcag gttaatggcg ttttttgatgt    9900
cattttcgcg gtggctgaga tcagccactt cttccccgat aacggagacc ggcacactgg    9960
ccatatcggt ggtcatcatg cgccagcttt catccccgat atgcaccacc gggtaaagtt   10020
cacgggagac tttatctgac agcagacgtg cactggccag ggggatcacc atccgtcgcc   10080
cgggcgtgtc aataatatca ctctgtacat ccacaaacag acgataacgg ctctctcttt   10140
tataggtgta aaccttaaac tgcatttcac cagtccctgt tctcgtcagc aaaagagccg   10200
ttcatttcaa taaccgggc gacctcagcc atcccttcct gattttccgc tttccagcgt   10260
tcggcacgca gacgacgggc ttcattctgc atggttgtgc ttaccagacc ggagatattg   10320
acatcatata tgccttgagc aactgatagc tgtcgctgtc aactgtcact gtaatacgct   10380
gcttcatagc acacctcttt ttgacatact tcgggtatac atatcagtat atattcttat   10440
accgcaaaaa tcagcgcgca aatacgcata ctgttatctg gcttttagta agccggatcc   10500
tctagattac gccccgccct gccactcatc gcagtactgt tgtaattcat taagcattct   10560
gccgacatgg aagccatcac agacggcatg atgaacctga atcgccagcg gcatcagcac   10620
```

```
cttgtcgcct tgcgtataat atttgcccat ggtgaaaacg ggggcgaaga agttgtccat   10680
attggccacg tttaaatcaa aactggtgaa actcacccag ggattggctg agacgaaaaa   10740
catattctca ataaacccct tagggaaata ggccaggttt tcaccgtaac acgccacatc   10800
ttgcgaatat atgtgtagaa actgccgaaa atcgtcgtgg tattcactcc agagcgatga   10860
aaacgtttca gtttgctcat ggaaaacggt gtaacaaggg tgaacactat cccatatcac   10920
cagctcaccg tctttcattg ccatacgaaa ttccggatga gcattcatca ggcgggcaag   10980
aatgtgaata aaggccggat aaaacttgtg cttatttttc tttacggtct ttaaaaaggc   11040
cgtaatatcc agctgaacgg tctgttata ggtacattga gcaactgact gaaatgcctc    11100
aaaatgttct ttacgatgcc attgggatat atcaacggtg gtatatccag tgatttttt    11160 ctccatttta gcttccttag ctcctgaaaa tctcgccgga tcctaactca aaatccacac   11220
attatacgag ccggaagcat aaagtgtaaa gcctggggtg cctaatgcgg ccgccatagt   11280
gactggatat gttgtgtttt acagtattat gtagtctgtt ttttatgcaa aatctaatt   11340 aatatattga tatttatatc attttacgtt tctcgttcag cttttttgta caaacttgtt   11400
tgataaccgg tactagtgtg cacgtcgagc gtgtcctctc caaatgaaat gaacttcctt   11460
atatagagga agggtcttgc gaaggatagt gggattgtgc gtcatccctt acgtcagtgg   11520
agatgtcaca tcaatccact tgctttgaag acgtggttgg aacgtcttct ttttccacga   11580
tgctcctcgt gggtgggggt ccatctttgg gaccactgtc ggcagaggca tcttgaatga   11640
tagccttccc tttatcgcaa tgatggcatt tgtaggagcc accttccttt tctactgtcc   11700
tttcgatgaa gtgacagata gctgggcaat ggaatccgag gaggtttccc gaaattatcc   11760
tttgttgaaa agtctcaata gcccttggt cttctgagac tgtatctttg acattttgg    11820 agtagaccag agtgtcgtgc tccaccatgt tgacgaagat tttcttcttg tcattgagtc   11880
gtaaaagact ctgtatgaac tgttcgccag tcttcacggc gagttctgtt agatcctcga   11940
tttgaatctt agactccatg catggcctta gattcagtag gaactacctt tttagagact   12000
ccaatctcta ttacttgcct tggtttatga agcaagcctt gaatcgtcca tactggaata   12060
gtacttctga tcttgagaaa tatgtctttc tctgtgttct tgatgcaatt agtcctgaat   12120
cttttgactg catctttaac cttcttggga aggtatttga tctcctggag attgttactc   12180
gggtagatcg tcttgatgag acctgctgcg taggcctctc taaccatctg tgggtcagca   12240
ttctttctga aattgaagag gctaaccttc tcattatcag tggtgaacat agtgtcgtca   12300
ccttcacctt cgaacttcct tcctagatcg taaagataga ggaaatcgtc cattgtaatc   12360
tccggggcaa aggagatctc ttttggggct ggatcactgc tgggcctttt ggttcctagc   12420
gtgagccagt gggcttttg ctttggtggg cttgttaggg ccttagcaaa gctcttgggc    12480
ttgagttgag cttctccttt ggggatgaag ttcaacctgt ctgtttgctg acttgttgtg   12540
tacgcgtcag ctgctgctct tgcctctgta atagtggcaa atttcttgtg tgcaactccg   12600
ggaacgccgt ttgttgccgc cttttgtacaa ccccagtcat cgtatatacc ggcatgtgga   12660
ccgttataca caacgtagta gttgatatga gggtgttgaa tacccgattc tgctctgaga   12720
ggagcaactg tgctgttaag ctcagatttt tgtgggattg gaattggatc ctctagagca   12780
aagcttggcg taatcatggt catagctgtt tcctgtgtga aattgttatc cgctcacaat   12840
tccacacaac atacgagccg gaagcataaa gtgtaaagcc tggggtgcct aatgagtgag   12900
ctaactcaca ttaattgcgt tgcgctcact gcccgctttc cagtcgggaa acctgtcgtg   12960
```

```
ccagctgcat taatgaatcg gccaacgcgc ggggagaggc ggtttgcgta ttgggccaaa    13020
gacaaaaggg cgacattcaa ccgattgagg gagggaaggt aaatattgac ggaaattatt    13080
cattaaaggt gaattatcac cgtcaccgac ttgagccatt tgggaattag agccagcaaa    13140
atcaccagta gcaccattac cattagcaag gccggaaacg tcaccaatga aaccatcatc    13200
tagtaacata gatgacaccg cgcgcgataa tttatcctag tttgcgcgct atattttgtt    13260
ttctatcgcg tattaaatgt ataattgcgg gactctaatc ataaaaaccc atctcataaa    13320
taacgtcatg cattacatgt taattattac atgcttaacg taattcaaca gaaattatat    13380
gataatcatc gcaagaccgg caacaggatt caatcttaag aaactttatt gccaaatgtt    13440
tgaacgatct gcttcgacgc actccttctt taggtacgga ctagatctcg gtgacgggca    13500
ggaccggacg gggcggtacc ggcaggctga agtccagctg ccagaaaccc acgtcatgcc    13560
agttcccgtg cttgaagccg gccgcccgca gcatgccgcg gggggcatat ccgagcgcct    13620
cgtgcatgcg cacgctcggg tcgttgggca gcccgatgac agcgaccacg ctcttgaagc    13680
cctgtgcctc cagggacttc agcaggtggg tgtagagcgt ggagcccagt cccgtccgct    13740
ggtggcgggg ggagacgtac acggtcgact cggccgtcca gtcgtaggcg ttgcgtgcct    13800
tccaggggcc cgcgtaggcg atgccggcga cctcgccgtc cacctcggcg acgagccagg    13860
gatagcgctc ccgcagacgg acgaggtcgt ccgtccactc ctgcggttcc tgcggctcgg    13920
tacgaagtt gaccgtgctt gtctcgatgt agtggttgac gatggtgcag accgccggca    13980
tgtccgcctc ggtggcacgg cggatgtcgg ccgggcgtcg ttctgggctc atggatctgg    14040
attgagagtg aatatgagac tctaattgga taccgagggg aatttatgga acgtcagtgg    14100
agcattttg acaagaaata tttgctagct gatagtgacc ttaggcgact tttgaacgcg    14160
caataatggt ttctgacgta tgtgcttagc tcattaaact ccagaaaccc gcggctgagt    14220
ggctccttca acgttgcggt tctgtcagtt ccaaacgtaa aacggcttgt cccgcgtcat    14280
cggcgggggt cataacgtga ctcccttaat tctccgctca tgatcagatt gtcgtttccc    14340
gccttcagtt taaactatca gtgtttgaca ggatatattg gcgggtaaac ctaagagaaa    14400
agagcgttta ttagaataat cggatattta aaagggcgtg aaaaggttta ccgttcgtc    14460
catttgtatg tgcatgccaa ccacagggtt ccccagatct ggcgccggcc agcgagacga    14520
gcaagattgg ccgccgcccg aaacgatccg acagcgcgcc cagcacaggt gcgcaggcaa    14580
attgcaccaa cgcatacagc gccagcagaa tgccatagtg ggcggtgacg tcgttcgagt    14640
gaaccagatc gcgcaggagg cccggcagca ccggcataat caggccgatg ccgacagcgt    14700
cgagcgcgac agtgctcaga attacgatca ggggtatgtt gggtttcacg tctggcctcc    14760
ggaccagcct ccgctggtcc gattgaacgc gcggattctt tatcactgat aagttggtgg    14820
acatattatg tttatcagtg ataaagtgtc aagcatgaca aagttgcagc cgaatacagt    14880
gatccgtgcc gccctggacc tgttgaacga ggtcggcgta gacggtctga cgacacgcaa    14940
actggcggaa cggttgggggg ttcagcagcc ggcgctttac tggcacttca ggaacaagcg    15000
ggcgctgctc gacgcactgg ccgaagccat gctggcggag aatcatacgc attcggtgcc    15060
gagagccgac gacgactggc gctcatttct gatcgggaat gcccgcagct tcaggcaggc    15120
gctgctcgcc taccgcgatg gcgcgcgcat ccatgccggc acgcgaccgg gcgcaccgca    15180
gatggaaacg gccgacgcgc agcttcgctt cctctgcgag gcgggttttt cggccgggga    15240
cgccgtcaat gcgctgatga caatcagcta cttcactgtt ggggccgtgc ttgaggagca    15300
ggccggcgac agcgatgccg gcgagcgcgg cggcaccgtt gaacaggctc cgctctcgcc    15360
```

```
gctgttgcgg gccgcgatag acgccttcga cgaagccggt ccggacgcag cgttcgagca    15420
gggactcgcg gtgattgtcg atggattggc gaaaaggagg ctcgttgtca ggaacgttga    15480
aggaccgaga aagggtgacg attgatcagg accgctgccg gagcgcaacc cactcactac    15540
agcagagcca tgtagacaac atcccctccc cctttccacc gcgtcagacg cccgtagcag    15600
cccgctacgg gcttttcat gccctgccct agcgtccaag cctcacggcc gcgctcggcc    15660
tctctggcgg ccttctggcg ctcttccgct tcctcgctca ctgactcgct gcgctcggtc    15720
gttcggctgc ggcgagcggt atcagctcac tcaaaggcgg taatacggtt atccacagaa    15780 tcagggggata acgcaggaaa gaacatgtga gcaaaaggcc agcaaaaggc caggaaccgt    15840
aaaaaggccg cgttgctggc gttttccat aggctccgcc cccctgacga gcatcacaaa    15900
aatcgacgct caagtcagag gtggcgaaac ccgacaggac tataaagata ccaggcgttt    15960
ccccctggaa gctccctcgt gcgctctcct gttccgaccc tgccgcttac cggatacctg    16020
tccgcctttc tcccttcggg aagcgtggcg cttttccgct gcataaccct gcttcggggt    16080
cattatagcg atttttcgg tatatccatc ctttttcgca cgatatacag gattttgcca    16140
aagggttcgt gtagactttc cttggtgtat ccaacggcgt cagccgggca ggataggtga    16200
agtaggccca cccgcgagcg ggtgttcctt cttcactgtc ccttattcgc acctggcggt    16260
gctcaacggg aatcctgctc tgcgaggctg gccggctacc gccggcgtaa cagatgaggg    16320
caagcggatg gctgatgaaa ccaagccaac caggaagggc agcccaccta tcaaggtgta    16380
ctgccttcca gacgaacgaa gagcgattga ggaaaaggcg gcggcggccg gcatgagcct    16440
gtcggcctac ctgctggccg tcggccaggg ctacaaaatc acgggcgtcg tggactatga    16500
gcacgtccgc gagctggccc gcatcaatgg cgacctgggc cgcctgggcg gcctgctgaa    16560
actctggctc accgacgacc cgcgcacggc gcggttcggt gatgccacga tcctcgccct    16620
gctggcgaag atcgaagaga agcaggacga gcttggcaag gtcatgatgg gcgtggtccg    16680
cccgagggca gagccatgac tttttagcc gctaaacgg ccgggggtg cgcgtgattg    16740 ccaagcacgt ccccatgcgc tccatcaaga agagcgactt cgcggagctg gtgaagtaca    16800
tcaccgacga gcaaggcaag accgagcgcc tttgcgacgc tca                     16843
```

<210> SEQ ID NO 5
<211> LENGTH: 9142
<212> TYPE: DNA
<213> ORGANISM: artificial sequence
<220> FEATURE:
<223> OTHER INFORMATION: vector

<400> SEQUENCE: 5

```
ctagttatct gaataaaaga gaaagagatc atccatattt cttatcctaa atgaatgtca      60
cgtgtcttta taattctttg atgaaccaga tgcatttcat taaccaaatc catatacata     120
taaatattaa tcatatataa ttaatatcaa ttgggttagc aaaacaaatc tagtctaggt     180
gtgttttgcg aattcgatat caagcttgat gggtaccggc gcgcccgatc atccggatat     240
agttcctcct ttcagcaaaa aacccctcaa gacccgttta gaggcccaa ggggttatgc     300 tagttattgc tcagcggtgg cagcagccaa ctcagcttcc tttcgggctt tgttagcagc     360
cggatcgatc caagctgtac ctcactattc ctttgccctc ggacgagtgc tggggcgtcg     420
gtttccacta tcggcgagta cttctacaca gccatcggtc cagacggccg cgcttctgcg     480
ggcgatttgt gtacgcccga cagtcccggc tccggatcgg acgattgcgt cgcatcgacc     540
```

```
ctgcgcccaa gctgcatcat cgaaattgcc gtcaaccaag ctctgataga gttggtcaag      600
accaatgcgg agcatatacg cccggagccg cggcgatcct gcaagctccg gatgcctccg      660
ctcgaagtag cgcgtctgct gctccataca agccaaccac ggcctccaga agaagatgtt      720
ggcgacctcg tatttgggaat ccccgaacat cgcctcgctc cagtcaatga ccgctgttat     780
gcggccattg tccgtcagga cattgttgga gccgaaatcc gcgtgcacga ggtgccggac      840
ttcggggcag tcctcggccc aaagcatcag ctcatcgaga gctgcgcga cggacgcact       900 gacggtgtcg tccatcacag tttgccagtg atacacatgg ggatcagcaa tcgcgcatat     960
gaaatcacgc catgtagtgt attgaccgat tccttgcggt ccgaatgggc cgaacccgct     1020
cgtctggcta agatcggccg cagcgatcgc atccatagcc tccgcgaccg gctgcagaac    1080
agcgggcagt tcggtttcag gcaggtcttg caacgtgaca ccctgtgcac ggcgggagat    1140
gcaataggtc aggctctcgc tgaattcccc aatgtcaagc acttccggaa tcgggagcgc    1200
ggccgatgca aagtgccgat aaacataacg atctttgtag aaaccatcgg cgcagctatt   1260
tacccgcagg acatatccac gccctcctac atcgaagctg aaagcacgag attcttcgcc    1320
ctccgagagc tgcatcaggt cggagacgct gtcgaacttt tcgatcagaa acttctcgac    1380
agacgtcgcg gtgagttcag gcttttccat gggtatatct ccttcttaaa gttaaacaaa    1440
attatttcta gagggaaacc gttgtggtct ccctatagtg agtcgtatta atttcgcggg    1500
atcgagatct gatcaacctg cattaatgaa tcggccaacg cgcggggaga ggcggtttgc    1560
gtattgggcg ctcttccgct tcctcgctca ctgactcgct gcgctcggtc gttcggctgc    1620
ggcgagcggt atcagctcac tcaaaggcgg taatacggtt atccacagaa tcaggggata   1680
acgcaggaaa gaacatgtga gcaaaaggcc agcaaaaggc caggaaccgt aaaaaggccg   1740
cgttgctggc gtttttccat aggctccgcc ccctgacga gcatcacaaa aatcgacgct      1800
caagtcagag gtggcgaaac ccgacaggac tataaagata ccaggcgttt ccccctggaa    1860 gctcccctcgt gcgctctcct gttccgaccc tgccgcttac cggatacctg tccgcctttc   1920
tcccttcggg aagcgtggcg ctttctcaat gctcacgctg taggtatctc agttcggtgt    1980
aggtcgttcg ctccaagctg ggctgtgtgc acgaaccccc cgttcagccc gaccgctgcg    2040
ccttatccgg taactatcgt cttgagtcca acccggtaag acacgactta tcgccactgg    2100
cagcagccac tggtaacagg attagcagag cgaggtatgt aggcggtgct acagagttct    2160
tgaagtggtg gcctaactac ggctacacta aaggacagt atttggtatc tgcgctctgc     2220
tgaagccagt taccttcgga aaagagttgg tagctcttg atccggcaaa caaaccaccg    2280
ctggtagcgg tggtttttttt gtttgcaagc agcagattac gcgcagaaaa aaaggatctc   2340
aagaagatcc tttgatcttt tctacggggt ctgacgctca gtggaacgaa aactcacgtt   2400
aagggatttt ggtcatgaca ttaacctata aaaataggcg tatcacgagg ccctttcgtc    2460
tcgcgcgttt cggtgatgac ggtgaaaacc tctgacacat gcagctcccg gagacggtca    2520
cagcttgtct gtaagcggat gccggagca gacaagcccg tcagggcgcg tcagcgggtg    2580
ttggcgggtg tcggggctgg cttaactatg cggcatcaga gcagattgta ctgagagtgc    2640
accatatgga catattgtcg ttagaacgcg gctacaatta atacataacc ttatgtatca    2700
tacacatacg atttaggtga cactatagaa cggcgcgcca agctgggtct agaactagaa    2760
acgtgatgcc acttgttatt gaagtcgatt acagcatcta ttctgtttta ctatttataa    2820
ctttgccatt tctgactttt gaaaactatc tctggatttc ggtatcgctt tgtgaagatc    2880
gagcaaaaga gacgttttgt ggacgcaatg gtccaaatcc gttctacatg aacaaattgg    2940
```

| | |
|---|---|
| tcacaatttc cactaaaagt aaataaatgg caagttaaaa aaggaatatg cattttactg | 3000 |
| attgcctagg tgagctccaa gagaagttga atctacacgt ctaccaaccg ctaaaaaaag | 3060 |
| aaaaacattg aatatgtaac ctgattccat tagcttttga cttcttcaac agattctcta | 3120 |
| cttagatttc taacagaaat attattacta gcacatcatt ttcagtctca ctacagcaaa | 3180 |
| aaatccaacg gcacaataca gacaacagga gatatcagac tacagagata gatagatgct | 3240 |
| actgcatgta gtaagttaaa taaaaggaaa ataaaatgtc ttgctaccaa aactactaca | 3300 |
| gactatgatg ctcaccacag gccaaatcct gcaactagga cagcattatc ttatatatat | 3360 |
| tgtacaaaac aagcatcaag gaacatttgg tctaggcaat cagtacctcg ttctaccatc | 3420 |
| accctcagtt atcacatcct tgaaggatcc attactggga atcatcggca acacatgctc | 3480 |
| ctgatggggc acaatgacat caagaaggta ggggccaggg gtgtccaaca ttctctgaat | 3540 |
| tgccgctcta agctcttcct tcttcgtcac tcgcgctgcc ggtatcccac aagcatcagc | 3600 |
| aaacttgagc atgtttggga atatctcgct ctcgctagac ggatctccaa gataggtgtg | 3660 |
| agctctattg gacttgtaga acctatcctc caactgaacc accatcccca aatgctgatt | 3720 |
| gttcaacaac aatatcttaa ctgggagatt ctccactctt atagtggcca actcctgaac | 3780 |
| attcatgatg aaactaccat ccccatcaat gtcaaccaca acagcccag ggttagcaac | 3840 |
| agcagcacca atagccgcag gcaatccaaa acccatggct ccaagacccc ctgaggtcaa | 3900 |
| ccactgcctc ggtctcttgt acttgtaaaa ctgcgcagcc cacatttgat gctgcccaac | 3960 |
| cccagtacta caatagcat ctccattagt caactcatca agaacctcga tagcatgctg | 4020 |
| cggagaaatc gcgtcctgga atgtcttgta acccaatgga aacttgtgtt tctgcacatt | 4080 |
| aatctcttct ctccaacctc caagatcaaa cttaccctcc actcctttct cctccaaaat | 4140 |
| catattaatt cccttcaagg ccaacttcaa atccgcgcaa accgacacgt gcgcctgctt | 4200 |
| gttcttccca atctcggcag aatcaatatc aatgtgaaca atcttagccc tactagcaaa | 4260 |
| agcctcaagc ttcccagtaa cacggtcatc aaaccttacc ccaaaggcaa gcaacaaatc | 4320 |
| actattgtca acagcatagt tagcataaac agtaccatgc ataccagca tctgaaggga | 4380 |
| atattcatca ccaataggaa aagttccaag acccattaaa gtgctagcaa cgggaatacc | 4440 |
| agtgagttca acaaagcgcc tcaattcagc actggaattc aaactgccac cgccgacgta | 4500 |
| gagaacgggc ttttgggcct ccatgatgag tctgacaatg tgttccaatt gggcctcggc | 4560 |
| gggggggcctg ggcagcctgg cgaggtaacc ggggaggtta acgggctcgt cccaattagg | 4620 |
| cacggcgagt tgctgctgaa cgtctttggg aatgtcgatg aggaccggac cggggcggcc | 4680 |
| ggaggtggcg acgaagaaag cctcggcgac gacgcggggg atgtcgtcga cgtcgaggat | 4740 |
| gaggtagttg tgcttcgtga tggatctgct cacctccacg atcggggttt cttggaaggc | 4800 |
| gtcggtgccg atcatccggc gggcgacctg gccggtgatg gcgacgactg gacgctgtc | 4860 |
| cattaaagcg tcggcgaggc cgctcacgag gttggtggcg ccggggccgg aggtggcaat | 4920 |
| gcagacgccg gggaggccgg aggaacgcgc gtagccttcg gcggcgaaga cgccgccctg | 4980 |
| ctcgtggcgc gggagcacgt tgcggatggc ggcggagcgc gtgagcgcct ggtggatctc | 5040 |
| catcgacgca ccgccggggt acgcgaacac cgtcgtcacg ccctgcctct ccagcgcctc | 5100 |
| cacaaggatg tccgcgccct tgcgaggttc gccggaggcg aaccgtgaca cgaagggctc | 5160 |
| cgtggtcggc gcttccttgg tgaagggcgc gccgtgggg ggtttggaga tggaacattt | 5220 |
| gattttgaga gcgtggttgg gtttggtgag ggtttgatga gagagaggga gggtggatct | 5280 |

```
agtaatgcgt ttggggaagg tggggtgtga agaggaagaa gagaatcggg tggttctgga   5340
agcggtggcc gccattgtgt tgtgtggcat ggttatactt caaaaactgc acaacaagcc   5400
tagagttagt acctaaacag taaatttaca acagagagca aagacacatg caaaaatttc   5460
agccataaaa aaagttataa tagaatttaa agcaaaagtt tcatttttta aacatatata   5520
caaacaaact ggatttgaag gaagggatta attcccctgc tcaaagtttg aattcctatt   5580
gtgacctata ctcgaataaa attgaagcct aaggaatgta tgagaaacaa gaaaacaaaa   5640
caaaactaca gacaaacaag tacaattaca aaattcgcta aaattctgta atcaccaaac   5700
cccatctcag tcagcacaag gcccaaggtt tattttgaaa taaaaaaaaa gtgattttat   5760
ttctcataag ctaaagaaaa gaaaggcaat tatgaaatga tttcgactag atctgaaagt   5820
caaacgcgta ttccgcagat attaaagaaa gagtagagtt tcacatggat cctagatgga   5880
cccagttgag gaaaaagcaa ggcaaagcaa accagaagtg caagatccga aattgaacca   5940
cggaatctag gatttggtag agggagaaga aaagtacctt gagaggtaga agagaagaga   6000
agagcagaga gatatatgaa cgagtgtgtc ttggtctcaa ctctgaagcg atacgagttt   6060
agaggggagc attgagttcc aatttatagg gaaaccgggt ggcaggggtg agttaatgac   6120
ggaaaagccc ctaagtaacg agattggatt gtgggttaga ttcaaccgtt tgcatccgcg   6180
gcttagattg gggaagtcag agtgaatctc aaccgttgac tgagttgaaa attgaatgta   6240
gcaaccaatt gagccaaccc cagccttttgc cctttgattt tgatttgttt gttgcatact   6300
ttttatttgt cttctggttc tgactctctt tctctcgttt caatgccagg ttgcctactc   6360
ccacaccact cacaagaaga ttctactgtt agtattaaat attttttaat gtattaaatg   6420
atgaatgctt ttgtaaacag aacaagacta tgtctaataa gtgtcttgca acatttttta   6480
agaaattaaa aaaaatatat ttattatcaa aatcaaatgt atgaaaaatc atgaataata   6540
taattttata cattttttta aaaaatcttt taatttctta attaatatct taaaaataat   6600
gattaatatt taacccaaaa taattagtat gattggtaag gaagatatcc atgttatgtt   6660
tggatgtgag tttgatctag agcaaagctt actagagtcg acctgcagcc cctccaccgc   6720
ggtggcggcc gctctagaga tccgtcaaca tggtggagca cgacactctc gtctactcca   6780
agaatatcaa agatacagtc tcagaagacc aaagggctat tgagactttt caacaaaggg   6840
taatatcggg aaacctcctc ggattccatt gcccagctat ctgtcacttc atcaaaagga   6900
cagtagaaaa ggaaggtggc acctacaaat gccatcattg cgataaagga aaggctatcg   6960
ttcaagatgc ctctgccgac agtggtccca aagatggacc cccacccacg aggagcatcg   7020
tggaaaaaga agacgttcca accacgtctt caaagcaagt ggattgatgt gatgatccta   7080
tgcgtatggt atgacgtgtg ttcaagatga tgacttcaaa cctacctatg acgtatggta   7140
tgacgtgtgt cgactgatga cttagatcca ctcgagcggc tataaatacg tacctacgca   7200
ccctgcgcta ccatccctag agctgcagct tattttttaca acaattacca acaacaacaa   7260
acaacaaaca acattacaat tactatttac aattacagtc gacccatcaa caagtttgta   7320
caaaaaagct gaacgagaaa cgtaaaatga tataaatatc aatatattaa attagatttt   7380
gcataaaaaa cagactacat aatactgtaa aacacaacat atccagtcat attggcggcc   7440
gcattaggca ccccaggctt tacactttat gcttccggct cgtataatgt gtggattttg   7500
agttaggatc cgtcgagatt ttcaggagct aaggaagcta aaatggagaa aaaaatcact   7560
ggatatacca ccgttgatat atcccaatgg catcgtaaag aacattttga ggcatttcag   7620
tcagttgctc aatgtaccta taaccagacc gttcagctgg atattacggc cttttttaaag   7680
```

```
accgtaaaga aaaataagca caagttttat ccggccttta ttcacattct tgcccgcctg    7740
atgaatgctc atccggaatt ccgtatggca atgaaagacg gtgagctggt gatatgggat    7800
agtgttcacc cttgttacac cgttttccat gagcaaactg aaacgttttc atcgctctgg    7860
agtgaatacc acgacgattt ccggcagttt ctacacatat attcgcaaga gtggcgtgt    7920 tacggtgaaa acctggccta tttccctaaa gggtttattg agaatatgtt tttcgtctca    7980
gccaatccct gggtgagttt caccagtttt gatttaaacg tggccaatat ggacaacttc    8040 ttcgccccg ttttcaccat gggcaaatat tatacgcaag gcgacaaggt gctgatgccg    8100
ctggcgattc aggttcatca tgccgtttgt gatggcttcc atgtcggcag aatgcttaat    8160
gaattacaac agtactgcga tgagtggcag ggcggggcgt aaagatctgg atccggctta    8220
ctaaaagcca gataacagta tgcgtatttg cgcgctgatt tttgcggtat aagaatatat    8280
actgatatgt atacccgaag tatgtcaaaa agaggtatgc tatgaagcag cgtattacag    8340
tgacagttga cagcgacagc tatcagttgc tcaaggcata tatgatgtca atatctccgg    8400
tctggtaagc acaaccatgc agaatgaagc ccgtcgtctg cgtgccgaac gctggaaagc    8460
ggaaaatcag gaagggatgg ctgaggtcgc ccggtttatt gaaatgaacg ctcttttgc    8520 tgacgagaac aggggctggt gaaatgcagt ttaaggttta cacctataaa agagagagcc    8580
gttatcgtct gtttgtggat gtacagagtg atattattga cacgcccggg cgacggatgg    8640
tgatccccct ggccagtgca cgtctgctgt cagataaagt ctcccgtgaa ctttacccgg    8700
tggtgcatat cggggatgaa agctggcgca tgatgaccac cgatatggcc agtgtgccgg    8760
tctccgttat cggggaagaa gtggctgatc tcagccaccg cgaaaatgac atcaaaaacg    8820
ccattaacct gatgttctgg ggaatataaa tgtcaggctc ccttatacac agccagtctg    8880
caggtcgacc atagtgactg gatatgttgt gttttacagt attatgtagt ctgtttttta    8940
tgcaaaatct aatttaatat attgatattt atatcatttt acgtttctcg ttcagctttc    9000
ttgtacaaag tggttgataa cctagacttg tccatcttct ggattggcca acttaattaa    9060
tgtatgaaat aaaaggatgc acacatagtg acatgctaat cactataatg tgggcatcaa    9120
agttgtgtgt tatgtgtaat ta                                              9142
```

<210> SEQ ID NO 6
<211> LENGTH: 49911
<212> TYPE: DNA
<213> ORGANISM: artificial sequence
<220> FEATURE:
<223> OTHER INFORMATION: vector

<400> SEQUENCE: 6

```
gtgcagcgtg acccggtcgt gcccctctct agagataatg agcattgcat gtctaagtta      60
taaaaaatta ccacatattt tttttgtcac acttgtttga agtgcagttt atctatcttt     120
atacatatat ttaaactta ctctacgaat aatataatct atagtactac aataatatca     180 gtgtttaga gaatcatata aatgaacagt tagacatggt ctaaaggaca attgagtatt     240
ttgacaacag gactctacag ttttatcttt ttagtgtgca tgtgttctcc tttttttttg     300
caaatagctt cacctatata atacttcatc cattttatta gtacatccat ttagggttta     360
gggttaatgg tttttataga ctaatttttt tagtacatct atttattct attttagcct     420 ctaaattaag aaaactaaaa ctctatttta gtttttttat ttaataattt agatataaaa     480
tagaataaaa taaagtgact aaaaattaaa caaatacccct ttaagaaatt aaaaaaacta     540
```

```
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggaccect ctcgagagtt ccgctccacc gttggacttg    720
ctccgctgtc ggcatccaga aattgcgtgg cggagcggca gacgtgagcc ggcacggcag    780
gcggcctcct cctcctctca cggcacggca gctacggggg attcctttcc caccgctcct    840
tcgctttccc ttcctcgccc gccgtaataa atagacaccc cctccacacc ctctttcccc    900
aacctcgtgt tgttcggagc gcacacacac acaaccagat ctcccccaaa tccacccgtc    960
ggcacctccg cttcaaggta cgccgctcgt cctccccccc cccccctctc taccttctct   1020
agatcggcgt tccggtccat ggttagggcc cggtagttct acttctgttc atgtttgtgt   1080
tagatccgtg tttgtgttag atccgtgctg ctagcgttcg tacacggatg cgacctgtac   1140
gtcagacacg ttctgattgc taacttgcca gtgtttctct ttggggaatc ctgggatggc   1200
tctagccgtt ccgcagacgg gatcgattte atgatttttt ttgtttcgtt gcatagggtt   1260
tggtttgccc ttttccttta tttcaatata tgccgtgcac ttgtttgtcg ggtcatcttt   1320
tcatgctttt ttttgtcttg gttgtgatga tgtggtctgg ttgggcggtc gttctagatc   1380
ggagtagaat tctgtttcaa actacctggt ggatttatta attttggatc tgtatgtgtg   1440
tgccatacat attcatagtt acgaattgaa gatgatggat ggaaatatcg atctaggata   1500
ggtatacatg ttgatgcggg ttttactgat gcatatacag agatgctttt tgttcgcttg   1560
gttgtgatga tgtggtgtgg ttgggcggtc gttcattcgt tctagatcgg agtagaatac   1620
tgtttcaaac tacctggtgt atttattaat tttggaactg tatgtgtgtg tcatacatct   1680
tcatagttac gagtttaaga tggatggaaa tatcgatcta ggataggtat acatgttgat   1740
gtgggtttta ctgatgcata tacatgatgg catatgcagc atctattcat atgctctaac   1800
cttgagtacc tatctattat aataaacaag tatgttttat aattattttg atcttgatat   1860
acttggatga tggcatatgc agcagctata tgtggatttt tttagccctg ccttcatacg   1920
ctatttattt gcttggtact gtttctttttg tcgatgctca ccctgttgtt tggtgttact   1980
tctgcaggtc gactctagag gatccacaag tttgtacaaa aaagctgaac gagaaacgta   2040
aaatgatata aatatcaata tattaaatta gattttgcat aaaaaacaga ctacataata   2100
ctgtaaaaca caacatatcc agtcactatg gcggccgcat taggcacccc aggctttaca   2160
ctttatgctt ccggctcgta taatgtgtgg attttgagtt aggatttaaa tacgcgttga   2220
tccggcttac taaaagccag ataacagtat gcgtatttgc gcgctgattt ttgcggtata   2280
agaatatata ctgatatgta tacccgaagt atgtcaaaaa gaggtatgct atgaagcagc   2340
gtattacagt gacagttgac agcgacagct atcagttgct caaggcatat atgatgtcaa   2400
tatctccggt ctggtaagca caaccatgca gaatgaagcc cgtcgtctgc gtgccgaacg   2460
ctggaaagcg gaaaatcagg aagggatggc tgaggtcgcc cggtttattg aaatgaacgg   2520
ctcttttgct gacgagaaca ggggctggtg aaatgcagtt taaggtttac acctataaaa   2580
gagagagccg ttatcgtctg tttgtggatg tacagagtga tatcattgac acgcccggtc   2640
gacggatggt gatcccectg ccagtgcac gtctgctgtc agataaagtc tcccgtgaac   2700
tttacccggt ggtgcatatc ggggatgaaa gctggcgcat gatgaccacc gatatggcca   2760
gtgtgccggt ctccgttatc ggggaagaag tggctgatct cagccaccgc gaaaatgaca   2820
tcaaaaacgc cattaacctg atgttctggg gaatataaat gtcaggctcc cttatacaca   2880
gccagtctgc aggtcgacca tagtgactgg atatgttgtg ttttacagta ttatgtagtc   2940
```

-continued

```
tgttttttat gcaaaatcta atttaatata ttgatattta tatcatttta cgtttctcgt    3000
tcagctttct tgtacaaagt ggtgttaacc tagacttgtc catcttctgg attggccaac    3060
ttaattaatg tatgaaataa aaggatgcac acatagtgac atgctaatca ctataatgtg    3120
ggcatcaaag ttgtgtgtta tgtgtaatta ctagttatct gaataaaaga gaaagagatc    3180
atccatattt cttatcctaa atgaatgtca cgtgtcttta taattctttg atgaaccaga    3240
tgcatttcat taaccaaatc catatacata taaatattaa tcatatataa ttaatatcaa    3300
ttgggttagc aaaacaaatc tagtctaggt gtgttttgcg aattgcggcc gccaccgcgg    3360
tggagctcga attccggtcc gggtcacctt tgtccaccaa gatggaactg cggccgctca    3420
ttaattaagt caggcgcgcc tctagttgaa gacacgttca tgtcttcatc gtaagaagac    3480
actcagtagt cttcggccag aatggccatc tggattcagc aggcctagaa ggccatttaa    3540
atcctgagga tctggtcttc ctaaggaccc gggatatcgg accgattaaa ctttaattcg    3600
gtccgaagct tgcatgcctg cagtgcagcg tgacccggtc gtgcccctct ctagagataa    3660
tgagcattgc atgtctaagt tataaaaaat taccacatat tttttttgtc acacttgttt    3720
gaagtgcagt ttatctatct ttatacatat atttaaactt tactctacga ataatataat    3780
ctatagtact acaataatat cagtgtttta gagaatcata taaatgaaca gttagacatg    3840
gtctaaagga caattgagta ttttgacaac aggactctac agttttatct ttttagtgtg    3900
catgtgttct ccttttttttt tgcaaatagc ttcacctata taatacttca tccattttat    3960
tagtacatcc atttagggtt tagggttaat ggttttttata gactaatttt tttagtacat    4020
ctattttatt ctattttagc ctctaaatta agaaaactaa aactctattt tagttttttt    4080
atttaataat ttagatataa aatagaataa aataaagtga ctaaaaatta aacaaatacc    4140
ctttaagaaa ttaaaaaaac taaggaaaca tttttcttgt ttcgagtaga taatgccagc    4200
ctgttaaacg ccgtcgacga gtctaacgga caccaaccag cgaaccagca gcgtcgcgtc    4260
gggccaagcg aagcagacgg cacggcatct ctgtcgctgc ctctggaccc ctctcgagag    4320
ttccgctcca ccgttggact tgctccgctg tcggcatcca gaaattgcgt ggcggagcgg    4380
cagacgtgag ccggcacggc aggcggcctc ctcctcctct cacggcaccg gcagctacgg    4440
gggattcctt tcccaccgct ccttcgcttt ccctttcctcg cccgccgtaa taaatagaca    4500 cccccctccac accctctttc cccaacctcg tgttgttcgg agcgcacaca cacacaacca    4560
gatctccccc aaatccaccc gtcggcacct ccgcttcaag gtacgccgct cgtcctcccc    4620 ccccccccctc tctaccttct ctagatcggc gttccggtcc atgcatggtt agggcccggt    4680
agttctactt ctgttcatgt ttgtgttaga tccgtgtttg tgttagatcc gtgctgctag    4740
cgttcgtaca cggatgcgac ctgtacgtca gacacgttct gattgctaac ttgccagtgt    4800
ttctctttgg ggaatcctgg gatggctcta gccgttccgc agacgggatc gatttcatga    4860
ttttttttgt ttcgttgcat agggtttggt ttgccctttt cctttatttc aatatatgcc    4920
gtgcacttgt ttgtcgggtc atcttttcat gctttttttt gtcttggttg tgatgatgtg    4980
gtctggttgg gcggtcgttc tagatcggag tagaattctg tttcaaacta cctggtggat    5040
ttattaattt tggatctgta tgtgtgtgcc atacatattc atagttacga attgaagatg    5100
atggatggaa atatcgatct aggataggta tacatgttga tgcgggtttt actgatgcat    5160
atacagagat gctttttgtt cgcttggttg tgatgatgtg gtgtggttgg gcggtcgttc    5220
attcgttcta gatcggagta gaatactgtt tcaaactacc tggtgtattt attaattttg    5280
```

```
gaactgtatg tgtgtgtcat acatcttcat agttacgagt ttaagatgga tggaaatatc    5340
gatctaggat aggtatacat gttgatgtgg gttttactga tgcatataca tgatggcata    5400
tgcagcatct attcatatgc tctaaccttg agtacctatc tattataata aacaagtatg    5460
ttttataatt attttgatct tgatatactt ggatgatggc atatgcagca gctatatgtg    5520
gatttttta gccctgcctt catacgctat ttatttgctt ggtactgttt cttttgtcga    5580
tgctcaccct gttgtttggt gttacttctg caggtcgact ttaacttagc ctaggatcca    5640
cacgacacca tgtcccccga gcgccgcccc gtcgagatcc gcccggccac cgccgccgac    5700
atggccgccg tgtgcgacat cgtgaaccac tacatcgaga cctccaccgt gaacttccgc    5760
accgagccgc agacccgca ggagtggatc gacgacctgg agcgcctcca ggaccgctac    5820
ccgtggctcg tggccgaggt ggagggcgtg gtggccggca tcgcctacgc cggcccgtgg    5880
aaggcccgca acgcctacga ctggaccgtg gagtccaccg tgtacgtgtc ccaccgccac    5940
cagcgcctcg gcctcggctc caccctctac acccacctcc tcaagagcat ggaggcccag    6000
ggcttcaagt ccgtggtggc cgtgatcggc ctcccgaacg accgtccgt gcgcctccac    6060
gaggccctcg gctacaccgc ccgcggcacc ctccgcgccg ccggctacaa gcacggcggc    6120
tggcacgacg tcggcttctg gcagcgcgac ttcgagctgc cggccccgcc gcgcccggtg    6180
cgcccggtga cgcagatctg agtcgaaacc tagacttgtc catcttctgg attggccaac    6240
ttaattaatg tatgaaataa aaggatgcac acatagtgac atgctaatca ctataatgtg    6300
ggcatcaaag ttgtgtgtta tgtgtaatta ctagttatct gaataaaaga gaagagatc    6360
atccatattt cttatcctaa atgaatgtca cgtgtcttta taattctttg atgaaccaga    6420
tgcatttcat taaccaaatc catatacata taaatattaa tcatatataa ttaatatcaa    6480
ttgggttagc aaaacaaatc tagtctaggt gtgttttgcg aattgcggcc gccaccgcgg    6540
tggagctcga attcattccg attaatcgtg gcctcttgct cttcaggatg aagagctatg    6600
tttaaacgtg caagcgctac tagacaattc agtacattaa aaacgtccgc aatgtgttat    6660
taagttgtct aagcgtcaat ttggtttaca ccacaatata tcctgccacc agccagccaa    6720
cagctccccg accggcagct cggcacaaaa tcaccactcg atacaggcag cccatcagtc    6780
cgggacggcg tcagcgggag agccgttgta aggcggcaga cttttgctcat gttaccgatg    6840
ctattcggaa gaacggcaac taagctgccg ggttttgaaac acggatgatc tcgcggaggg    6900
tagcatgttg attgtaacga tgacagagcg ttgctgcctg tgatcaaata tcatctccct    6960
cgcagagatc cgaattatca gccttcttat tcatttctcg cttaaccgtg acaggctgtc    7020
gatcttgaga actatgccga cataatagga aatcgctgga taaagccgct gaggaagctg    7080
agtggcgcta tttctttaga agtgaacgtt gacgatcgtc gaccgtaccc cgatgaatta    7140
attcggacgt acgttctgaa cacagctgga tacttacttg ggcgattgtc atacatgaca    7200
tcaacaatgt acccgtttgt gtaaccgtct cttggaggtt cgtatgacac tagtggttcc    7260
cctcagcttg cgactagatg ttgaggccta acatttttatt agagagcagg ctagttgctt    7320
agatacatga tcttcaggcc gttatctgtc agggcaagcg aaaattggcc atttatgacg    7380
accaatgccc cgcagaagct cccatctttg ccgccataga cgccgcgccc ccttttggg    7440
gtgtagaaca tccttttgcc agatgtggaa aagaagttcg ttgtcccatt gttggcaatg    7500
acgtagtagc cggcgaaagt gcgagaccca tttgcgctat atataagcct acgatttccg    7560
ttgcgactat tgtcgtaatt ggatgaacta ttatcgtagt tgctctcaga gttgtcgtaa    7620
tttgatggac tattgtcgta attgcttatg gagttgtcgt agttgcttgg agaaatgtcg    7680
```

```
tagttggatg gggagtagtc atagggaaga cgagcttcat ccactaaaac aattggcagg    7740
tcagcaagtg cctgccccga tgccatcgca agtacgaggc ttagaaccac cttcaacaga    7800
tcgcgcatag tcttccccag ctctctaacg cttgagttaa gccgcgccgc gaagcggcgt    7860
cggcttgaac gaattgttag acattatttg ccgactacct tggtgatctc gcctttcacg    7920
tagtgaacaa attcttccaa ctgatctgcg cgcgaggcca agcgatcttc ttgtccaaga    7980
taagcctgcc tagcttcaag tatgacgggc tgatactggg ccggcaggcg ctccattgcc    8040
cagtcggcag cgacatcctt cggcgcgatt ttgccggtta ctgcgctgta ccaaatgcgg    8100
gacaacgtaa gcactacatt tcgctcatcg ccagcccagt cgggcggcga gttccatagc    8160
gttaaggttt catttagcgc ctcaaataga tcctgttcag gaaccggatc aaagagttcc    8220
tccgccgctg gacctaccaa ggcaacgcta tgttctcttg cttttgtcag caagatagcc    8280
agatcaatgt cgatcgtggc tggctcgaag atacctgcaa gaatgtcatt gcgctgccat    8340
tctccaaatt gcagttcgcg cttagctgga taacgccacg gaatgatgtc gtcgtgcaca    8400
acaatggtga cttctacagc gcggagaatc tcgctctctc caggggaagc cgaagtttcc    8460
aaaaggtcgt tgatcaaagc tcgccgcgtt gtttcatcaa gccttacagt caccgtaacc    8520
agcaaatcaa tatcactgtg tggcttcagg ccgccatcca ctgcggagcc gtacaaatgt    8580
acggccagca acgtcggttc gagatggcgc tcgatgacgc caactacctc tgatagttga    8640
gtcgatactt cggcgatcac cgcttccctc atgatgttta actcctgaat taagccgcgc    8700
cgcgaagcgg tgtcggcttg aatgaattgt taggcgtcat cctgtgctcc cgagaaccag    8760
taccagtaca tcgctgtttc gttcgagact tgaggtctag ttttatacgt gaacaggtca    8820
atgccgccga gagtaaagcc acattttgcg tacaaattgc aggcaggtac attgttcgtt    8880
tgtgtctcta atcgtatgcc aaggagctgt ctgcttagtg cccactttt cgcaaattcg     8940
atgagactgt gcgcgactcc tttgcctcgg tgcgtgtgcg acacaacaat gtgttcgata    9000
gaggctagat cgttccatgt tgagttgagt tcaatcttcc cgacaagctc ttggtcgatg    9060
aatgcgccat agcaagcaga gtcttcatca gagtcatcat ccgagatgta atccttccgg    9120
taggggctca cacttctggt agatagttca aagccttggt cggataggtg cacatcgaac    9180
acttcacgaa caatgaaatg gttctcagca tccaatgttt ccgccacctg ctcagggatc    9240
accgaaatct tcatatgacg cctaacgcct ggcacagcgg atcgcaaacc tggcgcggct    9300
tttggcacaa aaggcgtgac aggtttgcga atccgttgct gccacttgtt aacccttttg    9360
ccagatttgg taactataat ttatgttaga ggcgaagtct tgggtaaaaa ctggcctaaa    9420
attgctgggg atttcaggaa agtaaacatc accttccggc tcgatgtcta ttgtagatat    9480
atgtagtgta tctacttgat cgggggatct gctgcctcgc gcgtttcggt gatgacggtg    9540
aaaacctctg acacatgcag ctcccggaga cggtcacagc ttgtctgtaa gcggatgccg    9600
ggagcagaca agcccgtcag ggcgcgtcag cgggtgttgg cgggtgtcgg ggcgcagcca    9660
tgacccagtc acgtagcgat agcggagtgt atactggctt aactatgcgg catcagagca    9720
gattgtactg agagtgcacc atatgcggtg tgaaataccg cacagatgcg taaggagaaa    9780
ataccgcatc aggcgctctt ccgcttcctc gctcactgac tcgctgcgct cggtcgttcg    9840
gctgcggcga gcggtatcag ctcactcaaa ggcggtaata cggttatcca cagaatcagg    9900
ggataacgca ggaaagaaca tgtgagcaaa aggccagcaa aaggccagga accgtaaaaa    9960
ggccgcgttg ctggcgtttt tccataggct ccgcccccct gacgagcatc acaaaaatcg   10020
```

```
acgctcaagt cagaggtggc gaaacccgac aggactataa agataccagg cgtttccccc   10080
tggaagctcc ctcgtgcgct ctcctgttcc gaccctgccg cttaccggat acctgtccgc   10140
ctttctccct tcgggaagcg tggcgctttc tcatagctca cgctgtaggt atctcagttc   10200
ggtgtaggtc gttcgctcca agctgggctg tgtgcacgaa ccccccgttc agcccgaccg   10260
ctgcgcctta tccggtaact atcgtcttga gtccaacccg gtaagacacg acttatcgcc   10320
actggcagca gccactggta acaggattag cagagcgagg tatgtaggcg gtgctacaga   10380
gttcttgaag tggtggccta actacggcta cactagaagg acagtatttg gtatctgcgc   10440
tctgctgaag ccagttacct tcggaaaaag agttggtagc tcttgatccg gcaaacaaac   10500
caccgctggt agcggtggtt ttttgtttg caagcagcag attacgcgca gaaaaaaagg   10560
atctcaagaa gatcctttga tcttttctac ggggtctgac gctcagtgga acgaaaactc   10620
acgttaaggg attttggtca tgagattatc aaaaaggatc ttcacctaga tccttttaaa   10680
ttaaaaatga agttttaaat caatctaaag tatatatgag taaacttggt ctgacagtta   10740
ccaatgctta atcagtgagg cacctatctc agcgatctgt ctatttcgtt catccatagt   10800
tgcctgactc cccgtcgtgt agataactac gatacgggag ggcttaccat ctggccccag   10860
tgctgcaatg ataccgcgag acccacgctc accggctcca gatttatcag caataaacca   10920
gccagccgga agggccgagc gcagaagtgg tcctgcaact ttatccgcct ccatccagtc   10980
tattaattgt tgccgggaag ctagagtaag tagttcgcca gttaatagtt tgcgcaacgt   11040
tgttgccatt gctgcagggg ggggggggg ggggacttc cattgttcat tccacggaca   11100
aaaacagaga aggaaacga cagaggccaa aaagcctcgc tttcagcacc tgtcgtttcc   11160
tttcttttca gagggtattt taaataaaaa cattaagtta tgacgaagaa gaacggaaac   11220
gccttaaacc ggaaaatttt cataaatagc gaaaacccgc gaggtcgccg ccccgtaacc   11280
tacctgtcgg atcaccggaa aggacccgta aagtgataat gattatcatc tacatatcac   11340
aacgtgcgtg gaggccatca aaccacgtca aataatcaat tatgacgcag gtatcgtatt   11400
aattgatctg catcaactta acgtaaaaac aacttcagac aatacaaatc agcgacactg   11460
aatacggggc aacctcatgt ccccccccc ccccccctg caggcatcgt ggtgtcacgc   11520
tcgtcgtttg gtatggcttc attcagctcc ggttcccaac gatcaaggcg agttacatga   11580
tcccccatgt tgtgcaaaaa agcggttagc tccttcggtc ctccgatcgt tgtcagaagt   11640
aagttggccg cagtgttatc actcatggtt atggcagcac tgcataattc tcttactgtc   11700
atgccatccg taagatgctt ttctgtgact ggtgagtact caaccaagtc attctgagaa   11760
tagtgtatgc ggcgaccgag ttgctcttgc ccggcgtcaa cacgggataa taccgcgcca   11820
catagcagaa ctttaaaagt gctcatcatt ggaaaacgtt cttcggggcg aaaactctca   11880
aggatcttac cgctgttgag atccagttcg atgtaaccca ctcgtgcacc caactgatct   11940
tcagcatctt ttactttcac cagcgtttct gggtgagcaa aaacaggaag gcaaaatgcc   12000
gcaaaaaagg gaataagggc gacacggaaa tgttgaatac tcatactctt cctttttcaa   12060
tattattgaa gcatttatca gggttattgt ctcatgagcg gatacatatt tgaatgtatt   12120
tagaaaaata aacaaatagg ggttccgcgc acatttcccc gaaaagtgcc acctgacgtc   12180
taagaaacca ttattatcat gacattaacc tataaaaata ggcgtatcac gaggcccttt   12240
cgtcttcaag aattcggagc ttttgccatt ctcaccggat tcagtcgtca ctcatggtga   12300
tttctcactt gataacctta ttttgacga ggggaaatta ataggttgta ttgatgttgg   12360
acgagtcgga atcgcagacc gataccagga tcttgccatc ctatggaact gcctcggtga   12420
```

```
gttttctcct tcattacaga aacggctttt tcaaaaatat ggtattgata atcctgatat   12480
gaataaattg cagtttcatt tgatgctcga tgagttttc taatcagaat tggttaattg    12540
gttgtaacac tggcagagca ttacgctgac ttgacgggac ggcggctttg ttgaataaat   12600
cgaacttttg ctgagttgaa ggatcagatc acgcatcttc ccgacaacgc agaccgttcc   12660
gtggcaaagc aaaagttcaa aatcaccaac tggtccacct acaacaaagc tctcatcaac   12720
cgtggctccc tcactttctg gctggatgat ggggcgattc aggcctggta tgagtcagca   12780
acaccttctt cacgaggcag acctcagcgc cagaaggccg ccagagaggc cgagcgcggc   12840
cgtgaggctt ggacgctagg gcagggcatg aaaaagcccg tagcgggctg ctacgggcgt   12900
ctgacgcggt ggaaaggggg aggggatgtt gtctacatgg ctctgctgta gtgagtgggt   12960
tgcgctccgg cagcggtcct gatcaatcgt cacccttcct cggtccttca acgttcctga   13020
caacgagcct cctttcgcc aatccatcga caatcaccgc gagtccctgc tcgaacgctg     13080
cgtccggacc ggcttcgtcg aaggcgtcta tcgcggcccg caacagcggc gagagcggag   13140
cctgttcaac ggtgccgccg cgctcgccgg catcgctgtc gccggcctgc tcctcaagca   13200
cggccccaac agtgaagtag ctgattgtca tcagcgcatt gacggcgtcc ccggccgaaa   13260
aacccgcctc gcagaggaag cgaagctgcg cgtcggccgt ttccatctgc ggtgcgcccg   13320
gtcgcgtgcc ggcatggatg cgcgcgccat cgcggtaggc gagcagcgcc tgcctgaagc   13380
tgcgggcatt cccgatcaga aatgagcgcc agtcgtcgtc ggctctcggc accgaatgcg   13440
tatgattctc cgccagcatg gcttcggcca gtgcgtcgag cagcgcccgc ttgttcctga   13500
agtgccagta aagcgccggc tgctgaaccc ccaaccgttc cgccagtttg cgtgtcgtca   13560
gaccgtctac gccgacctcg ttcaacaggt ccagggcggc acggatcact gtattcggct   13620
gcaactttgt catgcttgac actttatcac tgataaacat aatatgtcca ccaacttatc   13680
agtgataaag aatccgcgcg ttcaatcgga ccagcggagg ctggtccgga ggccagacgt   13740
gaaacccaac ataccctga tcgtaattct gagcactgtc gcgctcgacg ctgtcggcat     13800
cggcctgatt atgccggtgc tgccgggcct cctgcgcgat ctggttcact cgaacgacgt   13860
caccgcccac tatggcattc tgctggcgct gtatgcgttg gtgcaatttg cctgcgcacc   13920
tgtgctgggc gcgctgtcgg atcgtttcgg gcggcggcca atcttgctcg tctcgctggc   13980
cggcgccact gtcgactacg ccatcatggc gacagcgcct ttccttggg ttctctatat     14040 cgggcggatc gtggccggca tcaccggggc gactggggcg gtagccggcg cttatattgc   14100
cgatatcact gatggcgatg agcgcgcgcg gcacttcggc ttcatgagcg cctgtttcgg   14160
gttcgggatg gtcgcgggac ctgtgctcgg tgggctgatg ggcggttct ccccccacgc     14220 tccgttcttc gccgcggcag ccttgaacgg cctcaatttc ctgacgggct gtttcctttt   14280
gccggagtcg cacaaaggcg aacgccggcc gttacgccgg gaggctctca cccgctcgc    14340 ttcgttccgg tgggcccggg gcatgaccgt cgtcgccgcc ctgatggcgg tcttcttcat   14400
catgcaactt gtcggacagg tgccggccgc gctttgggtc attttcggcg aggatcgctt   14460
tcactgggac gcgaccacga tcggcatttc gcttgccgca tttggcattc tgcattcact   14520
cgcccaggca atgatcaccg gccctgtagc cgcccggctc ggcgaaaggc gggcactcat   14580
gctcggaatg attgccgacg gcacaggcta catcctgctt gccttcgcga cacggggatg   14640
gatggcgttc ccgatcatgg tcctgcttgc ttcgggtggc atcggaatgc cggcgctgca   14700
agcaatgttg tccaggcagg tggatgagga acgtcagggg cagctgcaag gctcactggc   14760
```

```
ggcgctcacc agcctgacct cgatcgtcgg acccctcctc ttcacggcga tctatgcggc   14820
ttctataaca acgtggaacg ggtgggcatg gattgcaggc gctgccctct acttgctctg   14880
cctgccggcg ctgcgtcgcg ggctttggag cggcgcaggg caacgagccg atcgctgatc   14940
gtggaaacga taggcctatg ccatgcgggt caaggcgact tccggcaagc tatacgcgcc   15000
ctaggagtgc ggttggaacg ttggcccagc cagatactcc cgatcacgag caggacgccg   15060
atgatttgaa gcgcactcag cgtctgatcc aagaacaacc atcctagcaa cacggcggtc   15120
cccgggctga gaaagcccag taaggaaaca actgtaggtt cgagtcgcga gatccccgg    15180
aaccaaagga agtaggttaa acccgctccg atcaggccga gccacgccag gccgagaaca   15240
ttggttcctg taggcatcgg gattggcgga tcaaacacta agctactgg aacgagcaga    15300
agtcctccgg ccgccagttg ccaggcgta aaggtgagca gaggcacggg aggttgccac    15360
ttgcgggtca gcacggttcc gaacgccatg gaaaccgccc ccgccaggcc cgctgcgacg   15420
ccgacaggat ctagcgctgc gtttggtgtc aacaccaaca cgccacgcc cgcagttccg    15480
caaatagccc ccaggaccgc catcaatcgt atcgggctac ctagcagagc ggcagagatg   15540
aacacgacca tcagcggctg cacagcgcct accgtcgccg cgaccccgcc cggcaggcgg   15600
tagaccgaaa taaacaacaa gctccagaat agcgaaatat taagtgcgcc gaggatgaag   15660
atgcgcatcc accagattcc cgttggaatc tgtcggacga tcatcacgag caataaaccc   15720
gccggcaacg cccgcagcag cataccggcg accctcggc ctcgctgttc gggctccacg    15780
aaaacgccgg acagatgcgc cttgtgagcg tccttggggc cgtcctcctg tttgaagacc   15840
gacagcccaa tgatctcgcc gtcgatgtag gcgccgaatg ccacggcatc tcgcaaccgt   15900
tcagcgaacg cctccatggg cttttctcc tcgtgctcgt aaacggaccc gaacatctct    15960
ggagctttct tcagggccga caatcggatc tcgcggaaat cctgcacgtc ggccgctcca   16020
agccgtcgaa tctgagcctt aatcacaatt gtcaatttta atcctctgtt tatcggcagt   16080
tcgtagagcg cgccgtgcgt cccgagcgat actgagcgaa gcaagtgcgt cgagcagtgc   16140
ccgcttgttc ctgaaatgcc agtaaagcgc tggctgctga accccagcc ggaactgacc    16200
ccacaaggcc ctagcgtttg caatgcacca ggtcatcatt gacccaggcg tgttccacca   16260
ggccgctgcc tcgcaactct tcgcaggctt cgccgacctg ctcgcgccac ttcttcacgc   16320
gggtggaatc cgatccgcac atgaggcgga aggtttccag cttgagcggg tacggctccc   16380
ggtgcgagct gaaatagtcg aacatccgtc gggccgtcgg cgacagcttg cggtacttct   16440
cccatatgaa tttcgtgtag tggtcgccag caaacagcac gacgatttcc tcgtcgatca   16500
ggacctggca acgggacgtt ttcttgccac ggtccaggac gcggaagcgg tgcagcagcg   16560
acaccgattc caggtgccca acgcggtcgg acgtgaagcc catcgccgtc gcctgtaggc   16620
gcgacaggca ttcctcggcc ttcgtgtaat accggccatt gatcgaccag cccaggtcct   16680
ggcaaagctc gtagaacgtg aaggtgatcg gctcgccgat aggggtgcgc ttcgcgtact   16740
ccaacacctg ctgccacacc agttcgtcat cgtcggcccg cagctcgacg ccggtgtagg   16800
tgatcttcac gtccttgttg acgtggaaaa tgaccttgtt ttgcagcgcc tcgcgcggga   16860
ttttcttgtt gcgcgtggtg aacagggcag agcgggccgt gtcgtttggc atcgctcgca   16920
tcgtgtccgg ccacggcgca atatcgaaca aggaaagctg catttccttg atctgctgct   16980
tcgtgtgttt cagcaacgcg gcctgcttgg cctcgctgac ctgttttgcc aggtcctcgc   17040
cggcggtttt tcgcttcttg gtcgtcatag ttcctcgcgt gtcgatggtc atcgacttcg   17100
ccaaacctgc cgcctcctgt tcgagacgac gcgaacgctc cacggcggcc gatggcgcgg   17160
```

```
gcagggcagg gggagccagt tgcacgctgt cgcgctcgat cttggccgta gcttgctgga   17220
ccatcgagcc gacggactgg aaggtttcgc ggggcgcacg catgacggtg cggcttgcga   17280
tggtttcggc atcctcggcg gaaaaccccg cgtcgatcag ttcttgcctg tatgccttcc   17340
ggtcaaacgt ccgattcatt caccctcctt gcgggattgc cccgactcac gccggggcaa   17400
tgtgccctta ttcctgattt gacccgcctg gtgccttggt gtccagataa tccaccttat   17460
cggcaatgaa gtcggtcccg tagaccgtct ggccgtcctt ctcgtacttg gtattccgaa   17520
tcttgccctg cacgaatacc agcgaccccct tgcccaaata cttgccgtgg gcctcggcct   17580
gagagccaaa acacttgatg cggaagaagt cggtgcgctc ctgcttgtcg ccggcatcgt   17640
tgcgccactc ttcattaacc gctatatcga aaattgcttg cggcttgtta gaattgccat   17700
gacgtacctc ggtgtcacgg gtaagattac cgataaactg gaactgatta tggctcatat   17760
cgaaagtctc cttgagaaag gagactctag tttagctaaa cattggttcc gctgtcaaga   17820
actttagcgg ctaaaatttt gcgggccgcg accaaaggtg cgaggggcgg cttccgctgt   17880
gtacaaccag atattttttca ccaacatcct tcgtctgctc gatgagcggg gcatgacgaa   17940
acatgagctg tcggagaggg caggggtttc aatttcgttt ttatcagact taaccaacgg   18000
taaggccaac ccctcgttga aggtgatgga ggccattgcc gacgccctgg aaactcccct   18060
acctcttctc ctggagtcca ccgaccttga ccgcgaggca ctcgcggaga ttgcgggtca   18120 tccttttcaag agcagcgtgc cgcccggata cgaacgcatc agtgtggttt tgccgtcaca   18180
taaggcgttt atcgtaaaga aatggggcga cgacacccga aaaaagctgc gtggaaggct   18240
ctgacgccaa gggttagggc ttgcacttcc ttctttagcc gctaaaacgg cccccttctct   18300 gcgggccgtc ggctcgcgca tcatatcgac atcctcaacg gaagccgtgc cgcgaatggc   18360
atcgggcggg tgcgctttga cagttgtttt ctatcagaac ccctacgtcg tgcggttcga   18420
ttagctgttt gtcttgcagg ctaaacactt tcggtatatc gtttgcctgt gcgataatgt   18480
tgctaatgat ttgttgcgta ggggttactg aaaagtgagc gggaaagaag agtttcagac   18540
catcaaggag cgggccaagc gcaagctgga acgcgacatg ggtgcggacc tgttggccgc   18600
gctcaacgac ccgaaaaccg ttgaagtcat gctcaacgcg gacggcaagg tgtggcacga   18660
acgccttggc gagccgatgc ggtacatctg cgacatgcgg cccagccagt cgcaggcgat   18720
tatagaaacg gtggccggat tccacggcaa agaggtcacg cggcattcgc ccatcctgga   18780
aggcgagttc cccttggatg gcagccgctt tgccggccaa ttgccgccgg tcgtggccgc   18840
gccaaccttt gcgatccgca agcgcgcggt cgccatcttc acgctggaac agtacgtcga   18900
ggcgggcatc atgacccgcg agcaatacga ggtcattaaa agcgccgtcg cggcgcatcg   18960
aaacatcctc gtcattggcg gtactggctc gggcaagacc acgctcgtca acgcgatcat   19020
caatgaaatg gtcgccttca acccgtctga gcgcgtcgtc atcatcgagg acaccggcga   19080
aatccagtgc gccgcagaga acgccgtcca ataccacacc agcatcgacg tctcgatgac   19140
gctgctgctc aagacaacgc tgcgtatgcg ccccgaccgc atcctggtcg gtgaggtacg   19200 tggcccccgaa gcccttgatc tgttgatggc ctggaacacc gggcatgaag gaggtgccgc   19260 cacccctgcac gcaaacaacc ccaaagcggg cctgagccgg ctcgccatgc ttatcagcat   19320
gcacccggat tcaccgaaaac ccattgagcc gctgattggc gaggcggttc atgtggtcgt   19380
ccatatcgcc aggaccccta gcggccgtcg agtgcaagaa attctcgaag ttcttggtta   19440
cgagaacggc cagtacatca ccaaaaccct gtaaggagta tttccaatga caacggctgt   19500
```

```
tccgttccgt ctgaccatga atcgcggcat tttgttctac cttgccgtgt tcttcgttct   19560
cgctctcgcg ttatccgcgc atccggcgat ggcctcggaa ggcaccggcg gcagcttgcc   19620
atatgagagc tggctgacga acctgcgcaa ctccgtaacc ggcccggtgg ccttcgcgct   19680
gtccatcatc ggcatcgtcg tcgccggcgg cgtgctgatc ttcggcggcg aactcaacgc   19740
cttcttccga accctgatct tcctggttct ggtgatggcg ctgctggtcg gcgcgcagaa   19800
cgtgatgagc accttcttcg gtcgtggtgc cgaaatcgcg ccctcggca acggggcgct   19860 gcaccaggtg caagtcgcgg cggcggatgc cgtgcgtgcg gtagcggctg gacggctcgc   19920
ctaatcatgg ctctgcgcac gatccccatc cgtcgcgcag gcaaccgaga aaacctgttc   19980
atgggtggtg atcgtgaact ggtgatgttc tcgggcctga tggcgtttgc gctgattttc   20040
agcgcccaag agctgcgggc caccgtggtc ggtctgatcc tgtggttcgg ggcgctctat   20100
gcgttccgaa tcatggcgaa ggccgatccg aagatgcggt tcgtgtacct gcgtcaccgc   20160
cggtacaagc cgtattaccc ggcccgctcg accccgttcc gcgagaacac caatagccaa   20220
gggaagcaat accgatgatc caagcaattg cgattgcaat cgcgggcctc ggcgcgcttc   20280
tgttgttcat cctctttgcc cgcatccgcg cggtcgatgc cgaactgaaa ctgaaaaagc   20340
atcgttccaa ggacgccggc ctggccgatc tgctcaacta cgccgctgtc gtcgatgacg   20400
gcgtaatcgt gggcaagaac ggcagcttta tggctgcctg gctgtacaag ggcgatgaca   20460
acgcaagcag caccgaccag cagcgcgaag tagtgtccgc ccgcatcaac caggccctcg   20520
cgggcctggg aagtgggtgg atgatccatg tggacgccgt gcggcgtcct gctccgaact   20580
acgcggagcg gggcctgtcg gcgttccctg accgtctgac ggcagcgatt gaagaagagc   20640
gctcggtctt gccttgctcg tcggtgatgt acttcaccag ctccgcgaag tcgctcttct   20700
tgatggagcg catggggacg tgcttggcaa tcacgcgcac ccccccggccg ttttagcggc   20760 taaaaaagtc atggctctgc cctcgggcgg accacgccca tcatgacctt gccaagctcg   20820
tcctgcttct cttcgatctt cgccagcagg gcgaggatcg tggcatcacc gaaccgcgcc   20880
gtgcgcgggt cgtcggtgag ccagagtttc agcaggccgc ccaggcggcc caggtcgcca   20940
ttgatgcggg ccagctcgcg gacgtgctca tagtccacga cgcccgtgat tttgtagccc   21000
tggccgacgg ccagcaggta ggccgacagg ctcatgccgg ccgccgccgc cttttcctca   21060
atcgctcttc gttcgtctgg aaggcagtac accttgatag gtgggctgcc cttcctggtt   21120
ggcttggttt catcagccat ccgcttgccc tcatctgtta cgccggcggt agccggccag   21180
cctcgcagag caggattccc gttgagcacc gccaggtgcg aataagggac agtgaagaag   21240
gaacacccgc tcgcgggtgg gcctacttca cctatcctgc ccggctgacg ccgttggata   21300
caccaaggaa agtctacacg aacccttttgg caaaatcctg tatatcgtgc gaaaaaggat   21360
ggatataccg aaaaaatcgc tataatgacc ccgaagcagg gttatgcagc ggaaaagcgc   21420
tgcttccctg ctgttttgtg gaatatctac cgactggaaa caggcaaatg caggaaatta   21480
ctgaactgag gggacaggcg agagacgatg ccaaagagct acaccgacga gctggccgag   21540
tgggttgaat cccgcgcggc caagaagcgc cggcgtgatg aggctgcggt tgcgttcctg   21600
gcggtgaggc cggatgtcga ggcggcgtta gcgtccggct atgcgctcgt caccatttgg   21660
gagcacatgc gggaaacggg gaaggtcaag ttctcctacg agacgttccg ctcgcacgcc   21720
aggcggcaca tcaaggccaa gcccgccgat gtgcccgcac cgcaggccaa ggctgcggaa   21780
cccgcgccgc cacccaagac gccggagcca cggcggccga agcaggggg caaggctgaa   21840 aagccggccc ccgctgcggc cccgaccggc ttcaccttca acccaacacc ggacaaaaag   21900
```

```
gatctactgt aatggcgaaa attcacatgg ttttgcaggg caagggcggg gtcggcaagt    21960
cggccatcgc cgcgatcatt gcgcagtaca agatggacaa ggggcagaca cccttgtgca    22020
tcgacaccga cccggtgaac gcgacgttcg agggctacaa ggccctgaac gtccgccggc    22080
tgaacatcat ggccggcgac gaaattaact cgcgcaactt cgacaccctg gtcgagctga    22140
ttgcgccgac caaggatgac gtggtgatcg acaacggtgc cagctcgttc gtgcctctgt    22200
cgcattacct catcagcaac caggtgccgg ctctgctgca agaaatgggg catgagctgg    22260
tcatccatac cgtcgtcacc ggcggccagg ctctcctgga cacggtgagc ggcttcgccc    22320
agctcgccag ccagttcccg gccgaagcgc ttttcgtggt ctggctgaac ccgtattggg    22380
ggcctatcga gcatgagggc aagagctttg agcagatgaa ggcgtacacg gccaacaagg    22440
cccgcgtgtc gtccatcatc cagattccgg ccctcaagga agaaacctac ggccgcgatt    22500
tcagcgacat gctgcaagag cggctgacgt tcgaccaggc gctggccgat gaatcgctca    22560
cgatcatgac gcggcaacgc ctcaagatcg tgcggcgcgg cctgtttgaa cagctcgacg    22620
cggcggccgt gctatgagcg accagattga agagctgatc cgggagattg cggccaagca    22680
cggcatcgcc gtcggccgcg acgacccggt gctgatcctg cataccatca cgcccggct    22740
catggccgac agtgcggcca agcaagagga aatccttgcc gcgttcaagg aagagctgga    22800
agggatcgcc catcgttggg gcgaggacgc caaggccaaa gcggagcgga tgctgaacgc    22860
ggccctggcg gccagcaagg acgcaatggc gaaggtaatg aaggacagcg ccgcgcaggc    22920
ggccgaagcg atccgcaggg aaatcgacga cggccttggc cgccagctcg cggccaaggt    22980
cgcggacgcg cggcgcgtgg cgatgatgaa catgatcgcc ggcggcatgg tgttgttcgc    23040
ggccgccctg gtggtgtggg cctcgttatg aatcgcagag gcgcagatga aaaagcccgg    23100
cgttgccggg cttttgttttt gcgttagctg ggcttgtttg acaggcccaa gctctgactg    23160
cgcccgcgct cgcgctcctg ggcctgtttc ttctcctgct cctgcttgcg catcagggcc    23220
tggtgccgtc gggctgcttc acgcatcgaa tcccagtcgc cggccagctc gggatgctcc    23280
gcgcgcatct tgcgcgtcgc cagttcctcg atcttgggcg cgtgaatgcc catgccttcc    23340
ttgatttcgc gcaccatgtc cagccgcgtg tgcagggtct gcaagcgggc ttgctgttgg    23400
gcctgctgct gctgccaggc ggcctttgta cgcggcaggg acagcaagcc ggggcattg    23460
gactgtagct gctgcaaacg cgcctgctga cggtctacga gctgttctag gcggtcctcg    23520
atgcgctcca cctggtcatg ctttgcctgc acgtagagcg caagggtctg ctggtaggtc    23580
tgctcgatgg gcgcggattc taagagggcc tgctgttccg tctcggcctc ctgggccgcc    23640
tgtagcaaat cctcgccgct gttgccgctg gactgcttta ctgccgggga ctgctgttgc    23700
cctgctcgcg ccgtcgtcgc agttcggctt gcccccactc gattgactgc ttcatttcga    23760
gccgcagcga tgcgatctcg gattgcgtca acggacgggg cagcgcggag gtgtccggct    23820
tctccttggg tgagtcggtc gatgccatag ccaaaggttt ccttccaaaa tgcgtccatt    23880
gctggaccgt gtttctcatt gatgcccgca agcatcttcg gcttgaccgc caggtcaagc    23940
gcgccttcat gggcggtcat gacggacgcc gccatgacct tgccgccgtt gttctcgatg    24000
tagccgcgta atgaggcaat ggtgccgccc atcgtcagcg tgtcatcgac aacgatgtac    24060
ttctggccgg ggatcaccte cccctcgaaa gtcgggttga acgccaggcg atgatctgaa    24120
ccggctccgg ttcgggcgac cttctcccgc tgcacaatgt ccgtttcgac ctcaaggcca    24180
aggcggtcgg ccagaacgac cgccatcatg gccggaatct tgttgttccc cgccgcctcg    24240
```

```
acggcgagga ctggaacgat gcggggcttg tcgtcgccga tcagcgtctt gagctgggca   24300
acagtgtcgt ccgaaatcag gcgctcgacc aaattaagcg ccgcttccgc gtcgccctgc   24360
ttcgcagcct ggtattcagg ctcgttggtc aaagaaccaa ggtcgccgtt gcgaaccacc   24420
ttcgggaagt ctccccacgg tgcgcgctcg gctctgctgt agctgctcaa gacgcctccc   24480
tttttagccg ctaaaactct aacgagtgcg cccgcgactc aacttgacgc tttcggcact   24540
tacctgtgcc ttgccacttg cgtcataggt gatgcttttc gcactcccga tttcaggtac   24600
tttatcgaaa tctgaccggg cgtgcattac aaagttcttc cccacctgtt ggtaaatgct   24660
gccgctatct gcgtggacga tgctgccgtc gtggcgctgc gacttatcgg ccttttgggc   24720
catatagatg ttgtaaatgc caggtttcag ggccccggct ttatctacct tctggttcgt   24780
ccatgcgcct tggttctcgg tctggacaat tctttgccca ttcatgacca ggaggcggtg   24840
tttcattggg tgactcctga cggttgcctc tggtgttaaa cgtgtcctgg tcgcttgccg   24900
gctaaaaaaa agccgacctc ggcagttcga ggccggcttt ccctagagcc gggcgcgtca   24960
aggttgttcc atctatttta gtgaactgcg ttcgatttat cagttacttt cctcccgctt   25020
tgtgtttcct cccactcgtt tccgcgtcta gccgaccect caacatagcg gcctcttctt   25080
gggctgcctt tgcctcttgc cgcgcttcgt cacgctcggc ttgcaccgtc gtaaagcgct   25140
cggcctgcct ggccgcctct tgcgccgcca acttcctttg ctcctggtgg gcctcggcgt   25200
cggcctgcgc cttcgctttc accgctgcca actccgtgcg caaactctcc gcttcgcgcc   25260
tggtggcgtc gcgctcgccg cgaagcgcct gcatttcctg gttggccgcg tccagggtct   25320
tgcggctctc ttctttgaat gcgcgggcgt cctggtgagc gtagtccagc tcggcgcgca   25380
gctcctgcgc tcgacgctcc acctcgtcgg cccgctgcgt cgccagcgcg gcccgctgct   25440
cggctcctgc cagggcggtg cgtgcttcgg ccagggcttg ccgctggcgt gcggccagct   25500
cggccgcctc ggcggcctgc tgctctagca atgtaacgcg cgcctgggct tcttccagct   25560
cgcgggcctg cgcctcgaag gcgtcggcca gctcccgcg cacggcttcc aactcgttgc   25620
gctcacgatc ccagccggct tgcgctgcct gcaacgattc attggcaagg gcctgggcgg   25680
cttgccagag ggcggccacg gcctggttgc cggcctgctg caccgcgtcc ggcacctgga   25740
ctgccagcgg ggcggcctgc gccgtgcgct ggcgtcgcca ttcgcgcatg ccggcgctgg   25800
cgtcgttcat gttgacgcgg gcggccttac gcactgcatc cacggtcggg aagttctccc   25860
ggtcgccttg ctcgaacagc tcgtccgcag ccgcaaaaat gcggtcgcgc gtctctttgt   25920
tcagttccat gttggctccg gtaattggta agaataataa tactcttacc taccttatca   25980
gcgcaagagt ttagctgaac agttctcgac ttaacggcag gttttttagc ggctgaaggg   26040
caggcaaaaa aagccccgca cggtcggcgg gggcaaaggg tcagcgggaa ggggattagc   26100
gggcgtcggg cttcttcatg cgtcggggcc gcgcttcttg ggatggagca cgacgaagcg   26160
cgcacgcgca tcgtcctcgg ccctatcggc ccgcgtcgcg gtcaggaact tgtcgcgcgc   26220
taggtcctcc ctggtgggca ccaggggcat gaactcggcc tgctcgatgt aggtccactc   26280
catgaccgca tcgcagtcga ggccgcgttc cttcaccgtc tcttgcaggt cgcggtacgc   26340
ccgctcgttg agcggctggt aacgggccaa ttggtcgtaa atggctgtcg gccatgagcg   26400
gcctttcctg ttgagccagc agccgacgac gaagccggca atgcaggccc ctggcacaac   26460
caggccgacg ccggggcag gggatggcag cagctcgcca accaggaacc ccgccgcgat   26520
gatgccgatg ccggtcaacc agcccttgaa actatccggc cccgaaacac ccctgcgcat   26580
tgcctggatg ctgcgccgga tagcttgcaa catcaggagc cgtttctttt gttcgtcagt   26640
```

```
catggtccgc cctcaccagt tgttcgtatc ggtgtcggac gaactgaaat cgcaagagct  26700
gccggtatcg gtccagccgc tgtccgtgtc gctgctgccg aagcacggcg aggggtccgc  26760
gaacgccgca gacggcgtat ccggccgcag cgcatcgccc agcatggccc cggtcagcga  26820
gccgccggcc aggtagccca gcatggtgct gttggtcgcc ccggccacca gggccgacgt  26880
gacgaaatcg ccgtcattcc ctctggattg ttcgctgctc ggcggggcag tgcgccgcgc  26940
cggcggcgtc gtggatggct cgggttggct ggcctgcgac ggccggcgaa aggtgcgcag  27000
cagctcgtta tcgaccggct gcggcgtcgg ggccgccgcc ttgcgctgcg gtcggtgttc  27060
cttcttcggc tcgcgcagct tgaacagcat gatcgcggaa accagcagca acgccgcgcc  27120
tacgcctccc gcgatgtaga acagcatcgg attcattctt cggtcctcct tgtagcggaa  27180
ccgttgtctg tgcggcgcgg gtggcccgcg ccgctgtctt tggggatcag ccctcgatga  27240
gcgcgaccag tttcacgtcg gcaaggttcg cctcgaactc ctggccgtcg tcctcgtact  27300
tcaaccaggc atagccttcc gccggcgccc gacggttgag gataaggcgg gcagggcgct  27360
cgtcgtgctc gacctggacg atggccttt tcagcttgtc cgggtccggc tccttcgcgc  27420
cctttccctt ggcgtcctta ccgtcctggt cgccgtcctc gccgtcctgg ccgtcgccgg  27480
cctccgcgtc acgctcggca tcagtctggc cgttgaaggc atcgacggtg ttgggatcgc  27540
ggcccttctc gtccaggaac tcgcgcagca gcttgaccgt gccgcgcgtg atttcctggg  27600
tgtcgtcgtc aagccacgcc tcgacttcct ccgggcgctt cttgaaggcc gtcaccagct  27660
cgttcaccac ggtcacgtcg cgcacgcggc cggtgttgaa cgcatcggcg atcttctccg  27720
gcaggtccag cagcgtgacg tgctgggtga tgaacgccgg cgacttgccg atttccttgg  27780
cgatatcgcc tttcttcttg cccttcgcca gctcgcggcc aatgaagtcg gcaatttcgc  27840
gcggggtcag ctcgttgcgt tgcaggttct cgataacctg gtcggcttcg ttgtagtcgt  27900
tgtcgatgaa cgccgggatg gacttcttgc cggcccactt cgagccacgg tagcggcggg  27960
cgccgtgatt gatgatatag cggcccggct gctcctggtt ctcgcgcacc gaaatgggtg  28020
acttcacccc gcgctctttg atcgtggcac cgatttccgc gatgctctcc ggggaaaagc  28080
cggggttgtc ggccgtccgc ggctgatgcg gatcttcgtc gatcaggtcc aggtccagct  28140
cgatagggcc ggaaccgccc tgagacgccg caggagcgtc caggaggctc gacaggtcgc  28200
cgatgctatc caaccccagg ccggacggct gcgccgcgcc tgcggcttcc tgagcggccg  28260
cagcggtgtt tttcttggtg gtcttggctt gagccgcagt cattgggaaa tctccatctt  28320
cgtgaacacg taatcagcca gggcgcgaac ctctttcgat gccttgcgcg cggccgtttt  28380
cttgatcttc cagaccggca caccggatgc gagggcatcg gcgatgctgc tgcgcaggcc  28440
aacggtggcc ggaatcatca tcttggggta cgcggccagc agctcggctt ggtgcgcgc  28500 gtggcgcgga ttccgcgcat cgaccttgct gggcaccatg ccaaggaatt gcagcttggc  28560
gttcttctgg cgcacgttcg caatggtcgt gaccatcttc ttgatgccct ggatgctgta  28620
cgcctcaagc tcgatggggg acagcacata gtcggccgcg aagagggcgg ccgccaggcc  28680
gacgccaagg gtcggggccg tgtcgatcag gcacacgtcg aagccttggt tcgccagggc  28740
cttgatgttc gccccgaaca gctcgcgggc gtcgtccagc gacagccgtt cggcgttcgc  28800
cagtaccggg ttggactcga tgagggcgag gcgcgcggcc tggccgtcgc cggctgcggg  28860
tgcggtttcg gtccagccgc cggcagggac agcgccgaac agcttgcttg catgcaggcc  28920
ggtagcaaag tccttgagcg tgtaggacgc attgccctgg gggtccaggt cgatcacggc  28980
```

```
aacccgcaag ccgcgctcga aaaagtcgaa ggcaagatgc acaagggtcg aagtcttgcc    29040
gacgccgcct ttctggttgg ccgtgaccaa agttttcatc gtttggtttc ctgttttttc    29100
ttggcgtccg cttcccactt ccggacgatg tacgcctgat gttccggcag aaccgccgtt    29160
acccgcgcgt acccctcggg caagttcttg tcctcgaacg cggcccacac gcgatgcacc    29220
gcttgcgaca ctgcgcccct ggtcagtccc agcgacgttg cgaacgtcgc ctgtggcttc    29280
ccatcgacta agacgcccg cgctatctcg atggtctgct gccccacttc agcccctgg     29340
atcgcctcct ggaactggct ttcggtaagc cgtttcttca tggataacac ccataatttg    29400
ctccgcgcct tggttgaaca tagcggtgac agccgccagc acatgagaga agtttagcta    29460
aacatttctc gcacgtcaac acctttagcc gctaaaactc gtccttggcg taacaaaaca    29520
aaagcccgga aaccgggctt tcgtctcttg ccgcttatgg ctctgcaccc ggctccatca    29580
ccaacaggtc gcgcacgcgc ttcactcggt tgcggatcga cactgccagc ccaacaaagc    29640
cggttgccgc cgccgccagg atcgcgccga tgatgccggc cacaccgcc atcgcccacc     29700
aggtcgccgc cttccggttc cattcctgct ggtactgctt cgcaatgctg gacctcggct    29760
caccataggc tgaccgctcg atggcgtatg ccgcttctcc ccttggcgta aacccagcg     29820
ccgcaggcgg cattgccatg ctgcccgccg cttccccgac cacgacgcgc gcaccaggct    29880
tgcggtccag accttcggcc acggcgagct gcgcaaggac ataatcagcc gccgacttgg    29940
ctccacgcgc ctcgatcagc tcttgcactc gcgcgaaatc cttggcctcc acggccgcca    30000
tgaatcgcgc acgcggcgaa ggctccgcag ggccggcgtc gtgatcgccg ccgagaatgc    30060
ccttcaccaa gttcgacgac acgaaaatca tgctgacggc tatcaccatc atgcagacgg    30120
atcgcacgaa cccgctgaat tgaacacgag cacggcaccc gcgaccacta tgccaagaat    30180
gcccaaggta aaaattgccg gccccgccat gaagtccgtg aatgcccga cggccgaagt     30240
gaagggcagg ccgccaccca ggccgccgcc ctcactgccc ggcacctggt cgctgaatgt    30300
cgatgccagc acctgcggca cgtcaatgct tccgggcgtc gcgctcgggc tgatcgccca    30360
tcccgttact gccccgatcc cggcaatggc aaggactgcc agcgctgcca tttttgggt     30420
gaggccgttc gcggccgagg ggcgcagccc tgggggggat gggaggcccg cgttagcggg    30480
ccgggagggt tcgagaaggg ggggcacccc ccttcggcgt gcgcggtcac gcgcacaggg    30540
cgcagccctg gttaaaaaca aggttttataa atattggttt aaaagcaggt taaaagacag    30600
gttagcggtg gccgaaaaac gggcggaaac ccttgcaaat gctggatttt ctgcctgtgg    30660
acagcccctc aaatgtcaat aggtgcgccc ctcatctgtc agcactctgc ccctcaagtg    30720
tcaaggatcg cgcccctcat ctgtcagtag tcgcgcccct caagtgtcaa taccgcaggg    30780
cacttatccc caggcttgtc cacatcatct gtgggaaact cgcgtaaaat caggcgtttt    30840
cgccgatttg cgaggctggc cagctccacg tcgccggccg aaatcgagcc tgcccctcat    30900
ctgtcaacgc cgcgccgggt gagtcggccc ctcaagtgtc aacgtccgcc cctcatctgt    30960
cagtgagggc caagttttcc gcgaggtatc cacaacgccg gcggccgcgg tgtctcgcac    31020
acggcttcga cggcgtttct ggcgcgtttg cagggccata gacggccgcc agcccagcgg    31080
cgagggcaac cagcccggtg agcgtcggaa aggcgctgga agcccgtag cgacgcgag     31140
aggggcgaga caagccaagg gcgcaggctc gatgcgcagc acgacatagc cggttctcgc    31200
aaggacgaga atttccctgc ggtgcccctc aagtgtcaat gaaagtttcc aacgcgagcc    31260
attcgcgaga gccttgagtc cacgctagat gagagctttt tgtaggtgg accagttggt     31320
gattttgaac ttttgctttg ccacggaacg gtctgcgttg tcgggaagat gcgtgatctg    31380
```

```
atccttcaac tcagcaaaag ttcgatttat tcaacaaagc cacgttgtgt ctcaaaatct   31440
ctgatgttac attgcacaag ataaaaatat atcatcatga acaataaaac tgtctgctta   31500
cataaacagt aatacaaggg gtgttatgag ccatattcaa cgggaaacgt cttgctcgac   31560
tctagagctc gttcctcgag gaacggtacc tgcggggaag cttacaataa tgtgtgttgt   31620
taagtcttgt tgcctgtcat cgtctgactg actttcgtca taaatcccgg cctccgtaac   31680
ccagctttgg gcaagctcac ggatttgatc cggcggaacg ggaatatcga gatgccgggc   31740
tgaacgctgc agttccagct ttccctttcg ggacaggtac tccagctgat tgattatctg   31800
ctgaagggtc ttggttccac ctcctggcac aatgcgaatg attacttgag cgcgatcggg   31860
catccaattt tctcccgtca ggtgcgtggt caagtgctac aaggcacctt tcagtaacga   31920
gcgaccgtcg atccgtcgcc gggatacgga caaaatggag cgcagtagtc catcgagggc   31980
ggcgaaagcc tcgccaaaag caatacgttc atctcgcaca gcctccagat ccgatcgagg   32040
gtcttcggcg taggcagata gaagcatgga tacattgctt gagagtattc cgatggactg   32100
aagtatggct tccatctttt ctcgtgtgtc tgcatctatt tcgagaaagc ccccgatgcg   32160
gcgcaccgca acgcgaattg ccatactatc cgaaagtccc agcaggcgcg cttgatagga   32220
aaaggtttca tactcggccg atcgcagacg ggcactcacg accttgaacc cttcaacttt   32280
cagggatcga tgctggttga tggtagtctc actcgacgtg gctctggtgt gttttgacat   32340
agcttcctcc aaagaaagcg gaaggtctgg atactccagc acgaaatgtg cccgggtaga   32400
cggatggaag tctagccctg ctcaatatga aatcaacagt acatttacag tcaatactga   32460
atatacttgc tacatttgca attgtcttat aacgaatgtg aaataaaaat agtgtaacaa   32520
cgcttttact catcgataat cacaaaaaca tttatacgaa caaaaataca aatgcactcc   32580
ggtttcacag gataggcggg atcagaatat gcaactttg acgttttgtt cttttcaaagg   32640 gggtgctggc aaaaccaccg cactcatggg cctttgcgct gctttggcaa atgacggtaa   32700
acgagtggcc ctctttgatg ccgacgaaaa ccggcctctg acgcgatgga gagaaaacgc   32760
cttacaaagc agtactggga tcctcgctgt gaagtctatt ccgccgacga aatgcccctt   32820
cttgaagcag cctatgaaaa tgccgagctc gaaggatttg attatgcgtt ggccgatacg   32880
cgtggcggct cgagcgagct caacaacaca atcatcgcta gctcaaacct gcttctgatc   32940
cccaccatgc taacgccgct cgacatcgat gaggcactat ctacctaccg ctacgtcatc   33000
gagctgctgt tgagtgaaaa tttggcaatt cctacagctg ttttgcgcca acgcgtcccg   33060
gtcggccgat tgacaacatc gcaacgcagg atgtcagaga cgctagagag ccttccagtt   33120
gtaccgtctc ccatgcatga aagagatgca tttgccgcga tgaaagaacg cggcatgttg   33180
catcttacat tactaaacac gggaactgat ccgacgatgc gcctcataga gaggaatctt   33240
cggattgcga tggaggaagt cgtggtcatt tcgaaactga tcagcaaaat cttggaggct   33300
tgaagatgga aattcgcaag cccgcattgt cggtcggcga agcacggcgg cttgctggtg   33360
ctcgacccga gatccaccat cccaacccga cacttgttcc ccagaagctg gacctccagc   33420
acttgcctga aaaagccgac gagaaagacc agcaacgtga gcctctcgtc gccgatcaca   33480
tttacagtcc cgatcgacaa cttaagctaa ctgtggatgc ccttagtcca cctccgtccc   33540
cgaaaaagct ccaggttttt ctttcagcgc gaccgcccgc gcctcaagtg tcgaaaacat   33600
atgcaacctt cgttcggcaa tacagtccct cgaagtcgct acaaatgatt ttaaggcgcg   33660
cgttggacga tttcgaaagc atgctggcag atggatcatt tcgcgtggcc ccgaaaagtt   33720
```

```
atccgatccc ttcaactaca gaaaaatccg ttctcgttca gacctcacgc atgttcccgg   33780
ttgcgttgct cgaggtcgct cgaagtcatt ttgatccgtt ggggttggag accgctcgag   33840
ctttcggcca caagctggct accgccgcgc tcgcgtcatt ctttgctgga gagaagccat   33900
cgagcaattg gtgaagaggg acctatcgga acccctcacc aaatattgag tgtaggtttg   33960
aggccgctgg ccgcgtcctc agtcaccttt tgagccagat aattaagagc caaatgcaat   34020
tggctcaggc tgccatcgtc cccccgtgcg aaacctgcac gtccgcgtca agaaataac    34080
cggcacctct tgctgttttt atcagttgag ggcttgacgg atccgcctca gtttgcggc    34140
gcagccgcaa aatgagaaca tctatactcc tgtcgtaaac ctcctcgtcg cgtactcgac   34200
tggcaatgag aagttgctcg cgcgatagaa cgtcgcgggg tttctctaaa aacgcgagga   34260
gaagattgaa ctcacctgcc gtaagtttca cctcaccgcc agcttcggac atcaagcgac   34320
gttgcctgag attaagtgtc cagtcagtaa aacaaaaaga ccgtcggtct ttggagcgga   34380
caacgttggg gcgcacgcgc aaggcaaccc gaatgcgtgc aagaaactct ctcgtactaa   34440
acggcttagc gataaaatca cttgctccta gctcgagtga acaacttta tccgtctcct    34500
caaggcggtc gccactgata attatgattg gaatatcaga ctttgccgcc agatttcgaa   34560
cgatctcaag cccatcttca cgacctaaat ttagatcaac aaccacgaca tcgaccgtcg   34620
cggaagagag tactctagtg aactgggtgc tgtcggctac cgcggtcact ttgaaggcgt   34680
ggatcgtaag gtattcgata taagatgcc gcatagcgac atcgtcatcg ataagaagaa    34740
cgtgtttcaa cggctcacct ttcaatctaa aatctgaacc cttgttcaca gcgcttgaga   34800
aattttcacg tgaaggatgt acaatcatct ccagctaaat gggcagttcg tcagaattgc   34860
ggctgaccgc ggatgacgaa aatgcgaacc aagtatttca atttatgac aaaagttctc    34920
aatcgttgtt acaagtgaaa cgcttcgagg ttacagctac tattgattaa ggagatcgcc   34980
tatggtctcg ccccggcgtc gtgcgtccgc cgcgagccag atctcgccta cttcataaac   35040
gtcctcatag gcacggaatg gaatgatgac atcgatcgcc gtagagagca tgtcaatcag   35100
tgtgcgatct tccaagctag caccttgggc gctacttttg acaagggaaa acagtttctt   35160
gaatccttgg attggattcg cgccgtgtat tgttgaaatc gatcccggat gtcccgagac   35220
gacttcactc agataagccc atgctgcatc gtcgcgcatc tcgccaagca atatccggtc   35280
cggccgcata cgcagacttg cttggagcaa gtgctcggcg ctcacagcac ccagcccagc   35340
accgttcttg gagtagagta gtctaacatg attatcgtgt ggaatgacga gttcgagcgt   35400
atcttctatg gtgattagcc tttcctgggg ggggatggcg ctgatcaagg tcttgctcat   35460
tgttgtcttg ccgcttccgg tagggccaca tagcaacatc gtcagtcggc tgacgacgca   35520
tgcgtgcaga aacgcttcca aatccccgtt gtcaaaatgc tgaaggatag cttcatcatc   35580
ctgattttgg cgtttccttc gtgtctgcca ctggttccac ctcgaagcat cataacggga   35640
ggagacttct ttaagaccag aaacacgcga gcttggccgt cgaatggtca agctgacggt   35700
gcccgaggga acgtcggcg gcagacagat ttgtagtcgt tcaccaccag gaagttcagt    35760
ggcgcagagg gggttacgtg gtccgacatc ctgctttctc agcgcgcccg ctaaaatagc   35820
gatatcttca agatcatcat aagagacggg caaaggcatc ttggtaaaaa tgccggcttg   35880
gcgcacaaat gcctctccag gtcgattgat cgcaatttct tcagtcttcg ggtcatcgag   35940
ccattccaaa atcggcttca gaagaaagcg tagttgcgga tccacttcca tttacaatgt   36000
atcctatctc taagcggaaa tttgaattca ttaagagcgg cggttcctcc cccgcgtggc   36060
gccgccagtc aggcggagct ggtaaacacc aaagaaatcg aggtcccgtg ctacgaaaat   36120
```

```
ggaaacggtg tcaccctgat tcttcttcag ggttggcggt atgttgatgg ttgccttaag   36180
ggctgtctca gttgtctgct caccgttatt ttgaaagctg ttgaagctca tcccgccacc   36240
cgagctgccg gcgtaggtgc tagctgcctg gaaggcgcct tgaacaacac tcaagagcat   36300
agctccgcta aaacgctgcc agaagtggct gtcgaccgag cccggcaatc ctgagcgacc   36360
gagttcgtcc gcgcttggcg atgttaacga gatcatcgca tggtcaggtg tctcggcgcg   36420
atcccacaac acaaaaacgc gcccatctcc ctgttgcaag ccacgctgta tttcgccaac   36480
aacggtggtg ccacgatcaa gaagcacgat attgttcgtt gttccacgaa tatcctgagg   36540
caagacacac tttacatagc ctgccaaatt tgtgtcgatt gcggtttgca agatgcacgg   36600
aattattgtc ccttgcgtta ccataaaatc ggggtgcggc aagagcgtgg cgctgctggg   36660
ctgcagctcg gtgggtttca tacgtatcga caaatcgttc tcgccggaca cttcgccatt   36720
cggcaaggag ttgtcgtcac gcttgccttc ttgtcttcgg cccgtgtcgc cctgaatggc   36780
gcgtttgctg accccttgat cgccgctgct atatgcaaaa atcggtgttt cttccggccg   36840
tggctcatgc cgctccggtt cgcccctcgg cggtagagga gcagcaggct gaacagcctc   36900
ttgaaccgct ggaggatccg gcggcacctc aatcggagct ggatgaaatg gcttggtgtt   36960
tgttgcgatc aaagttgacg gcgatgcgtt ctcattcacc ttcttttggc gcccacctag   37020
ccaaatgagg cttaatgata acgcgagaac gacacctccg acgatcaatt tctgagaccc   37080
cgaaagacgc cggcgatgtt tgtcggagac cagggatcca gatgcatcaa cctcatgtgc   37140
cgcttgctga ctatcgttat tcatcccttc gcccccttca ggacgcgttt cacatcgggc   37200
ctcaccgtgc ccgtttgcgg ccttggcca acgggatcgt aagcggtgtt ccagatacat   37260
agtactgtgt ggccatccct cagacgccaa cctcgggaaa ccgaagaaat ctcgacatcg   37320 ctcccttta actgaatagtt ggcaacagct tccttgccat caggattgat ggtgtagatg   37380
gagggtatgc gtacattgcc cggaaagtgg aataccgtcg taaatccatt gtcgaagact   37440
tcgagtggca acagcgaacg atcgccttgg gcgacgtagt gccaattact gtccgccgca   37500
ccaagggctg tgacaggctg atccaataaa ttctcagctt tccgttgata ttgtgcttcc   37560
gcgtgtagtc tgtccacaac agccttctgt tgtgcctccc ttcgccgagc cgccgcatcg   37620
tcggcggggt aggcgaattg gacgctgtaa tagagatcgg gctgctcttt atcgaggtgg   37680
gacagagtct tggaacttat actgaaaaca taacggcgca tcccgagtc gcttgcggtt   37740 agcacgatta ctggctgagg cgtgaggacc tggcttgcct tgaaaaatag ataatttccc   37800
cgcggtaggc ctgctagatc tttgctattt gaaacggcaa ccgctgtcac cgtttcgttc   37860
gtggcgaatg ttacgaccaa agtagctcca accgccgtcg agaggcgcac cacttgatcg   37920
ggattgtaag ccaaataacg catgcgcgga tctagcttgc ccgccattgg agtgtcttca   37980
gcctccgcac cagtcgcagc ggcaaataaa catgctaaaa tgaaaagtgc ttttctgatc   38040
atggttcgct gtggcctacg tttgaaacgg tatcttccga tgtctgatag gaggtgacaa   38100
ccagacctgc cgggttggtt agtctcaatc tgccgggcaa gctggtcacc ttttcgtagc   38160
gaactgtcgc ggtccacgta ctcaccacag gcattttgcc gtcaacgacg agggtccttt   38220
tatagcgaat ttgctgcgtg cttggagtta catcatttga agcgatgtgc tcgacctcca   38280
ccctgccgcg tttgccaaga atgacttgag gcgaactggg attgggatag ttgaagaatt   38340
gctggtaatc ctgcgcact gttggggcac tgaagttcga taccaggtcg taggcgtact   38400
gagcggtgtc ggcatcataa ctctcgcgca ggcgaacgta ctcccacaat gaggcgttaa   38460
```

```
cgacggcctc ctcttgagtt gcaggcaatc gcgagacaga cacctcgctg tcaacggtgc   38520
cgtccggccg tatccataga tatacgggca caagcctgct caacggcacc attgtggcta   38580
tagcgaacgc ttgagcaaca tttcccaaaa tcgcgatagc tgcgacagct gcaatgagtt   38640
tggagagacg tcgcgccgat ttcgctcgcg cggtttgaaa ggcttctact tccttatagt   38700
gctcggcaag gctttcgcgc gccactagca tggcatattc aggcccgtc atagcgtcca    38760 cccgaattgc cgagctgaag atctgacgga gtaggctgcc atcgcccac attcagcggg    38820 aagatcgggc ctttgcagct cgctaatgtg tcgtttgtct ggcagccgct caaagcgaca   38880
actaggcaca gcaggcaata cttcatgaa ttctccattg aggcgaattt ttgcgcgacc    38940
tagcctcgct caacctgagc gaagcgacgg tacaagctgc tggcagattg ggttgcgccg   39000
ctccagtaac tgcctccaat gttgccggcg atcgccggca aagcgacaat gagcgcatcc   39060
cctgtcagaa aaacatatc gagttcgtaa agaccaatga tcttggccgc ggtcgtaccg    39120
gcgaaggtga ttacaccaag cataagggtg agcgcagtcg cttcggttag gatgacgatc   39180
gttgccacga ggtttaagag gagaagcaag agaccgtagg tgataagttg cccgatccac   39240
ttagctgcga tgtcccgcgt gcgatcaaaa atatatccga cgaggatcag aggcccgatc   39300
gcgagaagca ctttcgtgag aattccaacg gcgtcgtaaa ctccgaaggc agaccagagc   39360
gtgccgtaaa ggacccactg tgcccccttgg aaagcaagga tgtcctggtc gttcatcgga  39420
ccgatttcgg atgcgatttt ctgaaaaacg gcctgggtca cggcgaacat tgtatccaac   39480
tgtgccggaa cagtctgcag aggcaagccg gttacactaa actgctgaac aaagtttggg   39540
accgtctttt cgaagatgga aaccacatag tcttggtagt tagcctgccc aacaattaga   39600
gcaacaacga tggtgaccgt gatcacccga gtgataccgc tacgggtatc gacttcgccg   39660
cgtatgacta aaataccctg aacaataatc caaagagtga cacaggcgat caatggcgca   39720
ctcaccgcct cctggatagt ctcaagcatc gagtccaagc ctgtcgtgaa ggctacatcg   39780
aagatcgtat gaatggccgt aaacggcgcc ggaatcgtga aattcatcga ttggacctga   39840
acttgactgg tttgtcgcat aatgttggat aaaatgagct cgcattcggc gaggatgcgg   39900
gcggatgaac aaatcgccca gccttagggg agggcaccaa agatgacagc ggtcttttga   39960
tgctccttgc gttgagcggc cgcctcttcc gcctcgtgaa ggccggcctg cgcggtagtc   40020
atcgttaata ggcttgtcgc ctgtacattt tgaatcattg cgtcatggat ctgcttgaga   40080
agcaaaccat tggtcacggt tgcctgcatg atattgcgag atcgggaaag ctgagcagac   40140
gtatcagcat tcgccgtcaa gcgtttgtcc atcgtttcca gattgtcagc cgcaatgcca   40200
gcgctgtttg cggaaccggt gatctgcgat cgcaacaggt ccgcttcagc atcactaccc   40260
acgactgcac gatctgtatc gctggtgatc gcacgtgccg tggtcgacat tggcattcgc   40320
ggcgaaaaca tttcattgtc taggtccttc gtcgaaggat actgattttt ctggttgagc   40380
gaagtcagta gtccagtaac gccgtaggcc gacgtcaaca tcgtaaccat cgctatagtc   40440
tgagtgagat tctccgcagt cgcgagcgca gtcgcgagcg tctcagcctc cgttgccggg   40500
tcgctaacaa caaactgcgc ccgcgcgggc tgaatatata gaaagctgca ggtcaaaact   40560
gttgcaataa gttgcgtcgt cttcatcgtt tcctaccta tcaatcttct gcctcgtggt    40620
gacgggccat gaattcgctg agccagccag atgagttgcc ttcttgtgcc tcgcgtagtc   40680
gagttgcaaa gcgcaccgtg ttggcacgcc ccgaaagcac ggcgacatat tcacgcatat   40740
cccgcagatc aaattcgcag atgacgcttc cactttctcg tttaagaaga aacttacggc   40800
tgccgaccgt catgtcttca cggatcgcct gaaattcctt ttcggtacat ttcagtccat   40860
```

```
cgacataagc cgatcgatct gcggttggtg atggatagaa aatcttcgtc atacattgcg    40920
caaccaagct ggctcctagc ggcgattcca gaacatgctc tggttgctgc gttgccagta    40980
ttagcatccc gttgttttt cgaacggtca ggaggaattt gtcgacgaca gtcgaaaatt     41040
tagggtttaa caaataggcg cgaaactcat cgcagctcat cacaaaacgg cggccgtcga    41100
tcatggctcc aatccgatgc aggagatatg ctgcagcggg agcgcatact tcctcgtatt    41160
cgagaagatg cgtcatgtcg aagccggtaa tcgacggatc taactttact tcgtcaactt    41220
cgccgtcaaa tgcccagcca agcgcatggc cccggcacca gcgttggagc gcgctcctg    41280
cgccttcggc gggcccatgc aacaaaaatt cacgtaaccc cgcgattgaa cgcatttgtg    41340
gatcaaacga gagctgacga tggataccac ggaccagacg gcggttctct tccggagaaa    41400
tcccaccccg accatcactc tcgatgagag ccacgatcca ttcgcgcaga aaatcgtgtg    41460
aggctgctgt gttttctagg ccacgcaacg gcgccaaccc gctgggtgtg cctctgtgaa    41520
gtgccaaata tgttcctcct gtggcgcgaa ccagcaattc gccaccccgg tccttgtcaa    41580
agaacacgac cgtacctgca cggtcgacca tgctctgttc gagcatggct agaacaaaca    41640
tcatgagcgt cgtcttaccc ctcccgatag gcccgaatat tgccgtcatg ccaacatcgt    41700
gctcatgcgg gatatagtcg aaaggcgttc cgccattggt acgaaatcgg gcaatcgcgt    41760
tgccccagtg gcctgagctg gcgccctctg gaaagttttc gaaagagaca accctgcga    41820
aattgcgtga agtgattgcg ccagggcgtg tgcgccactt aaaattcccc ggcaattggg    41880
accaataggc cgcttccata ccaataccct cttggacaac cacggcacct gcatccgcca    41940
ttcgtgtccg agcccgcgcg cccctgtccc caagactatt gagatcgtct gcatagacgc    42000
aaaggctcaa atgatgtgag cccataacga attcgttgct cgcaagtgcg tcctcagcct    42060
cggataattt gccgatttga gtcacggctt tatcgccgga actcagcatc tggctcgatt    42120
tgaggctaag tttcgcgtgc gcttgcgggc gagtcaggaa cgaaaaactc tgcgtgagaa    42180
caagtggaaa atcgagggat agcagcgcgt tgagcatgcc cggccgtgtt tttgcagggt    42240
attcgcgaaa cgaatagatg gatccaacgt aactgtcttt tggcgttctg atctcgagtc    42300
ctcgcttgcc gcaaatgact ctgtcggtat aaatcgaagc gccgagtgag ccgctgacga    42360
ccggaaccgg tgtgaaccga ccagtcatga tcaaccgtag cgcttcgcca atttcggtga    42420
agagcacacc ctgcttctcg cggatgccaa gacgatgcag gccatacgct ttaagagagc    42480
cagcgacaac atgccaaaga tcttccatgt tcctgatctg gcccgtgaga tcgtttttccc    42540
tttttccgct tagcttggtg aacctcctct ttaccttccc taaagccgcc tgtgggtaga    42600
caatcaacgt aaggaagtgt tcattgcgga ggagttggcc ggagagcacg cgctgttcaa    42660
aagcttcgtt caggctagcg gcgaaaacac tacggaagtg tcgcggcgcc gatgatggca    42720
cgtcggcatg acgtacgagg tgagcatata ttgacacatg atcatcagcg atattgcgca    42780
acagcgtgtt gaacgcacga caacgcgcat tgcgcatttc agtttcctca agctcgaatg    42840
caacgccatc aattctcgca atggtcatga tcgatccgtc ttcaagaagg acgatatggt    42900
cgctgaggtg gccaatataa gggagataga tctcaccgga tctttcggtc gttccactcg    42960
cgccgagcat cacaccattc ctctccctcg tgggggaacc ctaattggat ttgggctaac    43020
agtagcgccc ccccaaactg cactatcaat gcttcttccc gcggtccgca aaaatagcag    43080
gacgacgctc gccgcattgt agtctcgctc cacgatgagc cgggctgcaa accataacg    43140
cacgagaacg acttcgtaga gcgggttctg aacgataacg atgacaaagc cggcgaacat    43200
```

| | |
|---|---|
| catgaataac cctgccaatg tcagtggcac cccaagaaac aatgcgggcc gtgtggctgc | 43260 |
| gaggtaaagg gtcgattctt ccaaacgatc agccatcaac taccgccagt gagcgtttgg | 43320 |
| ccgaggaagc tcgccccaaa catgataaca atgccgccga cgacgccggc aaccagccca | 43380 |
| agcgaagccc gcccgaacat ccaggagatc ccgatagcga caatgccgag aacagcgagt | 43440 |
| gactggccga acggaccaag gataaacgtg catatattgt taaccattgt ggcggggtca | 43500 |
| gtgccgccac ccgcagattg cgctgcggcg ggtccggatg aggaaatgct ccatgcaatt | 43560 |
| gcaccgcaca agcttggggc gcagctcgat atcacgcgca tcatcgcatt cgagagcgag | 43620 |
| aggcgattta gatgtaaacg gtatctctca aagcatcgca tcaatgcgca cctccttagt | 43680 |
| ataagtcgaa taagacttga ttgtcgtctg cggatttgcc gttgtcctgg tgtggcggtg | 43740 |
| gcggagcgat taaccgcca gcgccatcct cctgcgagcg gcgctgatat gaccccaaa | 43800 |
| catcccacgt ctcttcggat tttagcgcct cgtgatcgtc ttttggaggc tcgattaacg | 43860 |
| cgggcaccag cgattgagca gctgtttcaa cttttcgcac gtagccgttt gcaaaaccgc | 43920 |
| cgatgaaatt accggtgttg taagcggaga tcgcccgacg aagcgcaaat tgcttctcgt | 43980 |
| caatcgtttc gccgcctgca taacgacttt tcagcatgtt tgcagcggca gataatgatg | 44040 |
| tgcacgcctg gagcgcaccg tcaggtgtca gaccgagcat agaaaaattt cgagagttta | 44100 |
| tttgcatgag gccaacatcc agcgaatgcc gtgcatcgag acggtgcctg acgacttggg | 44160 |
| ttgcttggct gtgatcttgc cagtgaagcg tttcgccggt cgtgttgtca tgaatcgcta | 44220 |
| aaggatcaaa gcgactctcc accttagcta tcgccgcaag cgtagatgtc gcaactgatg | 44280 |
| gggcacactt gcgagcaaca tggtcaaact cagcagatga gagtggcgtg gcaaggctcg | 44340 |
| acgaacagaa ggagaccatc aaggcaagag aaagcgaccc cgatctctta agcataccct | 44400 |
| atctccttag ctcgcaacta acaccgcctc tcccgttgga agaagtgcgt tgttttatgt | 44460 |
| tgaagattat cgggagggtc ggttactcga aaattttcaa ttgcttcttt atgatttcaa | 44520 |
| ttgaagcgag aaacctcgcc cggcgtcttg gaacgcaaca tggaccgaga accgcgcatc | 44580 |
| catgactaag caaccggatc gacctattca ggccgcagtt ggtcaggtca ggctcagaac | 44640 |
| gaaaatgctc ggcgaggtta cgctgtctgt aaacccattc gatgaacggg aagcttcctt | 44700 |
| ccgattgctc ttggcaggaa tattggccca tgcctgcttg cgcttttgcaa atgctcttat | 44760 |
| cgcgttggta tcatatgcct tgtccgccag cagaaacgca ctctaagcga ttatttgtaa | 44820 |
| aaatgtttcg gtcatgcggc ggtcatgggc ttgacccgct gtcagcgcaa gacggatcgg | 44880 |
| tcaaccgtcg gcatcgacaa cagcgtgaat cttggtggtc aaaccgccac gggaacgtcc | 44940 |
| catacagcca tcgtcttgat cccgctgttt cccgtcgccg catgttggtg gacgcggaca | 45000 |
| caggaactgt caatcatgac gacattctat cgaaagcctt ggaaatcaca ctcagaatat | 45060 |
| gatcccagac gtctgcctca cgccatcgta caaagcgatt gtagcaggtt gtacaggaac | 45120 |
| cgtatcgatc aggaacgtct gcccagggcg ggcccgtccg gaagcgccac aagatgacat | 45180 |
| tgatcacccg cgtcaacgcg cggcacgcga cgcggcttat ttgggaacaa aggactgaac | 45240 |
| aacagtccat tcgaaatcgg tgacatcaaa gcggggacgg gttatcagtg gcctccaagt | 45300 |
| caagcctcaa tgaatcaaaa tcagaccgat ttgcaaacct gatttatgag tgtgcggcct | 45360 |
| aaatgatgaa atcgtccttc tagatcgcct ccgtggtgta gcaacacctc gcagtatcgc | 45420 |
| cgtgctgacc ttggccaggg aattgactgg caagggtgct ttcacatgac cgctctttg | 45480 |
| gccgcgatag atgatttcgt tgctgctttg ggcacgtaga aggagagaag tcatatcgga | 45540 |
| gaaattcctc ctggcgcgag agcctgctct atcgcgacgg catcccactg tcgggaacag | 45600 |

```
accggatcat tcacgaggcg aaagtcgtca acacatgcgt tataggcatc ttcccttgaa    45660
ggatgatctt gttgctgcca atctggaggt gcggcagccg caggcagatg cgatctcagc    45720
gcaacttgcg gcaaaacatc tcactcacct gaaaaccact agcgagtctc gcgatcagac    45780
gaaggccttt tacttaacga cacaaatatcc gatgtctgca tcacaggcgt cgctatccca    45840
gtcaatacta aagcggtgca ggaactaaag attactgatg acttaggcgt gccacgaggc    45900
ctgagacgac gcgcgtagac agttttttga aatcattatc aaagtgatgg cctccgctga    45960
agcctatcac ctctgcgccg gtctgtcgga gagatgggca agcattatta cggtcttcgc    46020
gcccgtacat gcattggacg attgcagggt caatggatct gagatcatcc agaggattgc    46080
cgcccttacc ttccgtttcg agttggagcc agcccctaaa tgagacgaca tagtcgactt    46140
gatgtgacaa tgccaagaga gagatttgct taacccgatt ttttttgctca agcgtaagcc    46200
tattgaagct tgccggcatg acgtccgcgc cgaaagaata tcctacaagt aaaacattct    46260
gcacaccgaa atgcttggtg tagacatcga ttatgtgacc aagatcctta gcagtttcgc    46320
ttggggaccg ctccgaccag aaataccgaa gtgaactgac gccaatgaca ggaatccctt    46380
ccgtctgcag ataggtacca tcgatagatc tgctgcctcg cgcgtttcgg tgatgacggt    46440
gaaaacctct gacacatgca gctcccggag acggtcacag cttgtctgta agcggatgcc    46500
gggagcagac aagcccgtca gggcgcgtca gcgggtgttg gcgggtgtcg gggcgcagcc    46560
atgacccagt cacgtagcga tagcggagtg tatactggct taactatgcg gcatcagagc    46620
agattgtact gagagtgcac catatgcggt gtgaaatacc gcacagatgc gtaaggagaa    46680
aataccgcat caggcgctct tccgcttcct cgctcactga ctcgctgcgc tcggtcgttc    46740
ggctgcggcg agcggtatca gctcactcaa aggcggtaat acggttatcc acagaatcag    46800
gggataacgc aggaaagaac atgtgagcaa aaggccagca aaaggccagg aaccgtaaaa    46860
aggccgcgtt gctggcgttt ttccataggc tccgccccc tgacgagcat cacaaaaatc    46920
gacgctcaag tcagaggtgg cgaaacccga caggactata aagataccag gcgtttcccc    46980
ctggaagctc cctcgtgcgc tctcctgttc cgaccctgcc gcttaccgga tacctgtccg    47040
cctttctccc ttcgggaagc gtggcgcttt ctcatagctc acgctgtagg tatctcagtt    47100
cggtgtaggt cgttcgctcc aagctgggct gtgtgcacga accccccgtt cagcccgacc    47160
gctgcgcctt atccggtaac tatcgtcttg agtccaaccc ggtaagacac gacttatcgc    47220
cactggcagc agccactggt aacaggatta gcagagcgag gtatgtaggc ggtgctacag    47280
agttcttgaa gtggtggcct aactacggct acactagaag acagtatttt ggtatctgcg    47340
ctctgctgaa gccagttacc ttcggaaaaa gagttggtag ctcttgatcc ggcaaacaaa    47400
ccaccgctgg tagcggtggt ttttttgttt gcaagcagca gattacgcgc agaaaaaaag    47460
gatctcaaga agatcctttg atcttttcta cggggtctga cgctcagtgg aacgaaaact    47520
cacgttaagg gattttggtc atgagattat caaaaaggat cttcacctag atccttttaa    47580
attaaaaatg aagttttaaa tcaatctaaa gtatatatga gtaaacttgg tctgacagtt    47640
accaatgctt aatcagtgag gcacctatct cagcgatctg tctatttcgt tcatccatag    47700
ttgcctgact ccccgtcgtg tagataacta cgatacggga gggcttacca tctgccccca    47760
gtgctgcaat gataccgcga gacccacgct caccggctcc agatttatca gcaataaacc    47820
agccagccgg aagggccgag cgcagaagtg gtcctgcaac tttatccgcc tccatccagt    47880
ctattaattg ttgccgggaa gctagagtaa gtagttcgcc agttaatagt ttgcgcaacg    47940
```

-continued

```
ttgttgccat tgctgcaggg ggggggggg gggggactt ccattgttca ttccacggac    48000
aaaaacagag aaaggaaacg acagaggcca aaaagcctcg ctttcagcac ctgtcgtttc    48060
ctttcttttc agagggtatt ttaaataaaa acattaagtt atgacgaaga agaacggaaa    48120
cgccttaaac cggaaaattt tcataaatag cgaaaacccg cgaggtcgcc gccccgtagt    48180
cggatcaccg gaaaggaccc gtaaagtgat aatgattatc atctacatat cacaacgtgc    48240
gtggaggcca tcaaaccacg tcaaataatc aattatgacg caggtatcgt attaattgat    48300
ctgcatcaac ttaacgtaaa aacaacttca gacaatacaa atcagcgaca ctgaatacgg    48360
ggcaacctca tgtccccccc ccccccccc ctgcaggcat cgtggtgtca cgctcgtcgt    48420
ttggtatggc ttcattcagc tccggttccc aacgatcaag gcgagttaca tgatccccca    48480
tgttgtgcaa aaaagcggtt agctccttcg gtcctccgat cgttgtcaga agtaagttgg    48540
ccgcagtgtt atcactcatg gttatggcag cactgcataa ttctcttact gtcatgccat    48600
ccgtaagatg cttttctgtg actggtgagt actcaaccaa gtcattctga aatagtgta    48660 tgcggcgacc gagttgctct tgcccggcgt caacacggga taataccgcg ccacatagca    48720
gaactttaaa agtgctcatc attggaaaac gttcttcggg gcgaaaactc tcaaggatct    48780
taccgctgtt gagatccagt tcgatgtaac ccactcgtgc acccaactga tcttcagcat    48840
cttttacttt caccagcgtt tctgggtgag caaaaacagg aaggcaaaat gccgcaaaaa    48900
agggaataag ggcgacacgg aaatgttgaa tactcatact cttccttttt caatattatt    48960
gaagcattta tcagggttat tgtctcatga gcggatacat atttgaatgt atttagaaaa    49020
ataaacaaat agggggttccg cgcacatttc cccgaaaagt gccacctgac gtctaagaaa    49080
ccattattat catgacatta acctataaaa ataggcgtat cacgaggccc tttcgtcttc    49140
aagaattggt cgacgatctt gctgcgttcg gatattttcg tggagttccc gccacagacc    49200
cggattgaag gcgagatcca gcaactcgcg ccagatcatc ctgtgacgga actttggcgc    49260
gtgatgactg gccaggacgt cggccgaaag agcgacaagc agatcacgct tttcgacagc    49320
gtcggatttg cgatcgagga ttttcggcg ctgcgctacg tccgcgaccg cgttgaggga    49380
tcaagccaca gcagcccact cgaccttcta gccgacccag acgagccaag ggatcttttt    49440
ggaatgctgc tccgtcgtca ggcttccga cgtttgggtg gttgaacaga agtcattatc    49500
gtacggaatg ccaagcactc ccgaggggaa ccctgtggtt ggcatgcaca tacaaatgga    49560
cgaacggata aaccttttca cgccctttta aatatccgtt attctaataa acgctctttt    49620
ctcttaggtt tacccgccaa tatatcctgt caaacactga tagtttaaac tgaaggcggg    49680
aaacgacaat ctgatcatga gcggagaatt aagggagtca cgttatgacc cccgccgatg    49740
acgcgggaca agccgtttta cgtttggaac tgacagaacc gcaacgttga aggagccact    49800
cagcaagctg gtacgattgt aatacgactc actatagggc gaattgagcg ctgtttaaac    49860
gctcttcaac tggaagagcg gttacccgga ccgaagcttg catgcctgca g             49911
```

<210> SEQ ID NO 7
<211> LENGTH: 36909
<212> TYPE: DNA
<213> ORGANISM: artificial sequence
<220> FEATURE:
<223> OTHER INFORMATION: vector

<400> SEQUENCE: 7

```
tctagagctc gttcctcgag gcctcgaggc ctcgaggaac ggtacctgcg gggaagctta      60
caataatgtg tgttgttaag tcttgttgcc tgtcatcgtc tgactgactt tcgtcataaa     120
```

-continued

```
tcccggcctc cgtaacccag ctttgggcaa gctcacggat ttgatccggc ggaacgggaa      180
tatcgagatg ccgggctgaa cgctgcagtt ccagctttcc ctttcgggac aggtactcca      240
gctgattgat tatctgctga agggtcttgg ttccacctcc tggcacaatg cgaatgatta      300
cttgagcgcg atcgggcatc caattttctc ccgtcaggtg cgtggtcaag tgctacaagg      360
cacctttcag taacgagcga ccgtcgatcc gtcgccggga tacggacaaa atggagcgca      420
gtagtccatc gagggcggcg aaagcctcgc caaaagcaat acgttcatct cgcacagcct      480
ccagatccga tcgagggtct tcggcgtagg cagatagaag catggataca ttgcttgaga      540
gtattccgat ggactgaagt atggcttcca tcttttctcg tgtgtctgca tctatttcga      600
gaaagccccc gatgcggcgc accgcaacgc gaattgccat actatccgaa agtcccagca      660
ggcgcgcttg ataggaaaag gtttcatact cggccgatcg cagacgggca ctcacgacct      720
tgaacccttc aactttcagg gatcgatgct ggttgatggt agtctcactc gacgtggctc      780
tggtgtgttt tgacatagct tcctccaaag aaagcggaag gtctggatac tccagcacga      840
aatgtgcccg ggtagacgga tggaagtcta gccctgctca atatgaaatc aacagtacat      900
ttacagtcaa tactgaatat acttgctaca tttgcaattg tcttataacg aatgtgaaat      960
aaaaatagtg taacaacgct tttactcatc gataatcaca aaaacattta tacgaacaaa     1020
aatacaaatg cactccggtt tcacaggata ggcgggatca gaatatgcaa cttttgacgt     1080
tttgttcttt caaggggggt gctggcaaaa ccaccgcact catgggcctt tgcgctgctt     1140
tggcaaatga cggtaaacga gtggccctct ttgatgccga cgaaaaccgg cctctgacgc     1200
gatggagaga aaacgcctta caaagcagta ctgggatcct cgctgtgaag tctattccgc     1260
cgacgaaatg cccccttcttg aagcagccta tgaaaatgcc gagctcgaag gatttgatta     1320
tgcgttggcc gatacgcgtg gcggctcgag cgagctcaac aacacaatca tcgctagctc     1380
aaacctgctt ctgatcccca ccatgctaac gccgctcgac atcgatgagg cactatctac     1440
ctaccgctac gtcatcgagc tgctgttgag tgaaaatttg gcaattccta cagctgtttt     1500
gcgccaacgc gtcccggtcg gccgattgac aacatcgcaa cgcaggatgt cagagacgct     1560
agagagcctt ccagttgtac cgtctcccat gcatgaaaga gatgcatttg ccgcgatgaa     1620
agaacgcggc atgttgcatc ttacattact aaacacggga actgatccga cgatgcgcct     1680
catagagagg aatcttcgga ttgcgatgga ggaagtcgtg gtcatttcga aactgatcag     1740
caaaatcttg gaggcttgaa gatggcaatt cgcaagcccg cattgtcggt cggcgaagca     1800
cggcggcttg ctggtgctcg acccgagatc caccatccca acccgacact tgttccccag     1860
aagctggacc tccagcactt gcctgaaaaa gccgacgaga aagaccagca acgtgagcct     1920
ctcgtcgccg atcacattta cagtcccgat cgacaactta gctaactgt ggatgccctt      1980 agtccacctc cgtccccgaa aaagctccag ttttttcttt cagcgcgacc gcccgcgcct     2040
caagtgtcga aaacatatga caacctcgtt cggcaataca gtccctcgaa gtcgctacaa     2100 atgatttaa ggcgcgcgtt ggacgatttc gaaagcatgc tggcagatgg atcatttcgc      2160
gtggccccga aaagttatcc gatcccttca actacagaaa aatccgttct cgttcagacc     2220
tcacgcatgt tcccggttgc gttgctcgag gtcgctcgaa gtcatttga tccgttgggg      2280 ttggagaccg ctcgagcttt cggccacaag ctggctaccg ccgcgctcgc gtcattcttt     2340
gctggagaga agccatcgag caattggtga agagggaccc atcggaaccc ctcaccaaat     2400
attgagtgta ggtttgaggc cgctggccgc gtcctcagtc accttttgag ccagataatt     2460
```

```
aagagccaaa tgcaattggc tcaggctgcc atcgtccccc cgtgcgaaac ctgcacgtcc    2520
gcgtcaaaga aataaccggc acctcttgct gtttttatca gttgagggct tgacggatcc    2580
gcctcaagtt tgcggcgcag ccgcaaaatg agaacatcta tactcctgtc gtaaacctcc    2640
tcgtcgcgta ctcgactggc aatgagaagt tgctcgcgcg atagaacgtc gcggggtttc    2700
tctaaaaacg cgaggagaag attgaactca cctgccgtaa gtttcacctc accgccagct    2760
tcggacatca agcgacgttg cctgagatta agtgtccagt cagtaaaaca aaaagaccgt    2820
cggtctttgg agcggacaac gttggggcgc acgcgcaagg caacccgaat gcgtgcaaga    2880
aactctctcg tactaaacgg cttagcgata aaatcacttg ctcctagctc gagtgcaaca    2940
actttatccg tctcctcaag gcggtcgcca ctgataatta tgattggaat atcagacttt    3000
gccgccagat ttcgaacgat ctcaagccca tcttcacgac ctaaatttag atcaacaacc    3060
acgacatcga ccgtcgcgga agagagtact ctagtgaact gggtgctgtc ggctaccgcg    3120
gtcactttga aggcgtggat cgtaaggtat tcgataataa gatgccgcat agcgacatcg    3180
tcatcgataa gaagaacgtg tttcaacggc tcacctttca atctaaaatc tgaacccttg    3240
ttcacagcgc ttgagaaatt ttcacgtgaa ggatgtacaa tcatctccag ctaaatgggc    3300
agttcgtcag aattgcggct gaccgcggat gacgaaaatg cgaaccaagt atttcaattt    3360
tatgacaaaa gttctcaatc gttgttacaa gtgaaacgct tcgaggttac agctactatt    3420
gattaaggag atcgcctatg gtctcgcccc ggcgtcgtgc gtccgccgcg agccagatct    3480
cgcctacttc ataaacgtcc tcataggcac ggaatggaat gatgacatcg atcgccgtag    3540
agagcatgtc aatcagtgtg cgatcttcca agctagcacc ttgggcgcta cttttgacaa    3600
gggaaaacag tttcttgaat ccttggattg gattcgcgcc gtgtattgtt gaaatcgatc    3660
ccggatgtcc cgagacgact tcactcagat aagcccatgc tgcatcgtcg cgcatctcgc    3720
caagcaatat ccggtccggc cgcatacgca gacttgcttg gagcaagtgc tcggcgctca    3780
cagcacccag cccagcaccg ttcttggagt agagtagtct aacatgatta tcgtgtggaa    3840
tgacgagttc gagcgtatct tctatggtga ttagcctttc ctggggggg atggcgctga    3900 tcaaggtctt gctcattgtt gtcttgccgc ttccggtagg gccacatagc aacatcgtca    3960
gtcggctgac gacgcatgcg tgcagaaacg cttccaaatc cccgttgtca aaatgctgaa    4020
ggatagcttc atcatcctga ttttggcgtt ccttcgtgt ctgccactgg ttccacctcg    4080
aagcatcata acgggaggag acttcttaa gaccagaaac acgcgagctt ggccgtcgaa    4140
tggtcaagct gacggtgccc gagggaacgg tcggcggcag acagatttgt agtcgttcac    4200
caccaggaag ttcagtggcg cagaggggt tacgtggtcc gacatcctgc tttctcagcg    4260
cgcccgctaa aatagcgata tcttcaagat catcataaga gacgggcaaa ggcatcttgg    4320
taaaaatgcc ggcttggcgc acaaatgcct ctccaggtcg attgatcgca atttcttcag    4380
tcttcgggtc atcgagccat tccaaaatcg gcttcagaag aaagcgtagt tgcggatcca    4440 cttccatttta caatgtatcc tatctctaag cggaaatttg aattcattaa gagcggcggt    4500
tcctcccccg cgtggcgccg ccagtcaggc ggagctggta acaccaaag aaatcgaggt    4560 cccgtgctac gaaaatggaa acggtgtcac cctgattctt cttcagggtt ggcggtatgt    4620
tgatggttgc cttaagggct gtctcagttg tctgctcacc gttattttga aagctgttga    4680
agctcatccc gccacccgag ctgccggcgt aggtgctagc tgcctggaag gcgccttgaa    4740
caacactcaa gagcatagct ccgctaaaac gctgccagaa gtggctgtcg accgagcccg    4800
gcaatcctga gcgaccgagt tcgtccgcgc ttggcgatgt taacgagatc atcgcatggt    4860
```

```
caggtgtctc ggcgcgatcc cacaacacaa aaacgcgccc atctccctgt tgcaagccac   4920
gctgtatttc gccaacaacg gtggtgccac gatcaagaag cacgatattg ttcgttgttc   4980
cacgaatatc ctgaggcaag acacacttta catagcctgc caaatttgtg tcgattgcgg   5040
tttgcaagat gcacggaatt attgtccctt gcgttaccat aaaatcgggg tgcggcaaga   5100
gcgtggcgct gctgggctgc agctcggtgg gtttcatacg tatcgacaaa tcgttctcgc   5160
cggacacttc gccattcggc aaggagttgt cgtcacgctt gccttcttgt cttcggcccg   5220
tgtcgccctg aatggcgcgt ttgctgaccc cttgatcgcc gctgctatat gcaaaaatcg   5280
gtgtttcttc cggccgtggc tcatgccgct ccggttcgcc cctcggcggt agaggagcag   5340
caggctgaac agcctcttga accgctggag gatccggcgg cacctcaatc ggagctggat   5400
gaaatggctt ggtgtttgtt gcgatcaaag ttgacggcga tgcgttctca ttcaccttct   5460
tttggcgccc acctagccaa atgaggctta atgataacgc gagaacgaca cctccgacga   5520
tcaatttctg agaccccgaa agacgccggc gatgtttgtc ggagaccagg gatccagatg   5580
catcaacctc atgtgccgct tgctgactat cgttattcat cccttcgccc ccttcaggac   5640
gcgtttcaca tcgggcctca ccgtgccgtt tgcggccttt ggccaacgg gatcgtaagc    5700
ggtgttccag atacatagta ctgtgtggcc atccctcaga cgccaacctc gggaaaccga   5760
agaaatctcg acatcgctcc ctttaactga atagttggca acagcttcct tgccatcagg   5820
attgatggtg tagatggagg gtatgcgtac attgcccgga aagtggaata ccgtcgtaaa   5880
tccattgtcg aagacttcga gtggcaacag cgaacgatcg ccttgggcga cgtagtgcca   5940
attactgtcc gccgcaccaa gggctgtgac aggctgatcc aataaattct cagctttccg   6000
ttgatattgt gcttccgcgt gtagtctgtc cacaacagcc ttctgttgtg cctcccttcg   6060
ccgagccgcc gcatcgtcgg cggggtaggc gaattggacg ctgtaataga gatcgggctg   6120
ctctttatcg aggtgggaca gagtcttgga acttatactg aaaacataac ggcgcatccc   6180
ggagtcgctt gcggttagca cgattactgg ctgaggcgtg aggacctggc ttgccttgaa   6240
aaatagataa tttccccgcg gtagggctgc tagatctttg ctatttgaaa cggcaaccgc   6300
tgtcaccgtt tcgttcgtgg cgaatgttac gaccaaagta gctccaaccg ccgtcgagag   6360
gcgcaccact tgatcgggat tgtaagccaa ataacgcatg cgcggatcta gcttgcccgc   6420
cattggagtg tcttcagcct ccgcaccagt cgcagcggca aataaacatg ctaaaatgaa   6480
aagtgctttt ctgatcatgg ttcgctgtgg cctacgtttg aaacggtatc ttccgatgtc   6540
tgataggagg tgacaaccag acctgccggg ttggttagtc tcaatctgcc gggcaagctg   6600
gtcacctttt cgtagcgaac tgtcgcggtc cacgtactca ccacaggcat tttgccgtca   6660
acgacgaggg tccttttata gcgaatttgc tgcgtgcttg gagttacatc atttgaagcg   6720
atgtgctcga cctccaccct gccgcgtttg ccaagaatga cttgaggcga actgggattg   6780
ggatagttga agaattgctg gtaatcctgg cgcactgttg gggcactgaa gttcgatacc   6840
aggtcgtagg cgtactgagc ggtgtcggca tcataactct cgcgcaggcg aacgtactcc   6900
cacaatgagg cgttaacgac ggcctcctct tgagttgcag gcaatcgcga gacagacacc   6960
tcgctgtcaa cggtgccgtc cggccgtatc catagatata cgggcacaag cctgctcaac   7020
ggcaccattg tggctatagc gaacgcttga gcaacatttc ccaaaatcgc gatagctgcg   7080
acagctgcaa tgagtttgga gagacgtcgc gccgatttcg ctcgcgcggt ttgaaaggct   7140
tctacttcct tatagtgctc ggcaaggctt tcgcgcgcca ctagcatggc atattcaggc   7200
```

| | |
|---|---|
| cccgtcatag cgtccacccg aattgccgag ctgaagatct gacggagtag gctgccatcg | 7260 |
| ccccacattc agcgggaaga tcgggccttt gcagctcgct aatgtgtcgt ttgtctggca | 7320 |
| gccgctcaaa gcgacaacta ggcacagcag gcaatacttc atagaattct ccattgaggc | 7380 |
| gaatttttgc gcgacctagc ctcgctcaac ctgagcgaag cgacggtaca agctgctggc | 7440 |
| agattgggtt gcgccgctcc agtaactgcc tccaatgttg ccggcgatcg ccggcaaagc | 7500 |
| gacaatgagc gcatcccctg tcagaaaaaa catatcgagt tcgtaaagac caatgatctt | 7560 |
| ggccgcggtc gtaccggcga aggtgattac accaagcata agggtgagcg cagtcgcttc | 7620 |
| ggttaggatg acgatcgttg ccacgaggtt aagaggaga agcaagagac cgtaggtgat | 7680 |
| aagttgcccg atccacttag ctgcgatgtc ccgcgtgcga tcaaaatat atccgacgag | 7740 |
| gatcagaggc ccgatcgcga gaagcacttt cgtgagaatt ccaacggcgt cgtaaactcc | 7800 |
| gaaggcagac cagagcgtgc cgtaaaggac ccactgtgcc ccttggaaag caaggatgtc | 7860 |
| ctggtcgttc atcggaccga tttcggatgc gattttctga aaaacggcct gggtcacggc | 7920 |
| gaacattgta tccaactgtg ccggaacagt ctgcagaggc aagccggtta cactaaactg | 7980 |
| ctgaacaaag tttgggaccg tcttttcgaa gatggaaacc acatagtctt ggtagttagc | 8040 |
| ctgcccaaca attagagcaa caacgatggt gaccgtgatc acccgagtga taccgctacg | 8100 |
| ggtatcgact tcgccgcgta tgactaaaat accctgaaca ataatccaaa gagtgacaca | 8160 |
| ggcgatcaat ggcgcactca ccgcctcctg gatagtctca agcatcgagt ccaagcctgt | 8220 |
| cgtgaaggct acatcgaaga tcgtatgaat ggccgtaaac ggcgccggaa tcgtgaaatt | 8280 |
| catcgattgg acctgaactt gactggtttg tcgcataatg ttggataaaa tgagctcgca | 8340 |
| tcggcgagg atgcgggcgg atgaacaaat cgcccagcct tagggagggg caccaaagat | 8400 |
| gacagcggtc ttttgatgct ccttgcgttg agcggccgcc tcttccgcct cgtgaaggcc | 8460 |
| ggcctgcgcg gtagtcatcg ttaataggct tgtcgcctgt acattttgaa tcattgcgtc | 8520 |
| atggatctgc ttgagaagca aaccattggt cacggttgcc tgcatgatat tgcgagatcg | 8580 |
| ggaaagctga gcagacgtat cagcattcgc cgtcaagcgt ttgtccatcg tttccagatt | 8640 |
| gtcagccgca atgccagcgc tgtttgcgga accggtgatc tgcgatcgca acaggtccgc | 8700 |
| ttcagcatca ctacccacga ctgcacgatc tgtatcgctg gtgatcgcac gtgccgtggt | 8760 |
| cgacattggc attcgcggcg aaaacatttc attgtctagg tccttcgtcg aaggatactg | 8820 |
| atttttctgg ttgagcgaag tcagtagtcc agtaacgccg taggccgacg tcaacatcgt | 8880 |
| aaccatcgct atagtctgag tgagattctc cgcagtcgcg agcgcagtcg cgagcgtctc | 8940 |
| agcctccgtt gccgggtcgc taacaacaaa ctgcgcccgc gcgggctgaa tatatagaaa | 9000 |
| gctgcaggtc aaaactgttg caataagttg cgtcgtcttc atcgtttcct accttatcaa | 9060 |
| tcttctgcct cgtggtgacg ggccatgaat tcgctgagcc agccagatga gttgccttct | 9120 |
| tgtgcctcgc gtagtcgagt tgcaaagcgc accgtgttgg cacgccccga agcacggcg | 9180 |
| acatattcac gcatatcccg cagatcaaat tcgcagatga cgcttccact ttctcgttta | 9240 |
| agaagaaact tacggctgcc gaccgtcatg tcttcacgga tcgcctgaaa ttccttttcg | 9300 |
| gtacatttca gtccatcgac ataagccgat cgatctgcgg ttggtgatgg atagaaaatc | 9360 |
| ttcgtcatac attgcgcaac caagctggct cctagcggcg attccagaac atgctctggt | 9420 |
| tgctgcgttg ccagtattag catcccgttg ttttttcgaa cggtcaggag gaatttgtcg | 9480 |
| acgacagtcg aaaatttagg gtttaacaaa taggcgcgaa actcatcgca gctcatcaca | 9540 |
| aaacggcggc cgtcgatcat ggctccaatc cgatgcagga gatatgctgc agcgggagcg | 9600 |

```
catacttcct cgtattcgag aagatgcgtc atgtcgaagc cggtaatcga cggatctaac    9660
tttacttcgt caacttcgcc gtcaaatgcc cagccaagcg catggcccg gcaccagcgt     9720 tggagccgcg ctcctgcgcc ttcggcgggc ccatgcaaca aaaattcacg taaccccgcg    9780
attgaacgca tttgtggatc aaacgagagc tgacgatgga taccacgac cagacggcgg    9840 ttctcttccg gagaaatccc accccgacca tcactctcga tgagagccac gatccattcg    9900
cgcagaaaat cgtgtgaggc tgctgtgttt tctaggccac gcaacggcgc caacccgctg    9960
ggtgtgcctc tgtgaagtgc caaatatgtt cctcctgtgg cgcgaaccag caattcgcca   10020
ccccggtcct tgtcaaagaa cacgaccgta cctgcacggt cgaccatgct ctgttcgagc   10080
atggctagaa caaacatcat gagcgtcgtc ttacccctcc cgataggccc gaatattgcc   10140
gtcatgccaa catcgtgctc atgcgggata tagtcgaaag gcgttccgcc attggtacga   10200
aatcgggcaa tcgcgttgcc ccagtggcct gagctggcgc cctctggaaa gttttcgaaa   10260
gagacaaacc ctgcgaaatt gcgtgaagtg attgcgccag ggcgtgtgcg ccacttaaaa   10320
ttccccggca attgggacca ataggccgct tccataccaa taccttcttg gacaaccacg   10380
gcacctgcat ccgccattcg tgtccgagcc gcgcgcccc tgtccccaag actattgaga    10440
tcgtctgcat agacgcaaag gctcaaatga tgtgagccca taacgaattc gttgctcgca   10500
agtgcgtcct cagcctcgga taatttgccg atttgagtca cggctttatc gccgaactc    10560 agcatctggc tcgatttgag gctaagtttc gcgtgcgctt gcgggcgagt caggaacgaa   10620
aaactctgcg tgagaacaag tggaaaatcg agggatagca gcgcgttgag catgcccggc   10680
cgtgtttttg cagggtattc gcgaaacgaa tagatggatc caacgtaact gtcttttggc   10740
gttctgatct cgagtcctcg cttgccgcaa atgactctgt cggtataaat cgaagcgccg   10800
agtgagccgc tgacgaccgg aaccggtgtg aaccgaccag tcatgatcaa ccgtagcgct   10860
tcgccaattt cggtgaagag cacaccctgc ttctcgcgga tgccaagacg atgcaggcca   10920
tacgctttaa gagagccagc gacaacatgc caaagatctt ccatgttcct gatctggccc   10980
gtgagatcgt tttcccttt tccgcttagc ttggtgaacc tcctctttac cttccctaaa    11040
gccgcctgtg ggtagacaat caacgtaagg aagtgttcat tgcggaggag ttggccggag   11100
agcacgcgct gttcaaaagc ttcgttcagg ctagcggcga aaacactacg gaagtgtcgc   11160
ggcgccgatg atggcacgtc ggcatgacgt acgaggtgag catatattga cacatgatca   11220
tcagcgatat tgcgcaacag cgtgttgaac gcacgacaac gcgcattgcg catttcagtt   11280
tcctcaagct cgaatgcaac gccatcaatt ctcgcaatgg tcatgatcga tccgtcttca   11340
agaaggacga tatggtcgct gaggtggcca atataaggga gatagatctc accggatctt   11400
tcggtcgttc cactcgcgcc gagcatcaca ccattcctct ccctcgtggg ggaaccctaa   11460
ttggatttgg gctaacagta gcgcccccc aaactgcact atcaatgctt cttcccgcgg    11520
tccgcaaaaa tagcaggacg acgctcgccg cattgtagtc tcgctccacg atgagccggg   11580
ctgcaaacca taacggcacg agaacgactt cgtagagcgg gttctgaacg ataacgatga   11640
caaagccggc gaacatcatg aataaccctg ccaatgtcag tggcaccca agaaacaatg    11700 cgggccgtgt ggctgcgagg taaagggtcg attcttccaa acgatcagcc atcaactacc   11760
gccagtgagc gtttggccga ggaagctcgc cccaaacatg ataacaatgc cgccgacgac   11820
gccggcaacc agcccaagcg aagcccgccc gaacatccag gagatcccga tagcgacaat   11880
gccgagaaca gcgagtgact ggccgaacgg accaaggata aacgtgcata tattgttaac   11940
```

```
cattgtggcg gggtcagtgc cgccacccgc agattgcgct gcggcgggtc cggatgagga  12000
aatgctccat gcaattgcac cgcacaagct tggggcgcag ctcgatatca cgcgcatcat  12060
cgcattcgag agcgagaggc gatttagatg taaacggtat ctctcaaagc atcgcatcaa  12120
tgcgcacctc cttagtataa gtcgaataag acttgattgt cgtctgcgga tttgccgttg  12180
tcctggtgtg gcggtggcgg agcgattaaa ccgccagcgc catcctcctg cgagcggcgc  12240
tgatatgacc cccaaacatc ccacgtctct tcggatttta gcgcctcgtg atcgtctttt  12300
ggaggctcga ttaacgcggg caccagcgat tgagcagctg tttcaacttt tcgcacgtag  12360
ccgtttgcaa aaccgccgat gaaattaccg gtgttgtaag cggagatcgc ccgacgaagc  12420
gcaaattgct tctcgtcaat cgtttcgccg cctgcataac gacttttcag catgtttgca  12480
gcggcagata atgatgtgca cgcctggagc gcaccgtcag gtgtcagacc gagcatagaa  12540
aaatttcgag agtttatttg catgaggcca acatccagcg aatgccgtgc atcgagacgg  12600
tgcctgacga cttgggttgc ttggctgtga tcttgccagt gaagcgtttc gccggtcgtg  12660
ttgtcatgaa tcgctaaagg atcaaagcga ctctccacct tagctatcgc cgcaagcgta  12720
gatgtcgcaa ctgatggggc acacttgcga gcaacatggt caaactcagc agatgagagt  12780
ggcgtggcaa ggctcgacga acagaaggag accatcaagg caagagaaag cgaccccgat  12840
ctcttaagca taccttatct ccttagctcg caactaacac cgcctctccc gttggaagaa  12900
gtgcgttgtt ttatgttgaa gattatcggg agggtcggtt actcgaaaat ttcaattgc  12960 ttctttatga tttcaattga agcgagaaac ctcgcccggc gtcttggaac gcaacatgga  13020
ccgagaaccg cgcatccatg actaagcaac cggatcgacc tattcaggcc gcagttggtc  13080
aggtcaggct cagaacgaaa atgctcggcg aggttacgct gtctgtaaac ccattcgatg  13140
aacgggaagc ttccttccga ttgctcttgg caggaatatt ggcccatgcc tgcttgcgct  13200
ttgcaaatgc tcttatcgcg ttggtatcat atgccttgtc cgccagcaga aacgcactct  13260
aagcgattat ttgtaaaaat gtttcggtca tgcggcggtc atgggcttga cccgctgtca  13320
gcgcaagacg gatcggtcaa ccgtcggcat cgacaacagc gtgaatcttg gtggtcaaac  13380
cgccacggga acgtcccata cagccatcgt cttgatcccg ctgtttcccg tcgccgcatg  13440
ttggtggacg cggacacagg aactgtcaat catgacgaca ttctatcgaa agccttggaa  13500
atcacactca gaatatgatc ccagacgtct gcctcacgcc atcgtacaaa gcgattgtag  13560
caggttgtac aggaaccgta tcgatcagga acgtctgccc agggcgggcc cgtccggaag  13620
cgccacaaga tgacattgat cacccgcgtc aacgcgcggc acgcgacgcg cttatttgg  13680 gaacaaagga ctgaacaaca gtccattcga aatcggtgac atcaaagcgg ggacgggtta  13740
tcagtggcct ccaagtcaag cctcaatgaa tcaaaatcag accgatttgc aaacctgatt  13800
tatgagtgtg cggcctaaat gatgaaatcg tccttctaga tcgcctccgt ggtgtagcaa  13860
cacctcgcag tatcgccgtg ctgaccttgg ccagggaatt gactggcaag ggtgctttca  13920
catgaccgct ctttggccg cgatagatga tttcgttgct gctttgggca cgtagaagga  13980
gagaagtcat atcggagaaa ttcctcctgg cgcgagagcc tgctctatcg cgacggcatc  14040
ccactgtcgg gaacagaccg gatcattcac gaggcgaaag tcgtcaacac atgcgttata  14100
ggcatcttcc cttgaaggat gatcttgttg ctgccaatct ggaggtgcgg cagccgcagg  14160
cagatgcgat ctcagcgcaa cttgcggcaa acatctcac tcacctgaaa accactagcg  14220
agtctcgcga tcagacgaag gccttttact taacgcacaca atatccgatg tctgcatcac  14280
aggcgtcgct atcccagtca atactaaagc ggtgcaggaa ctaaagatta ctgatgactt  14340
```

```
aggcgtgcca cgaggcctga gacgacgcgc gtagacagtt ttttgaaatc attatcaaag   14400
tgatggcctc cgctgaagcc tatcacctct gcgccggtct gtcggagaga tgggcaagca   14460
ttattacggt cttcgcgccc gtacatgcat tggacgattg cagggtcaat ggatctgaga   14520
tcatccagag gattgccgcc cttaccttcc gtttcgagtt ggagccagcc cctaaatgag   14580
acgacatagt cgacttgatg tgacaatgcc aagagagaga tttgcttaac ccgattttt   14640 tgctcaagcg taagcctatt gaagcttgcc ggcatgacgt ccgcgccgaa agaatatcct   14700
acaagtaaaa cattctgcac accgaaatgc ttggtgtaga catcgattat gtgaccaaga   14760
tccttagcag tttcgcttgg ggaccgctcc gaccagaaat accgaagtga actgacgcca   14820
atgacaggaa tcccttccgt ctgcagatag gtaccatcga tagatctgct gcctcgcgcg   14880
tttcggtgat gacggtgaaa acctctgaca catgcagctc ccggagacgg tcacagcttg   14940
tctgtaagcg gatgccggga gcagacaagc ccgtcagggc gcgtcagcgg gtgttggcgg   15000 gtgtcgggc gcagccatga cccagtcacg tagcgatagc ggagtgtata ctggcttaac   15060
tatgcggcat cagagcagat tgtactgaga gtgcaccata tgcggtgtga aataccgcac   15120
agatgcgtaa ggagaaaata ccgcatcagg cgctcttccg cttcctcgct cactgactcg   15180
ctgcgctcgg tcgttcggct gcggcgagcg gtatcagctc actcaaaggc ggtaatacgg   15240
ttatccacag aatcagggga taacgcagga agaacatgt gagcaaaagg ccagcaaaag   15300
gccaggaacc gtaaaaaggc cgcgttgctg gcgttttcc ataggctccg ccccctgac    15360 gagcatcaca aaaatcgacg ctcaagtcag aggtggcgaa acccgacagg actataaaga   15420
taccaggcgt ttccccctgg aagctccctc gtgcgctctc ctgttccgac cctgccgctt   15480
accggatacc tgtccgcctt tctcccttcg ggaagcgtgg cgctttctca tagctcacgc   15540
tgtaggtatc tcagttcggt gtaggtcgtt cgctccaagc tgggctgtgt gcacgaaccc   15600
cccgttcagc ccgaccgctg cgccttatcc ggtaactatc gtcttgagtc aacccggta    15660 agacacgact tatcgccact ggcagcagcc actggtaaca ggattagcag agcgaggtat   15720
gtaggcggtg ctacagagtt cttgaagtgg tggcctaact acggctacac tagaaggaca   15780
gtatttggta tctgcgctct gctgaagcca gttaccttcg gaaaaagagt tggtagctct   15840
tgatccggca aacaaaccac cgctggtagc ggtggttttt ttgtttgcaa gcagcagatt   15900
acgcgcagaa aaaaaggatc tcaagaagat cctttgatct tttctacggg gtctgacgct   15960
cagtggaacg aaaactcacg ttaagggatt ttggtcatga gattatcaaa aaggatcttc   16020
acctagatcc ttttaaatta aaatgaagt tttaaatcaa tctaaagtat atatgagtaa   16080
acttggtctg acagttacca atgcttaatc agtgaggcac ctatctcagc gatctgtcta   16140
tttcgttcat ccatagttgc ctgactcccc gtcgtgtaga taactacgat acgggagggc   16200
ttaccatctg gccccagtgc tgcaatgata ccgcgagacc cacgctcacc ggctccagat   16260
ttatcagcaa taaaccagcc agccggaagg gccgagcgca gaagtggtcc tgcaacttta   16320
tccgcctcca tccagtctat taattgttgc cgggaagcta gagtaagtag ttcgccagtt   16380
aatagtttgc gcaacgttgt tgccattgct gcaggggggg ggggggggg gttccattgt   16440 tcattccacg gacaaaaaca gagaaaggaa acgacagagg ccaaaaagct cgctttcagc   16500
acctgtcgtt tcctttcttt tcagagggta ttttaaataa aaacattaag ttatgacgaa   16560
gaagaacgga aacgccttaa accggaaaat tttcataaat agcgaaaacc cgcgaggtcg   16620 ccgcccgta acctgtcgga tcaccggaaa ggacccgtaa agtgataatg attatcatct   16680
```

-continued

```
acatatcaca acgtgcgtgg aggccatcaa accacgtcaa ataatcaatt atgacgcagg    16740
tatcgtatta attgatctgc atcaacttaa cgtaaaaaca acttcagaca atacaaatca    16800
gcgacactga atacggggca acctcatgtc cccccccccc ccccccctgc aggcatcgtg    16860
gtgtcacgct cgtcgtttgg tatggcttca ttcagctccg gttcccaacg atcaaggcga    16920
gttacatgat cccccatgtt gtgcaaaaaa gcggttagct ccttcggtcc tccgatcgtt    16980
gtcagaagta agttggccgc agtgttatca ctcatggtta tggcagcact gcataattct    17040
cttactgtca tgccatccgt aagatgcttt tctgtgactg gtgagtactc aaccaagtca    17100
ttctgagaat agtgtatgcg gcgaccgagt tgctcttgcc cggcgtcaac acgggataat    17160
accgcgccac atagcagaac tttaaaagtg ctcatcattg gaaaacgttc ttcggggcga    17220
aaactctcaa ggatcttacc gctgttgaga tccagttcga tgtaacccac tcgtgcaccc    17280
aactgatctt cagcatcttt tactttcacc agcgtttctg ggtgagcaaa aacaggaagg    17340
caaaatgccg caaaaaaggg aataaggcg acacggaaat gttgaatact catactcttc    17400
cttttcaat attattgaag catttatcag ggttattgtc tcatgagcgg atacatattt    17460
gaatgtattt agaaaaataa acaaataggg gttccgcgca catttccccg aaaagtgcca    17520
cctgacgtct aagaaaccat tattatcatg acattaacct ataaaaatag gcgtatcacg    17580
aggccctttc gtcttcaaga attcggagct tttgccattc tcaccggatt cagtcgtcac    17640
tcatggtgat ttctcacttg ataaccttat ttttgacgag gggaaattaa taggttgtat    17700
tgatgttgga cgagtcggaa tcgcagaccg ataccaggat cttgccatcc tatggaactg    17760
cctcggtgag ttttctcctt cattacgaaa acggcttttt caaaaatatg gtattgataa    17820
tcctgatatg aataaattgc agtttcattt gatgctcgat gagttttct aatcagaatt    17880
ggttaattgg ttgtaacact ggcagagcat tacgctgact tgacgggacg gcggctttgt    17940
tgaataaatc gaacttttgc tgagttgaag gatcagatca cgcatcttcc cgacaacgca    18000
gaccgttccg tggcaaagca aaagttcaaa atcaccaact ggtccaccta caacaaagct    18060
ctcatcaacc gtggctccct cactttctgg ctggatgatg gggcgattca ggcctggtat    18120
gagtcagcaa caccttcttc acgaggcaga cctcagcgcc agaaggccgc cagagaggcc    18180
gagcgcggcc gtgaggcttg gacgctaggg cagggcatga aaaagcccgt agcgggctgc    18240
tacgggcgtc tgacgcggtg gaaaggggga ggggatgttg tctacatggc tctgctgtag    18300
tgagtgggtt gcgctccggc agcggtcctg atcaatcgtc accctttctc ggtccttcaa    18360
cgttcctgac aacagcctc cttttcgcca atccatcgac aatcaccgcg agtccctgct    18420
cgaacgctgc gtccggaccg gcttcgtcga aggcgtctat cgcggcccgc aacagcggcg    18480
agagcggagc ctgttcaacg gtgccgccgc gctcgccggc atcgctgtcg ccggcctgct    18540
cctcaagcac ggccccaaca gtgaagtagc tgattgtcat cagcgcattg acggcgtccc    18600
cggccgaaaa accgcctcg cagaggaagc gaagctgcgc gtcggccgtt tccatctgcg    18660
gtgcgcccgg tcgcgtgccg gcatggatgc gcgcgccatc gcggtaggcg agcagcgcct    18720
gcctgaagct gcgggcattc ccgatcagaa atgagcgcca gtcgtcgtcg gctctcggca    18780
ccgaatgcgt atgattctcc gccagcatgg cttcggccag tgcgtcgagc agcgccgct    18840
tgttcctgaa gtgccagtaa agcgccggct gctgaacccc caaccgttcc gccagtttgc    18900
gtgtcgtcag accgtctacg ccgacctcgt tcaacaggtc cagggcggca cggatcactg    18960
tattcggctg caactttgtc atgcttgaca ctttatcact gataaacata atatgtccac    19020
caacttatca gtgataaaga atccgcgcgt tcaatcggac cagcggaggc tggtccggag    19080
```

```
gccagacgtg aaacccaaca taccoctgat cgtaattctg agcactgtcg cgctcgacgc   19140
tgtcggcatc ggcctgatta tgccggtgct gccgggcctc ctgcgcgatc tggttcactc   19200
gaacgacgtc accgcccact atggcattct gctggcgctg tatgcgttgg tgcaatttgc   19260
ctgcgcacct gtgctgggcg cgctgtcgga tcgtttcggg cggcggccaa tcttgctcgt   19320
ctcgctggcc ggcgccactg tcgactacgc catcatggcg acagcgcctt cctttgggt    19380
tctctatatc gggcggatcg tggccggcat caccggggcg actggggcgg tagccggcgc   19440
ttatattgcc gatatcactg atggcgatga gcgcgcgcgg cacttcggct tcatgagcgc   19500
ctgtttcggg ttcgggatgg tcgcgggacc tgtgctcggt gggctgatgg gcggtttctc   19560
cccccacgct ccgttcttcg ccgcggcagc cttgaacggc ctcaatttcc tgacgggctg   19620
tttccttttg ccggagtcgc acaaaggcga acgccggccg ttacgccggg aggctctcaa   19680
cccgctcgct tcgttccggt gggcccgggg catgaccgtc gtcgccgccc tgatggcggt   19740
cttcttcatc atgcaacttg tcggacaggt gccggccgcg cttttgggtca tttttcggcga   19800
ggatcgcttt cactgggacg cgaccacgat cggcatttcg cttgccgcat ttggcattct   19860
gcattcactc gcccaggcaa tgatcaccgg ccctgtagcc gcccggctcg gcgaaaggcg   19920
ggcactcatg ctcggaatga ttgccgacgg cacaggctac atcctgcttg ccttcgcgac   19980
acggggatgg atgcgcgttcc cgatcatggt cctgcttgct cgggtggca tcggaatgcc    20040
ggcgctgcaa gcaatgttgt ccaggcaggt ggatgaggaa cgtcagggcc agctgcaagg   20100
ctcactggcg gcgctcacca gcctgacctc gatcgtcgga cccctcctct tcacggcgat   20160
ctatgcggct tctataacaa cgtggaacgg gtgggcatgg attgcaggcg ctgccctcta   20220
cttgctctgc ctgccggcgc tgcgtcgcgg gctttggagc ggcgcagggc aacgagccga   20280
tcgctgatcg tggaaacgat aggcctatgc catgcgggtc aaggcgactt ccggcaagct   20340
atacgcgccc taggagtgcg gttgaacgt tggcccagcc agatactccc gatcacgagc    20400
aggacgccga tgatttgaag cgcactcagc gtctgatcca agaacaacca tcctagcaac   20460
acggcggtcc ccgggctgag aaagcccagt aaggaaacaa ctgtaggttc gagtcgcgag   20520
atcccccgga accaaaggaa gtaggttaaa cccgctccga tcaggccgag ccacgccagg   20580
ccgagaacat tggttcctgt aggcatcggg attggcggat caaacactaa agctactgga   20640
acgagcagaa gtcctccggc cgccagttgc caggcggtaa aggtgagcag aggcacggga   20700
ggttgccact tgcgggtcag cacggttccg aacgccatgg aaaccgcccc cgccaggccc   20760
gctgcgacgc cgacaggatc tagcgctgcg tttggtgtca acaccaacag cgccacgccc   20820
gcagttccgc aaatagcccc caggaccgcc atcaatcgta tcgggctacc tagcagagcg   20880
gcagagatga acacgaccat cagcggctgc acagcgccta ccgtcgccgc gaccccgccc   20940
ggcaggcggt agaccgaaat aaacaacaag ctccagaata gcgaaatatt aagtgcgccg   21000
aggatgaaga tgcgcatcca ccagattccc gttggaatct gtcggacgat catcacgagc   21060
aataaacccg ccggcaacgc ccgcagcagc ataccggcga cccctcggcc tcgctgttcg   21120
ggctccacga aaacgccgga cagatgcgcc ttgtgagcgt ccttggggcc gtcctcctgt   21180
ttgaagaccc acagcccaat gatctcgccg tcgatgtagg cgccgaatgc cacggcatct   21240
cgcaaccgtt cagcgaacgc ctccatgggc ttttttctcct cgtgctcgta aacggacccg   21300
aacatctctg gagctttctt cagggccgac aatcggatct cgcggaaatc ctgcacgtcg   21360
gccgctccaa gccgtcgaat ctgagccctta atcacaattg tcaattttaa tcctctgttt   21420
```

```
atcggcagtt cgtagagcgc gccgtgcgtc ccgagcgata ctgagcgaag caagtgcgtc   21480
gagcagtgcc cgcttgttcc tgaaatgcca gtaaagcgct ggctgctgaa ccccagccg    21540 gaactgaccc cacaaggccc tagcgtttgc aatgcaccag gtcatcattg acccaggcgt   21600
gttccaccag gccgctgcct cgcaactctt cgcaggcttc gccgacctgc tcgcgccact   21660
tcttcacgcg ggtggaatcc gatccgcaca tgaggcggaa ggtttccagc ttgagcgggt   21720
acggctcccg gtgcgagctg aaatagtcga acatccgtcg ggccgtcggc gacagcttgc   21780
ggtacttctc ccatatgaat tcgtgtagt ggtcgccagc aaacagcacg acgatttcct    21840
cgtcgatcag gacctggcaa cgggacgttt tcttgccacg gtccaggacg cggaagcggt   21900
gcagcagcga caccgattcc aggtgcccaa cgcggtcgga cgtgaagccc atcgccgtcg   21960
cctgtaggcg cgacaggcat tcctcggcct tcgtgtaata ccggccattg atcgaccagc   22020
ccaggtcctg gcaaagctcg tagaacgtga aggtgatcgg ctcgccgata ggggtgcgct   22080
tcgcgtactc caacacctgc tgccacacca gttcgtcatc gtcggcccgc agctcgacgc   22140
cggtgtaggt gatcttcacg tccttgttga cgtggaaaat gaccttgttt tgcagcgcct   22200
cgcgcgggat tttcttgttg cgcgtggtga acagggcaga gcgggccgtg tcgtttggca   22260
tcgctcgcat cgtgtccggc cacggcgcaa tatcgaacaa ggaaagctgc atttccttga   22320
tctgctgctt cgtgtgtttc agcaacgcgg cctgcttggc ctcgctgacc tgttttgcca   22380
ggtcctcgcc ggcggttttt cgcttcttgg tcgtcatagt tcctcgcgtg tcgatggtca   22440
tcgacttcgc caaacctgcc gcctcctgtt cgagacgacg cgaacgctcc acggcggccg   22500
atggcgcggg cagggcaggg ggagccagtt gcacgctgtc gcgctcgatc ttggccgtag   22560
cttgctggac catcgagccg acggactgga aggtttcgcg gggcgcacgc atgacggtgc   22620
ggcttgcgat ggtttcggca tcctcggcgg aaaaccccgc gtcgatcagt tcttgcctgt   22680
atgccttccg gtcaaacgtc cgattcattc accctccttg cgggattgcc ccgactcacg   22740
ccggggcaat gtgcccttat tcctgatttg acccgcctgg tgccttggtg tccagataat   22800
ccaccttatc ggcaatgaag tcggtcccgt agaccgtctg gccgtccttc tcgtacttgg   22860
tattccgaat cttgccctgc acgaatacca gcgaccccct gcccaaatac ttgccgtggg   22920
cctcggcctg agagccaaaa cacttgatgc ggaagaagtc ggtgcgctcc tgcttgtcgc   22980
cggcatcgtt gcgccactct tcattaaccg ctatatcgaa aattgcttgc ggcttgttag   23040
aattgccatg acgtacctcg gtgtcacggg taagattacc gataaactgg aactgattat   23100
ggctcatatc gaaagtctcc ttgagaaagg agactctagt ttagctaaac attggttccg   23160
ctgtcaagaa ctttagcggc taaaattttg cgggccgcga ccaaaggtgc gagggcggc    23220 ttccgctgtg tacaaccaga tattttcac caacatcctt cgtctgctcg atgagcgggg    23280
catgacgaaa catgagctgt cggagagggc aggggtttca atttcgtttt tatcagactt   23340
aaccaacggt aaggccaacc cctcgttgaa ggtgatggag gccattgccg acgccctgga   23400
aactccccta cctcttctcc tggagtccac cgaccttgac cgcgaggcac tcgcggagat   23460
tgcgggtcat cctttcaaga gcagcgtgcc gcccggatac gaacgcatca gtgtggtttt   23520
gccgtcacat aaggcgttta tcgtaaagaa atggggcgac gacacccgaa aaaagctgcg   23580
tggaaggctc tgacgccaag ggttagggct tgcacttcct tctttagccg ctaaaacggc   23640
cccttctctg cgggccgtcg gctcgcgcat catatcgaca tcctcaacgg aagccgtgcc   23700
gcgaatggca tcgggcgggt gcgctttgac agttgttttc tatcagaacc cctacgtcgt   23760
gcggttcgat tagctgtttg tcttgcaggc taaacacttt cggtatatcg tttgcctgtg   23820
```

```
cgataatgtt gctaatgatt tgttgcgtag gggttactga aaagtgagcg ggaaagaaga    23880
gtttcagacc atcaaggagc gggccaagcg caagctggaa cgcgacatgg gtgcggacct    23940
gttggccgcg ctcaacgacc cgaaaaccgt tgaagtcatg ctcaacgcgg acggcaaggt    24000
gtggcacgaa cgccttggcg agccgatgcg gtacatctgc gacatgcggc ccagccagtc    24060
gcaggcgatt atagaaacgg tggccggatt ccacggcaaa gaggtcacgc ggcattcgcc    24120
catcctggaa ggcgagttcc ccttggatgg cagccgcttt gccggccaat tgccgccggt    24180
cgtggccgcg ccaacctttg cgatccgcaa gcgcgcggtc gccatcttca cgctggaaca    24240
gtacgtcgag gcgggcatca tgacccgcga gcaatacgag gtcattaaaa gcgccgtcgc    24300
ggcgcatcga aacatcctcg tcattggcgg tactggctcg gcaagacca cgctcgtcaa    24360
cgcgatcatc aatgaaatgg tcgccttcaa cccgtctgag cgcgtcgtca tcatcgagga    24420
caccggcgaa atccagtgcg ccgcagagaa cgccgtccaa taccacacca gcatcgacgt    24480
ctcgatgacg ctgctgctca agacaacgct gcgtatgcgc cccgaccgca tcctggtcgg    24540
tgaggtacgt ggccccgaag cccttgatct gttgatggcc tggaacaccg gcatgaagg    24600
aggtgccgcc accctgcacg caaacaaccc caaagcgggc ctgagccggc tcgccatgct    24660
tatcagcatg cacccggatt caccgaaacc cattgagccg ctgattggcg aggcggttca    24720
tgtggtcgtc catatcgcca ggaccccag cggccgtcga gtgcaagaaa ttctcgaagt    24780
tcttggttac gagaacggcc agtacatcac caaaaccctg taaggagtat ttccaatgac    24840
aacggctgtt ccgttccgtc tgaccatgaa tcgcggcatt ttgttctacc ttgccgtgtt    24900
cttcgttctc gctctcgcgt tatccgcgca tccggcgatg gcctcggaag gcaccggcgg    24960
cagcttgcca tatgagagct ggctgacgaa cctgcgcaac tccgtaaccg gcccggtggc    25020
cttcgcgctg tccatcatcg gcatcgtcgt cgccggcggc gtgctgatct tcggcggcga    25080
actcaacgcc ttcttccgaa ccctgatctt cctggttctg gtgatggcgc tgctggtcgg    25140
cgcgcagaac gtgatgagca ccttcttcgg tcgtggtgcc gaaatcgcgg ccctcggcaa    25200
cggggcgctg caccaggtgc aagtcgcggg ggcggatgcc gtgcgtgcgg tagcggctgg    25260
acggctcgcc taatcatggc tctgcgcacg atccccatcc gtcgcgcagg caaccgagaa    25320
aacctgttca tgggtggtga tcgtgaactg gtgatgttct cgggcctgat ggcgtttgcg    25380
ctgattttca gcgcccaaga gctgcgggcc accgtggtcg gtctgatcct gtggttcggg    25440
gcgctctatg cgttccgaat catggcgaag gccgatccga agatgcggtt cgtgtacctg    25500
cgtcaccgcc ggtacaagcc gtattaccg gcccgctcga ccccgttccg cgagaacacc    25560
aatagccaag ggaagcaata ccgatgatcc aagcaattgc gattgcaatc gcgggcctcg    25620
gcgcgcttct gttgttcatc ctctttgccc gcatccgcgc ggtcgatgcc gaactgaaac    25680
tgaaaaagca tcgttccaag gacgccggcc tggccgatct gctcaactac gccgctgtcg    25740
tcgatgacgg cgtaatcgtg ggcaagaacg gcagctttat ggctgcctgg ctgtacaagg    25800
gcgatgacaa cgcaagcagc accgaccagc agcgcgaagt agtgtccgcc cgcatcaacc    25860
aggccctcgc gggcctggga agtgggtgga tgatccatgt ggacgccgtg cggcgtcctg    25920
ctccgaacta cgcggagcgg ggcctgtcgg cgttccctga ccgtctgacg gcagcgattg    25980
aagaagagcg ctcggtcttg ccttgctcgt cggtgatgta cttcaccagc tccgcgaagt    26040
cgctcttctt gatggagcgc atggggacgg gcttggcaat cacgcgcacc ccccggccgt    26100
tttagcggct aaaaaagtca tggctctgcc ctcgggcgga ccacgcccat catgaccttg    26160
```

```
ccaagctcgt cctgcttctc ttcgatcttc gccagcaggg cgaggatcgt ggcatcaccg   26220
aaccgcgccg tgcgcgggtc gtcggtgagc cagagtttca gcaggccgcc caggcggccc   26280
aggtcgccat tgatgcgggc cagctcgcgg acgtgctcat agtccacgac gcccgtgatt   26340
ttgtagccct ggccgacggc cagcaggtag gccgacaggc tcatgccggc cgccgccgcc   26400
ttttcctcaa tcgctcttcg ttcgtctgga aggcagtaca ccttgatagg tgggctgccc   26460
ttcctggttg gcttggtttc atcagccatc cgcttgccct catctgttac gccggcggta   26520
gccggccagc ctcgcagagc aggattcccg ttgagcaccg ccaggtgcga ataagggaca   26580
gtgaagaagg aacacccgct cgcgggtggg cctacttcac ctatcctgcc cggctgacgc   26640
cgttggatac accaaggaaa gtctacacga acccctttggc aaaatcctgt atatcgtgcg   26700
aaaaaggatg atataccga aaaaatcgct ataatgaccc cgaagcaggg ttatgcagcg   26760
gaaaagcgct gcttccctgc tgttttgtgg aatatctacc gactggaaac aggcaaatgc   26820
aggaaattac tgaactgagg ggacaggcga gagacgatgc caaagagcta caccgacgag   26880
ctggccgagt gggttgaatc ccgcgcgcc aagaagcgcc ggcgtgatga ggctgcggtt   26940
gcgttcctgg cggtgagggc ggatgtcgag gcggcgttag cgtccggcta tgcgctcgtc   27000
accatttggg agcacatgcg ggaaacgggg aaggtcaagt tctcctacga gacgttccgc   27060
tcgcacgcca ggcggcacat caaggccaag cccgccgatg tgcccgcacc gcaggccaag   27120
gctgcggaac ccgcgccggc acccaagacg ccggagccac ggcggccgaa gcaggggggc   27180
aaggctgaaa agccggcccc cgctgcggcc ccgaccggct tcaccttcaa cccaacaccg   27240
gacaaaaagg atctactgta atggcgaaaa ttcacatggt tttgcagggc aagggcgggg   27300
tcggcaagtc ggccatcgcc gcgatcattg cgcagtacaa gatggacaag gggcagacac   27360
ccttgtgcat cgacaccgac ccggtgaacg cgacgttcga gggctacaag gccctgaacg   27420
tccgccggct gaacatcatg gccggcgacg aaattaactc gcgcaacttc gacaccctgg   27480
tcgagctgat tgcgccgacc aaggatgacg tggtgatcga caacggtgcc agctcgttcg   27540
tgcctctgtc gcattacctc atcagcaacc aggtgccggc tctgctgcaa gaaatggggc   27600
atgagctggt catccatacc gtcgtcaccg gcggccaggc tctcctggac acggtgagcg   27660
gcttcgccca gctcgccagc cagttcccgg ccgaagcgct tttcgtggtc tggctgaacc   27720
cgtattgggg gcctatcgag catgagggca agagctttga gcagatgaag gcgtacacgg   27780
ccaacaaggc ccgcgtgtcg tccatcatcc agattccggc cctcaaggaa gaaacctacg   27840
gccgcgattt cagcgacatg ctgcaagagc ggctgacgtt cgaccaggcg ctggccgatg   27900
aatcgctcac gatcatgacg cggcaacgcc tcaagatcgt gcggcgcggc ctgtttgaac   27960
agctcgacgc ggcggccgtg ctatgagcga ccagattgaa gagctgatcc gggagattgc   28020
ggccaagcac ggcatcgccg tcggccgcga cgacccggtg ctgatcctgc ataccatcaa   28080
cgccgggctc atggccgaca gtgcggccaa gcaagaggaa atccttgccg cgttcaagga   28140
agagctggaa gggatcgccc atcgttgggg cgaggacgcc aaggccaaag cggagcggat   28200
gctgaacgcg gccctggcgg ccagcaagga cgcaatggcg aaggtaatga aggacagcgc   28260
cgcgcaggcg gccgaagcga tccgcaggga aatcgacgac ggccttggcc gccagctcgc   28320
ggccaaggtc gcggacgcgc ggcgcgtggc gatgatgaac atgatcgccg gcggcatggt   28380
gttgttcgcg gccgccctgg tggtgtgggc ctcgttatga atcgcagagg cgcagatgaa   28440
aaagcccggc gttgccgggc tttgtttttg cgttagctgg gcttgtttga caggcccaag   28500
ctctgactgc gcccgcgctc gcgctcctgg gcctgtttct tctcctgctc ctgcttgcgc   28560
```

```
atcagggcct ggtgccgtcg ggctgcttca cgcatcgaat cccagtcgcc ggccagctcg   28620
ggatgctccg cgcgcatctt gcgcgtcgcc agttcctcga tcttgggcgc gtgaatgccc   28680
atgccttcct tgatttcgcg caccatgtcc agccgcgtgt gcagggtctg caagcgggct   28740
tgctgttggg cctgctgctg ctgccaggcg gcctttgtac gcggcaggga cagcaagccg   28800
ggggcattgg actgtagctg ctgcaaacgc gcctgctgac ggtctacgag ctgttctagg   28860
cggtcctcga tgcgctccac ctggtcatgc tttgcctgca cgtagagcgc aagggtctgc   28920
tggtaggtct gctcgatggg cgcggattct aagagggcct gctgttccgt ctcggcctcc   28980
tgggccgcct gtagcaaatc ctcgccgctg ttgccgctgg actgctttac tgccggggac   29040
tgctgttgcc ctgctcgcgc cgtcgtcgca gttcggcttg ccccactcg attgactgct    29100 tcatttcgag ccgcagcgat gcgatctcgg attgcgtcaa cggacggggc agcgcggagg   29160
tgtccggctt ctccttgggt gagtcggtcg atgccatagc caaaggtttc cttccaaaat   29220
gcgtccattg ctggaccgtg tttctcattg atgcccgcaa gcatcttcgg cttgaccgcc   29280
aggtcaagcg cgccttcatg ggcggtcatg acggacgccg ccatgacctt gccgccgttg   29340
ttctcgatgt agccgcgtaa tgaggcaatg gtgccgccca tcgtcagcgt gtcatcgaca   29400
acgatgtact tctggccggg gatcacctcc ccctcgaaag tcgggttgaa cgccaggcga   29460
tgatctgaac cggctccggt tcgggcgacc ttctcccgct gcacaatgtc cgtttcgacc   29520
tcaaggccaa ggcggtcggc cagaacgacc gccatcatgg ccggaatctt gttgttcccc   29580
gccgcctcga cggcgaggac tggaacgatg cggggcttgt cgtcgccgat cagcgtcttg   29640
agctgggcaa cagtgtcgtc cgaaatcagg cgctcgacca aattaagcgc cgcttccgcg   29700
tcgccctgct tcgcagcctg gtattcaggc tcgttggtca agaaccaag gtcgccgttg    29760 cgaaccacct tcgggaagtc tccccacggt gcgcgctcgg ctctgctgta gctgctcaag   29820
acgcctccct ttttagccgc taaaactcta acgagtgcgc ccgcgactca acttgacgct   29880
ttcggcactt acctgtgcct tgccacttgc gtcataggtg atgcttttcg cactcccgat   29940
ttcaggtact ttatcgaaat ctgaccgggc gtgcattaca aagttcttcc ccacctgttg   30000
gtaaatgctg ccgctatctg cgtggacgat gctgccgtcg tggcgctgcg acttatcggc   30060
cttttgggcc atatagatgt tgtaaatgcc aggtttcagg gccccggctt tatctaccct   30120
ctggttcgtc catgcgcctt ggttctcggt ctggacaatt ctttgcccat tcatgaccag   30180
gaggcggtgt ttcattgggt gactcctgac ggttgcctct ggtgttaaac gtgtcctggt   30240
cgcttgccgg ctaaaaaaaa gccgacctcg gcagttcgag gccggctttc cctagagccg   30300
ggcgcgtcaa ggttgttcca tctattttag tgaactgcgt tcgatttatc agttactttc   30360
ctcccgcttt gtgtttcctc ccactcgttt ccgcgtctag ccgaccccctc aacatagcgg   30420 cctcttcttg ggctgccttt gcctcttgcc gcgcttcgtc acgctcggct tgcaccgtcg   30480
taaagcgctc ggcctgcctg gccgcctctt gcgccgccaa cttcctttgc tcctggtggg   30540
cctcggcgtc ggcctgcgcc ttcgctttca ccgctgccaa ctccgtgcgc aaactctccg   30600
cttcgcgcct ggtggcgtcg cgctcgccgc gaagcgcctg catttcctgg ttggccgcgt   30660
ccagggtctt gcggctctct tctttgaatg cgcgggcgtc ctggtgagcg tagtccagct   30720
cggcgcgcag ctcctgcgct cgacgctcca cctcgtcggc ccgctgcgtc gccagcgcgg   30780
cccgctgctc ggctcctgcc agggcggtgc gtgcttcggc cagggcttgc cgctggcgtg   30840
cggccagctc ggccgcctcg gcggcctgct gctctagcaa tgtaacgcgc gcctgggctt   30900
```

```
cttccagctc gcgggcctgc gcctcgaagg cgtcggccag ctccccgcgc acggcttcca   30960
actcgttgcg ctcacgatcc cagccggctt gcgctgcctg caacgattca ttggcaaggg   31020
cctgggcggc ttgccagagg gcggccacgg cctggttgcc ggcctgctgc accgcgtccg   31080
gcacctggac tgccagcggg gcggcctgcg ccgtgcgctg gcgtcgccat cgcgcatgc    31140
cggcgctggc gtcgttcatg ttgacgcggg cggccttacg cactgcatcc acggtcggga   31200
agttctcccg gtcgccttgc tcgaacagct cgtccgcagc cgcaaaaatg cggtcgcgcg   31260
tctctttgtt cagttccatg ttggctccgg taattggtaa gaataataat actcttacct   31320
accttatcag cgcaagagtt tagctgaaca gttctcgact taacggcagg ttttttagcg   31380
gctgaagggc aggcaaaaaa agccccgcac ggtcggcggg ggcaaagggt cagcgggaag   31440
gggattagcg ggcgtcgggc ttcttcatgc gtcggggccg cgcttcttgg gatggagcac   31500
gacgaagcgc gcacgcgcat cgtcctcggc cctatcggcc cgcgtcgcgg tcaggaactt   31560
gtcgcgcgct aggtcctccc tggtgggcac caggggcatg aactcggcct gctcgatgta   31620
ggtccactcc atgaccgcat cgcagtcgag gccgcgttcc ttcaccgtct cttgcaggtc   31680
gcggtacgcc cgctcgttga gcggctggta acgggccaat tggtcgtaaa tggctgtcgg   31740
ccatgagcgg ccttttcctgt tgagccagca gccgacgacg aagccggcaa tgcaggcccc   31800
tggcacaacc aggccgacgc cgggggcagg ggatggcagc agctcgccaa ccaggaaccc   31860
cgccgcgatg atgccgatgc cggtcaacca gcccttgaaa ctatccggcc ccgaaacacc   31920
cctgcgcatt gcctggatgc tgcgccggat agcttgcaac atcaggagcc gtttcttttg   31980
ttcgtcagtc atggtccgcc ctcaccagtt gttcgtatcg gtgtcggacg aactgaaatc   32040
gcaagagctg ccggtatcgg tccagccgct gtccgtgtcg ctgctgccga agcacggcga   32100
ggggtccgcg aacgccgcag acggcgtatc cggccgcagc gcatcgccca gcatggcccc   32160
ggtcagcgag ccgccggcca ggtagcccag catggtgctg ttggtcgccc cggccaccag   32220
ggccgacgtg acgaaatcgc cgtcattccc tctggattgt tcgctgctcg gcggggcagt   32280
gcgccgcgcc ggcggcgtcg tggatggctc gggttggctg gcctgcgacg gccggcgaaa   32340
ggtgcgcagc agctcgttat cgaccggctg cggcgtcggg gccgccgcct tgcgctgcgg   32400
tcggtgttcc ttcttcggct cgcgcagctt gaacagcatg atcgcggaaa ccagcagcaa   32460
cgccgcgcct acgcctcccg cgatgtagaa cagcatcgga ttcattcttc ggtcctcctt   32520
gtagcggaac cgttgtctgt gcggcgcggg tggcccgcgc cgctgtcttt ggggatcagc   32580
cctcgatgag cgcgaccagt ttcacgtcgg caaggttcgc ctcgaactcc tggccgtcgt   32640
cctcgtactt caaccaggca tagccttccg ccggcggccg acggttgagg ataaggcggg   32700
cagggcgctc gtcgtgctcg acctggacga tggcctttt cagcttgtcc gggtccggct   32760
cctttcgcgcc cttttccttg gcgtccttac cgtcctggtc gccgtcctcg ccgtcctggc   32820
cgtcgccggc ctccgcgtca cgctcggcat cagtctggcc gttgaaggca tcgacggtgt   32880
tgggatcgcg gcccttctcg tccaggaact cgcgcagcag cttgaccgtg ccgcgcgtga   32940
tttcctgggt gtcgtcgtca agccacgcct cgacttcctc cgggcgcttc ttgaaggccg   33000
tcaccagctc gttcaccacg gtcacgtcgc gcacgcggcc ggtgttgaac gcatcggcga   33060
tcttctccgg caggtccagc agcgtgacgt gctgggtgat gaacgccggc gacttgccga   33120
tttccttggc gatatcgcct ttcttcttgc ccttcgccag ctcgcggcca atgaagtcgg   33180
caatttcgcg cggggtcagc tcgttgcgtt gcaggtctc gataacctgg tcggcttcgt   33240
tgtagtcgtt gtcgatgaac gccgggatgg acttcttgcc ggcccacttc gagccacggt   33300
```

```
agcggcgggc gccgtgattg atgatatagc ggcccggctg ctcctggttc tcgcgcaccg   33360
aaatgggtga cttcaccccg cgctctttga tcgtggcacc gatttccgcg atgctctccg   33420
gggaaaagcc ggggttgtcg gccgtccgcg gctgatgcgg atcttcgtcg atcaggtcca   33480
ggtccagctc gatagggccg gaaccgccct gagacgccgc aggagcgtcc aggaggctgc   33540
acaggtcgcc gatgctatcc aaccccaggc cggacggctg cgccgcgcct gcggcttcct   33600
gagcggccgc agcggtgttt ttcttggtgg tcttggcttg agccgcagtc attgggaaat   33660
ctccatcttc gtgaacacgt aatcagccag ggcgcgaacc tctttcgatg ccttgcgcgc   33720
ggccgttttc ttgatcttcc agaccggcac accggatgcg agggcatcgg cgatgctgct   33780
gcgcaggcca acggtggccg gaatcatcat cttggggtac gcggccagca gctcggcttg   33840
gtggcgcgcg tggcgcggat tccgcgcatc gaccttgctg gcaccatgc  caaggaattg   33900 cagcttggcg ttcttctggc gcacgttcgc aatggtcgtg accatcttct tgatgccctg   33960
gatgctgtac gcctcaagct cgatggggga cagcacatag tcggccgcga agagggcggc   34020
cgccaggccg acgccaaggg tcggggccgt gtcgatcagg cacacgtcga agccttggtt   34080
cgccagggcc ttgatgttcg ccccgaacag ctcgcgggcg tcgtccagcg acagccgttc   34140
ggcgttcgcc agtaccgggt tggactcgat gagggcgagg cgcgcggcct ggccgtcgcc   34200
ggctgcgggt gcggtttcgg tccagccgcc ggcaggaca  cgccgaaca gcttgcttgc   34260 atgcaggccg gtagcaaagt ccttgagcgt gtaggacgca ttgccctggg ggtccaggtc   34320
gatcacggca acccgcaagc cgcgctcgaa aaagtcgaag gcaagatgca caagggtcga   34380
agtcttgccg acgccgcctt tctggttggc cgtgaccaaa gttttcatcg tttggtttcc   34440
tgttttttct tggcgtccgc ttcccacttc cggacgatgt acgcctgatg ttccggcaga   34500
accgccgtta cccgcgcgta cccctcgggc aagttcttgt cctcgaacgc ggcccacacg   34560
cgatgcaccg cttgcgacac tgcgcccctg gtcagtccca gcgacgttgc gaacgtcgcc   34620
tgtggcttcc catcgactaa gacgccccgc gctatctcga tggtctgctg ccccacttcc   34680 agccctgga  tcgcctcctg gaactggctt tcggtaagcc gttcttcat  ggataacacc   34740 cataatttgc tccgcgcctt ggttgaacat agcggtgaca gccgcagca  catgagagaa   34800 gtttagctaa acatttctcg cacgtcaaca cctttagccg ctaaaactcg tccttggcgt   34860
aacaaaacaa aagcccggaa accgggcttt cgtctcttgc cgcttatggc tctgcacccg   34920
gctccatcac caacaggtcg cgcacgcgct tcactcggtt gcggatcgac actgccagcc   34980
caacaaagcc ggttgccgcc gccgccagga tcgcgccgat gatgccggcc acaccggcca   35040
tcgcccacca ggtcgccgcc ttccggttcc attcctgctg gtactgcttc gcaatgctgg   35100
acctcggctc accataggct gaccgctcga tggcgtatgc cgcttctccc cttggcgtaa   35160
aacccagcgc cgcaggcggc attgccatgc tgcccgccgc tttcccgacc acgacgcgcg   35220
caccaggctt gcggtccaga ccttcggcca cggcgagctg cgcaaggaca taatcagccg   35280
ccgacttggc tccacgcgcc tcgatcagct cttgcactcg cgcgaaatcc ttggcctcca   35340
cggccgccat gaatcgcgca cgcggcgaag gctccgcagg gccggcgtcg tgatcgccgc   35400
cgagaatgcc cttcaccaag ttcgacgaca cgaaaatcat gctgacggct atcaccatca   35460
tgcagacgga tcgcacgaac ccgctgaatt gaacacgagc acggcacccg cgaccactat   35520
gccaagaatg cccaaggtaa aaattgccgg ccccgccatg aagtccgtga atgcccgac   35580 ggccgaagtg aagggcaggc cgccacccag gccgccgccc tcactgcccg gcacctggtc   35640
```

| | |
|---|---|
| gctgaatgtc gatgccagca cctgcggcac gtcaatgctt ccgggcgtcg cgctcgggct | 35700 |
| gatcgcccat cccgttactg ccccgatccc ggcaatggca aggactgcca gcgctgccat | 35760 |
| ttttggggtg aggccgttcg cggccgaggg gcgcagcccc tgggggggatg ggaggcccgc | 35820 |
| gttagcgggc cgggagggtt cgagaagggg gggcaccccc cttcggcgtg cgcggtcacg | 35880 |
| cgcacagggc gcagccctgg ttaaaaacaa ggtttataaa tattggttta aaagcaggtt | 35940 |
| aaaagacagg ttagcggtgg ccgaaaaacg ggcggaaacc cttgcaaatg ctggattttc | 36000 |
| tgcctgtgga cagcccctca aatgtcaata ggtgcgcccc tcatctgtca gcactctgcc | 36060 |
| cctcaagtgt caaggatcgc gcccctcatc tgtcagtagt cgcgcccctc aagtgtcaat | 36120 |
| accgcagggc acttatcccc aggcttgtcc acatcatctg tgggaaactc gcgtaaaatc | 36180 |
| aggcgttttc gccgatttgc gaggctggcc agctccacgt cgccggccga atcgagcct | 36240 |
| gcccctcatc tgtcaacgcc gcgccgggtg agtcggcccc tcaagtgtca acgtccgccc | 36300 |
| ctcatctgtc agtgagggcc aagttttccg cgaggtatcc acaacgccgg cggccgcggt | 36360 |
| gtctcgcaca cggcttcgac ggcgtttctg gcgcgtttgc agggccatag acggccgcca | 36420 |
| gcccagcggc gagggcaacc agcccggtga gcgtcggaaa ggcgctggaa gccccgtagc | 36480 |
| gacgcggaga ggggcgagac aagccaaggg cgcaggctcg atgcgcagca cgacatagcc | 36540 |
| ggttctcgca aggacgagaa tttccctgcg gtgcccctca agtgtcaatg aaagtttcca | 36600 |
| acgcgagcca ttcgcgagag ccttgagtcc acgctagatg agagctttgt tgtaggtgga | 36660 |
| ccagttggtg attttgaact tttgctttgc cacggaacgg tctgcgttgt cgggaagatg | 36720 |
| cgtgatctga tccttcaact cagcaaaagt tcgatttatt caacaaagcc acgttgtgtc | 36780 |
| tcaaaatctc tgatgttaca ttgcacaaga taaaaatata tcatcatgaa caataaaact | 36840 |
| gtctgcttac ataaacagta atacaagggg tgttatgagc catattcaac gggaaacgtc | 36900 |
| ttgctcgac | 36909 |

<210> SEQ ID NO 8
<211> LENGTH: 13019
<212> TYPE: DNA
<213> ORGANISM: artificial sequence
<220> FEATURE:
<223> OTHER INFORMATION: vector

<400> SEQUENCE: 8

| | |
|---|---|
| gttacccgga ccgaagctta gcccgggcat gcctgcagtg cagcgtgacc cggtcgtgcc | 60 |
| cctctctaga gataatgagc attgcatgtc taagttataa aaaattacca catatttttt | 120 |
| ttgtcacact tgtttgaagt gcagtttatc tatctttata catatattta aactttactc | 180 |
| tacgaataat ataatctata gtactacaat aatatcagtg ttttagagaa tcatataaat | 240 |
| gaacagttag acatggtcta aaggacaatt gagtattttg acaacaggac tctacagttt | 300 |
| tatcttttta gtgtgcatgt gttctccttt ttttttgcaa atagcttcac ctatataata | 360 |
| cttcatccat tttattagta catccattta gggtttaggg ttaatggttt ttatagacta | 420 |
| atttttttag tacatctatt ttattctatt ttagcctcta aattaagaaa actaaaactc | 480 |
| tattttagtt tttttattta ataatttaga tataaaatag aataaaataa agtgactaaa | 540 |
| aattaaacaa ataccctttt agaaattaaa aaaactaagg aaacattttt cttgtttcga | 600 |
| gtagataatg ccagcctgtt aaacgccgtc gacgagtcta acggacacca accagcgaac | 660 |
| cagcagcgtc gcgtcgggcc aagcgaagca gacggcacgg catctctgtc gctgcctctg | 720 |
| gaccccctct cgagagttcc gctccaccgt tggacttgct ccgctgtcgg catccagaaat | 780 |

```
tgcgtggcgg agcggcagac gtgagccggc acggcaggcg gcctcctcct cctctcacgg      840
cacggcagct acgggggatt cctttcccac cgctccttcg ctttcccttc ctcgcccgcc      900
gtaataaata gacacccccct ccacaccctc tttccccaac ctcgtgttgt tcggagcgca     960
cacacacaca accagatctc ccccaaatcc acccgtcggc acctccgctt caaggtacgc     1020
cgctcgtcct cccccccccc ccctctctac cttctctaga tcggcgttcc ggtccatggt     1080
tagggcccgg tagttctact tctgttcatg tttgtgttag atccgtgttt gtgttagatc     1140
cgtgctgcta gcgttcgtac acggatgcga cctgtacgtc agacacgttc tgattgctaa     1200
cttgccagtg tttctctttg gggaatcctg ggatggctct agccgttccg cagacgggat     1260
cgatttcatg attttttttg tttcgttgca tagggtttgg tttgcccttt tcctttattt     1320
caatatatgc cgtgcacttg tttgtcgggt catcttttca tgctttttttt tgtcttggtt    1380 gtgatgatgt ggtctggttg ggcggtcgtt ctagatcgga gtagaattct gtttcaaact     1440
acctggtgga tttattaatt ttggatctgt atgtgtgtgc catacatatt catagttacg     1500
aattgaagat gatggatgga aatatcgatc taggataggt atacatgttg atgcgggttt     1560
tactgatgca tatacagaga tgcttttttgt tcgcttggtt gtgatgatgt ggtgtggttg    1620
ggcggtcgtt cattcgttct agatcggagt agaatactgt ttcaaactac ctggtgtatt     1680
tattaatttt ggaactgtat gtgtgtgtca tacatcttca tagttacgag tttaagatgg     1740
atggaaatat cgatctagga taggtataca tgttgatgtg ggttttactg atgcatatac     1800
atgatggcat atgcagcatc tattcatatg ctctaacctt gagtacctat ctattataat     1860
aaacaagtat gttttataat tattttgatc ttgatatact tggatgatgg catatgcagc    1920
agctatatgt ggattttttt agccctgcct tcatacgcta tttatttgct tggtactgtt     1980
tcttttgtcg atgctcaccc tgttgtttgg tgttacttct gcaggtcgac tctagaggat     2040
ccacaagttt gtacaaaaaa gctgaacgag aaacgtaaaa tgatataaat atcaatatat     2100
taaattagat tttgcataaa aaacagacta cataatactg taaaacacaa catatccagt     2160
cactatggcg gccgcattag gcaccccagg ctttacactt tatgcttccg gctcgtataa     2220
tgtgtggatt ttgagttagg atttaaatac gcgttgatcc ggcttactaa agccagata     2280 acagtatgcg tatttgcgcg ctgatttttg cggtataaga atatatactg atatgtatac     2340
ccgaagtatg tcaaaagag gtatgctatg aagcagcgta ttacagtgac agttgacagc     2400
gacagctatc agttgctcaa ggcatatatg atgtcaatat ctccggtctg gtaagcacaa     2460
ccatgcagaa tgaagcccgt cgtctgcgtg ccgaacgctg gaaagcggaa atcaggaag     2520 ggatggctga ggtcgcccgg tttattgaaa tgaacggctc ttttgctgac gagaacaggg     2580
gctggtgaaa tgcagtttaa ggtttacacc tataaaagag agagccgtta tcgtctgttt     2640
gtggatgtac agagtgatat cattgacacg cccggtcgac ggatggtgat cccctggcc     2700 agtgcacgtc tgctgtcaga taaagtctcc cgtgaacttt acccggtggt gcatatcggg     2760
gatgaaagct ggcgcatgat gaccaccgat atggccagtg tgccggtctc cgttatcggg     2820
gaagaagtgg ctgatctcag ccaccgcgaa aatgacatca aaaacgccat taacctgatg     2880
ttctggggaa tataaatgtc aggctcccct atacacagcc agtctgcagg tcgaccatag     2940
tgactggata tgttgtgttt tacagtatta tgtagtctgt tttttatgca aaatctaatt     3000
taatatattg atatttatat catttttacgt ttctcgttca gctttcttgt acaaagtggt     3060
gttaacctag acttgtccat cttctggatt ggccaactta attaatgtat gaaataaaag     3120
```

```
gatgcacaca tagtgacatg ctaatcacta taatgtgggc atcaaagttg tgtgttatgt    3180
gtaattacta gttatctgaa taaaagagaa agagatcatc catatttctt atcctaaatg    3240
aatgtcacgt gtctttataa ttctttgatg aaccagatgc atttcattaa ccaaatccat    3300
atacatataa atattaatca tatataatta atatcaattg ggttagcaaa acaaatctag    3360
tctaggtgtg ttttgcgaat tgcggccgcc accgcggtgg agctcgaatt ccggtccggg    3420
tcacctttgt ccaccaagat ggaactgcgg ccgctcatta attaagtcag gcgcgcctct    3480
agttgaagac acgttcatgt cttcatcgta agaagacact cagtagtctt cggccagaat    3540
ggccatctgg attcagcagg cctagaaggc catttaaatc ctgaggatct ggtcttccta    3600
aggacccggg atatcggacc gattaaactt taattcggtc cgaagcttgc atgcctgcag    3660
tgcagcgtga cccggtcgtg cccctctcta gagataatga gcattgcatg tctaagttat    3720
aaaaaattac cacatatttt ttttgtcaca cttgtttgaa gtgcagttta tctatcttta    3780
tacatatatt taaactttac tctacgaata atataatcta tagtactaca ataatatcag    3840
tgttttagag aatcatataa atgaacagtt agacatggtc taaaggacaa ttgagtattt    3900
tgacaacagg actctacagt tttatctttt tagtgtgcat gtgttctcct ttttttttgc    3960 aaaatagcttc acctatataa tacttcatcc attttattag tacatccatt tagggtttag    4020
ggttaatggt ttttatagac taatttttttt agtacatcta ttttattcta ttttagcctc    4080
taaattaaga aaactaaaac tctattttag tttttttatt taataattta gatataaaat    4140
agaataaaat aaagtgacta aaaattaaac aaatacccctt taagaaatta aaaaaactaa    4200
ggaaacattt ttcttgtttc gagtagataa tgccagcctg ttaaacgccg tcgacgagtc    4260
taacggacac caaccagcga accagcagcg tcgcgtcggg ccaagcgaag cagacggcac    4320
ggcatctctg tcgctgcctc tggacccctc tcgagagttc cgctccaccg ttggacttgc    4380
tccgctgtcg gcatccagaa attgcgtggc ggagcggcag acgtgagccg gcacggcagg    4440
cggcctcctc ctcctctcac ggcaccggca gctacggggg attcctttcc caccgctcct    4500
tcgctttccc ttcctcgccc gccgtaataa atagacaccc cctccacacc ctctttcccc    4560
aacctcgtgt tgttcggagc gcacacacac acaaccagat ctcccccaaa tccacccgtc    4620
ggcacctccg cttcaaggta cgccgctcgt cctcccccc ccccctctct accttctcta    4680
gatcggcgtt ccggtccatg catggttagg gcccggtagt tctacttctg ttcatgtttg    4740
tgttagatcc gtgtttgtgt tagatccgtg ctgctagcgt tcgtacacgg atgcgacctg    4800
tacgtcagac acgttctgat tgctaacttg ccagtgtttc tctttgggga atcctgggat    4860
ggctctagcc gttccgcaga cgggatcgat ttcatgattt tttttgtttc gttgcatagg    4920
gtttggtttg ccctttcct ttatttcaat atatgccgtg cacttgtttg tcgggtcatc    4980
ttttcatgct ttttttgtc ttggttgtga tgatgtggtc tggttgggcg tcgttctag    5040 atcggagtag aattctgttt caaactacct ggtggattta ttaattttgg atctgtatgt    5100
gtgtgccata catattcata gttacgaatt gaagatgatg gatggaaata tcgatctagg    5160
ataggtatac atgttgatgc gggttttact gatgcatata cagagatgct ttttgttcgc    5220
ttggttgtga tgatggtg tggttgggcg tcgttcatt cgttctagat cggagtagaa    5280
tactgtttca aactacctgg tgtatttatt aattttggaa ctgtatgtgt gtgtcataca    5340
tcttcatagt tacgagttta agatggatgg aaatatcgat ctaggatagg tatacatgtt    5400
gatgtgggtt ttactgatgc atatacatga tggcatatgc agcatctatt catatgctct    5460
aaccttgagt acctatctat tataataaac aagtatgttt tataattatt ttgatcttga    5520
```

-continued

```
tatacttgga tgatggcata tgcagcagct atatgtggat ttttttagcc ctgccttcat    5580
acgctattta tttgcttggt actgtttctt ttgtcgatgc tcaccctgtt gtttggtgtt    5640
acttctgcag gtcgacttta acttagccta ggatccacac gacaccatgt cccccgagcg    5700
ccgccccgtc gagatccgcc cggccaccgc cgccgacatg gccgccgtgt gcgacatcgt    5760
gaaccactac atcgagacct ccaccgtgaa cttccgcacc gagccgcaga ccccgcagga    5820
gtggatcgac gacctggagc gcctccagga ccgctacccg tggctcgtgg ccgaggtgga    5880
gggcgtggtg gccggcatcg cctacgccgg cccgtggaag gcccgcaacg cctacgactg    5940
gaccgtggag tccaccgtgt acgtgtccca ccgccaccag cgcctcggcc tcggctccac    6000
cctctacacc cacctcctca agagcatgga ggcccagggc ttcaagtccg tggtggccgt    6060
gatcggcctc ccgaacgacc cgtccgtgcg cctccacgag gccctcggct acaccgcccg    6120
cggcacccte cgcgccgccg gctacaagca cggcggctgg cacgacgtcg gcttctggca    6180
gcgcgacttc gagctgccgg ccccgccgcg cccggtgcgc ccggtgacgc agatctgagt    6240
cgaaacctag acttgtccat cttctggatt ggccaactta attaatgtat gaaataaaag    6300
gatgcacaca tagtgacatg ctaatcacta taatgtgggc atcaaagttg tgtgttatgt    6360
gtaattacta gttatctgaa taaaagagaa agagatcatc catatttctt atcctaaatg    6420
aatgtcacgt gtcttttataa ttctttgatg aaccagatgc atttcattaa ccaaatccat    6480
atacatataa atattaatca tatataatta atatcaattg ggttagcaaa acaaatctag    6540
tctaggtgtg ttttgcgaat tgcggccgcc accgcgtgg agctcgaatt cattccgatt    6600
aatcgtggcc tcttgctctt caggatgaag agctatgttt aaacgtgcaa gcgctactag    6660
acaattcagt acattaaaaa cgtccgcaat gtgttattaa gttgtctaag cgtcaatttg    6720
tttacaccac aatatatcct gccaccagcc agccaacagc tccccgaccg gcagctcggc    6780
acaaatcac cactcgatac aggcagccca tcagtccggg acggcgtcag cgggagagcc    6840
gttgtaaggc ggcagacttt gctcatgtta ccgatgctat tcggaagaac ggcaactaag    6900
ctgccgggtt tgaaacacgg atgatctcgc ggagggtagc atgttgattg taacgatgac    6960
agagcgttgc tgcctgtgat caaatatcat ctccctcgca gagatccgaa ttatcagcct    7020
tcttattcat ttctcgctta accgtgacag gctgtcgatc ttgagaacta tgccgacata    7080
ataggaaatc gctggataaa gccgctgagg aagctgagtg gcgctatttc tttagaagtg    7140
aacgttgacg atcgtcgacc gtaccccgat gaattaattc ggacgtacgt tctgaacaca    7200
gctggatact tacttgggcg attgtcatac atgacatcaa caatgtaccc gtttgtgtaa    7260
ccgtctcttg gaggttcgta tgacactagt ggttcccctc agcttgcgac tagatgttga    7320
ggcctaacat tttattagag agcaggctag ttgcttagat acatgatctt caggccgtta    7380
tctgtcaggg caagcgaaaa ttggccattt atgacgacca atgccccgca gaagctccca    7440
tctttgccgc catagacgcc gcgcccccct ttggggtgt agaacatcct tttgccagat    7500
gtggaaaaga agttcgttgt cccattgttg gcaatgacgt agtagccggc gaaagtgcga    7560
gacccatttg cgctatatat aagcctacga tttccgttgc gactattgtc gtaattggat    7620
gaactattat cgtagttgct ctcagagttg tcgtaatttg atggactatt gtcgtaattg    7680
cttatggagt tgtcgtagtt gcttggagaa atgtcgtagt tggatgggga gtagtcatag    7740
ggaagacgag cttcatccac taaaacaatt ggcaggtcag caagtgcctg ccccgatgcc    7800
atcgcaagta cgaggcttag aaccaccttc aacagatcgc gcatagtctt ccccagctct    7860
```

```
ctaacgcttg agttaagccg cgccgcgaag cggcgtcggc ttgaacgaat tgttagacat    7920
tatttgccga ctaccttggt gatctcgcct ttcacgtagt gaacaaattc ttccaactga    7980
tctgcgcgcg aggccaagcg atcttcttgt ccaagataag cctgcctagc ttcaagtatg    8040
acgggctgat actgggccgg caggcgctcc attgcccagt cggcagcgac atccttcggc    8100
gcgattttgc cggttactgc gctgtaccaa atgcgggaca acgtaagcac tacatttcgc    8160
tcatcgccag cccagtcggg cggcgagttc catagcgtta aggtttcatt tagcgcctca    8220
aatagatcct gttcaggaac cggatcaaag agttcctccg ccgctggacc taccaaggca    8280
acgctatgtt ctcttgcttt tgtcagcaag atagccagat caatgtcgat cgtggctggc    8340
tcgaagatac ctgcaagaat gtcattgcgc tgccattctc caaattgcag ttcgcgctta    8400
gctggataac gccacggaat gatgtcgtcg tgcacaacaa tggtgacttc tacagcgcgg    8460
agaatctcgc tctctccagg ggaagccgaa gtttccaaaa ggtcgttgat caaagctcgc    8520
cgcgttgttt catcaagcct tacagtcacc gtaaccagca aatcaatatc actgtgtggc    8580
ttcaggccgc catccactgc ggagccgtac aaatgtacgg ccagcaacgt cggttcgaga    8640
tggcgctcga tgacgccaac tacctctgat agttgagtcg atacttcggc gatcaccgct    8700
tccctcatga tgtttaactc ctgaattaag ccgcgccgcg aagcggtgtc ggcttgaatg    8760
aattgttagg cgtcatcctg tgctcccgag aaccagtacc agtacatcgc tgtttcgttc    8820
gagacttgag gtctagtttt atacgtgaac aggtcaatgc cgccgagagt aaagccacat    8880
tttgcgtaca aattgcaggc aggtacattg ttcgtttgtg tctctaatcg tatgccaagg    8940
agctgtctgc ttagtgccca cttttttcgca aattcgatga gactgtgcgc gactcctttg    9000
cctcggtgcg tgtgcgacac aacaatgtgt tcgatagagg ctagatcgtt ccatgttgag    9060
ttgagttcaa tcttcccgac aagctcttgg tcgatgaatg cgccatagca agcagagtct    9120
tcatcagagt catcatccga gatgtaatcc ttccggtagg ggctcacact tctggtagat    9180
agttcaaagc cttggtcgga taggtgcaca tcgaacactt cacgaacaat gaaatggttc    9240
tcagcatcca atgtttccgc cacctgctca gggatcaccg aaatcttcat atgacgccta    9300
acgcctggca cagcggatcg caaacctggc gcggcttttg gcacaaaagg cgtgacaggt    9360
ttgcgaatcc gttgctgcca cttgttaacc cttttgccag atttggtaac tataatttat    9420
gttagaggcg aagtcttggg taaaaactgg cctaaaattg ctggggattt caggaaagta    9480
aacatcacct tccggctcga tgtctattgt agatatatgt agtgtatcta cttgatcggg    9540
ggatctgctg cctcgcgcgt ttcggtgatg acggtgaaaa cctctgacac atgcagctcc    9600
cggagacggt cacagcttgt ctgtaagcgg atgccgggag cagacaagcc cgtcagggcg    9660
cgtcagcggg tgttggcggg tgtcgggcg cagccatgac ccagtcacgt agcgatagcg    9720
gagtgtatac tggcttaact atgcggcatc agagcagatt gtactgagag tgcaccatat    9780
gcggtgtgaa ataccgcaca gatgcgtaag gagaaaatac cgcatcaggc gctcttccgc    9840
ttcctcgctc actgactcgc tgcgctcggt cgttcggctg cggcgagcgg tatcagctca    9900
ctcaaaggcg gtaatacggt tatccacaga atcagggat aacgcaggaa agaacatgtg    9960
agcaaaaggc cagcaaaagg ccaggaaccg taaaaaggcc gcgttgctgg cgttttccca   10020
taggctccgc ccccctgacg agcatcacaa aaatcgacgc tcaagtcaga ggtggcgaaa   10080
cccgacagga ctataaagat accaggcgtt tcccctgga agctccctcg tgcgctctcc   10140
tgttccgacc ctgccgctta ccggatacct gtccgccttt ctcccttcgg gaagcgtggc   10200
gctttctcat agctcacgct gtaggtatct cagttcggtg taggtcgttc gctccaagct   10260
```

```
gggctgtgtg cacgaacccc ccgttcagcc cgaccgctgc gccttatccg gtaactatcg   10320
tcttgagtcc aacccggtaa gacacgactt atcgccactg gcagcagcca ctggtaacag   10380
gattagcaga gcgaggtatg taggcggtgc tacagagttc ttgaagtggt ggcctaacta   10440
cggctacact agaaggacag tatttggtat ctgcgctctg ctgaagccag ttaccttcgg   10500
aaaaagagtt ggtagctctt gatccggcaa acaaaccacc gctggtagcg gtggtttttt   10560
tgtttgcaag cagcagatta cgcgcagaaa aaaggatct caagaagatc ctttgatctt   10620
ttctacgggg tctgacgctc agtggaacga aaactcacgt taagggattt tggtcatgag   10680
attatcaaaa aggatcttca cctagatcct tttaaattaa aaatgaagtt ttaaatcaat   10740
ctaaagtata tatgagtaaa cttggtctga cagttaccaa tgcttaatca gtgaggcacc   10800
tatctcagcg atctgtctat ttcgttcatc catagttgcc tgactccccg tcgtgtagat   10860
aactacgata cgggagggct taccatctgg ccccagtgct gcaatgatac cgcgagaccc   10920
acgctcaccg gctccagatt tatcagcaat aaaccagcca gccggaaggg ccgagcgcag   10980
aagtggtcct gcaactttat ccgcctccat ccagtctatt aattgttgcc gggaagctag   11040
agtaagtagt tcgccagtta atagtttgcg caacgttgtt gccattgctg cagggggggg   11100
gggggggggg gacttccatt gttcattcca cggacaaaaa cagagaaagg aaacgacaga   11160
ggccaaaaag cctcgctttc agcacctgtc gtttcctttc ttttcagagg gtattttaaa   11220
taaaaacatt aagttatgac gaagaagaac ggaaacgcct taaaccggaa aattttcata   11280
aatagcgaaa acccgcgagg tcgccgcccc gtaacctgtc ggatcaccgg aaaggacccg   11340
taaagtgata atgattatca tctacatatc acaacgtgcg tggaggccat caaaccacgt   11400
caaataatca attatgacgc aggtatcgta ttaattgatc tgcatcaact taacgtaaaa   11460
acaacttcag acaatacaaa tcagcgacac tgaatacggg gcaacctcat gtccccccc   11520 cccccccccc tgcaggcatc gtggtgtcac gctcgtcgtt tggtatggct tcattcagct   11580
ccggttccca acgatcaagg cgagttacat gatcccccat gttgtgcaaa aaagcggtta   11640
gctccttcgg tcctccgatc gttgtcagaa gtaagttggc cgcagtgtta tcactcatgg   11700
ttatggcagc actgcataat tctcttactg tcatgccatc cgtaagatgc ttttctgtga   11760
ctggtgagta ctcaaccaag tcattctgag aatagtgtat gcggcgaccg agttgctctt   11820
gcccggcgtc aacacgggat aataccgcgc cacatagcag aactttaaaa gtgctcatca   11880
ttggaaaacg ttcttcgggg cgaaaactct caaggatctt accgctgttg agatccagtt   11940
cgatgtaacc cactcgtgca cccaactgat cttcagcatc ttttactttc accagcgttt   12000
ctgggtgagc aaaaacagga aggcaaaatg ccgcaaaaaa gggaataagg gcgacacgga   12060
aatgttgaat actcatactc ttcctttttc aatattattg aagcatttat cagggttatt   12120
gtctcatgag cggatacata tttgaatgta tttagaaaaa taaacaaata ggggttccgc   12180
gcacatttcc ccgaaaagtg ccacctgacg tctaagaaac cattattatc atgacattaa   12240
cctataaaaa taggcgtatc acgaggccct ttcgtcttca agaattggtc gacgatcttg   12300
ctgcgttcgg atattttcgt ggagttcccg ccacagaccc ggattgaagg cgagatccag   12360
caactcgcgc cagatcatcc tgtgacgaa ctttggcgcg tgatgactgg ccaggacgtc   12420
ggccgaaaga gcgacaagca gatcacgctt tcgacagcg tcggatttgc gatcgaggat   12480
ttttcggcgc tgcgctacgt ccgcgaccgc gttgagggat caagccacag cagcccactc   12540
gaccttctag ccgacccaga cgagccaagg gatcttttg gaatgctgct ccgtcgtcag   12600
```

```
gctttccgac gtttgggtgg ttgaacagaa gtcattatcg tacggaatgc caagcactcc   12660 cgagggaac  cctgtggttg gcatgcacat acaaatggac gaacggataa accttttcac   12720
gcccttttaa atatccgtta ttctaataaa cgctcttttc tcttaggttt acccgccaat   12780
atatcctgtc aaacactgat agtttaaact gaaggcggga aacgacaatc tgatcatgag   12840
cggagaatta agggagtcac gttatgaccc ccgccgatga cgcgggacaa gccgttttac   12900
gtttggaact gacagaaccg caacgttgaa ggagccactc agcaagctgg tacgattgta   12960
atacgactca ctatagggcg aattgagcgc tgtttaaacg ctcttcaact ggaagagcg    13019
```

<210> SEQ ID NO 9
<211> LENGTH: 2991
<212> TYPE: DNA
<213> ORGANISM: artificial sequence
<220> FEATURE:
<223> OTHER INFORMATION: vector

<400> SEQUENCE: 9

```
ctttcctgcg ttatcccctg attctgtgga taaccgtatt accgcctttg agtgagctga     60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcctg cagctctaga gctcgaattc tacaggtcac    600
taataccatc taagtagttg gttcatagtg actgcatatg ttgtgtttta cagtattatg    660
tagtctgttt tttatgcaaa atctaattta atatattgat atttatatca ttttacgttt    720
ctcgttcaac tttcttgtac aaagtggccg ttaacggatc cagacttgtc catcttctgg    780
attggccaac ttaattaatg tatgaaataa aaggatgcac acatagtgac atgctaatca    840
ctataatgtg ggcatcaaag ttgtgtgtta tgtgtaatta ctagttatct gaataaaaga    900
gaaagagatc atccatattt cttatcctaa atgaatgtca cgtgtcttta taattctttg    960
atgaaccaga tgcatttcat taaccaaatc catatacata taaatattaa tcatatataa   1020
ttaatatcaa ttgggttagc aaaacaaatc tagtctaggt gtgttttgcg aattgcggca   1080
agcttgcggc cgcccccggc aactttatta tacaaagttg gcattataaa aaagcattgc   1140
ttatcaattt gttgcaacga acaggtcact atcagtcaaa ataaaatcat tatttggagc   1200
tccatggtag cgttaacgcg gccgcgatat ccctatagt gagtcgtatt acatggtcat   1260 agctgttcc tggcagctct ggcccgtgtc tcaaaatctc tgatgttaca ttgcacaaga   1320
taaaaatata tcatcatgaa caataaaact gtctgcttac ataaacagta atacaagggg   1380
tgttatgagc catattcaac gggaaacgtc gaggccgcga ttaaattcca acatggatgc   1440
tgatttatat gggtataaat gggctcgcga taatgtcggg caatcaggtg cgacaatcta   1500
tcgcttgtat gggaagcccg atgcgccaga gttgtttctg aaacatggca aaggtagcgt   1560
tgccaatgat gttacagatg agatggtcag actaaactgg ctgacggaat ttatgcctct   1620
tccgaccatc aagcatttta tccgtactcc tgatgatgca tggttactca ccactgcgat   1680
```

```
cccggaaaa acagcattcc aggtattaga agaatatcct gattcaggtg aaaatattgt    1740
tgatgcgctg gcagtgttcc tgcgccggtt gcattcgatt cctgtttgta attgtccttt    1800
taacagcgat cgcgtatttc gtctcgctca ggcgcaatca cgaatgaata acggtttggt    1860
tgatgcgagt gattttgatg acgagcgtaa tggctggcct gttgaacaag tctggaaaga    1920
aatgcataaa cttttgccat tctcaccgga ttcagtcgtc actcatggtg atttctcact    1980
tgataacctt attttgacg aggggaaatt aataggttgt attgatgttg acgagtcgg      2040
aatcgcagac cgataccagg atcttgccat cctatggaac tgcctcggtg agttttctcc    2100
ttcattacag aaacggcttt tcaaaaata tggtattgat aatcctgata tgaataaatt     2160
gcagtttcat ttgatgctcg atgagttttt ctaatcagaa ttggttaatt ggttgtaaca    2220
ctggcagagc attacgctga cttgacggga cggcgcaagc tcatgaccaa aatcccttaa    2280
cgtgagttac gcgtcgttcc actgagcgtc agaccccgta gaaaagatca aggatcttc     2340
ttgagatcct ttttttctgc gcgtaatctg ctgcttgcaa acaaaaaaac caccgctacc    2400
agcggtggtt tgtttgccgg atcaagagct accaactctt tttccgaagg taactggctt    2460
cagcagagcg cagataccaa atactgtcct tctagtgtag ccgtagttag gccaccactt    2520
caagaactct gtagcaccgc ctacatacct cgctctgcta atcctgttac cagtggctgc    2580
tgccagtggc gataagtcgt gtcttaccgg gttggactca agacgatagt taccggataa    2640
ggcgcagcgg tcgggctgaa cggggggttc gtgcacacag cccagcttgg agcgaacgac    2700
ctacaccgaa ctgagatacc tacagcgtga gcattgagaa agcgccacgc ttcccgaagg    2760
gagaaaggcg gacaggtatc cggtaagcgg cagggtcgga acaggagagc gcacgaggga    2820
gcttccaggg ggaaacgcct ggtatcttta tagtcctgtc gggtttcgcc acctctgact    2880
tgagcgtcga ttttgtgat gctcgtcagg ggggcggagc ctatgaaaaa cgccagcaa     2940
cgcggccttt ttacggttcc tggccttttg ctggcctttt gctcacatgt t             2991
```

<210> SEQ ID NO 10
<211> LENGTH: 13807
<212> TYPE: DNA
<213> ORGANISM: artificial sequence
<220> FEATURE:
<223> OTHER INFORMATION: vector

<400> SEQUENCE: 10

```
aagctggtac gattgtaata cgactcacta tagggcgaat tgagcgctgt ttaaacgctc    60
ttcaactgga agagcggtta ccagagctgg tcacctttgt ccaccaagat ggaactgcgg    120
ccgctcatta attaagtcag gcgcgcctct agttgaagac acgttcatgt cttcatcgta    180
agaagacact cagtagtctt cggccagaat ggccgtaggt gaattaagag gagagaggag    240
gtaaacattt tcttctattt tttcatattt tcaggataaa ttattgtaaa gtttacaag    300
atttccattt gactagtgta aatgaggaat attctctagt aagatcatta tttcatctac    360
ttctttatc ttctaccagt agaggaataa acaatattta gctcctttgt aaatacaaat     420
taatttcgt tcttgacatc attcaatttt aattttacgt ataaaataaa agatcatacc     480
tattagaacg attaaggaga aatacaattc gaatgagaag gatgtgccgt tgttataat     540
aaacagccac acgacgtaaa cgtaaaatga ccacatgatg ggccaataga catggaccga    600
ctactaataa tagtaagtta cattttagga tggaataaat atcataccga catcagtttg    660
aaagaaaagg gaaaaaaga aaaataaat aaaagatata ctaccgacat gagttccaaa      720
```

```
aagcaaaaaa aaagatcaag ccgacacaga cacgcgtaga gagcaaaatg actttgacgt    780
cacaccacga aaacagacgc ttcatacgtg tccctttatc tctctcagtc tctctataaa    840
cttagtgaga ccctcctctg ttttactcag gatccccggg taccgagctc gaattcaccg    900
gtcgccacca tggcccacag caagcacggc ctgaaggagg agatgaccat gaagtaccac    960
atggagggct gcgtgaacgg ccacaagttc gtgatcaccg gcgagggcat cggctacccc   1020
ttcaagggca gcagaccat caacctgtgc gtgatcgagg gcggcccct gcccttcagc     1080
gaggacatcc tgagcgccgg cttcaagtac ggcgaccgga tcttcaccga gtaccccag    1140
gacatcgtgg actacttcaa gaacagctgc cccgccggct acacctgggg ccggagcttc   1200
ctgttcgagg acggcgccgt gtgcatctgt aacgtggaca tcaccgtgag cgtgaaggag   1260
aactgcatct accacaagag catcttcaac ggcgtgaact tccccgccga cggccccgtg   1320
atgaagaaga tgaccaccaa ctgggaggcc agctgcgaga gatcatgcc cgtgcctaag    1380
cagggcatcc tgaagggcga cgtgagcatg tacctgctgc tgaaggacgg cggccggtac   1440
cggtgccagt tcgacaccgt gtacaaggcc aagagcgtgc ccagcaagat gcccgagtgg   1500
cacttcatcc agcacaagct gctgcgggag gaccggagcg acgccaagaa ccagaagtgg   1560
cagctgaccg agcacgccat cgccttcccc agcgccctgg cctgaagcgg cccatggata   1620
ttcgaacgcg taggtaccac atggttaacc tagacttgtc catcttctgg attggccaac   1680
ttaattaatg tatgaaataa aaggatgcac acatagtgac atgctaatca ctataatgtg   1740
ggcatcaaag ttgtgtgtta tgtgtaatta ctagttatct gaataaaaga gaagagatc    1800
atccatattt cttatcctaa atgaatgtca cgtgtcttta taattctttg atgaaccaga   1860
tgcatttcat taaccaaatc catatacata taaatattaa tcatatataa ttaatatcaa   1920
ttgggttagc aaaacaaatc tagtctaggt gtgttttgcg aatgcggcca ttggcctaga   1980
aggccattta atcctgagg atctggtctt cctaaggacc cgggatatcg ctatcaactt    2040
tgtatagaaa agttgaacga gaaacgtaaa atgatataaa tatcaatata ttaaattaga   2100
ttttgcataa aaaacagact acataatact gtaaaacaca acatatccag tcactatggt   2160
cgacctgcag actggctgtg tataagggag cctgacattt atattcccca gaacatcagg   2220
ttaatggcgt ttttgatgtc atttttcgcgg tggctgagat cagccacttc ttccccgata   2280
acggagaccg gcacactggc catatcggtg gtcatcatgc gccagctttc atccccgata   2340
tgcaccaccg ggtaaagttc acgggggact ttatctgaca gcagacgtgc actggccagg   2400
gggatcacca tccgtcgccc gggcgtgtca ataatatcac tctgtacatc cacaaacaga   2460
cgataacggc tctctctttt ataggtgtaa accttaaact gcatttcacc agcccctgtt   2520
ctcgtcggca aaagagccgt tcatttcaat aaaccgggcg acctcagcca tcccttcctg   2580
attttccgct ttccagcgtt cggcacgcag acgacgggct tcattctgca tggttgtgct   2640
taccgaaccg gagatattga catcatatat gccttgagca actgatagct gtcgctgtca   2700
actgtcactg taatacgctg cttcatagca tacctctttt tgacatactt cgggtataca   2760
tatcagtata tattcttata ccgcaaaaat cagcgcgcaa atacgcatac tgttatctgg   2820
cttttagtaa gccggatcct ctagattacg ccccgcctgc cactcatcgc agtactgttg   2880
taattcatta agcattctgc cgacatggaa gccatcacaa acggcatgat gaacctgaat   2940
cgccagcggc atcagcacct tgtcgccttg cgtataatat ttgcccatgg tgaaaacggg   3000
ggcgaagaag ttgtccatat tggccacgtt taaatcaaaa ctggtgaaac tcacccaggg   3060
attggctgag acgaaaaaca tattctcaat aaaccctta gggaaatagg ccaggttttc    3120
```

```
accgtaacac gccacatctt gcgaatatat gtgtagaaac tgccggaaat cgtcgtggta    3180
ttcactccag agcgatgaaa acgtttcagt ttgctcatgg aaaacggtgt aacaagggtg    3240
aacactatcc catatcacca gctcaccgtc tttcattgcc atacggaatt ccggatgagc    3300
attcatcagg cgggcaagaa tgtgaataaa ggccggataa aacttgtgct tattttctt     3360 tacggtcttt aaaaaggccg taatatccag ctgaacggtc tggttatagg tacattgagc    3420
aactgactga aatgcctcaa aatgttcttt acgatgccat gggatatat caacggtggt     3480 atatccagtg attttttct ccattttagc ttccttagct cctgaaaatc tcgacggatc     3540
ctaactcaaa atccacacat tatacgagcc ggaagcataa agtgtaaagc ctggggtgcc    3600
ctaatgcggc cgccatagtg actggatatg ttgtgtttta cagtattatg tagtctgttt    3660
tttatgcaaa atcaatttta atatattgat atttatatca ttttacgttt ctcgttcaac    3720
tttattatac aaagttgata gatatcggac cgattaaact ttaattcggt ccgaagcttg    3780
catgcctgca gtgcagcgtg acccggtcgt gcccctctct agagataatg agcattgcat    3840
gtctaagtta taaaaaatta ccacatattt ttttgtcac acttgtttga agtgcagttt     3900
atctatcttt atacatatat ttaaacttta ctctacgaat aatataatct atagtactac    3960
aataatatca gtgttttaga gaatcatata aatgaacagt tagacatggt ctaaaggaca    4020
attgagtatt ttgacaacag gactctacag ttttatcttt ttagtgtgca tgtgttctcc    4080 ttttttttg caaatagctt cacctatata atacttcatc cattttatta gtacatccat     4140
ttagggttta gggttaatgg tttttataga ctaattttt tagtacatct attttattct     4200
attttagcct ctaaattaag aaaactaaaa ctctatttta gttttttat ttaataattt     4260 agatataaaa tagaataaaa taaagtgact aaaaattaaa caaatacccct ttaagaaatt    4320 aaaaaaacta aggaaacatt tttcttgttt cgagtagata atgccagcct gttaaacgcc    4380
gtcgacgagt ctaacggaca ccaaccagcg aaccagcagc gtcgcgtcgg gccaagcgaa    4440
gcagacggca cggcatctct gtcgctgcct ctggaccct ctcgagagtt ccgctccacc     4500
gttggacttg ctccgctgtc ggcatccaga aattgcgtgg cggagcggca gacgtgagcc    4560
ggcacggcag gcggcctcct cctcctctca cggcaccggc agctacgggg gattcctttc    4620
ccaccgctcc ttcgctttcc cttcctcgcc cgccgtaata aatagacacc ccctccacac    4680
cctctttccc caacctcgtg ttgttcggag cgcacacaca caaccaga tctcccccaa      4740 atccacccgt cggcacctcc gcttcaaggt acgccgctcg tcctcccccc cccccctctc    4800
taccttctct agatcggcgt tccggtccat gcatggttag ggcccggtag ttctacttct    4860
gttcatgttt gtgttagatc cgtgtttgtg ttagatccgt gctgctagcg ttcgtacacg    4920
gatgcgacct gtacgtcaga cacgttctga ttgctaactt gccagtgttt ctcttggggg    4980
aatcctggga tggctctagc cgttccgcag acgggatcga tttcatgatt ttttttgttt    5040
cgttgcatag ggtttggttt gccctttcc tttattccaa tatatgccgt gcacttgttt     5100
gtcgggtcat cttttcatgc tttttttgt cttggttgtg atgatgtggt ctggttgggc     5160
ggtcgttcta gatcggagta gaattctgtt tcaaactacc tggtggattt attaattttg    5220
gatctgtatg tgtgtgccat acatattcat agttacgaat tgaagatgat ggatggaaat    5280
atcgatctag gataggtata catgttgatg cgggttttac tgatgcatat acagagatgc    5340
tttttgttcg cttggttgtg atgatgtggt gtggttgggc ggtcgttcat tcgttctaga    5400
tcggagtaga atactgtttc aaactacctg gtgtatttat taattttgga actgtatgtg    5460
```

| | |
|---|---|
| tgtgtcatac atcttcatag ttacgagttt aagatggatg gaaatatcga tctaggatag | 5520 |
| gtatacatgt tgatgtgggt tttactgatg catatacatg atggcatatg cagcatctat | 5580 |
| tcatatgctc taaccttgag tacctatcta ttataataaa caagtatgtt ttataattat | 5640 |
| tttgatcttg atatacttgg atgatggcat atgcagcagc tatatgtgga ttttttttagc | 5700 |
| cctgccttca tacgctattt atttgcttgg tactgtttct tttgtcgatg ctcaccctgt | 5760 |
| tgtttggtgt tacttctgca ggtcgacttt aacttagcct aggatccaca cgacaccatg | 5820 |
| tcccccgagc gccgccccgt cgagatccgc ccggccaccg ccgccgacat ggccgccgtg | 5880 |
| tgcgacatcg tgaaccacta catcgagacc tccaccgtga acttccgcac cgagccgcag | 5940 |
| accccgcagg agtggatcga cgacctggag cgcctccagg accgctaccc gtggctcgtg | 6000 |
| gccgaggtgg agggcgtggt ggccggcatc gcctacgccg gccgtggaa ggcccgcaac | 6060 |
| gcctacgact ggaccgtgga gtccaccgtg tacgtgtccc accgccacca cgcctcggc | 6120 |
| ctcggctcca ccctctacac ccacctcctc aagagcatgg aggcccaggg cttcaagtcc | 6180 |
| gtggtggccg tgatcggcct cccgaacgac ccgtccgtgc gcctccacga ggccctcggc | 6240 |
| tacaccgccc gcggcaccct ccgcgccgcc ggctacaagc acggcggctg cacgacgtc | 6300 |
| ggcttctggc agcgcgactt cgagctgccg gccccgccgc gccggtgcg cccggtgacg | 6360 |
| cagatctccg gtggaggcgg cagcggtggc ggaggctccg gaggcggtgg ctccatggcc | 6420 |
| tcctccgagg acgtcatcaa ggagttcatg cgcttcaagg tgcgcatgga gggctccgtg | 6480 |
| aacggccacg agttcgagat cgagggcgag ggcgagggcc gccctacga gggcacccag | 6540 |
| accgccaagc tgaaggtgac caagggcggc cccctgccct tcgcctggga catcctgtcc | 6600 |
| ccccagttcc agtacggctc caaggtgtac gtgaagcacc ccgccgacat ccccgactac | 6660 |
| aagaagctgt ccttccccga gggcttcaag tgggagcgcg tgatgaactt cgaggacggc | 6720 |
| ggcgtggtga ccgtgaccca ggactcctcc ctgcaggacg gctccttcat ctacaaggtg | 6780 |
| aagttcatcg gcgtgaactt ccctccgac ggccccgtaa tgcagaagaa gactatgggc | 6840 |
| tgggaggcct ccaccgagcg cctgtacccc cgcgacggcg tgctgaaggg cgagatccac | 6900 |
| aaggccctga gctgaagga cggcggccac tacctggtgg agttcaagtc catctacatg | 6960 |
| gccaagaagc ccgtgcagct gcccggctac tactacgtgg actccaagct ggacatcacc | 7020 |
| tcccacaacg aggactacac catcgtggag cagtacgagc gcgccgaggg ccgccaccac | 7080 |
| ctgttcctgt agtcaggatc tgagtcgaaa cctagacttg tccatcttct ggattggcca | 7140 |
| acttaattaa tgtatgaaat aaaaggatgc acacatagtg acatgctaat cactataatg | 7200 |
| tgggcatcaa agttgtgtgt tatgtgtaat tactagttat ctgaataaaa gagaaagaga | 7260 |
| tcatccatat ttcttatcct aaatgaatgt cacgtgtctt tataattctt tgatgaacca | 7320 |
| gatgcatttc attaaccaaa tccatataca tataaatatt aatcatatat aattaatatc | 7380 |
| aattgggtta gcaaaacaaa tctagtctag gtgtgttttg cgaatgcggc cgccaccgcg | 7440 |
| gtggagctcg aattcattcc gattaatcgt ggcctcttgc tcttcaggat gaagagctat | 7500 |
| gtttaaacgt gcaagcgcta ctagacaatt cagtacatta aaaacgtccg caatgtgtta | 7560 |
| ttaagttgtc taagcgtcaa tttgtttaca ccacaatata tcctgccacc agccagccaa | 7620 |
| cagctccccg accggcagct cggcacaaaa tcaccactcg atacaggcag cccatcagtc | 7680 |
| cgggacggcg tcagcgggag agccgttgta aggcggcaga cttgctcat gttaccgatg | 7740 |
| ctattcggaa gaacggcaac taagctgccg ggtttgaaac acggatgatc tcgcggaggg | 7800 |
| tagcatgttg attgtaacga tgacagagcg ttgctgcctg tgatcaaata tcatctccct | 7860 |

```
cgcagagatc cgaattatca gccttcttat tcatttctcg cttaaccgtg acaggctgtc   7920
gatcttgaga actatgccga cataatagga aatcgctgga taaagccgct gaggaagctg   7980
agtggcgcta tttctttaga agtgaacgtt gacgatcgtc gaccgtaccc cgatgaatta   8040
attcggacgt acgttctgaa cacagctgga tacttacttg ggcgattgtc atacatgaca   8100
tcaacaatgt acccgtttgt gtaaccgtct cttggaggtt cgtatgacac tagtggttcc   8160
cctcagcttg cgactagatg ttgaggccta acatttatt agagagcagg ctagttgctt    8220
agatacatga tcttcaggcc gttatctgtc agggcaagcg aaaattggcc atttatgacg   8280
accaatgccc cgcagaagct cccatctttg ccgccataga cgccgcgccc ccttttggg    8340 gtgtagaaca tccttttgcc agatgtggaa aagaagttcg ttgtcccatt gttggcaatg   8400
acgtagtagc cggcgaaagt gcgagaccca tttgcgctat atataagcct acgatttccg   8460
ttgcgactat tgtcgtaatt ggatgaacta ttatcgtagt tgctctcaga gttgtcgtaa   8520
tttgatggac tattgtcgta attgcttatg gagttgtcgt agttgcttgg agaaatgtcg   8580
tagttggatg gggagtagtc atagggaaga cgagcttcat ccactaaaac aattggcagg   8640
tcagcaagtg cctgccccga tgccatcgca agtacgaggc ttagaaccac cttcaacaga   8700
tcgcgcatag tcttccccag ctctctaacg cttgagttaa gccgcgccgc gaagcggcgt   8760
cggcttgaac gaattgttag acattatttg ccgactacct tggtgatctc gcctttcacg   8820
tagtgaacaa attcttccaa ctgatctgcg cgcgaggcca agcgatcttc ttgtccaaga   8880
taagcctgcc tagcttcaag tatgacgggc tgatactggg ccggcaggcg ctccattgcc   8940
cagtcggcag cgacatcctt cggcgcgatt ttgccggtta ctgcgctgta ccaaatgcgg   9000
gacaacgtaa gcactacatt tcgctcatcg ccagcccagt cgggcggcga gttccatagc   9060
gttaaggttt catttagcgc ctcaaataga tcctgttcag gaaccggatc aaagagttcc   9120
tccgccgctg gacctaccaa ggcaacgcta tgttctcttg cttttgtcag caagatagcc   9180
agatcaatgt cgatcgtggc tggctcgaag atacctgcaa gaatgtcatt gcgctgccat   9240
tctccaaatt gcagttcgcg cttagctgga taacgccacg gaatgatgtc gtcgtgcaca   9300
acaatggtga cttctacagc gcggagaatc tcgctctctc caggggaagc cgaagtttcc   9360
aaaaggtcgt tgatcaaagc tcgccgcgtt gtttcatcaa gccttacagt caccgtaacc   9420
agcaaatcaa tatcactgtg tggcttcagg ccgccatcca ctgcggagcc gtacaaatgt   9480
acggccagca acgtcggttc gagatggcgc tcgatgacgc caactacctc tgatagttga   9540
gtcgatactt cggcgatcac cgcttccctc atgatgttta actcctgaat taagccgcgc   9600
cgcgaagcgg tgtcggcttg aatgaattgt taggcgtcat cctgtgctcc cgagaaccag   9660
taccagtaca tcgctgtttc gttcgagact tgaggtctag ttttatacgt gaacaggtca   9720
atgccgccga gagtaaagcc acattttgcg tacaaattgc aggcaggtac attgttcgtt   9780
tgtgtctcta atcgtatgcc aaggagctgt ctgcttagtg cccactttt cgcaaattcg     9840 atgagactgt gcgcgactcc tttgcctcgg tgcgtgtgcg acacaacaat gtgttcgata   9900
gaggctagat cgttccatgt tgagttgagt tcaatcttcc cgacaagctc ttggtcgatg   9960
aatgcgccat agcaagcaga gtcttcatca gagtcatcat ccgagatgta atccttccgg   10020 tagggctca cacttctggt agatagttca aagccttggt cggataggtg cacatcgaac     10080
acttcacgaa caatgaaatg gttctcagca tccaatgttt ccgccacctg ctcagggatc   10140
accgaaatct tcatatgacg cctaacgcct ggcacagcgg atcgcaaacc tggcgcggct   10200
```

```
tttggcacaa aaggcgtgac aggtttgcga atccgttgct gccacttgtt aacccttttg   10260
ccagatttgg taactataat ttatgttaga ggcgaagtct tgggtaaaaa ctggcctaaa   10320
attgctgggg atttcaggaa agtaaacatc accttccggc tcgatgtcta ttgtagatat   10380
atgtagtgta tctacttgat cgggggatct gctgcctcgc gcgtttcggt gatgacggtg   10440
aaaacctctg acacatgcag ctcccggaga cggtcacagc ttgtctgtaa gcggatgccg   10500
ggagcagaca gcccgtcag ggcgcgtcag cgggtgttgg cgggtgtcgg ggcgcagcca   10560
tgacccagtc acgtagcgat agcggagtgt atactggctt aactatgcgg catcagagca   10620
gattgtactg agagtgcacc atatgcggtg tgaaataccg cacagatgcg taaggagaaa   10680
ataccgcatc aggcgctctt ccgcttcctc gctcactgac tcgctgcgct cggtcgttcg   10740
gctgcggcga gcggtatcag ctcactcaaa ggcggtaata cggttatcca cagaatcagg   10800
ggataacgca ggaaagaaca tgtgagcaaa aggccagcaa aaggccagga accgtaaaaa   10860
ggccgcgttg ctggcgtttt tccataggct ccgcccccct gacgagcatc acaaaaatcg   10920
acgctcaagt cagaggtggc gaaacccgac aggactataa agataccagg cgtttccccc   10980
tggaagctcc ctcgtgcgct ctcctgttcc gaccctgccg cttaccggat acctgtccgc   11040
ctttctccct tcgggaagcg tggcgctttc tcatagctca cgctgtaggt atctcagttc   11100
ggtgtaggtc gttcgctcca agctgggctg tgtgcacgaa ccccccgttc agcccgaccg   11160
ctgcgcctta tccggtaact atcgtcttga gtccaacccg gtaagacacg acttatcgcc   11220
actggcagca gccactggta acaggattag cagagcgagg tatgtaggcg gtgctacaga   11280
gttcttgaag tggtggccta actacggcta cactagaagg acagtatttg gtatctgcgc   11340
tctgctgaag ccagttacct tcggaaaaag agttggtagc tcttgatccg gcaaacaaac   11400
caccgctggt agcggtggtt tttttgtttg caagcagcag attacgcgca gaaaaaaagg   11460
atctcaagaa gatcctttga tcttttctac ggggtctgac gctcagtgga acgaaaactc   11520
acgttaaggg attttggtca tgagattatc aaaaaggatc ttcacctaga tccttttaaa   11580
ttaaaaatga agttttaaat caatctaaag tatatatgag taaacttggt ctgacagtta   11640
ccaatgctta atcagtgagg cacctatctc agcgatctgt ctatttcgtt catccatagt   11700
tgcctgactc cccgtcgtgt agataactac gatacgggag ggcttaccat ctggccccag   11760
tgctgcaatg ataccgcgag acccacgctc accggctcca gatttatcag caataaacca   11820
gccagccgga agggccgagc gcagaagtgg tcctgcaact ttatccgcct ccatccagtc   11880
tattaattgt tgccgggaag ctagagtaag tagttcgcca gttaatagtt tgcgcaacgt   11940
tgttgccatt gctgcagggg ggggggggg ggggacttc cattgttcat tccacggaca   12000
aaaacagaga aggaaacga cagaggccaa aaagcctcgc tttcagcacc tgtcgtttcc   12060
tttcttttca gagggtattt taaataaaaa cattaagtta tgacgaagaa gaacggaaac   12120
gccttaaacc ggaaaatttt cataaatagc gaaaacccgc gaggtcgccg ccccgtaacc   12180
tgtcggatca ccggaaagga cccgtaaagt gataatgatt atcatctaca tatcacaacg   12240
tgcgtggagg ccatcaaacc acgtcaaata atcaattatg acgcaggtat cgtattaatt   12300
gatctgcatc aacttaacgt aaaaacaact tcagacaata caaatcagcg acactgaata   12360
cggggcaacc tcatgtcccc cccccccccc ccctgcagg catcgtggtg tcacgctcgt   12420
cgtttggtat ggcttcattc agctccggtt cccaacgatc aaggcgagtt acatgatccc   12480
ccatgttgtg caaaaaagcg gttagctcct tcggtcctcc gatcgttgtc agaagtaagt   12540
tggccgcagt gttatcactc atggttatgg cagcactgca taattctctt actgtcatgc   12600
```

```
catccgtaag atgctttct gtgactggtg agtactcaac caagtcattc tgagaatagt    12660
gtatgcggcg accgagttgc tcttgcccgg cgtcaacacg ggataatacc gcgccacata    12720
gcagaacttt aaaagtgctc atcattggaa aacgttcttc ggggcgaaaa ctctcaagga    12780
tcttaccgct gttgagatcc agttcgatgt aacccactcg tgcacccaac tgatcttcag    12840
catcttttac tttcaccagc gtttctgggt gagcaaaaac aggaaggcaa atgccgcaa     12900
aaaagggaat aagggcgaca cggaaatgtt gaatactcat actcttcctt tttcaatatt    12960
attgaagcat ttatcagggt tattgtctca tgagcggata catatttgaa tgtatttaga    13020
aaaataaaca aataggggtt ccgcgcacat ttccccgaaa agtgccacct gacgtctaag    13080
aaaccattat tatcatgaca ttaacctata aaaataggcg tatcacgagg ccctttcgtc    13140
ttcaagaatt ggtcgacgat cttgctgcgt tcggatattt tcgtggagtt cccgccacag    13200
acccggattg aaggcgagat ccagcaactc gcgccagatc atcctgtgac ggaactttgg    13260
cgcgtgatga ctggccagga cgtcggccga aagagcgaca agcagatcac gcttttcgac    13320
agcgtcggat ttgcgatcga ggattttttcg gcgctgcgct acgtccgcga ccgcgttgag    13380
ggatcaagcc acagcagccc actcgacctt ctagccgacc cagacgagcc aagggatctt    13440
tttggaatgc tgctccgtcg tcaggctttc cgacgtttgg gtggttgaac agaagtcatt    13500
atcgtacgga atgccaagca ctcccgaggg gaaccctgtg gttggcatgc acatacaaat    13560
ggacgaacgg ataaaccttt tcacgccctt ttaaatatcc gttattctaa taaacgctct    13620
tttctcttag gttacccgc caatatatcc tgtcaaacac tgatagttta aactgaaggc     13680
gggaaacgac aatctgatca tgagcggaga attaagggag tcacgttatg acccccgccg    13740
atgacgcggg acaagccgtt ttacgtttgg aactgacaga accgcaacgt tgaaggagcc    13800
actcagc                                                              13807

<210> SEQ ID NO 11
<211> LENGTH: 4678
<212> TYPE: DNA
<213> ORGANISM: artificial sequence
<220> FEATURE:
<223> OTHER INFORMATION: vector

<400> SEQUENCE: 11
gaaaggccca gtcttccgac tgagcctttc gttttatttg atgcctggca gttccctact      60
ctcgcgttaa cgctagcatg gatgttttcc cagtcacgac gttgtaaaac gacggccagt     120
cttaagctcg ggcccgcgtt aacgctacca tggagctcca ataatgatt ttattttgac      180
tgatagtgac ctgttcgttg caacaaattg ataagcaatg ctttttata atgccaactt      240
tgtatagaaa agttgggccg aattcgagct cggtacggcc agaatggccc ggaccgggtt     300
accgaattcg agctcggtac cctgggatcc ctggtaatta ttggctgtag gattctaaac     360
agagcctaaa tagctggaat agctctagcc ctcaatccaa actaatgata tctatactta     420
tgcaactcta aatttttatt ctaaaagtaa tatttcattt ttgtcaacga gattctctac     480
tctattccac aatcttttga agcaatattt accttaaatc tgtactctat accaataatc     540
atatattcta ttatttattt ttatctctct cctaaggagc atcccctat gtctgcatgg      600
ccccgcctc gggtcccaat ctcttgctct gctagtagca cagaagaaaa cactagaaat      660
gacttgcttg acttagagta tcagataaac atcatgttta cttaacttta atttgtatcg     720
gtttctacta tttttataat attttttgtct ctatagatac tacgtgcaac agtataatca    780
```

```
acctagttta atccagagcg aaggattttt tactaagtac gtgactccat atgcacagcg    840
ttccttttat ggttcctcac tgggcacagc ataaacgaac cctgtccaat gttttcagcg    900
cgaacaaaca gaaattccat cagcgaacaa acaacataca tgcgagatga aataaataa     960 taaaaaaagc tccgtctcga taggccggca cgaatcgaga gcctccatag ccagtttttt   1020
ccatcggaac ggcggttcgc gcacctaatt atatgcacca cacgcctata aagccaacca   1080
acccgtcgga ggggcgcaag ccagacagaa gacagcccgt cagcccctct cgttttcat    1140 ccgccttcgc ctccaaccgc gtgcgctcca cgcctcctcc aggaaagcga ggatctcccc   1200
caaatccacc cgtcggcacc tccgcttcaa ggtacgccgc tcgtcctccc ccccccccc    1260 tctctacctt ctctagatcg gcgttccggt ccatggttag ggcccggtag ttctacttct   1320
gttcatgttt gtgttagatc cgtgtttgtg ttagatccgt gctgctagcg ttcgtacacg   1380
gatgcgacct gtacgtcaga cacgttctga ttgctaactt gccagtgttt ctctttgggg   1440
aatcctggga tggctctagc cgttccgcag acgggatcga tttcatgatt ttttttgttt   1500
cgttgcatag ggtttggttt gccctttttcc tttatttcaa tatatgccgt gcacttgttt   1560
gtcgggtcat cttttcatgc ttttttttgt cttggttgtg atgatgtggt ctggttgggc   1620
ggtcgttcta gatcggagta gaattctgtt tcaaactacc tggtggattt attaattttg   1680
gatctgtatg tgtgtgccat acatattcat agttacgaat tgaagatgat ggatggaaat   1740
atcgatctag ataggtata catgttgatg cgggttttac tgatgcatat acagagatgc    1800 ttttttgttcg cttggttgtg atgatgtggt gtggttgggc ggtcgttcat tcgttctaga   1860
tcggagtaga atactgtttc aaactacctg gtgtatttat taattttgga actgtatgtg   1920
tgtgtcatac atcttcatag ttacgagttt aagatggatg gaaatatcga tctaggatag   1980
gtatacatgt tgatgtgggt tttactgatg catatacatg atggcatatg cagcatctat   2040
tcatatgctc taaccttgag tacctatcta ttataataaa caagtatgtt ttataattat   2100
tttgatcttg atatacttgg atgatggcat atgcagcagc tatatgtgga ttttttttagc   2160 cctgccttca tacgctattt atttgcttgg tactgtttct tttgtcgatg ctcaccctgt   2220
tgtttggtgt tacttctgca ggtcgactct agaagcttgg tcacccggtc cgggcctaga   2280
aggccagctt caagtttgta caaaaaagtt gaacgagaaa cgtaaaatga tataaatatc   2340
aatatattaa attagatttt gcataaaaaa cagactacat aatactgtaa acacaacat    2400 atgcagtcac tatgaatcaa ctacttagat ggtattagtg acctgtagaa ttcgagctct   2460
agagctgcag ggcggccgcg atatccccta tagtgagtcg tattacatgg tcatagctgt   2520
ttcctggcag ctctggcccg tgtctcaaaa tctctgatgt tacattgcac aagataaaaa   2580
tatatcatca tgaacaataa aactgtctgc ttacataaac agtaatacaa ggggtgttat   2640
gagccatatt caacgggaaa cgtcgaggcc gcgattaaat tccaacatgg atgctgattt   2700
atatgggtat aaatgggctc gcgataatgt cgggcaatca ggtgcgacaa tctatcgctt   2760
gtatgggaag cccgatgcgc cagagttgtt tctgaaacat ggcaaaggta gcgttgccaa   2820
tgatgttaca gatgagatgg tcagactaaa ctggctgacg gaatttatgc ctcttccgac   2880
catcaagcat tttatccgta ctcctgatga tgcatggtta ctcaccactg cgatccccgg   2940
aaaaacagca ttccaggtat tagaagaata tcctgattca ggtgaaaata ttgttgatgc   3000
gctggcagtg ttcctgcgcc ggttgcattc gattcctgtt tgtaattgtc cttttaacag   3060
cgatcgcgta tttcgtctcg ctcaggcgca atcacgaatg aataacggtt tggttgatgc   3120
gagtgatttt gatgacgagc gtaatggctg gcctgttgaa caagtctgga agaaatgca    3180
```

```
taaactttg ccattctcac cggattcagt cgtcactcat ggtgatttct cacttgataa    3240
ccttattttt gacgaggga aattaatagg ttgtattgat gttggacgag tcggaatcgc    3300
agaccgatac caggatcttg ccatcctatg gaactgcctc ggtgagtttt ctccttcatt   3360
acagaaacgg cttttcaaa aatatggtat tgataatcct gatatgaata aattgcagtt    3420
tcatttgatg ctcgatgagt ttttctaatc agaattggtt aattggttgt aacactggca   3480
gagcattacg ctgacttgac gggacggcgc aagctcatga ccaaaatccc ttaacgtgag   3540
ttacgcgtcg ttccactgag cgtcagaccc cgtagaaaag atcaaaggat cttcttgaga   3600
tcctttttt ctgcgcgtaa tctgctgctt gcaaacaaaa aaaccaccgc taccagcggt    3660
ggtttgtttg ccggatcaag agctaccaac tcttttccg aaggtaactg gcttcagcag    3720
agcgcagata ccaaatactg tccttctagt gtagccgtag ttaggccacc acttcaagaa   3780
ctctgtagca ccgcctacat acctcgctct gctaatcctg ttaccagtgg ctgctgccag   3840
tggcgataag tcgtgtctta ccgggttgga ctcaagacga tagttaccgg ataaggcgca   3900
gcggtcgggc tgaacggggg gttcgtgcac acagcccagc ttggagcgaa cgacctacac   3960
cgaactgaga tacctacagc gtgagcattg agaaagcgcc acgcttcccg aagggagaaa   4020
ggcggacagg tatccggtaa gcggcagggt cggaacagga gagcgcacga gggagcttcc   4080
agggggaaac gcctggtatc tttatagtcc tgtcgggttt cgccacctct gacttgagcg   4140
tcgatttttg tgatgctcgt caggggggcg gagcctatgg aaaaacgcca gcaacgcggc   4200
cttttacgg ttcctggcct tttgctggcc ttttgctcac atgttctttc ctgcgttatc    4260
ccctgattct gtggataacc gtattaccgc ctttgagtga gctgataccg ctcgccgcag   4320
ccgaacgacc gagcgcagcg agtcagtgag cgaggaagcg gaagagcgcc caatacgcaa   4380
accgcctctc cccgcgcgtt ggccgattca ttaatgcagc tggcacgaca ggtttcccga   4440
ctggaaagcg ggcagtgagc gcaacgcaat taatacgcgt accgctagcc aggaagagtt   4500
tgtagaaacg caaaaaggcc atccgtcagg atggccttct gcttagtttg atgcctggca   4560
gtttatggcg ggcgtcctgc ccgccaccct ccgggccgtt gcttcacaac gttcaaatcc   4620
gctcccggcg gatttgtcct actcaggaga gcgttcaccg acaaacaaca gataaaac    4678
```

<210> SEQ ID NO 12
<211> LENGTH: 3505
<212> TYPE: DNA
<213> ORGANISM: artificial sequence
<220> FEATURE:
<223> OTHER INFORMATION: vector

<400> SEQUENCE: 12

```
gatccccggg taccgagctc gaattcggcc caagtttgta caaaaaagtt gaacgagaaa    60
cgtaaaatga tataaatatc aatatattaa attagatttt gcataaaaaa cagactacat   120
aatactgtaa aacacaacat atgcagtcac tatgaatcaa ctactagat ggtattagtg    180
acctgtagaa ttcgagctct agagctgcag ggcggccgcg atatccccta tagtgagtcg   240
tattacatgg tcatagctgt ttcctggcag ctctggcccg tgtctcaaaa tctctgatgt   300
tacattgcac aagataaaaa tatatcatca tgaacaataa aactgtctgc ttacataaac   360
agtaatacaa ggggtgttat gagccatatt caacgggaaa cgtcgaggcc gcgattaaat   420
tccaacatgg atgctgattt atatgggtat aaatgggctc gcgataatgt cgggcaatca   480
ggtgcgacaa tctatcgctt gtatgggaag cccgatgcgc cagagttgtt tctgaaacat   540
```

```
ggcaaaggta gcgttgccaa tgatgttaca gatgagatgg tcagactaaa ctggctgacg    600
gaatttatgc ctcttccgac catcaagcat tttatccgta ctcctgatga tgcatggtta    660
ctcaccactg cgatccccgg aaaaacagca ttccaggtat tagaagaata tcctgattca    720
ggtgaaaata ttgttgatgc gctggcagtg ttcctgcgcc ggttgcattc gattcctgtt    780
tgtaattgtc cttttaacag cgatcgcgta tttcgtctcg ctcaggcgca atcacgaatg    840
aataacggtt tggttgatgc gagtgatttt tgatgacgag cgtaatggctg gcctgttgaa    900 caagtctgga agaaatgca taaacttttg ccattctcac cggattcagt cgtcactcat    960
ggtgatttct cacttgataa ccttattttt gacgagggga aattaatagg ttgtattgat   1020
gttggacgag tcggaatcgc agaccgatac caggatcttg ccatcctatg gaactgcctc   1080
ggtgagtttt ctccttcatt acagaaacgg ctttttcaaa aatatggtat tgataatcct   1140
gatatgaata aattgcagtt tcatttgatg ctcgatgagt ttttctaatc agaattggtt   1200
aattggttgt aacactggca gagcattacg ctgacttgac gggacggcgc aagctcatga   1260
ccaaaatccc ttaacgtgag ttacgcgtcg ttccactgag cgtcagaccc cgtagaaaag   1320
atcaaaggat cttcttgaga tcctttttt ctgcgcgtaa tctgctgctt gcaaacaaaa   1380
aaaccaccgc taccagcggt ggtttgtttg ccggatcaag agctaccaac tctttttccg   1440
aaggtaactg gcttcagcag agcgcagata ccaaatactg tccttctagt gtagccgtag   1500
ttaggccacc acttcaagaa ctctgtagca ccgcctacat acctcgctct gctaatcctg   1560
ttaccagtgg ctgctgccag tggcgataag tcgtgtctta ccgggttgga ctcaagacga   1620
tagttaccgg ataaggcgca gcggtcgggc tgaacggggg gttcgtgcac acagcccagc   1680
ttggagcgaa cgacctacac cgaactgaga tacctacagc gtgagcattg agaaagcgcc   1740
acgcttcccg aagggagaaa ggcggacagg tatccggtaa gcggcagggt cggaacagga   1800
gagcgcacga gggagcttcc aggggggaaac gcctggtatc tttatagtcc tgtcgggttt   1860
cgccacctct gacttgagcg tcgatttttg tgatgctcgt caggggggcg agcctatgg   1920 aaaaacgcca gcaacgcggc ctttttacgg ttcctggcct tttgctggcc ttttgctcac   1980
atgttctttc ctgcgttatc ccctgattct gtggataacc gtattaccgc ctttgagtga   2040
gctgataccg ctcgccgcag ccgaacgacc gagcgcagcg agtcagtgag cgaggaagcg   2100
gaagagcgcc caatacgcaa accgcctctc cccgcgcgtt ggccgattca ttaatgcagc   2160
tggcacgaca ggtttcccga ctggaaagcg ggcagtgagc gcaacgcaat taatacgcgt   2220
accgctagcc aggaagagtt tgtagaaacg caaaaaggcc atccgtcagg atggccttct   2280
gcttagtttg atgcctggca gtttatggcg ggcgtcctgc ccgccaccct ccgggccgtt   2340
gcttcacaac gttcaaatcc gctcccggcg gatttgtcct actcaggaga gcgttcaccg   2400
acaaacaaca gataaaacga aaggcccagt cttccgactg agcctttcgt tttatttgat   2460
gcctggcagt tccctactct cgcgttaacg ctagcatgga tgttttccca gtcacgacgt   2520
tgtaaaacga cggccagtct taagctcggg cccgcgttaa cgctaccatg gagctccaaa   2580
taatgatttt attttgactg atagtgacct gttcgttgca acaaattgat aagcaatgct   2640
tttttataat gccaactttg tatagaaaag ttgaagctta atccttaca gaattgctgt   2700 agtttcatag tgctagatgt ggacagcaaa gcgccgctgt atgcttctgc ttttcttttt   2760
tggtgtgtgt agccacatcc tttgttcctg cccggcgcca tcccacttgg ttgttttttt   2820
ttatgattga aagccttcat gcttcctcgg tcaatcaccg gtgcgcactg ggagcatcgc   2880
cggaaaaaaa attcttcggc taagagtaac ttctttctcc ttttcttctc tgatctcgcg   2940
```

| | | | | |
|---|---|---|---|---|
| agcagtgctg | ataacgtgtt | gtaatctact | tagcggtaac | gagattgaga gagacaaaat | 3000 |
| gacagaacta | ttgtctttat | tgcagagtgt | catgtattta | tacaggggat acaaagtctc | 3060 |
| ccaaggggtg | tgtcccttgg | gagtaactgc | cagttgatca | caggacaata ttttgtaaca | 3120 |
| aaacgtacac | atcgtcaaaa | tagcgaggca | tgaaactggc | cttggccatg gacgcgtgaa | 3180 |
| gcgcgccatg | cgttggatat | gtggtcaata | agtatataca | atacaatgtt taacagagct | 3240 |
| gatagtactg | ctttggcaca | ttttttgtcca | cgcttcatga | gagataaaac acctgcacgt | 3300 |
| aaattcacat | gctgcactga | aggcccgatc | actgaggagc | gaactgccgt aactcccttc | 3360 |
| tatatatacc | cccagtccct | gtttcagttt | tcgtcaagct | agcagcacca agttgtcgat | 3420 |
| cacttgcctg | ctcttgagct | cgattaagct | atcatcagct | acagcatccg atcccaaact | 3480 |
| gcaactgtag | cagcgacaac | tgccg | | | 3505 |

<210> SEQ ID NO 13
<211> LENGTH: 49765
<212> TYPE: DNA
<213> ORGANISM: artificial sequence
<220> FEATURE:
<223> OTHER INFORMATION: vector

<400> SEQUENCE: 13

| | | | | |
|---|---|---|---|---|
| gggggggggg | gggggggtt | ccattgttca | ttccacggac | aaaaacagag aaaggaaacg | 60 |
| acagaggcca | aaaagctcgc | tttcagcacc | tgtcgtttcc | tttcttttca gagggtattt | 120 |
| taaataaaaa | cattaagtta | tgacgaagaa | gaacggaaac | gccttaaacc ggaaaatttt | 180 |
| cataaatagc | gaaaacccgc | gaggtcgccg | ccccgtaacc | tgtcggatca ccggaaagga | 240 |
| cccgtaaagt | gataatgatt | atcatctaca | tatcacaacg | tgcgtggagg ccatcaaacc | 300 |
| acgtcaaata | atcaattatg | acgcaggtat | cgtattaatt | gatctgcatc aacttaacgt | 360 |
| aaaaacaact | tcagacaata | caaatcagcg | acactgaata | cggggcaacc tcatgtcccc | 420 |
| cccccccccc | ccctgcagg | catcgtggtg | tcacgctcgt | cgtttggtat ggcttcattc | 480 |
| agctccggtt | cccaacgatc | aaggcgagtt | acatgatccc | ccatgttgtg caaaaaagcg | 540 |
| gttagctcct | tcggtcctcc | gatcgttgtc | agaagtaagt | tggccgcagt gttatcactc | 600 |
| atggttatgg | cagcactgca | taattctctt | actgtcatgc | catccgtaag atgcttttct | 660 |
| gtgactggtg | agtactcaac | caagtcattc | tgagaatagt | gtatgcggcg accgagttgc | 720 |
| tcttgcccgg | cgtcaacacg | ggataatacc | gcgccacata | gcagaacttt aaaagtgctc | 780 |
| atcattggaa | aacgttcttc | ggggcgaaaa | ctctcaagga | tcttaccgct gttgagatcc | 840 |
| agttcgatgt | aacccactcg | tgcacccaac | tgatcttcag | catcttttac tttcaccagc | 900 |
| gtttctgggt | gagcaaaaac | aggaaggcaa | aatgccgcaa | aaaagggaat aagggcgaca | 960 |
| cggaaatgtt | gaatactcat | actcttcctt | tttcaatatt | attgaagcat ttatcagggt | 1020 |
| tattgtctca | tgagcggata | catatttgaa | tgtatttaga | aaaataaaca aataggggtt | 1080 |
| ccgcgcacat | ttccccgaaa | agtgccacct | gacgtctaag | aaaccattat tatcatgaca | 1140 |
| ttaacctata | aaaataggcg | tatcacgagg | ccctttcgtc | ttcaagaatt cggagctttt | 1200 |
| gccattctca | ccggattcag | tcgtcactca | tggtgatttc | tcacttgata accttatttt | 1260 |
| tgacgagggg | aaattaatag | gttgtattga | tgttggacga | gtcggaatcg cagaccgata | 1320 |
| ccaggatctt | gccatcctat | ggaactgcct | cggtgagttt | tctccttcat tacagaaacg | 1380 |
| gctttttcaa | aaatatggta | ttgataatcc | tgatatgaat | aaattgcagt ttcatttgat | 1440 |

```
gctcgatgag ttttctaat cagaattggt taattggttg taacactggc agagcattac   1500
gctgacttga cgggacggcg gctttgttga ataaatcgaa cttttgctga gttgaaggat   1560
cagatcacgc atcttcccga caacgcagac cgttccgtgg caaagcaaaa gttcaaaatc   1620
accaactggt ccacctacaa caaagctctc atcaaccgtg gctccctcac tttctggctg   1680
gatgatgggg cgattcaggc ctggtatgag tcagcaacac cttcttcacg aggcagacct   1740
cagcgccaga aggccgccag agaggccgag cgcggccgtg aggcttggac gctagggcag   1800
ggcatgaaaa agcccgtagc gggctgctac gggcgtctga cgcggtggaa aggggagggg   1860
gatgttgtct acatggctct gctgtagtga gtgggttgcg ctccggcagc ggtcctgatc   1920
aatcgtcacc ctttctcggt ccttcaacgt tcctgacaac gagcctcctt ttcgccaatc   1980
catcgacaat caccgcgagt ccctgctcga acgctgcgtc cggaccggct tcgtcgaagg   2040
cgtctatcgc ggcccgcaac agcggcgaga gcggagcctg ttcaacggtg ccgccgcgct   2100
cgccggcatc gctgtcgccg gcctgctcct caagcacggc cccaacagtg aagtagctga   2160
ttgtcatcag cgcattgacg gcgtcccggg ccgaaaaacc cgcctcgcag aggaagcgaa   2220
gctgcgcgtc ggccgtttcc atctgcggtg cgcccggtcg cgtgccggca tggatgcgcg   2280
cgccatcgcg gtaggcgagc agcgcctgcc tgaagctgcg ggcattcccg atcagaaatg   2340
agcgccagtc gtcgtcggct ctcggcaccg aatgcgtatg attctccgcc agcatggctt   2400
cggccagtgc gtcgagcagc gcccgcttgt tcctgaagtg ccagtaaagc gccggctgct   2460
gaaccccccaa ccgttccgcc agtttgcgtg tcgtcagacc gtctacgccg acctcgttca   2520
acaggtccag ggcggcacgg atcactgtat tcggctgcaa ctttgtcatg cttgacactt   2580
tatcactgat aaacataata tgtccaccaa cttatcagtg ataaagaatc gcgcgttca    2640
atcgaccag cggaggctgg tccggaggcc agacgtgaaa cccaacatac ccctgatcgt    2700
aattctgagc actgtcgcgc tcgacgctgt cggcatcggc ctgattatgc cggtgctgcc   2760
gggcctcctg cgccgatctgg ttcactcgaa cgacgtcacc gcccactatg gcattctgct   2820
ggcgctgtat gcgttggtgc aatttgcctg cgcacctgtg ctgggcgcgc tgtcggatcg   2880
tttcgggcgg cggccaatct tgctcgtctc gctggccggc gccactgtcg actacgccat   2940
catggcgaca gcgcctttcc tttgggttct ctatatcggg cggatcgtgg ccggcatcac   3000
cggggcgact ggggcggtag ccggcgctta tattgccgat atcactgatg gcgatgagcg   3060
cgcgcggcac ttcggcttca tgagcgcctg tttcggggtc gggatggtcg cgggacctgt   3120
gctcggtggg ctgatgggcg gtttctcccc ccacgctccg ttcttcgccg cggcagcctt   3180
gaacggcctc aatttcctga cgggctgttt ccttttgccg gagtcgcaca aaggcgaacg   3240
ccggccgtta cgccgggagg ctctcaaccc gctcgcttcg ttccggtggg cccgggggcat  3300
gaccgtcgtc gccgccctga tggcggtctt cttcatcatg caacttgtcg acaggtgcc   3360
ggccgcgctt tgggtcattt tcggcgagga tcgctttcac tgggacgcga ccacgatcgg   3420
catttcgctt gccgcatttg gcattctgca ttcactcgcc caggcaatga tcaccggccc   3480
tgtagccgcc cggctcggcg aaaggcgggc actcatgctc ggaatgattg ccgacggcac   3540
aggctacatc ctgcttgcct tcgcgacacg gggatggatg gcgttcccga tcatggtcct   3600
gcttgcttcg ggtggcatcg gaatgccggc gctgcaagca atgttgtcca ggcaggtgga   3660
tgaggaacgt caggggcagc tgcaaggctc actggcggcg ctcaccagcc tgacctcgat   3720
cgtcggaccc ctcctcttca cggcgatcta tgcggcttct ataacaacgt ggaacgggtg   3780
ggcatggatt gcaggcgctg ccctctactt gctctgcctg ccggcgctgc gtcgcgggct   3840
```

```
ttggagcggc gcagggcaac gagccgatcg ctgatcgtgg aaacgatagg cctatgccat    3900
gcgggtcaag gcgacttccg gcaagctata cgcgccctag gagtgcggtt ggaacgttgg    3960
cccagccaga tactcccgat cacgagcagg acgccgatga tttgaagcgc actcagcgtc    4020
tgatccaaga acaaccatcc tagcaacacg gcggtcccg gctgagaaa gcccagtaag    4080 gaaacaactg taggttcgag tcgcgagatc ccccggaacc aaaggaagta ggttaaaccc    4140
gctccgatca ggccgagcca cgccaggccg agaacattgg ttcctgtagg catcgggatt    4200
ggcggatcaa acactaaagc tactggaacg agcagaagtc ctccggccgc cagttgccag    4260
gcggtaaagg tgagcagagg cacggaggt tgccacttgc gggtcagcac ggttccgaac    4320
gccatggaaa ccgccccgc caggcccgct gcgacgccga caggatctag cgctgcgttt    4380
ggtgtcaaca ccaacagcgc cacgcccgca gttccgcaaa tagcccccag gaccgccatc    4440
aatcgtatcg ggctacctag cagagcggca gagatgaaca cgaccatcag cggctgcaca    4500
gcgcctaccg tcgccgcgac cccgcccggc aggcggtaga ccgaaataaa caacaagctc    4560
cagaatagcg aaatattaag tgcgccgagg atgaagatgc gcatccacca gattcccgtt    4620
ggaatctgtc ggacgatcat cacgagcaat aaacccgccg gcaacgcccg cagcagcata    4680
ccggcgaccc ctcggcctcg ctgttcgggc tccacgaaaa cgccggacag atgcgccttg    4740
tgagcgtcct tggggccgtc ctcctgtttg aagaccgaca gcccaatgat ctcgccgtcg    4800
atgtaggcgc cgaatgccac ggcatctcgc aaccgttcag cgaacgcctc catgggcttt    4860
ttctcctcgt gctcgtaaac ggacccgaac atctctggag ctttcttcag gccgacaat    4920 cggatctcgc ggaaatcctg cacgtcggcc gctccaagcc gtcgaatctg agccttaatc    4980
acaattgtca atttaatcc tctgtttatc ggcagttcgt agagcgcgcc gtgcgtcccg    5040
agcgatactg agcgaagcaa gtgcgtcgag cagtgcccgc ttgttcctga aatgccagta    5100
aagcgctggc tgctgaaccc ccagccgaa ctgaccccac aaggccctag cgtttgcaat    5160
gcaccaggtc atcattgacc caggcgtgtt ccaccaggcc gctgcctcgc aactcttcgc    5220
aggcttcgcc gacctgctcg cgccacttct tcacgcgggt ggaatccgat ccgcacatga    5280
ggcggaaggt ttccagcttg agcgggtacg gctcccggtg cgagctgaaa tagtcgaaca    5340
tccgtcgggc cgtcggcgac agcttgcggt acttctccca tatgaatttc gtgtagtggt    5400
cgccagcaaa cagcacgacg atttcctcgt cgatcaggac ctggcaacgg acgttttct    5460 tgccacggtc caggacgcgg aagcggtgca gcagcgacac cgattccagg tgcccaacgc    5520
ggtcggacgt gaagcccatc gccgtcgcct gtaggcgcga caggcattcc tcggccttcg    5580
tgtaataccg gccattgatc gaccagccca ggtcctggca aagctcgtag aacgtgaagg    5640
tgatcggctc gccgataggg gtgcgcttcg cgtactccaa cacctgctgc cacaccagtt    5700
cgtcatcgtc ggcccgcagc tcgacgccgg tgtaggtgat cttcacgtcc ttgttgacgt    5760
ggaaaatgac cttgttttgc agcgcctcgc gcgggatttt cttgttgcgc gtggtgaaca    5820
gggcagagcg ggccgtgtcg tttggcatcg ctcgcatcgt gtccggccac ggcgcaatat    5880
cgaacaagga aagctgcatt tccttgatct gctgcttcgt gtgtttcagc aacgcggcct    5940
gcttggcctc gctgacctgt tttgccaggt cctcgccggc ggttttcgc ttcttggtcg    6000 tcatagttcc tcgcgtgtcg atggtcatcg acttcgccaa acctgccgcc tcctgttcga    6060
gacgacgcga acgctccacg gcggccgatg gcgcgggcag gcaggggga gccagttgca    6120 cgctgtcgcg ctcgatcttg gccgtagctt gctggaccat cgagccgacg gactggaagg    6180
```

```
tttcgcgggg cgcacgcatg acggtgcggc ttgcgatggt tcggcatcc tcggcggaaa    6240 acccccgcgtc gatcagttct tgcctgtatg ccttccggtc aaacgtccga ttcattcacc   6300
ctccttgcgg gattgccccg actcacgccg gggcaatgtg cccttattcc tgatttgacc   6360
cgcctggtgc cttggtgtcc agataatcca ccttatcggc aatgaagtcg gtcccgtaga   6420
ccgtctggcc gtccttctcg tacttggtat tccgaatctt gccctgcacg aataccagcg   6480 acccctttgcc caaatacttg ccgtgggcct cggcctgaga gccaaaacac ttgatgcgga   6540
agaagtcggt gcgctcctgc ttgtcgccgg catcgttgcg ccactcttca ttaaccgcta   6600
tatcgaaaat tgcttgcggc ttgttagaat tgccatgacg tacctcggtg tcacgggtaa   6660
gattaccgat aaactggaac tgattatggc tcatatcgaa agtctccttg agaaaggaga   6720
ctctagttta gctaaacatt ggttccgctg tcaagaactt tagcggctaa aattttgcgg   6780
gccgcgacca aaggtgcgag gggcggcttc cgctgtgtac aaccagatat ttttcaccaa   6840
catccttcgt ctgctcgatg agcggggcat gacgaaacat gagctgtcgg agagggcagg   6900
ggtttcaatt tcgtttttat cagacttaac caacggtaag gccaacccct cgttgaaggt   6960
gatggaggcc attgccgacg ccctggaaac tcccctacct cttctcctgg agtccaccga   7020
ccttgaccgc gaggcactcg cggagattgc gggtcatcct ttcaagagca gcgtgccgcc   7080
cggatacgaa cgcatcagtg tggttttgcc gtcacataag gcgtttatcg taaagaaatg   7140
gggcgacgac acccgaaaaa agctgcgtgg aaggctctga cgccaagggt tagggcttgc   7200
acttccttct ttagccgcta aaacggcccc ttctctgcgg gccgtcggct cgcgcatcat   7260
atcgacatcc tcaacggaag ccgtgccgcg aatggcatcg ggcgggtgcg ctttgacagt   7320
tgttttctat cagaacccct acgtcgtgcg gttcgattag ctgtttgtct tgcaggctaa   7380
acactttcgg tatatcgttt gcctgtgcga taatgttgct aatgatttgt tgcgtagggg   7440
ttactgaaaa gtgagcggga aagaagagtt tcagaccatc aaggagcggg ccaagcgcaa   7500
gctggaacgc gacatgggtg cggacctgtt ggccgcgctc aacgacccga aaaccgttga   7560
agtcatgctc aacgcggacg gcaaggtgtg gcacgaacgc cttggcgagc cgatgcggta   7620
catctgcgac atgcggccca gccagtcgca ggcgattata gaaacggtgg ccggattcca   7680
cggcaaagag gtcacgcggc attcgcccat cctggaaggc gagttcccct tggatggcag   7740
ccgctttgcc ggccaattgc cgccggtcgt ggccgcgcca acctttgcga tccgcaagcg   7800
cgcggtcgcc atcttcacgc tggaacagta cgtcgaggcg ggcatcatga cccgcgagca   7860
atacgaggtc attaaaagcg ccgtcgcggc gcatcgaaac atcctcgtca ttggcggtac   7920
tggctcgggc aagaccacgc tcgtcaacgc gatcatcaat gaaatggtcg ccttcaaccc   7980
gtctgagcgc gtcgtcatca tcgaggacac cggcgaaatc cagtgcgccg cagagaacgc   8040
cgtccaatac cacaccagca tcgacgtctc tgatgacgctg ctgctcaaga caacgctgcg   8100
tatgcgcccc gaccgcatcc tggtcggtga ggtacgtggc cccgaagccc ttgatctgtt   8160
gatggcctgg aacaccgggc atgaaggagg tgccgccacc ctgcacgcaa acaacccaa    8220 agcgggcctg agccggctcg ccatgcttat cagcatgcac ccggattcac cgaaacccat   8280
tgagccgctg attggcgagg cggttcatgt ggtcgtccat atcgccagga cccctagcgg   8340
ccgtcgagtg caagaaattc tcgaagttct tggttacgag aacggccagt acatcaccaa   8400
aaccctgtaa ggagtatttc caatgacaac ggctgttccg ttccgtctga ccatgaatcg   8460
cggcattttg ttctaccttg ccgtgttctt cgttctcgct ctcgcgttat ccgcgcatcc   8520
ggcgatggcc tcggaaggca ccggcggcag cttgccatat gagagctggc tgacgaacct   8580
```

```
gcgcaactcc gtaaccggcc cggtggcctt cgcgctgtcc atcatcggca tcgtcgtcgc   8640
cggcggcgtg ctgatcttcg gcggcgaact caacgccttc ttccgaaccc tgatcttcct   8700
ggttctggtg atggcgctgc tggtcggcgc gcagaacgtg atgagcacct tcttcggtcg   8760
tggtgccgaa atcgcggccc tcggcaacgg ggcgctgcac caggtgcaag tcgcggcggc   8820
ggatgccgtg cgtgcggtag cggctggacg gctcgcctaa tcatggctct gcgcacgatc   8880
cccatccgtc gcgcaggcaa ccgagaaaac ctgttcatgg gtggtgatcg tgaactggtg   8940
atgttctcgg gcctgatggc gtttgcgctg attttcagcg cccaagagct gcgggccacc   9000
gtggtcggtc tgatcctgtg gttcggggcg ctctatgcgt tccgaatcat ggcgaaggcc   9060
gatccgaaga tgcggttcgt gtacctgcgt caccgccggt acaagccgta ttacccggcc   9120
cgctcgaccc cgttccgcga gaacaccaat agccaaggga gcaataccg atgatccaag   9180 caattgcgat tgcaatcgcg ggcctcggcg cgcttctgtt gttcatcctc tttgcccgca   9240
tccgcgcggc cgatgccgaa ctgaaactga aaaagcatcg ttccaaggac gccggcctgg   9300
ccgatctgct caactacgcc gctgtcgtcg atgacggcgt aatcgtgggc aagaacggca   9360
gctttatggc tgcctggctg tacaaggcg atgacaacgc aagcagcacc gaccagcagc   9420
gcgaagtagt gtccgcccgc atcaaccagg ccctcgcggg cctgggaagt gggtggatga   9480
tccatgtgga cgccgtgcgg cgtcctgctc cgaactacgc ggagcggggc ctgtcggcgt   9540
tccctgaccg tctgacggca gcgattgaag aagagcgctc ggtcttgcct tgctcgtcgg   9600
tgatgtactt caccagctcc gcgaagtcgc tcttcttgat ggagcgcatg gggacgtgct   9660
tggcaatcac gcgcaccccc cggccgtttt agcggctaaa aaagtcatgg ctctgccctc   9720
gggcggacca cgcccatcat gaccttgcca agctcgtcct gcttctcttc gatcttcgcc   9780
agcagggcga ggatcgtggc atcaccgaac cgcgccgtgc gcgggtcgtc ggtgagccag   9840
agtttcagca ggccgcccag gcggcccagg tcgccattga tgcgggccag ctcgcggacg   9900
tgctcatagt ccacgacgcc cgtgattttg tagccctggc cgacggccag caggtaggcc   9960
gacaggctca tgccggccgc cgccgccttt tcctcaatcg ctcttcgttc gtctggaagg   10020
cagtacacct tgataggtgg gctgcccttc ctggttggct tggtttcatc agccatccgc   10080
ttgccctcat ctgttacgcc ggcggtagcc ggccagcctc gcagagcagg attcccgttg   10140
agcaccgcca ggtgcgaata agggacagtg aagaaggaac acccgctcgc gggtgggcct   10200
acttcaccta tcctgcccgg ctgacgccgt tggatacacc aaggaaagtc tacacgaacc   10260
ctttggcaaa atcctgtata tcgtgcgaaa aaggatggat ataccgaaaa atcgctata   10320 atgaccccga agcagggtta tgcagcggaa aagcgctgct tccctgctgt tttgtggaat   10380
atctaccgac tggaaacagg caaatgcagg aaattactga actgagggga caggcgagag   10440
acgatgccaa agagctacac cgacgagctg gccgagtggg ttgaatcccg cgcggccaag   10500
aagcgccggc gtgatgaggc tgcggttgcg ttcctggcgg tgagggcgga tgtcgaggcg   10560
gcgttagcgt ccggctatgc gctcgtcacc atttgggagc acatgcggga aacgggaag   10620 gtcaagttct cctacgagac gttccgctcg cacgccaggc ggcacatcaa ggccaagccc   10680
gccgatgtgc ccgcaccgca ggccaaggct gcggaacccg cgccggcacc caagacgccg   10740
gagccacggc ggccgaagca ggggggcaag gctgaaaagc cggccccgc tgcggccccg   10800 accggcttca ccttcaaccc aacaccggac aaaaaggatc tactgtaatg gcgaaaattc   10860
acatggtttt gcagggcaag ggcggggtcg gcaagtcggc catcgccgcg atcattgcgc   10920
```

```
agtacaagat ggacaagggg cagacaccct tgtgcatcga caccgacccg gtgaacgcga   10980
cgttcgaggg ctacaaggcc ctgaacgtcc gccggctgaa catcatggcc ggcgacgaaa   11040
ttaactcgcg caacttcgac accctggtcg agctgattgc gccgaccaag gatgacgtgg   11100
tgatcgacaa cggtgccagc tcgttcgtgc ctctgtcgca ttacctcatc agcaaccagg   11160
tgccggctct gctgcaagaa atggggcatg agctggtcat ccataccgtc gtcaccggcg   11220
gccaggctct cctggacacg gtgagcggct cgcccagct cgccagccag ttccggccg    11280
aagcgctttt cgtggtctgg ctgaacccgt attgggggcc tatcgagcat gagggcaaga   11340
gctttgagca gatgaaggcg tacacggcca acaaggcccg cgtgtcgtcc atcatccaga   11400
ttccggccct caaggaagaa acctacggcc gcgatttcag cgacatgctg caagagcggc   11460
tgacgttcga ccaggcgctg gccgatgaat cgctcacgat catgacgcgg caacgcctca   11520
agatcgtgcg gcgcggcctg tttgaacagc tcgacgcggc ggccgtgcta tgagcgacca   11580
gattgaagag ctgatccggg agattgcggc caagacggc atcgccgtcg gccgcgacga    11640
cccggtgctg atcctgcata ccatcaacgc ccggctcatg gccgacagtg cggccaagca   11700
agaggaaatc cttgccgcgt tcaaggaaga gctggaaggg atcgcccatc gttggggcga   11760
ggacgccaag gccaaagcgg agcggatgct gaacgcggcc ctggcggcca gcaaggacgc   11820
aatggcgaag gtaatgaagg acagcgccgc gcaggcggcc gaagcgatcc gcagggaaat   11880
cgacgacggc cttggccgcc agctcgcggc caaggtcgcg gacgcgcggc gcgtggcgat   11940
gatgaacatg atcgccggcg gcatggtgtt gttcgcggcc gccctggtgg tgtgggcctc   12000
gttatgaatc gcagaggcgc agatgaaaaa gcccggcgtt gccgggcttt gttttttgcgt   12060
tagctgggct tgtttgacag gcccaagctc tgactgcgcc cgcgctcgcg ctcctgggcc   12120
tgtttcttct cctgctcctg cttgcgcatc agggcctggt gccgtcgggc tgcttcacgc   12180
atcgaatccc agtcgccggc cagctcggga tgctccgcgc gcatcttgcg cgtcgccagt   12240
tcctcgatct tgggcgcgtg aatgcccatg ccttccttga tttcgcgcac catgtccagc   12300
cgcgtgtgca gggtctgcaa gcgggcttgc tgtttgggcct gctgctgctg ccaggcggcc   12360
tttgtacgcg gcagggacag caagccgggg gcattggact gtagctgctg caaacgcgcc   12420
tgctgacggt ctacgagctg ttctaggcgg tcctcgatgc gctccacctg gtcatgcttt   12480
gcctgcacgt agagcgcaag ggtctgctgg taggtctgct cgatgggcgc ggattctaag   12540
agggcctgct gttccgtctc ggcctcctgg gccgcctgta gcaaatcctc gccgctgttg   12600
ccgctggact gctttactgc cggggactgc tgttgccctg ctcgcgccgt cgtcgcagtt   12660
cggcttgccc ccactcgatt gactgcttca tttcgagccg cagcgatgcg atctcggatt   12720
gcgtcaacgg acggggcagc gcggaggtgt ccggcttctc cttgggtgag tcggtcgatg   12780
ccatagccaa aggtttcctt ccaaaatgcg tccattgctg gaccgtgttt ctcattgatg   12840
cccgcaagca tcttcggctt gaccgccagg tcaagcgcgc cttcatgggc ggtcatgacg   12900
gacgccgcca tgaccttgcc gccgttgttc tcgatgtagc cgcgtaatga ggcaatggtg   12960
ccgcccatcg tcagcgtgtc atcgacaacg atgtacttct ggccggggat cacctccccc   13020
tcgaaagtcg ggttgaacgc caggcgatga tctgaaccgg ctccggttcg ggcgaccttc   13080
tcccgctgca caatgtccgt ttcgacctca aggccaaggc ggtcggccag aacgaccgcc   13140
atcatggccg gaatcttgtt gttccccgcc gcctcgacgg cgaggactgg aacgatgcgg   13200
ggcttgtcgt cgccgatcag cgtcttgagc tgggcaacag tgtcgtccga aatcaggcgc   13260
tcgaccaaat taagcgccgc ttccgcgtcg ccctgcttcg cagcctggta ttcaggctcg   13320
```

```
ttggtcaaag aaccaaggtc gccgttgcga accaccttcg ggaagtctcc ccacggtgcg   13380
cgctcggctc tgctgtagct gctcaagacg cctcccttt  tagccgctaa aactctaacg   13440
agtgcgcccg cgactcaact tgacgctttc ggcacttacc tgtgccttgc cacttgcgtc   13500
ataggtgatg cttttcgcac tcccgatttc aggtacttta tcgaaatctg accgggcgtg   13560
cattacaaag ttcttcccca cctgttggta aatgctgccg ctatctgcgt ggacgatgct   13620
gccgtcgtgg cgctgcgact tatcggcctt ttgggccata tagatgttgt aaatgccagg   13680
tttcagggcc ccggctttat ctaccttctg gttcgtccat gcgccttggt tctcggtctg   13740
gacaattctt tgcccattca tgaccaggag gcggtgtttc attgggtgac tcctgacggt   13800
tgcctctggt gttaaacgtg tcctggtcgc ttgccggcta aaaaaaagcc gacctcggca   13860
gttcgaggcc ggctttccct agagccgggc gcgtcaaggt tgttccatct attttagtga   13920
actgcgttcg atttatcagt tactttcctc ccgctttgtg tttcctccca ctcgtttccg   13980
cgtctagccg accccctcaac atagcggcct cttcttgggc tgcctttgcc tcttgccgcg   14040
cttcgtcacg ctcggcttgc accgtcgtaa agcgctcggc ctgcctggcc gcctcttgcg   14100
ccgccaactt cctttgctcc tggtgggcct cggcgtcggc ctgcgccttc gctttcaccg   14160
ctgccaactc cgtgcgcaaa ctctccgctt cgcgcctggt ggcgtcgcgc tcgccgcgaa   14220
gcgcctgcat ttcctggttg gccgcgtcca gggtcttgcg gctctcttct ttgaatgcgc   14280
gggcgtcctg gtgagcgtag tccagctcgg cgcgcagctc ctgcgctcga cgctccacct   14340
cgtcggcccg ctgcgtcgcc agcgcggcc  gctgctcggc tcctgccagg gcggtgcgtg   14400
cttcggccag ggcttgccgc tggcgtgcgg ccagctcggc cgcctcggcg gcctgctgct   14460
ctagcaatgt aacgcgcgcc tgggcttctt ccagctcgcg ggcctgcgcc tcgaaggcgt   14520
cggccagctc cccgcgcacg gcttccaact cgttgcgctc acgatcccag ccggcttgcg   14580
ctgcctgcaa cgattcattg gcaagggcct gggcggcttg ccagagggcg gccacggcct   14640
ggttgccggc ctgctgcacc gcgtccggca cctggactgc cagcggggcg gcctgcgccg   14700
tgcgctggcg tcgccattcg cgcatgccgg cgctggcgtc gttcatgttg acgcgggcgg   14760
ccttacgcac tgcatccacg gtcgggaagt tctcccggtc gccttgctcg aacagctcgt   14820
ccgcagccgc aaaaatgcgg tcgcgcgtct ctttgttcag ttccatgttg gctccggtaa   14880
ttggtaagaa taataatact cttacctacc ttatcagcgc aagagtttag ctgaacagtt   14940
ctcgacttaa cggcaggttt tttagcggct gaagggcagg caaaaaaagc cccgcacggt   15000
cggcggggc  aaagggtcag cgggaagggg attagcgggc gtcgggcttc ttcatgcgtc   15060
ggggccgcgc ttcttgggat ggagcacgac gaagcgcgca cgcgcatcgt cctcggccct   15120
atcggccgc  gtcgcggtca ggaacttgtc gcgcgctagg tcctccctgg tgggcaccag   15180
gggcatgaac tcggcctgct cgatgtaggt ccactccatg accgcatcgc agtcgaggcc   15240
gcgttccttc accgtctctt gcaggtcgcg gtacgcccgc tcgttgagcg gctggtaacg   15300
ggccaattgg tcgtaaatgg ctgtcggcca tgagcggcct ttcctgttga gccagcagcc   15360
gacgacgaag ccggcaatgc aggccccctgg cacaaccagg ccgacgccgg ggcaggggga   15420
tggcagcagc tcgccaacca ggaacccgc  cgcgatgatg ccgatgccgg tcaaccagcc   15480
cttgaaacta tccggccccg aaacacccct gcgcattgcc tggatgctgc gccggatagc   15540
ttgcaacatc aggagccgtt tcttttgttc gtcagtcatg gtccgccctc accagttgtt   15600
cgtatcggtg tcggacgaac tgaaatcgca agagctgccg gtatcggtcc agccgctgtc   15660
```

```
cgtgtcgctg ctgccgaagc acggcgaggg gtccgcgaac gccgcagacg gcgtatccgg   15720
ccgcagcgca tcgcccagca tggcccggt cagcgagccg ccggccaggt agcccagcat   15780
ggtgctgttg gtcgccccgg ccaccagggc cgacgtgacg aaatcgccgt cattccctct   15840
ggattgttcg ctgctcggcg gggcagtgcg ccgcgccggc ggcgtcgtgg atggctcggg   15900
ttggctggcc tgcgacggcc ggcgaaaggt gcgcagcagc tcgttatcga ccggctgcgg   15960
cgtcggggcc gccgccttgc gctgcggtcg gtgttccttc ttcggctcgc gcagcttgaa   16020
cagcatgatc gcggaaacca gcagcaacgc cgcgcctacg cctcccgcga tgtagaacag   16080
catcggattc attcttcggt cctccttgta gcggaaccgt tgtctgtgcg gcgcgggtgg   16140
cccgcgccgc tgtctttggg gatcagccct cgatgagcgc gaccagtttc acgtcggcaa   16200
ggttcgcctc gaactcctgg ccgtcgtcct cgtacttcaa ccaggcatag ccttccgccg   16260
gcggccgacg gttgaggata aggcgggcag ggcgctcgtc gtgctcgacc tggacgatgg   16320
cctttttcag cttgtccggg tccggctcct tcgcgccctt ttccttggcg tccttaccgt   16380
cctggtcgcc gtcctcgccg tcctggccgt cgccggcctc cgcgtcacgc tcggcatcag   16440
tctggccgtt gaaggcatcg acggtgttgg gatcgcggcc cttctcgtcc aggaactcgc   16500
gcagcagctt gaccgtgccg cgcgtgattt cctgggtgtc gtcgtcaagc cacgcctcga   16560
cttcctccgg gcgcttcttg aaggccgtca ccagctcgtt caccacggtc acgtcgcgca   16620
cgcggccggt gttgaacgca tcggcgatct tctccggcag gtccagcagc gtgacgtgct   16680
gggtgatgaa cgccggcgac ttgccgattt ccttggcgat atcgcctttc ttcttgccct   16740
tcgccagctc gcggccaatg aagtcggcaa tttcgcgcgg ggtcagctcg ttgcgttgca   16800
ggttctcgat aacctggtcg gcttcgttgt agtcgttgtc gatgaacgcc gggatggact   16860
tcttgccggc ccactcgag ccacggtagc ggcgggcgcc gtgattgatg atatagcggc   16920
ccggctgctc ctggttctcg cgcaccgaaa tgggtgactt caccccgcgc tctttgatcg   16980
tggcaccgat ttccgcgatg ctctccgggg aaaagccggg gttgtcggcc gtccgcggct   17040
gatgcggatc ttcgtcgatc aggtccaggt ccagctcgat agggccggaa ccgccctgag   17100
acgccgcagg agcgtccagg aggctcgaca ggtcgccgat gctatccaac cccaggccgg   17160
acggctgcgc cgcgcctgcg gcttcctgag cggccgcagc ggtgtttttc ttggtggtct   17220
tggcttgagc cgcagtcatt gggaaatctc catcttcgtg aacacgtaat cagccagggc   17280
gcgaacctct ttcgatgcct tgcgcgcggc cgttttcttg atcttccaga ccggcacacc   17340
ggatgcgagg gcatcggcga tgctgctgcg caggccaacg gtggccggaa tcatcatctt   17400
ggggtacgcg gccagcagct cggcttggtg gcgcgcgtgg cgcggattcc gcgcatcgac   17460
cttgctgggc accatgccaa ggaattgcag cttggcgttc ttctggcgca cgttcgcaat   17520
ggtcgtgacc atcttcttga tgccctggat gctgtacgcc tcaagctcga tgggggacag   17580
cacatagtcg gccgcgaaga gggcggccgc caggccgacg ccaagggtcg gggccgtgtc   17640
gatcaggcac acgtcgaagc cttggttcgc cagggccttg atgttcgccc cgaacagctc   17700
gcgggcgtcg tccagcgaca gccgttcggc gttcgccagt accgggttgg actcgatgag   17760
ggcgaggcgc gcggcctggc cgtcgccggc tgcgggtgcg gtttcggtcc agccgccggc   17820
agggacagcg ccgaacagct tgcttgcatg caggccggta gcaaagtcct tgagcgtgta   17880
ggacgcattg ccctgggggt ccaggtcgat cacggcaacc cgcaagccgc gctcgaaaaa   17940
gtcgaaggca agatgcacaa gggtcgaagt cttgccgacg ccgcctttct ggttggccgt   18000
gaccaaagtt ttcatcgttt ggtttcctgt tttttcttgg cgtccgcttc ccacttccgg   18060
```

```
acgatgtacg cctgatgttc cggcagaacc gccgttaccc gcgcgtaccc ctcgggcaag   18120
ttcttgtcct cgaacgcggc ccacacgcga tgcaccgctt cgacactgc gccctggtc    18180 agtcccagcg acgttgcgaa cgtcgcctgt ggcttcccat cgactaagac gccccgcgct   18240
atctcgatgg tctgctgccc cacttccagc ccctggatcg cctcctggaa ctggctttcg   18300
gtaagccgtt tcttcatgga taacacccat aatttgctcc gcgccttggt tgaacatagc   18360
ggtgacagcc gccagcacat gagagaagtt tagctaaaca tttctcgcac gtcaacacct   18420
ttagccgcta aaactcgtcc ttggcgtaac aaaacaaaag cccggaaacc gggctttcgt   18480
ctcttgccgc ttatggctct gcacccggct ccatcaccaa caggtcgcgc acgcgcttca   18540
ctcggttgcg gatcgacact gccagcccaa caaagccggt tgccgccgcc gccaggatcg   18600
cgccgatgat gccggccaca ccggccatcg cccaccaggt cgccgccttc cggttccatt   18660
cctgctggta ctgcttcgca atgctggacc tcggctcacc ataggctgac cgctcgatgg   18720
cgtatgccgc ttctccccctt ggcgtaaaac ccagcgccgc aggcggcatt gccatgctgc   18780
ccgccgcttt cccgaccacg acgcgcgcac caggcttgcg gtccagacct tcggccacgg   18840
cgagctgcgc aaggacataa tcagccgccg acttggctcc acgcgcctcg atcagctctt   18900
gcactcgcgc gaaatccttg gcctccacgg ccgccatgaa tcgcgcacgc ggcgaaggct   18960
ccgcagggcc ggcgtcgtga tcgccgccga gaatgcccctt caccaagttc gacgacacga   19020
aaatcatgct gacggctatc accatcatgc agacggatcg cacgaacccg ctgaattgaa   19080
cacgagcacg gcaccgcga ccactatgcc aagaatgccc aaggtaaaaa ttgccggccc   19140
cgccatgaag tccgtgaatg ccccgacggc cgaagtgaag ggcaggccgc cacccaggcc   19200
gccgccctca ctgcccggca cctggtcgct gaatgtcgat gccagcacct gcggcacgtc   19260
aatgcttccg ggcgtcgcgc tcgggctgat cgcccatccc gttactgccc cgatcccggc   19320
aatggcaagg actgccagcg ctgccatttt tggggtgagg ccgttcgcgg ccgaggggcg   19380
cagcccctgg ggggatggga ggcccgcgtt agcgggccgg gagggttcga aaggggggg    19440 cacccccctt cggcgtgcgc ggtcacgcgc acagggcgca gccctggtta aaaacaaggt   19500
ttataaatat tggtttaaaa gcaggttaaa agacaggtta gcggtggccg aaaaacgggc   19560
ggaaacccct gcaaatgctg gattttctgc ctgtggacag ccctcaaat gtcaataggt    19620 gcgcccctca tctgtcagca ctctgcccct caagtgtcaa ggatcgcgcc cctcatctgt   19680
cagtagtcgc gccctcaag tgtcaatacc gcagggcact tatccccagg cttgtccaca    19740
tcatctgtgg gaaactcgcg taaaatcagg cgttttcgcc gatttgcgag gctggccagc   19800
tccacgtcgc cggccgaaat cgagcctgcc cctcatctgt caacgccgcg ccgggtgagt   19860
cggcccctca agtgtcaacg tccgccctc atctgtcagt gagggccaag ttttccgcga    19920
ggtatccaca acgccggcgg ccgcggtgtc tcgcacacgg cttcgacggc gtttctggcg   19980
cgtttgcagg gccatagacg gccgccagcc cagcggcgag ggcaaccagc ccggtgagcg   20040
tcggaaaggc gctggaagcc ccgtagcgac gcggagaggg gcgagacaag ccaagggcgc   20100
aggctcgatg cgcagcacga catagccggt tctcgcaagg acgagaattt ccctgcggtg   20160
cccctcaagt gtcaatgaaa gtttccaacg cgagccattc gcgagagcct tgagtccacg   20220
ctagatgaga gctttgttgt aggtggacca gttggtgatt ttgaactttt gctttgccac   20280
ggaacggtct gcgttgtcgg gaagatgcgt gatctgatcc ttcaactcag caaaagttcg   20340
atttattcaa caaagccacg ttgtgtctca aaatctctga tgttacattg cacaagataa   20400
```

```
aaatatatca tcatgaacaa taaaactgtc tgcttacata aacagtaata caaggggtgt   20460
tatgagccat attcaacggg aaacgtcttg ctcgactcta gagctcgttc ctcgaggcct   20520
cgaggcctcg aggaacggta cctgcgggga agcttacaat aatgtgtgtt gttaagtctt   20580
gttgcctgtc atcgtctgac tgactttcgt cataaatccc ggcctccgta acccagcttt   20640
gggcaagctc acggatttga tccggcggaa cgggaatatc gagatgccgg gctgaacgct   20700
gcagttccag cttccccttt cgggacaggt actccagctg attgattatc tgctgaaggg   20760
tcttggttcc acctcctggc acaatgcgaa tgattacttg agcgcgatcg ggcatccaat   20820
tttctcccgt caggtgcgtg gtcaagtgct acaaggcacc tttcagtaac gagcgaccgt   20880
cgatccgtcg ccgggatacg gacaaaatgg agcgcagtag tccatcgagg gcggcgaaag   20940
cctcgccaaa agcaatacgt tcatctcgca cagcctccag atccgatcga gggtcttcgg   21000
cgtaggcaga tagaagcatg gatacattgc ttgagagtat tccgatggac tgaagtatgg   21060
cttccatctt ttctcgtgtg tctgcatcta tttcgagaaa gccccgatg cggcgcaccg   21120
caacgcgaat tgccatacta tccgaaagtc ccagcaggcg cgcttgatag gaaaaggttt   21180
catactcggc cgatcgcaga cgggcactca cgaccttgaa cccttcaact ttcagggatc   21240
gatgctggtt gatggtagtc tcactcgacg tggctctggt gtgttttgac atagcttcct   21300
ccaaagaaag cggaaggtct ggatactcca gcacgaaatg tgcccgggta cggatgga    21360
agtctagccc tgctcaatat gaaatcaaca gtacatttac agtcaatact gaatatactt   21420
gctacatttg caattgtctt ataacgaatg tgaaataaaa atagtgtaac aacgctttta   21480
ctcatcgata atcacaaaaa catttatacg aacaaaaata caaatgcact ccggtttcac   21540
aggataggcg ggatcagaat atgcaacttt tgacgttttg ttctttcaaa gggggtgctg   21600
gcaaaaccac cgcactcatg ggcctttgcg ctgctttggc aaatgacggt aaacgagtgg   21660
ccctctttga tgccgacgaa aaccggcctc tgacgcgatg gagagaaaac gccttacaaa   21720
gcagtactgg gatcctcgct gtgaagtcta ttccgccgac gaaatgcccc ttcttgaagc   21780
agcctatgaa aatgccgagc tcgaaggatt tgattatgcg ttggccgata cgcgtggcgg   21840
ctcgagcgag ctcaacaaca caatcatcgc tagctcaaac ctgcttctga tccccaccat   21900
gctaacgccg ctcgacatcg atgaggcact atctacctac cgctacgtca tcgagctgct   21960
gttgagtgaa aatttggcaa ttcctacagc tgttttgcgc caacgcgtcc cggtcggccg   22020
attgacaaca tcgcaacgca ggatgtcaga gacgctagag agccttccag ttgtaccgtc   22080
tcccatgcat gaaagagatg catttgccgc gatgaaagaa cgcggcatgt tgcatcttac   22140
attactaaac acgggaactg atccgacgat gcgcctcata gagaggaatc ttcggattgc   22200
gatggaggaa gtcgtggtca tttcgaaact gatcagcaaa atcttggagg cttgaagatg   22260
gcaattcgca agcccgcatt gtcggtcggc gaagcacggc ggcttgctgg tgctcgaccc   22320
gagatccacc atcccaaccc gacacttgtt ccccagaagc tggacctcca gcacttgcct   22380
gaaaaagccg acgagaaaga ccagcaacgt gagcctctcg tcgccgatca catttacagt   22440
cccgatcgac aacttaagct aactgtggat gcccttagtc cacctccgtc cccgaaaaag   22500
ctccaggttt ttctttcagc gcgaccgccc gcgcctcaag tgtcgaaaac atatgacaac   22560
ctcgttcggc aatacagtcc ctcgaagtcg ctacaaatga ttttaaggcg cgcgttggac   22620
gatttcgaaa gcatgctggc agatggatca tttcgcgtgg ccccgaaaag ttatccgatc   22680
ccttcaacta cagaaaaatc cgttctcgtt cagacctcac gcatgttccc ggttgcgttg   22740
ctcgaggtcg ctcgaagtca ttttgatccg ttggggttgg agaccgctcg agctttcggc   22800
```

```
cacaagctgg ctaccgccgc gctcgcgtca ttctttgctg gagagaagcc atcgagcaat   22860
tggtgaagag ggacctatcg gaacccctca ccaaatattg agtgtaggtt tgaggccgct   22920
ggccgcgtcc tcagtcacct tttgagccag ataattaaga gccaaatgca attggctcag   22980
gctgccatcg tcccccgtg cgaaacctgc acgtccgcgt caaagaaata accggcacct    23040
cttgctgttt ttatcagttg agggcttgac ggatccgcct caagtttgcg gcgcagccgc   23100
aaaatgagaa catctatact cctgtcgtaa acctcctcgt cgcgtactcg actggcaatg   23160
agaagttgct cgcgcgatag aacgtcgcgg ggtttctcta aaaacgcgag gagaagattg   23220
aactcacctg ccgtaagttt cacctcaccg ccagcttcgg acatcaagcg acgttgcctg   23280
agattaagtg tccagtcagt aaaacaaaaa gaccgtcggt ctttggagcg gacaacgttg   23340
gggcgcacgc gcaaggcaac ccgaatgcgt gcaagaaact ctctcgtact aaacggctta   23400
gcgataaaat cacttgctcc tagctcgagt gcaacaactt tatccgtctc ctcaaggcgg   23460
tcgccactga taattatgat tggaatatca gactttgccg ccagatttcg aacgatctca   23520
agcccatctt cacgacctaa atttagatca acaaccacga catcgaccgt cgcggaagag   23580
agtactctag tgaactgggt gctgtcggct accgcggtca cttttgaaggc gtggatcgta   23640 aggtattcga taataagatg ccgcatagcg acatcgtcat cgataagaag aacgtgtttc   23700
aacggctcac ctttcaatct aaaatctgaa cccttgttca cagcgcttga gaaattttca   23760
cgtgaaggat gtacaatcat ctccagctaa atgggcagtt cgtcagaatt gcggctgacc   23820
gcggatgacg aaaatgcgaa ccaagtattt caattttatg acaaaagttc tcaatcgttg   23880
ttacaagtga aacgcttcga ggttacagct actattgatt aaggagatcg cctatggtct   23940
cgccccggcg tcgtgcgtcc gccgcgagcc agatctcgcc tacttcataa acgtcctcat   24000
aggcacggaa tggaatgatg acatcgatcg ccgtagagag catgtcaatc agtgtgcgat   24060
cttccaagct agcaccttgg gcgctacttt tgacaaggga aaacagtttc ttgaatcctt   24120
ggattggatt cgcgccgtgt attgttgaaa tcgatcccgg atgtcccgag acgacttcac   24180
tcagataagc ccatgctgca tcgtcgcgca tctcgccaag caatatccgg tccggccgca   24240
tacgcagact tgcttggagc aagtgctcgg cgctcacagc acccagccca gcaccgttct   24300
tggagtagag tagtctaaca tgattatcgt gtggaatgac gagttcgagc gtatcttcta   24360
tggtgattag ccttttcctgg ggggggatgg cgctgatcaa ggtcttgctc attgttgtct   24420
tgccgcttcc ggtagggcca catagcaaca tcgtcagtcg gctgacgacg catgcgtgca   24480
gaaacgcttc caaatccccg ttgtcaaaat gctgaaggat agcttcatca tcctgatttt   24540
ggcgtttcct tcgtgtctgc cactggttcc acctcgaagc atcataacgg gaggagactt   24600
ctttaagacc agaaacacgc gagccttgcc gtcgaatggt caagctgacg gtgcccgagg   24660
gaacggtcgg cggcagacag atttgtagtc gttcaccacc aggaagttca gtggcgcaga   24720
gggggttacg tggtccgaca tcctgctttc tcagcgcgcc cgctaaaata gcgatatctt   24780
caagatcatc ataagagacg ggcaaaggca tcttggtaaa aatgccggct tggcgcacaa   24840
atgcctctcc aggtcgattg atcgcaattt cttcagtctt cgggtcatcg agccattcca   24900
aaatcggctt cagaagaaag cgtagttgcg gatccacttc catttacaat gtatcctatc   24960
tctaagcgga aatttgaatt cattaagagc ggcggttcct ccccgcgtg gcgccgccag   25020 tcaggcggag ctggtaaaca ccaaagaaat cgaggtcccg tgctacgaaa atggaaacgg   25080
tgtcaccctg attcttcttc agggttggcg gtatgttgat ggttgcctta agggctgtct   25140
```

```
cagttgtctg ctcaccgtta tttttgaaagc tgttgaagct catcccgcca cccgagctgc    25200
cggcgtaggt gctagctgcc tggaaggcgc cttgaacaac actcaagagc atagctccgc    25260
taaaacgctg ccagaagtgg ctgtcgaccg agcccggcaa tcctgagcga ccgagttcgt    25320
ccgcgcttgg cgatgttaac gagatcatcg catggtcagg tgtctcggcg cgatcccaca    25380
acacaaaaac gcgcccatct ccctgttgca agccacgctg tatttcgcca acaacggtgg    25440
tgccacgatc aagaagcacg atattgttcg ttgttccacg aatatcctga ggcaagacac    25500
actttacata gcctgccaaa tttgtgtcga ttgcggtttg caagatgcac ggaattattg    25560
tcccttgcgt taccataaaa tcggggtgcg gcaagagcgt ggcgctgctg ggctgcagct    25620
cggtgggttt catacgtatc gacaaatcgt tctcgccgga cacttcgcca ttcggcaagg    25680
agttgtcgtc acgcttgcct tcttgtcttc ggcccgtgtc gccctgaatg gcgcgtttgc    25740
tgaccccttg atcgccgctg ctatatgcaa aaatcggtgt ttcttccggc cgtggctcat    25800
gccgctccgg ttcgcccctc ggcggtagag gagcagcagg ctgaacagcc tcttgaaccg    25860
ctggaggatc cggcggcacc tcaatcgag ctggatgaaa tggcttggtg tttgttgcga    25920
tcaaagttga cggcgatgcg ttctcattca ccttcttttg gcgcccacct agccaaatga    25980
ggcttaatga taacgcgaga acgacacctc cgacgatcaa tttctgagac cccgaaagac    26040
gccggcgatg tttgtcggag accagggatc cagatgcatc aacctcatgt gccgcttgct    26100
gactatcgtt attcatccct tcgcccccctt caggacgcgt ttcacatcgg gcctcaccgt    26160
gcccgtttgc ggcctttggc caacgggatc gtaagcggtg ttccagatac atagtactgt    26220
gtggccatcc ctcagacgcc aacctcggga aaccgaagaa atctcgacat cgctccctt    26280
aactgaatag ttggcaacag cttccttgcc atcaggattg atggtgtaga tggagggtat    26340
gcgtacattg cccggaaagt ggaataccgt cgtaaatcca ttgtcgaaga cttcgagtgg    26400
caacagcgaa cgatcgcctt gggcgacgta gtgccaatta ctgtccgccg caccaagggc    26460
tgtgacaggc tgatccaata aattctcagc tttccgttga tattgtgctt ccgcgtgtag    26520
tctgtccaca acagccttct gttgtgcctc ccttcgccga gccgccgcat cgtcggcggg    26580
gtaggcgaat tggacgctgt aatagagatc gggctgctct ttatcgaggt gggacagagt    26640
cttgaacttt atactgaaaa cataacggcg catcccggag tcgcttgcgg ttagcacgat    26700
tactggctga ggcgtgagga cctggcttgc cttgaaaaat agataatttc cccgcggtag    26760
ggctgctaga tctttgctat ttgaaacggc aaccgctgtc accgtttcgt tcgtggcgaa    26820
tgttacgacc aaagtagctc caaccgccgt cgagaggcgc accacttgat cgggattgta    26880
agccaaataa cgcatgcgcg gatctagctt gcccgccatt ggagtgtctt cagcctccgc    26940
accagtcgca gcgcaaata aacatgctaa aatgaaaagt gcttttctga tcatggttcg    27000
ctgtggccta cgtttgaaac ggtatcttcc gatgtctgat aggaggtgac aaccagacct    27060
gccgggttgg ttagtctcaa tctgccgggc aagctggtca cctttcgta gcgaactgtc    27120
gcggtccacg tactcaccac aggcattttg ccgtcaacga cgagggtcct tttatagcga    27180
atttgctgcg tgcttggagt tacatcattt gaagcgatgt gctcgacctc caccctgccg    27240
cgtttgccaa gaatgacttg aggcgaactg ggattgggat agttgaagaa ttgctggtaa    27300
tcctggcgca ctgttggggc actgaagttc gataccaggt cgtaggcgta ctgagcggtg    27360
tcggcatcat aactctcgcg caggcgaacg tactcccaca atgaggcgtt aacgacggcc    27420
tcctcttgag ttgcaggcaa tcgcgagaca gacacctcgc tgtcaacggt gccgtccggc    27480
cgtatccata gatatacggg cacaagcctg ctcaacggca ccattgtggc tatagcgaac    27540
```

```
gcttgagcaa catttcccaa aatcgcgata gctgcgacag ctgcaatgag tttggagaga    27600
cgtcgcgccg atttcgctcg cgcggtttga aaggcttcta cttccttata gtgctcggca    27660
aggctttcgc gcgccactag catggcatat tcaggccccg tcatagcgtc cacccgaatt    27720
gccgagctga agatctgacg gagtaggctg ccatcgcccc acattcagcg ggaagatcgg    27780
gcctttgcag ctcgctaatg tgtcgtttgt ctggcagccg ctcaaagcga caactaggca    27840
cagcaggcaa tacttcatag aattctccat tgaggcgaat ttttgcgcga cctagcctcg    27900
ctcaacctga gcgaagcgac ggtacaagct gctggcagat tgggttgcgc cgctccagta    27960
actgcctcca atgttgccgg cgatcgccgg caaagcgaca atgagcgcat cccctgtcag    28020
aaaaaacata tcgagttcgt aaagaccaat gatcttggcc gcggtcgtac cggcgaaggt    28080
gattacacca agcataaggg tgagcgcagt cgcttcggtt aggatgacga tcgttgccac    28140
gaggtttaag aggagaagca agagaccgta ggtgataagt tgcccgatcc acttagctgc    28200
gatgtcccgc gtgcgatcaa aaatatatcc gacgaggatc agaggcccga tcgcgagaag    28260
cactttcgtg agaattccaa cggcgtcgta aactccgaag gcagaccaga gcgtgccgta    28320
aaggacccac tgtgccccctt ggaaagcaag gatgtcctgg tcgttcatcg gaccgatttc    28380
ggatgcgatt ttctgaaaaa cggcctgggt cacggcgaac attgtatcca actgtgccgg    28440
aacagtctgc agaggcaagc cggttacact aaactgctga acaaagtttg ggaccgtctt    28500
ttcgaagatg gaaaccacat agtcttggta gttagcctgc ccaacaatta gagcaacaac    28560
gatggtgacc gtgatcaccc gagtgatacc gctacgggta tcgacttcgc cgcgtatgac    28620
taaaataccc tgaacaataa tccaaagagt gacacaggcg atcaatggcg cactcaccgc    28680
ctcctggata gtctcaagca tcgagtccaa gcctgtcgtg aaggctacat cgaagatcgt    28740
atgaatggcc gtaaacggcg ccggaatcgt gaaattcatc gattggacct gaacttgact    28800
ggtttgtcgc ataatgttgg ataaaatgag ctcgcattcg gcgaggatgc gggcggatga    28860
acaaatcgcc cagccttagg ggagggcacc aaagatgaca gcggtctttt gatgctcctt    28920
gcgttgagcg gccgcctctt ccgcctcgtg aaggccggcc tgcgcggtag tcatcgttaa    28980
taggcttgtc gcctgtacat tttgaatcat tgcgtcatgg atctgcttga gaagcaaacc    29040
attggtcacg gttgcctgca tgatattgcg agatcgggaa agctgagcag acgtatcagc    29100
attcgccgtc aagcgtttgt ccatcgtttc cagattgtca gccgcaatgc cagcgctgtt    29160
tgcggaaccg gtgatctgcg atcgcaacag gtccgcttca gcatcactac ccacgactgc    29220
acgatctgta tcgctggtga tcgcacgtgc cgtggtcgac attggcattc gcggcgaaaa    29280
catttcattg tctaggtcct tcgtcgaagg atactgattt ttctggttga gcgaagtcag    29340
tagtccagta acgccgtagg ccgacgtcaa catcgtaacc atcgctatag tctgagtgag    29400
attctccgca gtcgcgagcg cagtcgcgag cgtctcagcc tccgttgccg ggtcgctaac    29460
aacaaactgc gcccgcgcgg gctgaatata tagaaagctg caggtcaaaa ctgttgcaat    29520
aagttgcgtc gtcttcatcg tttcctacct tatcaatctt ctgcctcgtg gtgacgggcc    29580
atgaattcgc tgagccagcc agatgagttg ccttcttgtg cctcgcgtag tcgagttgca    29640
aagcgcaccg tgttggcacg ccccgaaagc acggcgacat attcacgcat atcccgcaga    29700
tcaaattcgc agatgacgct tccactttct cgtttaagaa gaaacttacg gctgccgacc    29760
gtcatgtctt cacggatcgc ctgaaattcc ttttcggtac atttcagtcc atcgacataa    29820
gccgatcgat ctgcggttgg tgatggatag aaaatcttcg tcatacattg cgcaaccaag    29880
```

```
ctggctccta gcggcgattc cagaacatgc tctggttgct gcgttgccag tattagcatc    29940
ccgttgtttt ttcgaacggt caggaggaat ttgtcgacga cagtcgaaaa tttagggttt    30000
aacaaatagg cgcgaaactc atcgcagctc atcacaaaac ggcggccgtc gatcatggct    30060
ccaatccgat gcaggagata tgctgcagcg ggagcgcata cttcctcgta ttcgagaaga    30120
tgcgtcatgt cgaagccggt aatcgacgga tctaacttta cttcgtcaac ttcgccgtca    30180
aatgcccagc caagcgcatg gccccggcac cagcgttgga gccgcgctcc tgcgccttcg    30240
gcgggcccat gcaacaaaaa ttcacgtaac cccgcgattg aacgcatttg tggatcaaac    30300
gagagctgac gatggatacc acggaccaga cggcggttct cttccggaga atcccaccc    30360
cgaccatcac tctcgatgag agccacgatc cattcgcgca gaaaatcgtg tgaggctgct    30420
gtgttttcta ggccacgcaa cggcgccaac ccgctgggtg tgcctctgtg aagtgccaaa    30480
tatgttcctc ctgtggcgcg aaccagcaat tcgccacccc ggtccttgtc aaagaacacg    30540
accgtacctg cacggtcgac catgctctgt tcgagcatgg ctagaacaaa catcatgagc    30600
gtcgtcttac ccctcccgat aggcccgaat attgccgtca tgccaacatc gtgctcatgc    30660
gggatatagt cgaaaggcgt tccgccattg gtacgaaatc gggcaatcgc gttgccccag    30720
tggcctgagc tggcgccctc tggaaagttt tcgaaagaga caaaccctgc gaaattgcgt    30780
gaagtgattg cgccagggcg tgtgcgccac ttaaaattcc ccggcaattg ggaccaatag    30840
gccgcttcca taccaatacc ttcttggaca accacggcac ctgcatccgc cattcgtgtc    30900
cgagcccgcg cgcccctgtc cccaagacta ttgagatcgt ctgcatagac gcaaaggctc    30960
aaatgatgtg agcccataac gaattcgttg ctcgcaagtg cgtcctcagc ctcggataat    31020
ttgccgattt gagtcacggc tttatcgccg gaactcagca tctggctcga tttgaggcta    31080
agtttcgcgt gcgcttgcgg gcgagtcagg aacgaaaaac tctgcgtgag aacaagtgga    31140
aaatcgaggg atagcagcgc gttgagcatg cccggccgtg ttttgcagg gtattcgcga    31200
aacgaataga tggatccaac gtaactgtct tttggcgttc tgatctcgag tcctcgcttg    31260
ccgcaaatga ctctgtcggt ataaatcgaa gcgccgagtg agccgctgac gaccggaacc    31320
ggtgtgaacc gaccagtcat gatcaaccgt agcgcttcgc caatttcggt gaagagcaca    31380
ccctgcttct cgcggatgcc aagacgatgc aggccatacg ctttaagaga gccagcgaca    31440
acatgccaaa gatcttccat gttcctgatc tggcccgtga gatcgttttc cctttttccg    31500
cttagcttgg tgaacctcct ctttaccttc cctaaagccg cctgtgggta gacaatcaac    31560
gtaaggaagt gttcattgcg gaggagttgg ccggagagca cgcgctgttc aaaagcttcg    31620
ttcaggctag cggcgaaaac actacggaag tgtcgcggcg ccgatgatgg cacgtcggca    31680
tgacgtacga ggtgagcata tattgacaca tgatcatcag cgatattgcg caacagcgtg    31740
ttgaacgcac gacaacgcgc attgcgcatt tcagtttcct caagctcgaa tgcaacgcca    31800
tcaattctcg caatggtcat gatcgatccg tcttcaagaa ggacgatatg gtcgctgagg    31860
tggccaatat aagggagata gatctcaccg gatctttcgg tcgttccact cgcgccgagc    31920
atcacaccat tcctctccct cgtggggaa ccctaattgg atttgggcta acagtagcgc    31980
cccccccaaac tgcactatca atgcttcttc ccgcggtccg caaaaatagc aggacgacgc    32040
tcgccgcatt gtagtctcgc tccacgatga gccgggctgc aaaccataac ggcacgagaa    32100
cgacttcgta gagcgggttc tgaacgataa cgatgacaaa gccggcgaac atcatgaata    32160
accctgccaa tgtcagtggc accccaagaa acaatgcggg ccgtgtggct gcgaggtaaa    32220
gggtcgattc ttccaaaacga tcagccatca actaccgcca gtgagcgttt ggccgaggaa    32280
```

```
gctcgcccca aacatgataa caatgccgcc gacgacgccg gcaaccagcc caagcgaagc   32340
ccgcccgaac atccaggaga tcccgatagc gacaatgccg agaacagcga gtgactggcc   32400
gaacggacca aggataaacg tgcatatatt gttaaccatt gtggcggggt cagtgccgcc   32460
acccgcagat tgcgctgcgg cgggtccgga tgaggaaatg ctccatgcaa ttgcaccgca   32520
caagcttggg gcgcagctcg atatcacgcg catcatcgca ttcgagagcg agaggcgatt   32580
tagatgtaaa cggtatctct caaagcatcg catcaatgcg cacctcctta gtataagtcg   32640
aataagactt gattgtcgtc tgcggatttg ccgttgtcct ggtgtggcgg tggcggagcg   32700
attaaaccgc cagcgccatc ctcctgcgag cggcgctgat atgaccccca aacatcccac   32760
gtctcttcgg attttagcgc ctcgtgatcg tcttttggag gctcgattaa cgcgggcacc   32820
agcgattgag cagctgtttc aacttttcgc acgtagccgt ttgcaaaacc gccgatgaaa   32880
ttaccggtgt tgtaagcgga gatcgcccga cgaagcgcaa attgcttctc gtcaatcgtt   32940
tcgccgcctg cataacgact tttcagcatg tttgcagcgg cagataatga tgtgcacgcc   33000
tggagcgcac cgtcaggtgt cagaccgagc atagaaaaat tcgagagtt tatttgcatg    33060 aggccaacat ccagcgaatg ccgtgcatcg agacggtgcc tgacgacttg ggttgcttgg   33120
ctgtgatctt gccagtgaag cgtttcgccg gtcgtgttgt catgaatcgc taaaggatca   33180
aagcgactct ccaccttagc tatcgccgca agcgtagatg tcgcaactga tggggcacac   33240
ttgcgagcaa catggtcaaa ctcagcagat gagagtggcg tggcaaggct cgacgaacag   33300
aaggagacca tcaaggcaag agaaagcgac cccgatctct taagcatacc ttatctcctt   33360
agctcgcaac taacaccgcc tctcccgttg gaagaagtgc gttgttttat gttgaagatt   33420
atcgggaggg tcggttactc gaaaattttc aattgcttct ttatgatttc aattgaagcg   33480
agaaacctcg cccggcgtct tggaacgcaa catggaccga gaaccgcgca tccatgacta   33540
agcaaccgga tcgacctatt caggccgcag ttggtcaggt caggctcaga acgaaaatgc   33600
tcggcgaggt tacgctgtct gtaaacccat tcgatgaacg ggaagcttcc ttccgattgc   33660
tcttggcagg aatattggcc catgcctgct tgcgctttgc aaatgctctt atcgcgttgg   33720
tatcatatgc cttgtccgcc agcagaaacg cactctaagc gattatttgt aaaaatgttt   33780
cggtcatgcg gcggtcatgg gcttgacccg ctgtcagcgc aagacggatc ggtcaaccgt   33840
cggcatcgac aacagcgtga atcttggtgg tcaaaccgcc acgggaacgt cccatacagc   33900
catcgtcttg atcccgctgt ttccgtcgc cgcatgttgg tggacgcgga cacaggaact    33960
gtcaatcatg acgacattct atcgaaagcc ttggaaatca cactcagaat atgatcccag   34020
acgtctgcct cacgccatcg tacaaagcga ttgtagcagg ttgtacagga accgtatcga   34080
tcaggaacgt ctgcccaggg cgggcccgtc cggaagcgcc acaagatgac attgatcacc   34140
cgcgtcaacg cgcggcacgc gacgcggctt atttgggaac aaaggactga acaacagtcc   34200
attcgaaatc ggtgacatca aagcggggac gggttatcag tggcctccaa gtcaagcctc   34260
aatgaatcaa aatcagaccg atttgcaaac ctgatttatg agtgtgcggc ctaaatgatg   34320
aaatcgtcct tctagatcgc ctccgtggtg tagcaacacc tcgcagtatc gccgtgctga   34380
ccttggccag ggaattgact ggcaagggtg cttttcacatg accgctcttt tggccgcgat   34440
agatgatttc gttgctgctt tgggcacgta aaggagaga agtcatatcg gagaaattcc    34500
tcctggcgcg agagcctgct ctatcgcgac ggcatcccac tgtcgggaac agaccggatc   34560
attcacgagg cgaaagtcgt caacacatgc gttataggca tcttcccttg aaggatgatc   34620
```

```
ttgttgctgc aatctggag gtgcggcagc cgcaggcaga tgcgatctca gcgcaacttg    34680
cggcaaaaca tctcactcac ctgaaaacca ctagcgagtc tcgcgatcag acgaaggcct    34740
tttacttaac gacacaatat ccgatgtctg catcacaggc gtcgctatcc cagtcaatac    34800
taaagcggtg caggaactaa agattactga tgacttaggc gtgccacgag gcctgagacg    34860
acgcgcgtag acagtttttt gaaatcatta tcaaagtgat ggcctccgct gaagcctatc    34920
acctctgcgc cggtctgtcg gagagatggg caagcattat tacggtcttc gcgcccgtac    34980
atgcattgga cgattgcagg gtcaatggat ctgagatcat ccagaggatt gccgccctta    35040
ccttccgttt cgagttggag ccagccccta aatgagacga catagtcgac ttgatgtgac    35100
aatgccaaga gagagatttg cttaacccga tttttttgct caagcgtaag cctattgaag    35160
cttgccggca tgacgtccgc gccgaaagaa tatcctacaa gtaaaacatt ctgcacaccg    35220
aaatgcttgg tgtagacatc gattatgtga ccaagatcct tagcagtttc gcttggggac    35280
cgctccgacc agaaatacgg aagtgaactg acgccaatga caggaatccc ttccgtctgc    35340
agataggtac catcgataga tctgctgcct cgcgcgtttc ggtgatgacg gtgaaaacct    35400
ctgacacatg cagctcccgg agacggtcac agcttgtctg taagcggatg ccgggagcag    35460
acaagcccgt cagggcgcgt cagcgggtgt tggcgggtgt cggggcgcag ccatgaccca    35520
gtcacgtagc gatagcggag tgtatactgg cttaactatg cggcatcaga gcagattgta    35580
ctgagagtgc accatatgcg gtgtgaaata ccgcacagat gcgtaaggag aaaataccgc    35640
atcaggcgct cttccgcttc ctcgctcact gactcgctgc gctcggtcgt tcggctgcgg    35700
cgagcggtat cagctcactc aaaggcggta atacggttat ccacagaatc agggggataac    35760
gcaggaaaga acatgtgagc aaaaggccag caaaaggcca ggaaccgtaa aaaggccgcg    35820
ttgctggcgt ttttccatag gctccgcccc cctgacgagc atcacaaaaa tcgacgctca    35880
agtcagaggt ggcgaaaccc gacaggacta taaagatacc aggcgtttcc ccctggaagc    35940
tccctcgtgc gctctcctgt tccgaccctg ccgcttaccg gatacctgtc cgcctttctc    36000
ccttcgggaa gcgtggcgct ttctcatagc tcacgctgta ggtatctcag ttcggtgtag    36060
gtcgttcgct ccaagctggg ctgtgtgcac gaaccccccg ttcagcccga ccgctgcgcc    36120
ttatccggta actatcgtct tgagtccaac ccggtaagac acgacttatc gccactggca    36180
gcagccactg gtaacaggat tagcagagcg aggtatgtag cggtgctac agagttcttg    36240
aagtggtggc ctaactacgg ctacactaga aggacagtat ttggtatctg cgctctgctg    36300
aagccagtta ccttcggaaa aagagttggt agctcttgat ccggcaaaca accaccgct    36360
ggtagcggtg gttttttgt ttgcaagcag cagattacgc gcagaaaaaa aggatctcaa    36420
gaagatcctt tgatctttc tacggggtct gacgctcagt ggaacgaaaa ctcacgttaa    36480
gggattttgg tcatgagatt atcaaaaagg atcttcacct agatcctttt aaattaaaaa    36540
tgaagtttta aatcaatcta agtatatat gagtaaactt ggtctgacag ttaccaatgc    36600
ttaatcagtg aggcacctat ctcagcgatc tgtctatttc gttcatccat agttgcctga    36660
ctccccgtcg tgtagataac tacgatacgg gagggcttac catctggccc cagtgctgca    36720
atgataccgc gagacccacg ctcaccggct ccagatttat cagcaataaa ccagccagcc    36780
ggaagggccg agcgcagaag tggtcctgca actttatccg cctccatcca gtctattaat    36840
tgttgccggg aagctagagt aagtagttcg ccagttaata gtttgcgcaa cgttgttgcc    36900
attgctgcag gggggggggg gggggggac ttccattgtt cattccacgg acaaaaacag    36960
agaaaggaaa cgacagaggc caaaaagcct cgctttcagc acctgtcgtt tcctttcttt    37020
```

```
tcagagggta ttttaaataa aaacattaag ttatgacgaa gaagaacgga aacgccttaa  37080
accggaaaat tttcataaat agcgaaaacc cgcgaggtcg ccgccccgta acctgtcgga  37140
tcaccggaaa ggacccgtaa agtgataatg attatcatct acatatcaca acgtgcgtgg  37200
aggccatcaa accacgtcaa ataatcaatt atgacgcagg tatcgtatta attgatctgc  37260
atcaacttaa cgtaaaaaca acttcagaca atacaaatca gcgacactga atacggggca  37320
acctcatgtc ccccccccccc cccccctgc aggcatcgtg gtgtcacgct cgtcgtttgg  37380
tatggcttca ttcagctccg gttcccaacg atcaaggcga gttacatgat cccccatgtt  37440
gtgcaaaaaa gcggttagct ccttcggtcc tccgatcgtt gtcagaagta agttggccgc  37500
agtgttatca ctcatggtta tggcagcact gcataattct cttactgtca tgccatccgt  37560
aagatgcttt tctgtgactg gtgagtactc aaccaagtca ttctgagaat agtgtatgcg  37620
gcgaccgagt tgctcttgcc cggcgtcaac acgggataat accgcgccac atagcagaac  37680
tttaaaagtg ctcatcattg gaaaacgttc ttcggggcga aaactctcaa ggatcttacc  37740
gctgttgaga tccagttcga tgtaacccac tcgtgcaccc aactgatctt cagcatcttt  37800
tactttcacc agcgtttctg ggtgagcaaa aacaggaagg caaaatgccg caaaaaaggg  37860
aataagggcg acacggaaat gttgaatact catactcttc cttttcaat attattgaag  37920 catttatcag ggttattgtc tcatgagcgg atacatattt gaatgtattt agaaaaataa  37980
acaaataggg gttccgcgca catttccccg aaaagtgcca cctgacgtct aagaaaccat  38040
tattatcatg acattaacct ataaaaatag gcgtatcacg aggcccttc gtcttcaaga  38100 attggtcgac gatcttgctg cgttcggata ttttcgtgga gttcccgcca cagacccgga  38160
ttgaaggcga gatccagcaa ctcgcgccag atcatcctgt gacggaactt tggcgcgtga  38220
tgactggcca ggacgtcggc cgaaagagcg acaagcagat cacgcttttc gacagcgtcg  38280
gatttgcgat cgaggatttt tcggcgctgc gctacgtccg cgaccgcgtt gagggatcaa  38340
gccacagcag cccactcgac cttctagccg acccagacga gccaagggat cttttggaa  38400 tgctgctccg tcgtcaggct ttccgacgtt tgggtggttg aacagaagtc attatcgtac  38460
ggaatgccaa gcactcccga ggggaaccct gtggttggca tgcacataca aatggacgaa  38520
cggataaacc ttttcacgcc cttttaaata tccgttattc taataaacgc tcttttctct  38580
taggtttacc cgccaatata tcctgtcaaa cactgatagt ttaaactgaa ggcgggaaac  38640
gacaatctga tcatgagcgg agaattaagg gagtcacgtt atgacccccg ccgatgacgc  38700
gggacaagcc gttttacgtt tggaactgac agaaccgcaa cgttgaagga ccactcagc  38760 aagctggtac gattgtaata cgactcacta tagggcgaat tgagcgctgt ttaaacgctc  38820
ttcaactgga gagcggtta cccggaccga agcttgaagt tcctattccg aagttcctat  38880
tctctagaaa gtataggaac ttcagatctc gatgctcacc ctgttgtttg gtgttacttc  38940
tgcaggtcga ctctagagga tccaccatga gcccagaacg acgcccggcc gacatccgcc  39000
gtgccaccga ggcggacatg ccggcggtct gcaccatcgt caaccactac atcgagacaa  39060
gcacggtcaa cttccgtacc gagccgcagg aaccgcagga ctggacggac gacctcgtcc  39120
gtctgcggga gcgctatccc tggctcgtcg ccgaggtgga cggcgaggtc gccggcatcg  39180
cctacgcggg ccctggaag gcacgcaacg cctacgactg gacggccgag tcgaccgtgt  39240
acgtctcccc ccgccaccag cggacgggac tgggctccac gctctacacc cacctgctga  39300
agtccctgga ggcacagggc ttcaagagcg tggtcgctgt catcgggctg cccaacgacc  39360
```

```
cgagcgtgcg catgcacgag gcgctcggat atgcccccccg cggcatgctg cgggcggccg   39420
gcttcaagca cgggaactgg catgacgtgg gtttctggca gctggacttc agcctgccgg   39480
taccgccccg tccggtcctg cccgtcaccg agatctgatc cgtcgaccaa cctagacttg   39540
tccatcttct ggattggcca acttaattaa tgtatgaaat aaaaggatgc acacatagtg   39600
acatgctaat cactataatg tgggcatcaa agttgtgtgt tatgtgtaat tactagttat   39660
ctgaataaaa gagaaagaga tcatccatat ttcttatcct aaatgaatgt cacgtgtctt   39720
tataattctt tgatgaacca gatgcatttc attaaccaaa tccatataca tataaatatt   39780
aatcatatat aattaatatc aattgggtta gcaaaacaaa tctagtctag gtgtgttttg   39840
cgaattgcgg ccgcgatctg gggaattccc atggacaccg gtaattccca tgatcttctc   39900
tccttcatca atggatgcca tgtttcataa caataacacc aaatgtttga tgagctacca   39960
acaattgcgc aaagactatg gctaagctcg agctcgctcg ctacaagttg ttgactttca   40020
aatacaagtt tgttttttgga acaccaaata ttctacatga tctttcacta agttgcgcac   40080
cactatcaaa agattatcta ggccattatt caagtaaaga gtgaacacgt ctaagaccca   40140
caaccacacc aaatagaata cgcatacatg caacatattg tgcaagaagt atccaactgg   40200
actcccatgt attctaaaac tattttcgta gagttaaagt tatgacaaac ttatcaaata   40260
aaaatttgaa cgctggacca aaactttcat cttttcaaatc caccatcgtc tatcctcata   40320
aattgttttg attataacac atctacgtaa atcatttgtt ttgaacaata ctaatttaat   40380
tttattaagt caaataaccct gcttagaaaa taatccctcc acctcattta acaatttctt   40440
gtcaaacaca caccaagaaa aaaattaatg aaagagaaaa gaaatgaaaa ggacatggag   40500
ttgaatacta gcaaaattga ttgaaggaag attcacaatt gaaattgaaa ccatttaatt   40560
tattttcggg tccataataa taaattggta agaataaaaa cccgatcaag tccggtacag   40620
tacaattcca ctccaccaac tccttactta aaccctatt tatacccact ctcatcctca   40680
ctcttccttc acctctcaca ctctcttctc tctctcaaaa ccctcacaca aacgctgcgt   40740
ttagtgtaag aaattcaatc cggcgccttg gcgcgccgat catccacaag tttgtacaaa   40800
aaagctgaac gagaaacgta aaatgatata aatatcaata tattaaatta gattttgcat   40860
aaaaaacaga ctacataata ctgtaaaaca caacatatcc agtcactatg gcggccgcat   40920
taggcacccc aggcttttaca ctttatgctt ccggctcgta taatgtgtgg attttgagtt   40980
aggatttaaa tacgcgttga tccggcttac taaaagccag ataacagtat gcgtatttgc   41040
gcgctgattt ttgcggtata agaatatata ctgatatgta tacccgaagt atgtcaaaaa   41100
gaggtatgct atgaagcagc gtattacagt gacagttgac agcgacagct atcagttgct   41160
caaggcatat atgatgtcaa tatctccggt ctggtaagca caaccatgca gaatgaagcc   41220
cgtcgtctgc gtgccgaacg ctggaaagcg gaaaatcagg aagggatggc tgaggtcgcc   41280
cggtttattg aaatgaacgg ctcttttgct gacgagaaca ggggctggtg aaatgcagtt   41340
taaggtttac acctataaaa gagagagccg ttatcgtctg tttgtggatg tacagagtga   41400
tatcattgac acgcccggtc gacggatggt gatcccccctg gccagtgcac gtctgctgtc   41460
agataaagtc tcccgtgaac tttacccggt ggtgcatatc ggggatgaaa gctggcgcat   41520
gatgaccacc gatatggcca gtgtgccggt ctccgttatc ggggaagaag tggctgatct   41580
cagccaccgc gaaaatgaca tcaaaaacgc cattaacctg atgttctggg gaatataaat   41640
gtcaggctcc cttatacaca gccagtctgc aggtcgacca tagtgactgg atatgttgtg   41700
ttttacagta ttatgtagtc tgttttttat gcaaaatcta atttaatata ttgatattta   41760
```

```
tatcatttta cgtttctcgt tcagctttct tgtacaaagt ggtgttaacc tagacttgtc    41820
catcttctgg attggccaac ttaattaatg tatgaaataa aaggatgcac acatagtgac    41880
atgctaatca ctataatgtg ggcatcaaag ttgtgtgtta tgtgtaatta ctagttatct    41940
gaataaaaga gaaagagatc atccatattt cttatcctaa atgaatgtca cgtgtcttta    42000
taattctttg atgaaccaga tgcatttcat taaccaaatc catatacata taaatattaa    42060
tcatatataa ttaatatcaa ttgggttagc aaaacaaatc tagtctaggt gtgttttgcg    42120
aattgcggcc gccaccgcgg tggagctcga attccggtcc gggtcacctt tgtccaccaa    42180
gatgaaactg cggccgctca ttaattaagt caggcgcgcc tctagttgaa gacacgttca    42240
tgtcttcatc gtaagaagac actcagtagt cttcggccag aatggccatc tggattcagc    42300
aggcctagaa ggccatttaa atcctgagga tctggtcttc ctaaggaccc gggatatcgg    42360
accgattaaa ctttaattcg gtccgaagct tgaagttcct attccgaagt tcctattctc    42420
cagaaagtat aggaacttcg catgcctgca gtgcagcgtg acccggtcgt gcccctctct    42480
agagataatg agcattgcat gtctaagtta taaaaaatta ccacatattt ttttgtcac    42540 acttgtttga agtgcagttt atctatcttt atacatatat ttaaacttta ctctacgaat    42600
aatataatct atagtactac aataatatca gtgttttaga gaatcatata aatgaacagt    42660
tagacatggt ctaaaggaca attgagtatt ttgacaacag gactctacag ttttatcttt    42720
ttagtgtgca tgtgttctcc tttttttttg caaatagctt cacctatata atacttcatc    42780
cattttatta gtcatccat ttagggttta gggttaatgg ttttatataga ctaatttttt    42840 tagtacatct attttattct attttagcct ctaaattaag aaaactaaaa ctctatttta    42900
gtttttttat ttaataattt agatataaaa tagaataaaa taaagtgact aaaaattaaa    42960 caaatacccct ttaagaaatt aaaaaaacta aggaaacatt tttcttgttt cgagtagata    43020
atgccagcct gttaaacgcc gtcgacgagt ctaacggaca ccaaccagcg aaccagcagc    43080
gtcgcgtcgg gccaagcgaa gcagacggca cggcatctct gtcgctgcct ctggaccct    43140 ctcgagagtt ccgctccacc gttggacttg ctccgctgtc ggcatccaga aattgcgtgg    43200
cggagcggca gacgtgagcc ggcacggcag gcggcctcct cctcctctca ggcaccggc    43260 agctacgggg gattcctttc ccaccgctcc ttcgctttcc cttcctcgcc cgccgtaata    43320
aatagacacc cctccacac cctctttccc caacctcgtg ttgttcggag cgcacacaca    43380
cacaaccaga tctcccccaa atccacccgt cggcacctcc gcttcaaggt acgccgctcg    43440
tcctcccccc cccccctctc taccttctct agatcggcgt tccggtccat gcatggtag    43500 ggcccggtag ttctacttct gttcatgttt gtgttagatc cgtgtttgtg ttagatccgt    43560
gctgctagcg ttcgtacacg gatgcgacct gtacgtcaga cacgttctga ttgctaactt    43620
gccagtgttt ctctttgggg aatcctggga tggctctagc cgttccgcag acgggatcga    43680
tttcatgatt ttttttgttt cgttgcatag ggtttggttt gccctttttcc tttatttcaa    43740 tatatgccgt gcacttgttt gtcgggtcat cttttcatgc ttttttttgt cttggttgtg    43800
atgatgtggt ctggttgggc ggtcgttcta gatcggagta gaattctgtt tcaaactacc    43860
tggtggattt attaattttg gatctgtatg tgtgtgccat acatattcat agttacgaat    43920
tgaagatgat ggatggaaat atcgatctag gataggtata catgttgatg cgggttttac    43980
tgatgcatat acagagatgc ttttgttccg cttggttgtg atgatgtggt gtggttgggc    44040
ggtcgttcat tcgttctaga tcggagtaga atactgtttc aaactacctg gtgtatttat    44100
```

```
taattttgga actgtatgtg tgtgtcatac atcttcatag ttacgagttt aagatggatg   44160
gaaatatcga tctaggatag gtatacatgt tgatgtgggt tttactgatg catatacatg   44220
atggcatatg cagcatctat tcatatgctc taaccttgag tacctatcta ttataataaa   44280
caagtatgtt ttataattat tttgatcttg atatacttgg atgatggcat atgcagcagc   44340
tatatgtgga ttttttttagc cctgccttca tacgctattt atttgcttgg tactgtttct   44400
tttgtcgatg ctcaccctgt tgtttggtgt tacttctgca ggtcgacttt aacttagcct   44460
aggatccaca cgacaccatg atagaggtga aaccgattaa cgcagaggat acctatgaac   44520
taaggcatag aatactcaga ccaaaccagc cgatagaagc gtgtatgttt gaaagcgatt   44580
tacttcgtgg tgcatttcac ttaggcggct attacggggg caaactgatt tccatagctt   44640
cattccacca ggccgagcac tcagaactcc aaggccagaa acagtaccag ctccgaggta   44700
tggctacctt ggaaggttat cgtgagcaga aggcgggatc gagtctaatt aaacacgctg   44760
aagaaattct tcgtaagagg ggggcggact tgctttggtg taatgcgcgg acatccgcct   44820
caggctacta caaaaagtta ggcttcagcg agcaggagga ggtattcgac acgccgccag   44880
taggacctca catcctgatg tataaaagga tcacataact agctagtcag ttaacctaga   44940
cttgtccatc ttctggattg gccaacttaa ttaatgtatg aaataaaagg atgcacacat   45000
agtgacatgc taatcactat aatgtgggca tcaaagttgt gtgttatgtg taattactag   45060
ttatctgaat aaaagagaaa gagatcatcc atatttctta tcctaaatga atgtcacgtg   45120 tcttttataat tctttgatga accagatgca tttcattaac caaatccata tacatataaa   45180
tattaatcat atataattaa tatcaattgg gttagcaaaa caaatctagt ctaggtgtgt   45240
tttgcgaatt cagagctcga attcattccg attaatcgtg gcctcttgct cttcaggatg   45300
aagagctatg tttaaacgtg caagcgctac tagacaattc agtacattaa aaacgtccgc   45360
aatgtgttat taagttgtct aagcgtcaat ttgtttacac cacaatatat cctgccacca   45420
gccagccaac agctccccga ccggcagctc ggcacaaaat caccactcga tacaggcagc   45480
ccatcagtcc gggacggcgt cagcgggaga gccgttgtaa ggcggcagac tttgctcatg   45540
ttaccgatgc tattcggaag aacggcaact aagctgccgg gtttgaaaca cggatgatct   45600
cgcggagggt agcatgttga ttgtaacgat gacagagcgt tgctgcctgt gatcaaatat   45660
catctccctc gcagagatcc gaattatcag ccttcttatt catttctcgc ttaaccgtga   45720
caggctgtcg atcttgagaa ctatgccgac ataataggaa atcgctggat aaagccgctg   45780
aggaagctga gtggcgctat ttcttttagaa gtgaacgttg acgatcgtcg accgtacccc   45840
gatgaattaa ttcggacgta cgttctgaac acagctggat acttacttgg gcgattgtca   45900
tacatgacat caacaatgta cccgtttgtg taaccgtctc ttggaggttc gtatgacact   45960
agtggttccc ctcagcttgc gactagatgt tgaggcctaa cattttatta gagagcaggc   46020
tagttgctta gatacatgat cttcaggccg ttatctgtca gggcaagcga aaattggcca   46080
tttatgacga ccaatgcccc gcagaagctc ccatctttgc cgcccatagac gccgcgcccc   46140 ccttttgggg tgtagaacat cctttttgcca gatgtggaaa agaagttcgt tgtcccattg   46200
ttggcaatga cgtagtagcc ggcgaaagtg cgagacccat ttgcgctata tataagccta   46260
cgatttccgt tgcgactatt gtcgtaattg gatgaactat tatcgtagtt gctctcagag   46320
ttgtcgtaat ttgatggact attgtcgtaa ttgcttatgg agttgtcgta gttgcttgga   46380
gaaatgtcgt agttggatgg ggagtagtca tagggaagac gagcttcatc cactaaaaca   46440
attggcaggt cagcaagtgc ctgccccgat gccatcgcaa gtacgaggct tagaaccacc   46500
```

```
ttcaacagat cgcgcatagt cttccccagc tctctaacgc ttgagttaag ccgcgccgcg   46560
aagcggcgtc ggcttgaacg aattgttaga cattatttgc cgactacctt ggtgatctcg   46620
cctttcacgt agtgaacaaa ttcttccaac tgatctgcgc gcgaggccaa gcgatcttct   46680
tgtccaagat aagcctgcct agcttcaagt atgacgggct gatactgggc cggcaggcgc   46740
tccattgccc agtcggcagc gacatccttc ggcgcgattt tgccggttac tgcgctgtac   46800
caaatgcggg acaacgtaag cactacattt cgctcatcgc cagcccagtc gggcggcgag   46860
ttccatagcg ttaaggtttc atttagcgcc tcaaatagat cctgttcagg aaccggatca   46920
aagagttcct ccgccgctgg acctaccaag gcaacgctat gttctcttgc ttttgtcagc   46980
aagatagcca gatcaatgtc gatcgtggct ggctcgaaga tacctgcaag aatgtcattg   47040
cgctgccatt ctccaaattg cagttcgcgc ttagctggat aacgccacgg aatgatgtcg   47100
tcgtgcacaa caatggtgac ttctacagcg cggagaatct cgctctctcc aggggaagcc   47160
gaagtttcca aaaggtcgtt gatcaaagct cgccgcgttg tttcatcaag ccttacagtc   47220
accgtaacca gcaaatcaat atcactgtgt ggcttcaggc cgccatccac tgcggagccg   47280
tacaaatgta cggccagcaa cgtcggttcg agatggcgct cgatgacgcc aactacctct   47340
gatagttgag tcgatacttc ggcgatcacc gcttccctca tgatgtttaa ctcctgaatt   47400
aagccgcgcc gcgaagcggt gtcggcttga atgaattgtt aggcgtcatc ctgtgctccc   47460
gagaaccagt accagtacat cgctgtttcg ttcgagactt gaggtctagt tttatacgtg   47520
aacaggtcaa tgccgccgag agtaaagcca cattttgcgt acaaattgca ggcaggtaca   47580
ttgttcgttt gtgtctctaa tcgtatgcca aggagctgtc tgcttagtgc ccactttttc   47640
gcaaattcga tgagactgtg cgcgactcct ttgcctcggt gcgtgtgcga cacaacaatg   47700
tgttcgatag aggctagatc gttccatgtt gagttgagtt caatcttccc gacaagctct   47760
tggtcgatga atgcgccata gcaagcagag tcttcatcag agtcatcatc cgagatgtaa   47820
tccttccggt aggggctcac acttctggta gatagttcaa agccttggtc ggataggtgc   47880
acatcgaaca cttcacgaac aatgaaatgg ttctcagcat ccaatgtttc cgccacctgc   47940
tcagggatca ccgaaatctt catatgacgc ctaacgcctg gcacagcgga tcgcaaacct   48000
ggcgcggctt ttggcacaaa aggcgtgaca ggtttgcgaa tccgttgctg ccacttgtta   48060 accctttgc cagatttggt aactataatt tatgttagag gcgaagtctt gggtaaaaac     48120
tggcctaaaa ttgctgggga tttcaggaaa gtaaacatca ccttccggct cgatgtctat   48180
tgtagatata tgtagtgtat ctacttgatc gggggatctg ctgcctcgcg cgtttcggtg   48240
atgacggtga aaacctctga cacatgcagc tcccggagac ggtcacagct tgtctgtaag   48300
cggatgccgg gagcagacaa gcccgtcagg gcgcgtcagc gggtgttggc gggtgtcggg   48360
gcgcagccat gacccagtca cgtagcgata gcggagtgta tactggctta actatgcggc   48420
atcagagcag attgtactga gagtgcacca tatgcggtgt gaaataccgc acagatgcgt   48480
aaggagaaaa taccgcatca ggcgctcttc cgcttcctcg ctcactgact cgctgcgctc   48540
ggtcgttcgg ctgcggcgag cggtatcagc tcactcaaag gcggtaatac ggttatccac   48600
agaatcaggg gataacgcag gaaagaacat gtgagcaaaa ggccagcaaa aggccaggaa   48660
ccgtaaaaag gccgcgttgc tggcgttttt ccataggctc cgcccccctg acgagcatca   48720
caaaaatcga cgctcaagtc agaggtggcg aaacccgaca ggactataaa gataccaggc   48780
gtttccccct ggaagctccc tcgtgcgctc tcctgttccg accctgccgc ttaccggata   48840
```

```
cctgtccgcc tttctcccttt cgggaagcgt ggcgctttct catagctcac gctgtaggta    48900
tctcagttcg gtgtaggtcg ttcgctccaa gctgggctgt gtgcacgaac ccccgttca    48960 gcccgaccgc tgcgccttat ccggtaacta tcgtcttgag tccaacccgg taagacacga    49020
cttatcgcca ctggcagcag ccactggtaa caggattagc agagcgaggt atgtaggcgg    49080
tgctacagag ttcttgaagt ggtggcctaa ctacggctac actagaagga cagtatttgg    49140
tatctgcgct ctgctgaagc cagttacctt cggaaaaaga gttggtagct cttgatccgg    49200
caaacaaacc accgctggta gcggtggttt ttttgtttgc aagcagcaga ttacgcgcag    49260
aaaaaaagga tctcaagaag atcctttgat cttttctacg gggtctgacg ctcagtggaa    49320
cgaaaactca cgttaaggga ttttggtcat gagattatca aaaaggatct tcacctagat    49380
ccttttaaat taaaaatgaa gttttaaatc aatctaaagt atatatgagt aaacttggtc    49440
tgacagttac caatgcttaa tcagtgaggc acctatctca gcgatctgtc tatttcgttc    49500
atccatagtt gcctgactcc ccgtcgtgta gataactacg atacgggagg gcttaccatc    49560
tggccccagt gctgcaatga taccgcgaga cccacgctca ccggctccag atttatcagc    49620
aataaaccag ccagccggaa gggccgagcg cagaagtggt cctgcaactt tatccgcctc    49680
catccagtct attaattgtt gccgggaagc tagagtaagt agttcgccag ttaatagttt    49740
gcgcaacgtt gttgccattg ctgca                                         49765
```

<210> SEQ ID NO 14
<211> LENGTH: 1670
<212> TYPE: DNA
<213> ORGANISM: Zea Mays
<220> FEATURE:
<221> NAME/KEY: misc_feature
<222> LOCATION: (1660)..(1660)
<223> OTHER INFORMATION: n is a, c, g, or t

<400> SEQUENCE: 14

```
atggcgcccc gcggccgcac cctcctcccg ctcgccgcgg ccaccgtcct cgtcgcttcc      60
accatcttcc tcttcgccgc cgccggtgcg cgctggcggc ccgccgacac cgacctcccc     120
gtcccgccac acgccttccc cacggccgtc cccgcggccg tgaccgcttc ttcttactcc     180
aacgccaccg ccggcaagga gctctccttt ctcgacgaga acggccgccc cgatgacccc     240
tcctccgcct cagcatccag ctccacctcc ggcgccaccc cggccgctgg tgtcgtcaga     300
tgtgaccccc gcgacgccgt cagggtattc atgtacgaca tgccgcccga gttccacttc     360
ggcctcctcg gctggtcgcc gccgtcccct gactccgtct ggccagacgt caccgccgcc     420
tccccgccgc cgcgctaccc cgggggggctc aaccagcagc acagcgtgga gtactggctc     480
acgctcgacc tcctctcctc ctcgcccccc tgcggccgtc actccgcagt gcgggtctcc     540
gattcccgcg atgccgacct cgtcttcgtc cccttcttcg cgtccctcag ctacaaycgc     600
cactaccggc ccgtgccgcc cgagaagggc agcagggaca gggccatcca ggagaagctg     660
gtgcgggacc tcgcggcgcg gccggagtgg aggaggtacg gtggtgccga ccacgtcatc     720
gtcgcgcacc accccaacag cttgctgcac gcccgggcgg tgctgcaccc cgccgtgttc     780
gtgctgtcag acttcgggag gtacccaccg agggtggcca gcttggagaa ggatgtcatt     840
gcgccataca agcacatggc caagacgttc gtcaatgact cggccgggtt cgatgaccgg     900 ccgacccttgt tatacttccg gggagcaatt tacaggaagg aggggaggag cattcgacag     960
gagctatatt atatgctsaa agaagaaaag gatgtttact tttcctttgg aagtgtccag    1020
gaccatgggg ccagcaaagc tagccaagga atgcactcat caaaatttgtg cctaaatatt    1080
```

```
gctgggggaca cccccttcttc caatcgtctg tttgatgcga tagttaccca ctgtgtccct   1140
gttatcatca gtgacgacat tgagctacct tatgaggatg tgttggatta ttcaaaattc   1200
tccatctttg tccgttcgtc tgatgctgtt aagaaaggtt acctgatgag actgctcagt   1260
ggtgtaagca agcaacaatg gacaaagatg tgggataggc tcaaagaggt ggataaacat   1320
tttgagtatc agtatccatc acagaaggat gatgcagtcc agatgatctg caagcattg   1380 tctagaaagg tgccatcaat taagctgaag gttcacagat ctaatagatt ttcaagatct   1440
aacagaggaa ataaacaga aggggtgtg tctatcttgt ctctattggc taatctaatg   1500
taacacattt cactgacaca ggctctcagc ctttcccagt tgcacaaaat agatagattg   1560
taatactcag gttatcttta ggaaaggttt gtaccttaag atttgttggt tcagttgaag   1620
catatactgt caagtcaaag gttgttttgt aaggtatgtn aaatgtaatc             1670
```

<210> SEQ ID NO 15
<211> LENGTH: 484
<212> TYPE: PRT
<213> ORGANISM: Zea Mays

<400> SEQUENCE: 15

```
Met Ala Pro Arg Gly Arg Thr Leu Leu Pro Leu Ala Ala Ala Thr Val
1               5                   10                  15

Leu Val Ala Ser Thr Ile Phe Leu Phe Ala Ala Gly Ala Arg Trp
                20                  25                  30

Arg Pro Ala Asp Thr Asp Leu Pro Val Pro Pro His Ala Phe Pro Thr
            35                  40                  45

Ala Val Pro Ala Ala Val Thr Ala Ser Ser Tyr Ser Asn Ala Thr Ala
        50                  55                  60

Gly Lys Glu Leu Ser Phe Leu Asp Glu Asn Gly Arg Pro Asp Asp Pro
65                  70                  75                  80

Ser Ser Ala Ser Ala Ser Ser Thr Ser Gly Ala Thr Pro Ala Ala
                85                  90                  95

Gly Val Val Arg Cys Asp Pro Arg Asp Ala Val Arg Val Phe Met Tyr
            100                 105                 110

Asp Met Pro Pro Glu Phe His Phe Gly Leu Leu Gly Trp Ser Pro Pro
        115                 120                 125

Ser Pro Asp Ser Val Trp Pro Asp Val Thr Ala Ala Ser Pro Pro
    130                 135                 140

Arg Tyr Pro Gly Gly Leu Asn Gln Gln His Ser Val Glu Tyr Trp Leu
145                 150                 155                 160

Thr Leu Asp Leu Leu Ser Ser Pro Pro Cys Gly Arg His Ser Ala
                165                 170                 175

Val Arg Val Ser Asp Ser Arg Asp Ala Asp Leu Val Phe Val Pro Phe
            180                 185                 190

Phe Ala Ser Leu Ser Tyr Asn Arg His Tyr Arg Pro Val Pro Pro Glu
        195                 200                 205

Lys Gly Ser Arg Asp Arg Ala Ile Gln Glu Lys Leu Val Arg Asp Leu
    210                 215                 220

Ala Ala Arg Pro Glu Trp Arg Arg Tyr Gly Gly Ala Asp His Val Ile
225                 230                 235                 240

Val Ala His His Pro Asn Ser Leu Leu His Ala Arg Ala Val Leu His
                245                 250                 255

Pro Ala Val Phe Val Leu Ser Asp Phe Gly Arg Tyr Pro Pro Arg Val
            260                 265                 270
```

```
Ala Ser Leu Glu Lys Asp Val Ile Ala Pro Tyr Lys His Met Ala Lys
        275                 280                 285
Thr Phe Val Asn Asp Ser Ala Gly Phe Asp Asp Arg Pro Thr Leu Leu
    290                 295                 300
Tyr Phe Arg Gly Ala Ile Tyr Arg Lys Glu Gly Gly Ser Ile Arg Gln
305                 310                 315                 320
Glu Leu Tyr Tyr Met Leu Lys Glu Gly Lys Asp Val Tyr Phe Ser Phe
                325                 330                 335
Gly Ser Val Gln Asp His Gly Ala Ser Lys Ala Ser Gln Gly Met His
            340                 345                 350
Ser Ser Lys Phe Cys Leu Asn Ile Ala Gly Asp Thr Pro Ser Ser Asn
        355                 360                 365
Arg Leu Phe Asp Ala Ile Val Thr His Cys Val Pro Val Ile Ile Ser
370                 375                 380
Asp Asp Ile Glu Leu Pro Tyr Glu Asp Val Leu Asp Tyr Ser Lys Phe
385                 390                 395                 400
Ser Ile Phe Val Arg Ser Ser Asp Ala Val Lys Lys Gly Tyr Leu Met
                405                 410                 415
Arg Leu Leu Ser Gly Val Ser Lys Gln Gln Trp Thr Lys Met Trp Asp
            420                 425                 430
Arg Leu Lys Glu Val Asp Lys His Phe Glu Tyr Gln Tyr Pro Ser Gln
        435                 440                 445
Lys Asp Asp Ala Val Gln Met Ile Trp Gln Ala Leu Ser Arg Lys Val
450                 455                 460
Pro Ser Ile Lys Leu Lys Val His Arg Ser Asn Arg Phe Ser Arg Ser
465                 470                 475                 480
Asn Arg Gly Lys

<210> SEQ ID NO 16
<211> LENGTH: 1776
<212> TYPE: DNA
<213> ORGANISM: Zea Mays
<220> FEATURE:
<221> NAME/KEY: misc_feature
<222> LOCATION: (764)..(924)
<223> OTHER INFORMATION: n is a, c, g, or t

<400> SEQUENCE: 16
cccctcccca gctagccatg ccgcgcccc gctctggtcg ccgcccgcac tgccactgct     60
agccatggcc gccgccgccg cctgccggag cccgctggtc tggctcttcg cgctcgtcac    120
cgcactcttc ttcttctcct ggtacctcct cctcgactcc gccgcgggtc cagccgccgc    180
ccgccgcccc aaccagtggc tccgcctcgg cggcggcggg cggcgctccg gtcccggtag    240
gaaatgcgac cccgcggagg cgctgctgcg agtgttcatg tacgacctgc ccccgagtt    300 ccacttcgga ctgctcgact ggaagccccc cggcttcggc ggcggcgtgt ggcccgacat    360
cagggacggc gtgcctgact acccgggggg cctcaacctg cagcacagca tcgagtattg    420
gctcaccctc gacctcctgg cctccgagca gggcgcgccc acgccctgcg cagtggcgcg    480
ggtgcgccac gcgcgcggacg ccgacgtcgt cttcgtgccc ttcttcgcct cgctcagctt    540
caaccgccac tcccgggtgg taccgcccgc gcgggacagc gaggaccgcg cgctgcagcg    600
gaggctcctc gagttcctcg ccgcgcggcc cgagtggcgg aggactggcg gcgggacca    660 cgtcgtgctc gcgcatcacc ccaacgggat gctcgacgcg cgctacaggt tctgccctg    720 cgtcttcgtg ctctgcgact tcgggaggta cccgcccagc gtcnnnnnnn nnnnnnnnn    780
```

```
nnnnnnnnnn nnnnnnnnnn nnnnnnnnnn nnnnnnnnnn nnnnnnnnnn nnnnnnnnnn      840
nnnnnnnnnn nnnnnnnnnn nnnnnnnnnn nnnnnnnnnn nnnnnnnnnn nnnnnnnnnn      900
nnnnnnnnnn nnnnnnnnnn nnnngaaaga cgagaaagat gtgcatttct catttggaag      960
cgtagccggt aatgggatcg agcaagcaac acaaggdatg cggtcatcca agttctgcct     1020
caacattgca ggtgacactc catcctccaa ccgcctcttt gactccatag tcagtcactg     1080
tgttcccgtc acgatcagcg atgagattga gctcccgttt gaggatgtcc tcgactactc     1140
gaagttcagt gtcatagtac gtggcgcaga cgcagtcaag aagggggtttc taatgaacct    1200 gatcaaaggg atcagccgag aagagtggac acgcatgtgg aacaggctaa ggaagtgga     1260 aaagcacttt gagtaccaat acccatctca gaccgatgat gccgtgcaga tgatatggaa    1320
ggccattgct cggaaggtgc cgtctatccg gctgaagatt aacagactgc aaagattttc    1380
tctgtttgag actaacagga cagatgagac tctaccccca tcttcttctt ggctacagaa    1440
tcaggctcct tgattttgga ctagcaagct caggctttcg ccatgttttc aatctcgtag    1500
aatcaagagt tgatactgaa gaccaaatct taatcgcttg actgggggca gatgttagta    1560
tgttacagct gcagacatta gcggatagta aagttgaaac actttagcat agcagaatta    1620
catatccagt ggcacatcat tttcttcatt ttttttttctt ttgcttgcga ttcatccaaa   1680
gtgtcctcgg ctgcagacta aggacaatga attttgtatg tgaagctgta tattctaggc    1740
ggcaatatag ttactgatca gttacagttg ctgggc                              1776
```

<210> SEQ ID NO 17
<211> LENGTH: 462
<212> TYPE: PRT
<213> ORGANISM: Zea mays
<220> FEATURE:
<221> NAME/KEY: misc_feature
<222> LOCATION: (234)..(287)
<223> OTHER INFORMATION: Xaa can be any naturally occurring amino acid

<400> SEQUENCE: 17

```
Met Ala Ala Ala Ala Cys Arg Ser Pro Leu Val Trp Leu Phe Ala
1               5                   10                  15

Leu Val Thr Ala Leu Phe Phe Phe Ser Trp Tyr Leu Leu Asp Ser
                20                  25                  30

Ala Ala Gly Pro Ala Ala Ala Arg Arg Pro Asn Gln Trp Leu Arg Leu
                35                  40                  45

Gly Gly Gly Gly Arg Arg Ser Gly Pro Gly Arg Lys Cys Asp Pro Ala
        50                  55                  60

Glu Ala Leu Leu Arg Val Phe Met Tyr Asp Leu Pro Pro Glu Phe His
65                  70                  75                  80

Phe Gly Leu Leu Asp Trp Lys Pro Pro Gly Phe Gly Gly Val Trp
                85                  90                  95

Pro Asp Ile Arg Asp Gly Val Pro Asp Tyr Pro Gly Gly Leu Asn Leu
                100                 105                 110

Gln His Ser Ile Glu Tyr Trp Leu Thr Leu Asp Leu Leu Ala Ser Glu
            115                 120                 125

Gln Gly Ala Pro Thr Pro Cys Ala Val Ala Arg Val Arg His Ala Ala
        130                 135                 140

Asp Ala Asp Val Val Phe Val Pro Phe Phe Ala Ser Leu Ser Phe Asn
145                 150                 155                 160

Arg His Ser Arg Val Val Pro Pro Ala Arg Asp Ser Glu Asp Arg Ala
                165                 170                 175
```

Leu Gln Arg Arg Leu Leu Glu Phe Leu Ala Ala Arg Pro Glu Trp Arg
    180                 185                 190

Arg Thr Gly Gly Arg Asp His Val Leu Ala His His Pro Asn Gly
            195                 200                 205

Met Leu Asp Ala Arg Tyr Arg Phe Trp Pro Cys Val Phe Val Leu Cys
    210                 215                 220

Asp Phe Gly Arg Tyr Pro Pro Ser Val Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa
            245                 250                 255

Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Lys
    275                 280                 285

Asp Glu Lys Asp Val His Phe Ser Phe Gly Ser Val Ala Gly Asn Gly
    290                 295                 300

Ile Glu Gln Ala Thr Gln Gly Met Arg Ser Ser Lys Phe Cys Leu Asn
305                 310                 315                 320

Ile Ala Gly Asp Thr Pro Ser Ser Asn Arg Leu Phe Asp Ser Ile Val
            325                 330                 335

Ser His Cys Val Pro Val Thr Ile Ser Asp Glu Ile Glu Leu Pro Phe
            340                 345                 350

Glu Asp Val Leu Asp Tyr Ser Lys Phe Ser Val Ile Val Arg Gly Ala
            355                 360                 365

Asp Ala Val Lys Lys Gly Phe Leu Met Asn Leu Ile Lys Gly Ile Ser
    370                 375                 380

Arg Glu Glu Trp Thr Arg Met Trp Asn Arg Leu Lys Glu Val Glu Lys
385                 390                 395                 400

His Phe Glu Tyr Gln Tyr Pro Ser Gln Thr Asp Asp Ala Val Gln Met
            405                 410                 415

Ile Trp Lys Ala Ile Ala Arg Lys Val Pro Ser Ile Arg Leu Lys Ile
            420                 425                 430

Asn Arg Leu Gln Arg Phe Ser Leu Phe Glu Thr Asn Arg Thr Asp Glu
    435                 440                 445

Thr Leu Pro Pro Ser Ser Ser Trp Leu Gln Asn Gln Ala Pro
    450                 455                 460

<210> SEQ ID NO 18
<211> LENGTH: 1174
<212> TYPE: DNA
<213> ORGANISM: Zea mays

<400> SEQUENCE: 18
gcacgagtct tcgtgcccctt cttctcctcg ctcagcttca acgtgcacgg tcgcaacatg     60
accgaccctg acaccgaggc cgaccgcctc ctgcaggttg aacttgtgga tattctctgg    120
aagtctaaat attggcaacg ttctgcgggc cgtgaccatg tcattcctat gcatcaccct    180
aatgctttca gattcctgcg agcaatggtg aatgcatcta ttcttatagt ttcagacttt    240
gggagataca caaaggaact ggcttccctg aggaaagatg ttgtggcacc atatgtgcat    300 gttgtggggtt ccttccttga tgacgatcca cctgatccat ttgaggctcg ccatacactg    360
cttttctttc gaggccgtac tgtcaggaaa gatgaaggga aaatccggtc aaaacttgag    420
aagatattaa aaggcaagga aggggtgcgc tttgaggata gcattgccac gggcgacggc    480

```
attaacatat ctacagaagg tatgcggtca tcaaagtttt gtctccaccc tgctggggac    540
actccttcct catgccgcct gtttgatgcc atagtcagtc attgtgttcc tgtgatagtc    600
agcagtcgaa tcgagctccc ttttgaagat gagattgatt acagtgagtt ctcccttttc    660
ttctccgttg aagaggctct aagacctgat tacttgctga acgagctcag acaggtcccc    720
aaaaggaagt gggttgatat gtggttgaag cttaagaatg tctcccatca ttatgaattc    780
cagtatcccc ccaggaaggg cgacgcggtg aacatgatat ggaggcaggt gaggcacaag    840
atccccgcag ttaaccttgc tattcacagg aacagaagac tgaaaattcc agactggtgg    900
ggataatgat tggtggtgaa tcgtgtacat attaccatat ccactgttag tcctggttat    960
tttcggtgcg ttatgatgga acattgctc accgtccttt gtgaaccaaa gtgttcatct   1020
taagatccaa ggaccgagtc cacaactatt tgctgacagg aactgagatt atcacctctt   1080
ttttggtcga tttttgtgac ggcttcctat ttccccccct gatgctacaa aatagagggg   1140
acaaataaac ttacagtaac attatagagg agtc                              1174
```

<210> SEQ ID NO 19
<211> LENGTH: 282
<212> TYPE: PRT
<213> ORGANISM: Zea mays

<400> SEQUENCE: 19

```
Met Thr Asp Pro Asp Thr Glu Ala Asp Arg Leu Leu Gln Val Glu Leu
1               5                   10                  15

Val Asp Ile Leu Trp Lys Ser Lys Tyr Trp Gln Arg Ser Ala Gly Arg
            20                  25                  30

Asp His Val Ile Pro Met His His Pro Asn Ala Phe Arg Phe Leu Arg
        35                  40                  45

Ala Met Val Asn Ala Ser Ile Leu Ile Val Ser Asp Phe Gly Arg Tyr
    50                  55                  60

Thr Lys Glu Leu Ala Ser Leu Arg Lys Asp Val Val Ala Pro Tyr Val
65                  70                  75                  80

His Val Val Gly Ser Phe Leu Asp Asp Pro Pro Asp Pro Phe Glu
            85                  90                  95

Ala Arg His Thr Leu Leu Phe Phe Arg Gly Arg Thr Val Arg Lys Asp
            100                 105                 110

Glu Gly Lys Ile Arg Ser Lys Leu Glu Lys Ile Leu Lys Gly Lys Glu
        115                 120                 125

Gly Val Arg Phe Glu Asp Ser Ile Ala Thr Gly Asp Gly Ile Asn Ile
    130                 135                 140

Ser Thr Glu Gly Met Arg Ser Ser Lys Phe Cys Leu His Pro Ala Gly
145                 150                 155                 160

Asp Thr Pro Ser Ser Cys Arg Leu Phe Asp Ala Ile Val Ser His Cys
                165                 170                 175

Val Pro Val Ile Val Ser Ser Arg Ile Glu Leu Pro Phe Glu Asp Glu
            180                 185                 190

Ile Asp Tyr Ser Glu Phe Ser Leu Phe Phe Ser Val Glu Glu Ala Leu
        195                 200                 205

Arg Pro Asp Tyr Leu Leu Asn Glu Leu Arg Gln Val Pro Lys Arg Lys
    210                 215                 220

Trp Val Asp Met Trp Leu Lys Leu Lys Asn Val Ser His His Tyr Glu
225                 230                 235                 240

Phe Gln Tyr Pro Pro Arg Lys Gly Asp Ala Val Asn Met Ile Trp Arg
                245                 250                 255
```

Gln Val Arg His Lys Ile Pro Ala Val Asn Leu Ala Ile His Arg Asn
        260                 265                 270

Arg Arg Leu Lys Ile Pro Asp Trp Trp Gly
        275                 280

<210> SEQ ID NO 20
<211> LENGTH: 1834
<212> TYPE: DNA
<213> ORGANISM: Zea mays

<400> SEQUENCE: 20

| | | | | | |
|---|---|---|---|---|---|
| ctccatagcg | accaaccggc | cgccgcgggt | gaccaaccca | gccgcgcttt | ccccccgtcag | 60 |
| atcccctcct | agccagccat | ggccgagccc | cgttccgccc | tccgcccgca | ttgccactgt | 120 |
| tagtgccatg | gccaccgcct | gccggagccc | gctcgtctgg | ctcttcgcgc | tcgccgccgc | 180 |
| gctattcttc | ctctcctggt | acctcctcct | caactccgcc | gcgggcccaa | ccgccgcccg | 240 |
| ccgcccaac | caggggctcc | gcctcggcgg | ccccggtagg | aaatgcgacc | cgcggaggc | 300 |
| gctgctgcga | gtgttcatgt | acgacctgcc | ccccgagttc | cacttcggac | tgctcgactg | 360 |
| gaagcccccg | ggcttcggcg | gcggcgtgtg | gcccgacgtc | agggacggcg | tgccggacta | 420 |
| cccgggggg | ctcaaccttc | agcacagcat | cgagtactgg | ctcaccctcg | acctcttggc | 480 |
| ctccgagcag | ggcgcgccca | cgccctgcgc | agcggcgcgg | gtgcgccacg | cggcggacgc | 540 |
| cgacgtcgtc | ttcgtgcctt | tcttcgcctc | gctcagcttc | aaccgccact | cccgggtggt | 600 |
| gccgcccgcg | cggaacagcg | aggaccgcgc | gctgcaacgg | aggctcctcg | agttcctcgc | 660 |
| cgcgcggcct | gagtggcgca | ggaccggcgg | gcgggaccac | gtcgtgctcg | cgcatcaccc | 720 |
| caacggtatg | ctcgacgcgc | gctacaggtt | ctggccctgc | gtcttcgtgc | tctgcgactt | 780 |
| cgggaggtac | ccgcccagcg | tcgccaacct | cgacaaggac | atcatcgcgc | cctatcggca | 840 |
| cctcgtcgcc | aacttcgcta | atgacaccgc | cggatacgac | gaccggccga | cgctgctcta | 900 |
| cttccaaggc | gccatctaca | ggaaggatgg | tggttccatt | cggcaagaac | tgtattacct | 960 |
| tctgaaagac | gagaaagatg | tgcatttctc | atttggaagt | gtagctggta | atgggatcga | 1020 |
| gcaggcaaca | caaggtatgc | ggtcatccaa | gttctgcctc | aacattgcag | gtgacactcc | 1080 |
| atcctccaac | cgcctcttcg | actccattgt | cagtcactgt | gttcccgtca | tcatcagcga | 1140 |
| tgagattgag | ctcccgtttg | aggatgtcct | cgactattca | aagttcagcg | tcatagtacg | 1200 |
| tggcgcagat | gcagtcaaga | aggggtttct | aaagagcctg | atcaaaggga | tcagccaaga | 1260 |
| agagtggaca | cgcatgtgga | acaagctaaa | ggaagtagaa | aagcacttcg | agtaccaata | 1320 |
| cccatctcag | actgatgatg | ccgtgcagat | gatatggaag | gctattgctc | ggaaggtgcc | 1380 |
| ctctatccgt | ctgaagatta | acagactacg | agattttct | cggtttgata | ctaataggac | 1440 |
| agatgaaact | ctacccagtc | cttcttggct | acagaatcag | gcttcttgat | ttttggacta | 1500 |
| gcaaactcca | gctttcacca | tgttttcaat | cctgccgaaa | caagagttga | tactgaagac | 1560 |
| caaaccttaa | tcgcatgact | gggggcagat | gttacagctg | cagacattaa | cggagagtaa | 1620 |
| agttgaaaca | ctctagcata | acagaattac | atatccaatg | gcacatcatt | tttcttcatt | 1680 |
| tttcttactt | aagattcatc | caaatgtcc | ttggctgcag | actaaggaca | atgaattttg | 1740 |
| tatgaaaagc | tgtacattct | aggcggcaat | ataattactg | accagttaca | gttgctgaaa | 1800 |
| aaaaaaaaa | aaaaaaaaaa | aaaaaaaaaa | aaag | | | 1834 |

<210> SEQ ID NO 21

<211> LENGTH: 453
<212> TYPE: PRT
<213> ORGANISM: Zea mays

<400> SEQUENCE: 21

```
Met Ala Thr Ala Cys Arg Ser Pro Leu Val Trp Leu Phe Ala Leu Ala
1               5                   10                  15

Ala Ala Leu Phe Phe Leu Ser Trp Tyr Leu Leu Asn Ser Ala Ala
            20                  25                  30

Gly Pro Thr Ala Ala Arg Arg Pro Asn Gln Gly Leu Arg Leu Gly Gly
        35                  40                  45

Pro Gly Arg Lys Cys Asp Pro Ala Glu Ala Leu Leu Arg Val Phe Met
    50                  55                  60

Tyr Asp Leu Pro Pro Glu Phe His Phe Gly Leu Leu Asp Trp Lys Pro
65                  70                  75                  80

Pro Gly Phe Gly Gly Val Trp Pro Asp Val Arg Asp Gly Val Pro
                85                  90                  95

Asp Tyr Pro Gly Gly Leu Asn Leu Gln His Ser Ile Glu Tyr Trp Leu
            100                 105                 110

Thr Leu Asp Leu Leu Ala Ser Glu Gln Gly Ala Pro Thr Pro Cys Ala
        115                 120                 125

Ala Ala Arg Val Arg His Ala Ala Asp Ala Asp Val Val Phe Val Pro
    130                 135                 140

Phe Phe Ala Ser Leu Ser Phe Asn Arg His Ser Arg Val Val Pro Pro
145                 150                 155                 160

Ala Arg Asn Ser Glu Asp Arg Ala Leu Gln Arg Arg Leu Leu Glu Phe
                165                 170                 175

Leu Ala Ala Arg Pro Glu Trp Arg Arg Thr Gly Gly Arg Asp His Val
            180                 185                 190

Val Leu Ala His His Pro Asn Gly Met Leu Asp Ala Arg Tyr Arg Phe
        195                 200                 205

Trp Pro Cys Val Phe Val Leu Cys Asp Phe Gly Arg Tyr Pro Pro Ser
    210                 215                 220

Val Ala Asn Leu Asp Lys Asp Ile Ile Ala Pro Tyr Arg His Leu Val
225                 230                 235                 240

Ala Asn Phe Ala Asn Asp Thr Ala Gly Tyr Asp Asp Arg Pro Thr Leu
                245                 250                 255

Leu Tyr Phe Gln Gly Ala Ile Tyr Arg Lys Asp Gly Ser Ile Arg
            260                 265                 270

Gln Glu Leu Tyr Tyr Leu Leu Lys Asp Glu Lys Asp Val His Phe Ser
        275                 280                 285

Phe Gly Ser Val Ala Gly Asn Gly Ile Glu Gln Ala Thr Gln Gly Met
    290                 295                 300

Arg Ser Ser Lys Phe Cys Leu Asn Ile Ala Gly Asp Thr Pro Ser Ser
305                 310                 315                 320

Asn Arg Leu Phe Asp Ser Ile Val Ser His Cys Val Pro Val Ile Ile
                325                 330                 335

Ser Asp Glu Ile Glu Leu Pro Phe Glu Asp Val Leu Asp Tyr Ser Lys
            340                 345                 350

Phe Ser Val Ile Val Arg Gly Ala Asp Ala Val Lys Lys Gly Phe Leu
        355                 360                 365

Lys Ser Leu Ile Lys Gly Ile Ser Gln Glu Glu Trp Thr Arg Met Trp
    370                 375                 380

Asn Lys Leu Lys Glu Val Glu Lys His Phe Glu Tyr Gln Tyr Pro Ser
```

```
                385                 390                 395                 400

Gln Thr Asp Asp Ala Val Gln Met Ile Trp Lys Ala Ile Ala Arg Lys
                    405                 410                 415

Val Pro Ser Ile Arg Leu Lys Ile Asn Arg Leu Arg Arg Phe Ser Arg
                    420                 425                 430

Phe Asp Thr Asn Arg Thr Asp Glu Thr Leu Pro Ser Pro Ser Trp Leu
                    435                 440                 445

Gln Asn Gln Ala Ser
    450

<210> SEQ ID NO 22
<211> LENGTH: 2080
<212> TYPE: DNA
<213> ORGANISM: Oryza sativa

<400> SEQUENCE: 22
ggcatagcgg catgcatcgc agcataggcc ggtcaagaag acgatggccc tgacgaggcg      60
cctcctcatc gatctctcgt caagacgccg ccttttcaac gccggcaaat tctccaccac     120
gcacaagaag aaaccagtgc tccatgaagg agggagcag gggtgttgtt gaaatggagc      180
agcagctcgt ttctttgatt tgatctttgg cagtaagtaa ttcggggttt gaatttatta     240
tttttgtttt gggcgaattt cattccagcg gtgagtttgg ctggattctt gcgctgctcg     300
cgcgcgctgg tgtcgtggat ggtggcgag aggaagatgc agccatcgcc ggcggcgccg      360
ccggcggcgg agcaccggag gcgggcgctg ctgcgctacg tggtgttcct cgcggtctcc     420
ctcctcgcct tctcctgctg ggctctcgtc agctcgcgga tcgacggcgc cgtcctcgcg     480
gcgaccgccg gcggcgagca tgacgaccac gatggcatta ttgttagaag cagcacccaa     540
gcggagatgc cagcgagagg cgggaacgcg acgtcgcgcg gcgccgtcga ggtgggtgtg     600
ggtactccgg cggcgatgat cacccggcag ccgtcgtcgg gagagacgac gacgacggcg     660
gcgttggcgc gacgtgcga cgcggagagc gcgctgctga gggtgtacct ctacgacctc     720
ccgccggagt tccacttcgg catgctgggg tgggacggca aggcggccgg cgcggcgtgg     780
ccggacgtgg ccggcgaccc gcgcgccgtg ccgcgctacc gggcggcct gaacctgcag      840 cacagcgtcg agtactggct caccctggac atcctctcct ccaccacctc cggcgaccac     900
cgccgccgcc gtccgtgcac cgccgtgagg gtgacgaacg cgagccttgc cgacgtgttc     960
ctggtgccgt tcttcgcgtc gctgagctac aaccggcagt cgaagtcgcc gcacggcggc    1020
catgggagtg gcggccggag cgacaggcag ctgcagggcg agctggtgag gtacctggcg    1080
aggcgggagg agtggcggcg gtggggcggc gcggaccacc tcgtcgtgcc gcaccacccg    1140
aacagcatga tggacgcccg gcggcggctc agcgccgcca tgttcgtcct ctccgacttc    1200
ggcaggtacc cgccggacgt cgccaacctg aggaaggacg tgatcgcgcc gtacaagcac    1260
gtcgtcccct ccctcggcga cggcgactcg ccggggttcg agcagcgccc cgtcctcgct    1320
tacttccagg gcgccattca taggaaaaat ggtggaaggg ttcgtcagag gctgtaccag    1380
ctgatcaagg acgagaagga cgtccacttc acctacggca gcgtccgtca gaacggcatc    1440
aggcgcgcca ccaaggggat ggcctcctcc aagttctgcc tcaacatcgc cggcgacacc    1500
ccctcctcca accgcctctt cgacgccatc gtcagccact gcgtcccgt gatcatcagc     1560 gacgacatcg agctccccct cgaggacgtc ctcgactact ccgccttctg cgtgttcgtc    1620
cgcgcctccg acgcgtcaa gaggggcttc ctgctgcatc tcctcagggg gatctcccag     1680
gaagaatgga cggcaatgtg gaggaggctg aaggaggttg cacaccactt cgagtaccag    1740
```

```
taccottcgc agcctggtga cgctgttcag atgatctggg gagctgtagc tcggaagatg   1800
catttggtga agctgcaact tcacaagcgt ggtagatatc agaggacatt ttctgaatca   1860
taaaaggtta gggtagcaaa gcatggagga gattcagagc tataggttgc agttttgat    1920 caataattt catgtggctg gtaaagttct atggtcattt tgcaatctaa gttgcaagga    1980
ctatgtgcag ccagtctttg tccaagaggt aattattaga cagttagtta taaattatat   2040
tattcttatt aaaaaaaaaa aaaaaaaaaa aaaaaaaaa                          2080
```

<210> SEQ ID NO 23
<211> LENGTH: 514
<212> TYPE: PRT
<213> ORGANISM: Oryza sativa

<400> SEQUENCE: 23

```
Met Val Ala Glu Arg Lys Met Gln Pro Ser Pro Ala Ala Pro Pro Ala
1               5                   10                  15

Ala Glu His Arg Arg Ala Leu Leu Arg Tyr Val Val Phe Leu Ala
            20                  25                  30

Val Ser Leu Leu Ala Phe Ser Cys Trp Ala Leu Val Ser Ser Arg Ile
    35                  40                  45

Asp Gly Ala Val Leu Ala Ala Thr Ala Gly Gly Glu His Asp Asp His
50                  55                  60

Asp Gly Ile Ile Val Arg Ser Ser Thr Gln Ala Glu Met Pro Ala Arg
65                  70                  75                  80

Gly Gly Asn Ala Thr Ser Arg Gly Ala Val Glu Val Gly Val Gly Thr
                85                  90                  95

Pro Ala Ala Met Ile Thr Arg Gln Pro Ser Ser Gly Glu Thr Thr Thr
            100                 105                 110

Thr Ala Ala Leu Ala Ala Thr Cys Asp Ala Glu Ser Ala Leu Leu Arg
        115                 120                 125

Val Tyr Leu Tyr Asp Leu Pro Pro Glu Phe His Phe Gly Met Leu Gly
    130                 135                 140

Trp Asp Gly Lys Ala Ala Gly Ala Ala Trp Pro Asp Val Ala Gly Asp
145                 150                 155                 160

Pro Arg Ala Val Pro Arg Tyr Pro Gly Gly Leu Asn Leu Gln His Ser
                165                 170                 175

Val Glu Tyr Trp Leu Thr Leu Asp Ile Leu Ser Ser Thr Ser Gly
            180                 185                 190

Asp His Arg Arg Arg Pro Cys Thr Ala Val Arg Val Thr Asn Ala
        195                 200                 205

Ser Leu Ala Asp Val Phe Leu Val Pro Phe Phe Ala Ser Leu Ser Tyr
    210                 215                 220

Asn Arg Gln Ser Lys Ser Pro His Gly Gly His Gly Ser Gly Gly Arg
225                 230                 235                 240

Ser Asp Arg Gln Leu Gln Gly Glu Leu Val Arg Tyr Leu Ala Arg Arg
                245                 250                 255

Glu Glu Trp Arg Arg Trp Gly Gly Ala Asp His Leu Val Val Pro His
            260                 265                 270

His Pro Asn Ser Met Met Asp Ala Arg Arg Leu Ser Ala Ala Met
        275                 280                 285

Phe Val Leu Ser Asp Phe Gly Arg Tyr Pro Pro Asp Val Ala Asn Leu
    290                 295                 300

Arg Lys Asp Val Ile Ala Pro Tyr Lys His Val Val Pro Ser Leu Gly
```

```
                305                 310                 315                 320
Asp Gly Asp Ser Pro Gly Phe Glu Gln Arg Pro Val Leu Ala Tyr Phe
                325                 330                 335
Gln Gly Ala Ile His Arg Lys Asn Gly Gly Arg Val Arg Gln Arg Leu
                340                 345                 350
Tyr Gln Leu Ile Lys Asp Glu Lys Asp Val His Phe Thr Tyr Gly Ser
                355                 360                 365
Val Arg Gln Asn Gly Ile Arg Arg Ala Thr Lys Gly Met Ala Ser Ser
            370                 375                 380
Lys Phe Cys Leu Asn Ile Ala Gly Asp Thr Pro Ser Ser Asn Arg Leu
385                 390                 395                 400
Phe Asp Ala Ile Val Ser His Cys Val Pro Val Ile Ile Ser Asp Asp
                405                 410                 415
Ile Glu Leu Pro Phe Glu Asp Val Leu Asp Tyr Ser Ala Phe Cys Val
                420                 425                 430
Phe Val Arg Ala Ser Asp Ala Val Lys Arg Gly Phe Leu Leu His Leu
                435                 440                 445
Leu Arg Gly Ile Ser Gln Glu Glu Trp Thr Ala Met Trp Arg Arg Leu
        450                 455                 460
Lys Glu Val Ala His His Phe Glu Tyr Gln Tyr Pro Ser Gln Pro Gly
465                 470                 475                 480
Asp Ala Val Gln Met Ile Trp Gly Ala Val Ala Arg Lys Met His Leu
                485                 490                 495
Val Lys Leu Gln Leu His Lys Arg Gly Arg Tyr Gln Arg Thr Phe Ser
                500                 505                 510
Glu Ser

<210> SEQ ID NO 24
<211> LENGTH: 1802
<212> TYPE: DNA
<213> ORGANISM: Zea mays

<400> SEQUENCE: 24 cccccctccca gctagccatg gccgcgcccc gctctggtcg ccgcccgcac tgccactgct      60
agccatggcc gccgccgccg cctgccggag cccgctggtc tggctcttcg cgctcgtcac     120
cgcactcttc ttcttctcct ggtacctcct cctcgactcc gccgcgggtc cagccgccgc     180
ccgccgcccc aaccagtggc tccgcctcgg cggcggcggg cggcgctccg gtcccggtag     240
gaaatgcgac cccgcggagg cgctgctgcg agtgttcatg tacgacctgc ccccgagtt      300
ccacttcgga ctgctcgact ggaagccccc cggcttcggc ggcggcgtgt ggcccgacat     360
cagggacggc gtgcctgact acccgggggg cctcaacctg cagcacagca tcgagtattg     420
gctcacccct gacctcctgg cctccgagca gggcgcgccc acgccctgcg cagtggcgcg     480
ggtgcgccac gcggcggacg ccgacgtcgt cttcgtgccc ttcttcgcct cgctcagctt     540
caaccgccac tcccgggtgg taccgcccgc gcgggacagc gaggaccgcg cgctgcagcg     600
gaggctcctc gagttcctcg ccgcgcggcc cgagtggcgg aggactggcg gcgggaccga     660
cgtcgtgctc gcgcatcacc ccaacgggat gctcgacgcg cgctacaggt tctggccctg     720
cgtcttcgtg ctctgcgact cgggaggta cccgcccagc gtcgccaacc tcgacaagga     780
cgtcatcgcg ccctaccggc acctcgtcgc caacttcgct aatgacaccg ccggatacga     840
cgaccggccg acattgctct acttccaagg cgccatctac aggaaggacg gtggtttcat     900
ccggcaagaa ctgtattacc ttctgaaaga cgagaaagat gtgcatttct catttggaag     960
```

```
cgtagccggt aatgggatcg agcaagcaac acaagggatg cggtcatcca agttctgcct    1020
caacattgca ggtgacactc catcctccaa ccgcctcttt gactccatag tcagtcactg    1080
tgttcccgtc acgatcagcg atgagattga gctcccgttt gaggatgtcc tcgactactc    1140
gaagttcagt gtcatagtac gtggcgcaga cgcagtcaag aagggggtttc taatgaacct    1200 gatcaaaggg atcagccgag aagagtggac acgcatgtgg aacaggctaa aggaagtgga    1260
aaagcacttt gagtaccaat acccatctca gaccgatgat gccgtgcaga tgatatggaa    1320
ggccattgct cggaaggtgc cgtctatccg gctgaagatt aacagactgc aaagattttc    1380
tctgtttgag actaacagga cagatgagac tctaccccca tcttcttctt ggctacagaa    1440
tcaggctcct tgattttgga ctagcaagct caggctttcg ccatgttttc aatctcgtag    1500
aatcaagagt tgatactgaa gaccaaatct taatcgcttg actgggggca gatgttagta    1560
tgttacagct gcagacatta gcggatagta agttgaaaac actttagcat agcagaatta    1620
catatccagt ggcacatcat tttcttcatt ttttttttct tttgcttgcg attcatccaa    1680
agtgtcctcg gctgcagact aaggacaatg aatttttgtat gtgaagctgt atattctagg    1740
cggcaatata gttactgatc agttacagtt gctgagcaaa aaaaaaaaaa aaaaaaaaa    1800 aa                                                                   1802
```

<210> SEQ ID NO 25
<211> LENGTH: 462
<212> TYPE: PRT
<213> ORGANISM: Zea mays

<400> SEQUENCE: 25

```
Met Ala Ala Ala Ala Cys Arg Ser Pro Leu Val Trp Leu Phe Ala
1               5                   10                  15

Leu Val Thr Ala Leu Phe Phe Ser Trp Tyr Leu Leu Asp Ser
                20                  25                  30

Ala Ala Gly Pro Ala Ala Ala Arg Arg Pro Asn Gln Trp Leu Arg Leu
                35                  40                  45

Gly Gly Gly Gly Arg Arg Ser Gly Pro Gly Arg Lys Cys Asp Pro Ala
    50                  55                  60

Glu Ala Leu Leu Arg Val Phe Met Tyr Asp Leu Pro Pro Glu Phe His
65                  70                  75                  80

Phe Gly Leu Leu Asp Trp Lys Pro Pro Gly Phe Gly Gly Gly Val Trp
                85                  90                  95

Pro Asp Ile Arg Asp Gly Val Pro Asp Tyr Pro Gly Gly Leu Asn Leu
                100                 105                 110

Gln His Ser Ile Glu Tyr Trp Leu Thr Leu Asp Leu Leu Ala Ser Glu
            115                 120                 125

Gln Gly Ala Pro Thr Pro Cys Ala Val Ala Arg Val Arg His Ala Ala
    130                 135                 140

Asp Ala Asp Val Val Phe Val Pro Phe Ala Ser Leu Ser Phe Asn
145                 150                 155                 160

Arg His Ser Arg Val Val Pro Pro Ala Arg Asp Ser Glu Asp Arg Ala
                165                 170                 175

Leu Gln Arg Arg Leu Leu Glu Phe Leu Ala Ala Arg Pro Glu Trp Arg
                180                 185                 190

Arg Thr Gly Gly Arg Asp His Val Val Leu Ala His His Pro Asn Gly
            195                 200                 205

Met Leu Asp Ala Arg Tyr Arg Phe Trp Pro Cys Val Phe Val Leu Cys
```

```
                     210                 215                 220
Asp Phe Gly Arg Tyr Pro Pro Ser Val Ala Asn Leu Asp Lys Asp Val
225                 230                 235                 240

Ile Ala Pro Tyr Arg His Leu Val Ala Asn Phe Ala Asn Asp Thr Ala
                245                 250                 255

Gly Tyr Asp Asp Arg Pro Thr Leu Leu Tyr Phe Gln Gly Ala Ile Tyr
            260                 265                 270

Arg Lys Asp Gly Gly Phe Ile Arg Gln Glu Leu Tyr Tyr Leu Leu Lys
        275                 280                 285

Asp Glu Lys Asp Val His Phe Ser Phe Gly Ser Val Ala Gly Asn Gly
    290                 295                 300

Ile Glu Gln Ala Thr Gln Gly Met Arg Ser Ser Lys Phe Cys Leu Asn
305                 310                 315                 320

Ile Ala Gly Asp Thr Pro Ser Ser Asn Arg Leu Phe Asp Ser Ile Val
                325                 330                 335

Ser His Cys Val Pro Val Thr Ile Ser Asp Glu Ile Glu Leu Pro Phe
            340                 345                 350

Glu Asp Val Leu Asp Tyr Ser Lys Phe Ser Val Ile Val Arg Gly Ala
        355                 360                 365

Asp Ala Val Lys Lys Gly Phe Leu Met Asn Leu Ile Lys Gly Ile Ser
    370                 375                 380

Arg Glu Glu Trp Thr Arg Met Trp Asn Arg Leu Lys Glu Val Glu Lys
385                 390                 395                 400

His Phe Glu Tyr Gln Tyr Pro Ser Gln Thr Asp Asp Ala Val Gln Met
                405                 410                 415

Ile Trp Lys Ala Ile Ala Arg Lys Val Pro Ser Ile Arg Leu Lys Ile
            420                 425                 430

Asn Arg Leu Gln Arg Phe Ser Leu Phe Glu Thr Asn Arg Thr Asp Glu
        435                 440                 445

Thr Leu Pro Pro Ser Ser Ser Trp Leu Gln Asn Gln Ala Pro
    450                 455                 460

<210> SEQ ID NO 26
<211> LENGTH: 1674
<212> TYPE: DNA
<213> ORGANISM: Zea mays

<400> SEQUENCE: 26
ctagcatctc ttttctcata tgcagtacca catatatttc gttttacctc tattgagtat    60
aaaatcttta aatcgtagag tcttctaccg taactctatt tccctattta ctattgtacg   120
acttttaaca actagcacta catcgtcgac aaaaggtata caccaaggga tttcccctct   180
acgcccctg tgaccttatt catcacaaag gcgaaaaggt aagtgcttaa agttgatctt    240
tgatgtagta ctgtcctaat tgtgaagttg tatatgtcca tattacttgt tcgaacacta   300
gtcacaacat tggtccttag gagtatcttc atgaaggtgc ctcaaaataa tgctcccaaa   360
attaaaatac tacaacataa agtgtttagg gtactaaaaa aacaaatcga actccaccag   420
ttaagcccta tcatgtatt tttagaaaat aaagtatatt attagaaaac aaaaggttca    480
gtatattgta gaaaaatag gacactaatc tagggtgtag tatatctgga tcactttatt    540
gtctaaccta tgttttttg ttaaaaaatt tataaaacag gattacctgt ttttatgagt    600
tgaacccaat atcttaaaac aacacaatga ttaaaggctt tattggagat attctaatga   660
gcccaatgta tttcattaaa atttatgttt gtccaaatcc atttcataac atttttggt    720
```

```
actttatcat aaaccttaat caaatcaata aaaacatgtg tagatcatcc ttttgttctc    780
tatactggtc tatcacttgt cttattaaaa atgactttca tggttgatct tttaggtatg    840
aaaccgattt ggttagaaga gatcctcgct attccattga gggagggagc attcgacagg    900
agctatatta tatgctcaaa gaagaaaagg atgtttactt ttcctttgga agtgtccagg    960 accatgggc cagcaaagct agccaaggaa tgcactcatc aaaattttgc ctaaatattg    1020
ctggggacac cccttcttcc aatcgtctgt tgatgcgat agttaccac tgtgtccctg    1080 ttatcatcag tgacgacatt gagctacctt atgaggatgt gttggattat tcaaaattct    1140
ccatctttgt ccgttcgtct gatgctgtta agaaaggtta cctgatgaga ctgctcagtg    1200
gtgtaagcaa gcaacaatgg acaaagatgt gggataggct caaagaggtg gataaacatt    1260
ttgagtatca gtatccatca cagaaggatg atgcagtcca gatgatctgg caagcattgt    1320
ctagaaaggt gccatcaatt aagctgaagg ttcacagatc taatagattt tcaagatcta    1380
acagaggaaa ataaacagaa aggggtgtgt ctatcttgtc tctattggct aatctaatgt    1440
aacacatttc actgacacag gctctcagcc tttcccagtt gcacaaaata gatagattgt    1500
aatactcagg ttatctttag gaaaggtttg taccttaaga tttgttggtt cagttgaagc    1560
atatactgtc aagtcaaagg ttgttttgta aggtatgtta aatgtaatca tgaaagaaag    1620
acttggtttt gctgtttcaa aaaaaaaaaa aaaaaaaaa aaaaaaaaaa aaaa           1674
```

```
<210> SEQ ID NO 27
<211> LENGTH: 1674
<212> TYPE: PRT
<213> ORGANISM: Zea mays

<400> SEQUENCE: 27
```

```
Cys Thr Ala Gly Cys Ala Thr Cys Thr Cys Thr Thr Thr Cys Thr
1               5                   10                  15

Cys Ala Thr Ala Thr Gly Cys Ala Gly Thr Ala Cys Cys Ala Cys Ala
            20                  25                  30

Thr Ala Thr Ala Thr Thr Cys Gly Thr Thr Thr Ala Cys Cys
        35                  40                  45

Thr Cys Thr Ala Thr Thr Gly Ala Gly Thr Ala Thr Ala Ala Ala
    50                  55                  60

Thr Cys Thr Thr Thr Ala Ala Ala Thr Cys Gly Thr Ala Gly Ala Gly
65                  70                  75                  80

Thr Cys Thr Thr Cys Thr Ala Cys Cys Gly Thr Ala Ala Cys Thr Cys
                85                  90                  95

Thr Ala Thr Thr Thr Cys Cys Cys Thr Ala Thr Thr Ala Cys Thr
            100                 105                 110

Ala Thr Thr Gly Thr Ala Cys Gly Ala Cys Thr Thr Thr Ala Ala
        115                 120                 125

Cys Ala Ala Cys Thr Ala Gly Cys Ala Cys Thr Ala Cys Ala Thr Cys
130                 135                 140

Gly Thr Cys Gly Ala Cys Ala Ala Ala Gly Gly Thr Ala Thr Ala
145                 150                 155                 160

Cys Ala Cys Cys Ala Ala Gly Gly Gly Ala Thr Thr Cys Cys Cys
            165                 170                 175

Cys Thr Cys Thr Ala Cys Gly Cys Cys Cys Cys Thr Gly Thr Gly
        180                 185                 190

Ala Cys Cys Thr Thr Ala Thr Thr Cys Ala Thr Cys Ala Ala
    195                 200                 205
```

```
Ala Gly Gly Cys Gly Ala Ala Ala Gly Gly Thr Ala Ala Gly Thr
    210                 215                 220

Gly Cys Thr Thr Ala Ala Ala Gly Thr Thr Gly Ala Thr Cys Thr Thr
225                 230                 235                 240

Thr Gly Ala Thr Gly Thr Ala Gly Thr Ala Cys Thr Gly Thr Cys Cys
                245                 250                 255

Thr Ala Ala Thr Thr Gly Thr Gly Ala Ala Gly Thr Thr Gly Thr Ala
            260                 265                 270

Thr Ala Thr Gly Thr Cys Cys Ala Thr Ala Thr Ala Cys Thr Thr
        275                 280                 285

Gly Thr Thr Cys Gly Ala Ala Cys Ala Cys Thr Ala Gly Thr Cys Ala
    290                 295                 300

Cys Ala Ala Cys Ala Thr Thr Gly Gly Thr Cys Cys Thr Thr Ala Gly
305                 310                 315                 320

Gly Ala Gly Thr Ala Thr Cys Thr Thr Cys Ala Thr Gly Ala Ala Gly
                325                 330                 335

Gly Thr Gly Cys Cys Thr Cys Ala Ala Ala Thr Ala Ala Thr Gly
    340                 345                 350

Cys Thr Cys Cys Cys Ala Ala Ala Thr Thr Ala Ala Ala Ala Thr
        355                 360                 365

Ala Cys Thr Ala Cys Ala Ala Cys Ala Thr Ala Ala Ala Gly Thr Gly
    370                 375                 380

Thr Thr Thr Ala Gly Gly Gly Thr Ala Cys Thr Ala Ala Ala Ala Ala
385                 390                 395                 400

Ala Ala Cys Ala Ala Ala Thr Cys Gly Ala Ala Cys Thr Cys Cys Ala
                405                 410                 415

Cys Cys Ala Gly Thr Thr Ala Ala Gly Cys Cys Cys Thr Ala Thr Ala
            420                 425                 430

Thr Cys Ala Thr Gly Thr Ala Thr Thr Thr Ala Gly Ala Ala Ala
        435                 440                 445

Ala Thr Ala Ala Ala Gly Thr Ala Thr Ala Thr Thr Ala Thr Thr Ala
    450                 455                 460

Gly Ala Ala Ala Cys Ala Ala Ala Gly Gly Thr Thr Cys Ala
465                 470                 475                 480

Gly Thr Ala Thr Ala Thr Thr Gly Thr Ala Gly Ala Ala Ala Ala
                485                 490                 495

Ala Thr Ala Gly Gly Ala Cys Ala Cys Thr Ala Ala Thr Cys Thr Ala
            500                 505                 510

Gly Gly Gly Thr Gly Thr Ala Gly Thr Ala Thr Ala Cys Thr Gly
        515                 520                 525

Gly Ala Thr Cys Ala Cys Thr Thr Ala Thr Gly Thr Cys Thr
530                 535                 540

Ala Ala Cys Cys Thr Ala Thr Gly Thr Thr Thr Thr Thr Thr Thr Gly
545                 550                 555                 560

Thr Thr Ala Ala Ala Ala Ala Thr Thr Ala Thr Ala Ala Ala
                565                 570                 575

Ala Cys Ala Gly Gly Ala Thr Thr Ala Cys Cys Thr Gly Thr Thr Thr
            580                 585                 590

Thr Thr Ala Thr Gly Ala Gly Thr Gly Ala Ala Cys Cys Cys Ala
        595                 600                 605

Ala Thr Ala Thr Cys Thr Thr Ala Ala Ala Cys Ala Ala Cys Ala
    610                 615                 620

Cys Ala Ala Thr Gly Ala Thr Thr Ala Ala Ala Gly Gly Cys Thr Thr
```

-continued

```
              625                 630                 635                 640
Thr Ala Thr Thr Gly Gly Ala Gly Ala Thr Ala Thr Thr Cys Thr Ala
                    645                 650                 655
Ala Thr Gly Ala Gly Cys Cys Cys Ala Ala Thr Gly Thr Ala Thr Thr
                    660                 665                 670
Thr Cys Ala Thr Thr Ala Ala Ala Thr Thr Thr Ala Thr Gly Thr
                    675                 680                 685
Thr Thr Gly Thr Cys Cys Ala Ala Ala Thr Cys Cys Ala Thr Thr Thr
                    690                 695                 700
Cys Ala Thr Ala Ala Cys Ala Thr Thr Thr Thr Thr Gly Gly Thr
705                 710                 715                 720
Ala Cys Thr Thr Thr Ala Thr Cys Ala Thr Ala Ala Ala Cys Cys Thr
                    725                 730                 735
Thr Ala Ala Thr Cys Ala Ala Ala Thr Cys Ala Ala Thr Ala Ala Ala
                    740                 745                 750
Ala Ala Cys Ala Thr Gly Thr Gly Thr Ala Gly Ala Thr Cys Ala Thr
                    755                 760                 765
Cys Cys Thr Thr Thr Thr Gly Thr Cys Thr Cys Thr Ala Thr Ala
770                 775                 780
Cys Thr Gly Gly Thr Cys Thr Ala Thr Cys Ala Cys Thr Thr Gly Thr
785                 790                 795                 800
Cys Thr Thr Ala Thr Thr Ala Ala Ala Ala Thr Gly Ala Cys Thr
                    805                 810                 815
Thr Thr Cys Ala Thr Gly Gly Thr Thr Gly Ala Thr Cys Thr Thr Thr
                    820                 825                 830
Thr Ala Gly Gly Thr Ala Thr Gly Ala Ala Ala Cys Cys Gly Ala Thr
                    835                 840                 845
Thr Thr Gly Gly Thr Thr Ala Gly Ala Ala Ala Gly Ala Thr Cys
                    850                 855                 860
Cys Thr Cys Gly Cys Thr Ala Thr Thr Cys Cys Ala Thr Thr Gly Ala
865                 870                 875                 880
Gly Gly Gly Ala Gly Gly Ala Gly Cys Ala Thr Thr Cys Gly Ala
                    885                 890                 895
Cys Ala Gly Gly Ala Gly Cys Thr Ala Thr Ala Thr Thr Ala Thr Ala
                    900                 905                 910
Thr Gly Cys Thr Cys Ala Ala Ala Gly Ala Ala Gly Ala Ala Ala Ala
                    915                 920                 925
Gly Gly Ala Thr Gly Thr Thr Thr Ala Cys Thr Thr Thr Thr Cys Cys
930                 935                 940
Thr Thr Thr Gly Gly Ala Ala Gly Thr Gly Thr Cys Cys Ala Gly Gly
945                 950                 955                 960
Ala Cys Cys Ala Thr Gly Gly Gly Gly Cys Cys Ala Gly Cys Ala Ala
                    965                 970                 975
Ala Gly Cys Thr Ala Gly Cys Cys Ala Ala Gly Gly Ala Ala Thr Gly
                    980                 985                 990
Cys Ala Cys Thr Cys Ala Thr Cys Ala Ala Ala Ala Thr Thr Thr Thr
        995                 1000                1005
Gly Cys Cys Thr Ala Ala Ala Thr Ala Thr Thr Gly Cys Thr Gly
    1010                1015                1020
Gly Gly Gly Ala Cys Ala Cys Cys Cys Thr Thr Cys Thr Thr
    1025                1030                1035
Cys Cys Ala Ala Thr Cys Gly Thr Cys Thr Gly Thr Thr Thr Gly
    1040                1045                1050
```

Ala Thr Gly Cys Gly Ala Thr Ala Gly Thr Thr Ala Cys Cys Cys
1055                1060                1065

Ala Cys Thr Gly Thr Gly Thr Cys Cys Cys Thr Gly Thr Thr Ala
1070                1075                1080

Thr Cys Ala Thr Cys Ala Gly Thr Gly Ala Cys Gly Ala Cys Ala
1085                1090                1095

Thr Thr Gly Ala Gly Cys Thr Ala Cys Cys Thr Ala Thr Gly
1100                1105                1110

Ala Gly Gly Ala Thr Gly Thr Gly Thr Thr Gly Gly Ala Thr Thr
1115                1120                1125

Ala Thr Thr Cys Ala Ala Ala Ala Thr Thr Cys Thr Cys Cys Ala
1130                1135                1140

Thr Cys Thr Thr Thr Gly Thr Cys Cys Gly Thr Cys Gly Thr
1145                1150                1155

Cys Thr Gly Ala Thr Gly Cys Thr Gly Thr Thr Ala Ala Gly Ala
1160                1165                1170

Ala Ala Gly Gly Thr Thr Ala Cys Cys Thr Gly Ala Thr Gly Ala
1175                1180                1185

Gly Ala Cys Thr Gly Cys Thr Cys Ala Gly Thr Gly Gly Thr Gly
1190                1195                1200

Thr Ala Ala Gly Cys Ala Ala Gly Cys Ala Ala Cys Ala Ala Thr
1205                1210                1215

Gly Gly Ala Cys Ala Ala Ala Gly Ala Thr Gly Thr Gly Gly Gly
1220                1225                1230

Ala Thr Ala Gly Gly Cys Thr Cys Ala Ala Ala Gly Ala Gly Gly
1235                1240                1245

Thr Gly Gly Ala Thr Ala Ala Cys Ala Thr Thr Thr Thr Gly
1250                1255                1260

Ala Gly Thr Ala Thr Cys Ala Gly Thr Ala Thr Cys Cys Ala Thr
1265                1270                1275

Cys Ala Cys Ala Gly Ala Ala Gly Gly Ala Thr Gly Ala Thr Gly
1280                1285                1290

Cys Ala Gly Thr Cys Cys Ala Gly Ala Thr Gly Ala Thr Cys Thr
1295                1300                1305

Gly Gly Cys Ala Ala Gly Cys Ala Thr Thr Gly Thr Cys Thr Ala
1310                1315                1320

Gly Ala Ala Ala Gly Gly Thr Gly Cys Cys Ala Thr Cys Ala Ala
1325                1330                1335

Thr Thr Ala Ala Gly Cys Thr Gly Ala Ala Gly Gly Thr Thr Cys
1340                1345                1350

Ala Cys Ala Gly Ala Thr Cys Thr Ala Thr Ala Gly Ala Thr
1355                1360                1365

Thr Thr Thr Cys Ala Ala Gly Ala Thr Cys Thr Ala Ala Cys Ala
1370                1375                1380

Gly Ala Gly Gly Ala Ala Ala Thr Ala Ala Ala Cys Ala Gly
1385                1390                1395

Ala Ala Ala Gly Gly Gly Gly Thr Gly Thr Gly Thr Cys Thr Ala
1400                1405                1410

Thr Cys Thr Thr Gly Thr Cys Thr Cys Thr Ala Thr Thr Gly Gly
1415                1420                1425

Cys Thr Ala Ala Thr Cys Thr Ala Ala Thr Gly Thr Ala Ala Cys
1430                1435                1440

```
Ala Cys  Ala Thr Thr Thr Cys  Ala Cys Thr Gly Ala  Cys Ala Cys
    1445             1450                 1455

Ala Gly  Gly Cys Thr Cys Thr  Cys Ala Gly Cys Cys  Thr Thr Thr
    1460             1465                 1470

Cys Cys  Cys Ala Gly Thr Thr  Gly Cys Ala Cys Ala  Ala Ala Ala
    1475             1480                 1485

Thr Ala  Gly Ala Thr Ala Gly  Ala Thr Gly Thr Ala  Ala Ala Thr
    1490             1495                 1500

Ala Cys  Thr Cys Ala Gly Gly  Thr Thr Ala Thr Cys  Thr Thr Thr
    1505             1510                 1515

Ala Gly  Gly Ala Ala Ala Gly  Gly Thr Thr Thr Gly  Thr Ala Cys
    1520             1525                 1530

Cys Thr  Thr Ala Ala Gly Ala  Thr Thr Thr Gly Thr  Thr Gly Gly
    1535             1540                 1545

Thr Thr  Cys Ala Gly Thr Thr  Gly Ala Ala Gly Cys  Ala Thr Ala
    1550             1555                 1560

Thr Ala  Cys Thr Gly Thr Cys  Ala Ala Gly Thr Cys  Ala Ala Ala
    1565             1570                 1575

Gly Gly  Thr Thr Gly Thr Thr  Thr Thr Gly Thr Ala  Ala Gly Gly
    1580             1585                 1590

Thr Ala  Thr Gly Thr Thr Ala  Ala Ala Thr Gly Thr  Ala Ala Thr
    1595             1600                 1605

Cys Ala  Thr Gly Ala Ala Ala  Gly Ala Ala Ala Gly  Ala Cys Thr
    1610             1615                 1620

Thr Gly  Gly Thr Thr Thr Thr  Gly Cys Thr Gly Thr  Thr Thr Cys
    1625             1630                 1635

Ala Ala  Ala Ala Ala Ala Ala  Ala Ala Ala Ala Ala  Ala Ala Ala
    1640             1645                 1650

Ala Ala  Ala Ala Ala Ala Ala  Ala Ala Ala Ala Ala  Ala Ala Ala
    1655             1660                 1665

Ala Ala  Ala Ala Ala Ala
    1670

<210> SEQ ID NO 28
<211> LENGTH: 1893
<212> TYPE: DNA
<213> ORGANISM: Rye

<400> SEQUENCE: 28
caccagatcg acgattcgcc atgctccccc gtgcaccact ccggccatga gcctcgcgct      60
ccatggcgcc gccccgtgct cgcgccctac tcctgccgct ggcggcggcc accgtcctag     120
tcgcctccac catcttcctc ttcgccgccg ccggcgccgg ccgctggcgc cccgccgaca     180
ccggcctccc cgtcccggca accccgccg acttctcggc cgtccctatc ggtgtgagtg      240
taacatccac cgccaagggt aaagagctct cctttcttga tgagaatggc cgccccgacg     300
accccagctc cggctcggcg gcggctgctg aacctgggag atgcgacccc cgcgacgccg     360
ccgtcagggt gttcgtttac gacatgccgc cggagttcca cttcgggctg ctcggctggg     420
cgccacctcc cgggaacggc ggcggcgtct ggcctgacgt caggggcggc acagtcccgc     480
gctaccccgg tgggcttaac cagcagcaca gcgtggagta ctggctcacg ctggacctcc     540
tggcatcctc gtcggcagca ccgtgcggtc cggctgtgag ggttgccgac tctcgtgatg     600
cggacctgat cttcgtcccc ttcttcgcgt ccctcagtta caaccgccac tccaaggccg     660
tgccgccgga gaaggtaagc agagacatgt acctacagga gaagctcgtc aggtatctgg     720
```

-continued

```
tggcgcaacc ggagtggaag aggtccgggg gtgccgacca tgtcgtcgtc gcgcaccacc    780
ccaacagctt actccacgcc cggtcggcgc tgttcccagc agtgttcgtg ctgtctgact    840
tcgggaggta ccaccccagg gttgccagct tggagaagga tctcattgcg ccataccgac    900
atatggcaaa gacatttgtg aatgacacgg ccgggtttga tgatcggccg acattgttat    960
acttccgggg agccatttac agaaaggagg gaggaaacat tcggcaggaa ctatataata   1020
tgctcaaaga tgagagggat gttttctttt ccttcggaag cgtccaggac catggtgtca   1080
gcaaagccag ccagggaatg cactcatcaa agttttgcct aaacattgct ggggataccc   1140
catcttccaa tcgtctcttt gacgctatag taagccactg tgtccctgtt atcataagtg   1200
acgacattga gctcccttac gaggatatcc tagattattc aaagttctcc atctttgttc   1260
ggtcgtctga tgctattaaa aagggttact tgatgagact gattaaaggc ataaacaagc   1320
atcgatggac aaggatgtgg aagaggctca agaagtggga taaacatttt gagtaccagt   1380
tcccatctca taaggatgat gcggcccaga tgatctggca agcattggct aggaaggtgc   1440
cttcgatccg actgaaggca cataggttta gaagatcttc aagatctgaa agaggaaaca   1500
aataaacagg aaggaggtgt atgtattgat gatgtgctcc agatgatagg gcaagcagtg   1560
gctaggaaag gtgccttgat tcggatgaag gcacatatgt ttagtggatt tcaagatct    1620
gaaagaggaa ccaagtaaac aggaaaagtg tgtatgtatc gtgtttctag gctaatctaa   1680
cacagcattc actgacactg gcacgccagt tgcactttcc cttcgaggaa cattgtgaag   1740
tagaagattc aggttgagtg ttggttatac cttggaacaa acacaggttg agtgttgagt   1800
gttgaatgta tgttagcaag gcaaaaaaaa aaaaaaaaaa aaaaaaaaaa aaaaaaaaaa   1860
aaaaaaaaaa aaaaaaaaaa aaaaaaaaaa aaa                                1893
```

<210> SEQ ID NO 29
<211> LENGTH: 480
<212> TYPE: PRT
<213> ORGANISM: Rye

<400> SEQUENCE: 29

```
Met Ala Pro Pro Arg Ala Arg Ala Leu Leu Pro Leu Ala Ala Ala
1               5                   10                  15

Thr Val Leu Val Ala Ser Thr Ile Phe Leu Phe Ala Ala Gly Ala
                20                  25                  30

Gly Arg Trp Arg Pro Ala Asp Thr Gly Leu Pro Val Pro Ala Thr Pro
            35                  40                  45

Ala Asp Phe Ser Ala Val Pro Ile Gly Val Ser Val Thr Ser Thr Ala
50                  55                  60

Lys Gly Lys Glu Leu Ser Phe Leu Asp Glu Asn Gly Arg Pro Asp Asp
65                  70                  75                  80

Pro Ser Ser Gly Ser Ala Ala Ala Glu Pro Gly Arg Cys Asp Pro
                85                  90                  95

Arg Asp Ala Ala Val Arg Val Phe Val Tyr Asp Met Pro Pro Glu Phe
            100                 105                 110

His Phe Gly Leu Leu Gly Trp Ala Pro Pro Gly Asn Gly Gly Gly
            115                 120                 125

Val Trp Pro Asp Val Arg Gly Gly Thr Val Pro Arg Tyr Pro Gly Gly
        130                 135                 140

Leu Asn Gln Gln His Ser Val Glu Tyr Trp Leu Thr Leu Asp Leu Leu
145                 150                 155                 160
```

| | | | | | | | | | | | |
|---|---|---|---|---|---|---|---|---|---|---|---|
|Ala|Ser|Ser|Ser|Ala|Ala|Pro|Cys|Gly|Pro|Ala|Val|Arg|Val|Ala|Asp|
| | | |165| | | |170| | | |175| | | | |

Ala Ser Ser Ser Ala Ala Pro Cys Gly Pro Ala Val Arg Val Ala Asp
            165                 170                 175

Ser Arg Asp Ala Asp Leu Ile Phe Val Pro Phe Phe Ala Ser Leu Ser
        180                 185                 190

Tyr Asn Arg His Ser Lys Ala Val Pro Pro Glu Lys Val Ser Arg Asp
        195                 200                 205

Met Tyr Leu Gln Glu Lys Leu Val Arg Tyr Leu Val Ala Gln Pro Glu
    210                 215                 220

Trp Lys Arg Ser Gly Gly Ala Asp His Val Val Ala His His Pro
225                 230                 235                 240

Asn Ser Leu Leu His Ala Arg Ser Ala Leu Phe Pro Ala Val Phe Val
            245                 250                 255

Leu Ser Asp Phe Gly Arg Tyr His Pro Arg Val Ala Ser Leu Glu Lys
        260                 265                 270

Asp Leu Ile Ala Pro Tyr Arg His Met Ala Lys Thr Phe Val Asn Asp
        275                 280                 285

Thr Ala Gly Phe Asp Asp Arg Pro Thr Leu Leu Tyr Phe Arg Gly Ala
    290                 295                 300

Ile Tyr Arg Lys Glu Gly Gly Asn Ile Arg Gln Glu Leu Tyr Asn Met
305                 310                 315                 320

Leu Lys Asp Glu Arg Asp Val Phe Phe Ser Phe Gly Ser Val Gln Asp
                325                 330                 335

His Gly Val Ser Lys Ala Ser Gln Gly Met His Ser Ser Lys Phe Cys
            340                 345                 350

Leu Asn Ile Ala Gly Asp Thr Pro Ser Ser Asn Arg Leu Phe Asp Ala
        355                 360                 365

Ile Val Ser His Cys Val Pro Val Ile Ile Ser Asp Asp Ile Glu Leu
        370                 375                 380

Pro Tyr Glu Asp Ile Leu Asp Tyr Ser Lys Phe Ser Ile Phe Val Arg
385                 390                 395                 400

Ser Ser Asp Ala Ile Lys Lys Gly Tyr Leu Met Arg Leu Ile Lys Gly
                405                 410                 415

Ile Asn Lys His Arg Trp Thr Arg Met Trp Lys Arg Leu Lys Glu Val
            420                 425                 430

Asp Lys His Phe Glu Tyr Gln Phe Pro Ser His Lys Asp Asp Ala Ala
        435                 440                 445

Gln Met Ile Trp Gln Ala Leu Ala Arg Lys Val Pro Ser Ile Arg Leu
    450                 455                 460

Lys Ala His Arg Phe Arg Arg Ser Ser Arg Ser Glu Arg Gly Asn Lys
465                 470                 475                 480

<210> SEQ ID NO 30
<211> LENGTH: 1869
<212> TYPE: DNA
<213> ORGANISM: Zea mays

<400> SEQUENCE: 30

```
agctaccgct ccgttcttgt acgatggttc ctgaggatgc aaaatggtga gttgaatttg      60
attcacctgc gtgctgtttt gctgcatggt ggtggtggag aggaagatgc agccattgcc     120
gccgcctgag cgccggaggg tcgttcgttt cgtggtcttc atggccgtct ccctcctggc     180
cctgttctgc tgggctctcg tcaattccag gatcaacgtc gccatgcctt actctgcttt     240
cgtgatgcgc gatgtcgaca agacgcccgc attcacaggc ctagaagaca ggcagaggca     300
ccccgccggc gacccagcgt ggacctcggc ggcgccgcag gccgtgccgg tgaccagtaa     360
```

```
cgtcacggcg ggctcggtga aattgggtga tccggtgctc cgggagccgc tggcaggaga    420
agcggaacgg gaacggagcg agaggtgcga cgcggacagc gcggcgctca gggtgtatat    480
gtacgacctg ccggcggagt tccatttcgg catgctcggg tgggaacgga aggggaagct    540
ggcgtggccc gacgtccgcg acgcccacgc cgcgccgcac taccccggcg ggctcaacct    600
gcagcacagc gtggcgtact ggctcacgct ggacatcctg tcctccgccc tgccgcccgg    660
cagcgacgtg tcagagaca ggccctgtgt cgccgtcagg gtgacgaacg cgagcctcgc    720
caacgtcttc ttcgtgccgt tcttcgcgtc actgagctac aaccgccact cgaagctccg    780
ccgcggggag agggtgagca ggaacagggt cctgcaggcc gagctggtca agtacctgat    840
gcggaaggag gagtggagga ggtggggcgg caagaaccac ctcatcgtgc cgcaccaccc    900
caacagcttg atggaggcac ggaagaagct cagcgccgcc atgttcgtgt tgtctgactt    960
cgggaggtac tcgccggacg ttgccaacct caagaaggac gtcatcgcac cgtacaagca   1020
cgtcctccgc tccttaggcg atggcgactg ccatcgttc gagcaacgtc ccatcctcgc   1080
atacttccaa ggggccatcc atcggaaagc tggcgggaag gttcgccaga agctgtacca   1140
tctgctcaag gacgagcgcg acgtgcactt cacctacggc agcgtccggc agaacggcat   1200
ccggcgcgcc accgccggga tgtccacgtc gaagttctgc ctcaacatcg ccggcgacac   1260
gccgtcctcg aaccggctct tcgacgccat cgtcagccac tgtgtcccgg tcatcatcag   1320
cgacgacatc gagttgccat tgaggacat gctcgactac tcggagttct gcgtgttcgt   1380
gcgctccgcc gacgccgcca agaagggatt cctactacgg ctgctacggg gcatatcgcg   1440
cgaggagtgg accaagatgt ggatgagatt gaagaaggtg actcaccatt tcgagtacca   1500 gtaccccttca cggtcaggtg atgctgtcca gatgacatgg agcgcagtgg cgcggaagat   1560
gcattcggtg cagctgcagc ttcacaagcg cgctagattc cacaggacgg tttctgtatg   1620
aatatgatca aggccaccga gcgcggaagt ctggatgtgg caagattcgt cagttgcact   1680
gtgcagatga ttttttaga cttaactgac ataaaggtaa taacgggtga ataggtgtca   1740
tttttgtaat gtttacttcc ctaaaagaaa tagagatgtg agacttgaaa gcataaaatg   1800
cactatctta atctagtatt aaaaaaaaaa aaaaaaaaaa aaaaaaaaaa aaaaaaaaaa   1860
aaaaaaaaa                                                           1869
```

<210> SEQ ID NO 31
<211> LENGTH: 511
<212> TYPE: PRT
<213> ORGANISM: Zea mays

<400> SEQUENCE: 31

```
Met Val Val Glu Arg Lys Met Gln Pro Leu Pro Pro Glu Arg
1               5                   10                  15

Arg Arg Val Val Arg Phe Val Val Phe Met Ala Val Ser Leu Leu Ala
            20                  25                  30

Leu Phe Cys Trp Ala Leu Val Asn Ser Arg Ile Asn Val Ala Met Pro
        35                  40                  45

Tyr Ser Ala Phe Val Met Arg Asp Val Asp Lys Thr Pro Ala Phe Thr
    50                  55                  60

Gly Leu Glu Asp Arg Gln Arg His Pro Ala Gly Asp Pro Ala Trp Thr
65                  70                  75                  80

Ser Ala Ala Pro Gln Ala Val Pro Val Thr Ser Asn Val Thr Ala Gly
                85                  90                  95
```

```
Ser Val Lys Leu Gly Asp Pro Val Leu Arg Glu Pro Leu Ala Gly Glu
            100                 105                 110

Ala Glu Arg Glu Arg Ser Glu Arg Cys Asp Ala Asp Ser Ala Ala Leu
        115                 120                 125

Arg Val Tyr Met Tyr Asp Leu Pro Ala Glu Phe His Phe Gly Met Leu
    130                 135                 140

Gly Trp Glu Arg Lys Gly Lys Leu Ala Trp Pro Asp Val Arg Asp Ala
145                 150                 155                 160

His Ala Ala Pro His Tyr Pro Gly Gly Leu Asn Leu Gln His Ser Val
                165                 170                 175

Ala Tyr Trp Leu Thr Leu Asp Ile Leu Ser Ser Ala Leu Pro Pro Gly
            180                 185                 190

Ser Asp Val Val Arg Asp Arg Pro Cys Val Ala Val Arg Val Thr Asn
        195                 200                 205

Ala Ser Leu Ala Asn Val Phe Phe Val Pro Phe Phe Ala Ser Leu Ser
    210                 215                 220

Tyr Asn Arg His Ser Lys Leu Arg Arg Gly Glu Arg Val Ser Arg Asn
225                 230                 235                 240

Arg Val Leu Gln Ala Glu Leu Val Lys Tyr Leu Met Arg Lys Glu Glu
                245                 250                 255

Trp Arg Arg Trp Gly Gly Lys Asn His Leu Ile Val Pro His His Pro
            260                 265                 270

Asn Ser Leu Met Glu Ala Arg Lys Leu Ser Ala Ala Met Phe Val
        275                 280                 285

Leu Ser Asp Phe Gly Arg Tyr Ser Pro Asp Val Ala Asn Leu Lys Lys
    290                 295                 300

Asp Val Ile Ala Pro Tyr Lys His Val Leu Arg Ser Leu Gly Asp Gly
305                 310                 315                 320

Asp Ser Pro Ser Phe Glu Gln Arg Pro Ile Leu Ala Tyr Phe Gln Gly
                325                 330                 335

Ala Ile His Arg Lys Ala Gly Lys Val Arg Gln Lys Leu Tyr His
            340                 345                 350

Leu Leu Lys Asp Glu Arg Asp Val His Phe Thr Tyr Gly Ser Val Arg
    355                 360                 365

Gln Asn Gly Ile Arg Arg Ala Thr Ala Gly Met Ser Thr Ser Lys Phe
370                 375                 380

Cys Leu Asn Ile Ala Gly Asp Thr Pro Ser Ser Asn Arg Leu Phe Asp
385                 390                 395                 400

Ala Ile Val Ser His Cys Val Pro Val Ile Ile Ser Asp Asp Ile Glu
                405                 410                 415

Leu Pro Phe Glu Asp Met Leu Asp Tyr Ser Glu Phe Cys Val Phe Val
            420                 425                 430

Arg Ser Ala Asp Ala Ala Lys Lys Gly Phe Leu Leu Arg Leu Leu Arg
    435                 440                 445

Gly Ile Ser Arg Glu Glu Trp Thr Lys Met Trp Met Arg Leu Lys Lys
450                 455                 460

Val Thr His His Phe Glu Tyr Gln Tyr Pro Ser Arg Ser Gly Asp Ala
465                 470                 475                 480

Val Gln Met Thr Trp Ser Ala Val Ala Arg Lys Met His Ser Val Gln
                485                 490                 495

Leu Gln Leu His Lys Arg Ala Arg Phe His Arg Thr Val Ser Val
            500                 505                 510
```

```
<210> SEQ ID NO 32
<211> LENGTH: 1744
<212> TYPE: DNA
<213> ORGANISM: Arabidopsis thaliana

<400> SEQUENCE: 32
cttcggcgtt tcatcgtttt ctcatctacc tcgaaatttt ctcgtcactc taatcaaaaa     60
tctcacttcg ttattttctc gggaaaaatt tcccgatcac taaacctagt ttttagatat    120
tttctctcct ggattctgga tctacacaat ctttcttcct cttcttctat gaatctgttc    180
atcgtaattt cagattcttg atatatgatt ccttttctcc aatctcttct cttagctctc    240
agagatgggt gagaaaacaa actcacgtta tctcggtgta atcatcactc gaaaatctat    300
aattttcttg ttcatatcaa tcatcaccgt cctttcttgg ttttttatct tttcttccac    360
aaaccctaac cgagttctcg atcacatctc agtatcagaa tccacagatg tacctctcat    420
catcatcaag aactcaaaca gttctccaca aaacaacgca ccaaaacccc aaaacagaga    480
aggagcagaa acagaggaac ccattaaaga aacagagga ggaacaaaaa cagagtcatc    540
catgaatcaa acagaggcg aaaccctccg gtgtatccaa agggtttctc cttctccaag    600
gccattgaaa gtctacatgt atgatatgag tccagagttt cattttgggt tattgggttg    660
gaaaccagag agaaacggtg tcgtttggcc tgatatcaga gtcaatgttc ctcaccatcc    720
aggtggtctt aacttgcagc acagtgttga gtattggctc acattagatc ttttgttctc    780
tgagcttcca gaagattcta gaagctctcg ggccgcgata cgtgtaaaga actcgagcga    840
agctgatgtc gtgttcgtgc ccttcttctc ttcattgagc tataaccgat tctctaaggt    900
taaccaaaag cagaagaaga gccaggacaa agagttgcag gaaaatgtgg tgaaatacgt    960
aacgtcccaa aaagagtgga agacctcagg agggaaggat catgtgatca tggcgcatca   1020
tccgaatagt atgtcgacgg caaggcataa gctatttccg gcgatgtttg tggtcgctga   1080
ctttggtaga tactcgccac atgttgccaa tgttgacaaa gacattgtgg ctccatacaa   1140
acaccttgtt ccatcgtatg ttaatgacac atcgggcttt gatggccgtc cgatcttgct   1200
ctacttccaa ggagccatct accgcaaagc tggtggattt gtgagacaag agctatataa   1260
tcttctcaaa gaagaaaaag acgtccactt ctctttcgga agcgtaagga accacggcat   1320
atctaaagcc ggcgaaggaa tgagatcgtc caagttctgt ctcaacatag ccggggatac   1380
accatcctcg aatcgcctct tcgacgccat agctagtcac tgtatacccg tgatcattag   1440
cgatgacatc gagttaccat atgaggatgt cctcaactac aatgagttct gtctctttgt   1500
cagatcatca gacgctttaa agaaagggtt tctgatgggt cttgtcagga gtattggcag   1560
agaagagtat aataagatgt ggcttcggtt gaaggaagtg gagaggtatt tcgatttgcg   1620
ttttccggtg aaggatgacg agggagatta tgcagttcag atgatttgga aagctgttgc   1680
caggaaagct cctttggtga agatgaaggt tcacagattt cagaggttta caaggccttt   1740
ttag                                                                1744

<210> SEQ ID NO 33
<211> LENGTH: 1500
<212> TYPE: DNA
<213> ORGANISM: Arabidopsis thaliana

<400> SEQUENCE: 33
atgggtgaga aaacaaactc acgttatctc ggtgtaatca tcactcgaaa atctataatt     60
ttcttgttca tatcaatcat caccgtcctt tcttggtttt tatcttttc ttccacaaac    120
```

```
cctaaccgag ttctcgatca catctcagta tcagaatcca cagatgtacc tctcatcatc    180
atcaagaact caaacagttc tccacaaaac aacgcaccaa aaccccaaaa cagagaagga    240
gcagaaacag aggaacccat taaagaaaac agaggaggaa caaaaacaga gtcatccatg    300
aatcaaaaca gaggcgaaac cctccggtgt atccaaaggg tttctccttc tccaaggcca    360
ttgaaagtct acatgtatga tatgagtcca gagtttcatt ttgggttatt gggttggaaa    420
ccagagagaa acggtgtcgt ttggcctgat atcagagtca atgttcctca ccatccaggt    480
ggtcttaact tgcagcacag tgttgagtat tggctcacat tagatctttt gttctctgag    540
cttccagaag attctagaag ctctcgggcc gcgatacgtg taaagaactc gagcgaagct    600
gatgtcgtgt tcgtgcccct tcttctcttca ttgagctata accgattctc taaggttaac    660
caaaagcaga agaagagcca ggacaaagag ttgcaggaaa atgtggtgaa atacgtaacg    720
tcccaaaaag agtggaagac ctcaggaggg aaggatcatg tgatcatggc gcatcatccg    780
aatagtatgt cgacggcaag gcataagcta tttccggcga tgtttgtggt cgctgacttt    840
ggtagatact cgccacatgt tgccaatgtt gacaaagaca ttgtggctcc atacaaacac    900
cttgttccat cgtatgttaa tgacacatcg ggctttgatg gccgtccgat cttgctctac    960
ttccaaggag ccatctaccg caaagctggt ggatttgtga acaagagct atataatctt   1020
ctcaaagaag aaaaagacgt ccacttctct ttcggaagcg taaggaacca cggcatatct   1080
aaagccggcg aaggaatgag atcgtccaag ttctgtctca acatagccgg ggatacacca   1140
tcctcgaatc gcctcttcga cgccatagct agtcactgta tacccgtgat cattagcgat   1200
gacatcgagt taccatatga ggatgtcctc aactacaatg agttctgtct ctttgtcaga   1260
tcatcagacg ctttaaagaa agggtttctg atgggtcttg tcaggagtat tggcagagaa   1320
gagtataata agatgtggct tcggttgaag gaagtggaga ggtatttcga tttgcgtttt   1380
ccggtgaagg atgacgaggg agattatgca gttcagatga ttttggaaagc tgttgccagg   1440
aaagctcctt tggtgaagat gaaggttcac agatttcaga ggtttacaag gcctttttag   1500
```

<210> SEQ ID NO 34
<211> LENGTH: 499
<212> TYPE: PRT
<213> ORGANISM: Arabidopsis thaliana

<400> SEQUENCE: 34

```
Met Gly Glu Lys Thr Asn Ser Arg Tyr Leu Gly Val Ile Ile Thr Arg
1               5                   10                  15

Lys Ser Ile Ile Phe Leu Phe Ser Ile Ile Thr Val Leu Ser Trp
            20                  25                  30

Phe Phe Ile Phe Ser Ser Thr Asn Pro Asn Arg Val Leu Asp His Ile
        35                  40                  45

Ser Val Ser Glu Ser Thr Asp Val Pro Leu Ile Ile Lys Asn Ser
    50                  55                  60

Asn Ser Ser Pro Gln Asn Asn Ala Pro Lys Pro Gln Asn Arg Glu Gly
65                  70                  75                  80

Ala Glu Thr Glu Glu Pro Ile Lys Glu Asn Arg Gly Gly Thr Lys Thr
                85                  90                  95

Glu Ser Ser Met Asn Gln Asn Arg Gly Glu Thr Leu Arg Cys Ile Gln
            100                 105                 110

Arg Val Ser Pro Ser Pro Arg Pro Leu Lys Val Tyr Met Tyr Asp Met
        115                 120                 125

Ser Pro Glu Phe His Phe Gly Leu Leu Gly Trp Lys Pro Glu Arg Asn
```

```
            130                 135                 140
Gly Val Val Trp Pro Asp Ile Arg Val Asn Val Pro His His Pro Gly
145                 150                 155                 160

Gly Leu Asn Leu Gln His Ser Val Glu Tyr Trp Leu Thr Leu Asp Leu
                165                 170                 175

Leu Phe Ser Glu Leu Pro Glu Asp Ser Arg Ser Arg Ala Ala Ile
                180                 185                 190

Arg Val Lys Asn Ser Ser Glu Ala Asp Val Val Phe Val Pro Phe Phe
                195                 200                 205

Ser Ser Leu Ser Tyr Asn Arg Phe Ser Lys Val Asn Gln Lys Gln Lys
210                 215                 220

Lys Ser Gln Asp Lys Glu Leu Gln Glu Asn Val Val Lys Tyr Val Thr
225                 230                 235                 240

Ser Gln Lys Glu Trp Lys Thr Ser Gly Gly Lys Asp His Val Ile Met
                245                 250                 255

Ala His His Pro Asn Ser Met Ser Thr Ala Arg His Lys Leu Phe Pro
                260                 265                 270

Ala Met Phe Val Val Ala Asp Phe Gly Arg Tyr Ser Pro His Val Ala
                275                 280                 285

Asn Val Asp Lys Asp Ile Val Ala Pro Tyr Lys His Leu Val Pro Ser
290                 295                 300

Tyr Val Asn Asp Thr Ser Gly Phe Asp Gly Arg Pro Ile Leu Leu Tyr
305                 310                 315                 320

Phe Gln Gly Ala Ile Tyr Arg Lys Ala Gly Gly Phe Val Arg Gln Glu
                325                 330                 335

Leu Tyr Asn Leu Leu Lys Glu Glu Lys Asp Val His Phe Ser Phe Gly
                340                 345                 350

Ser Val Arg Asn His Gly Ile Ser Lys Ala Gly Glu Gly Met Arg Ser
                355                 360                 365

Ser Lys Phe Cys Leu Asn Ile Ala Gly Asp Thr Pro Ser Ser Asn Arg
                370                 375                 380

Leu Phe Asp Ala Ile Ala Ser His Cys Ile Pro Val Ile Ile Ser Asp
385                 390                 395                 400

Asp Ile Glu Leu Pro Tyr Glu Asp Val Leu Asn Tyr Asn Glu Phe Cys
                405                 410                 415

Leu Phe Val Arg Ser Ser Asp Ala Leu Lys Lys Gly Phe Leu Met Gly
                420                 425                 430

Leu Val Arg Ser Ile Gly Arg Glu Glu Tyr Asn Lys Met Trp Leu Arg
                435                 440                 445

Leu Lys Glu Val Glu Arg Tyr Phe Asp Leu Arg Phe Pro Val Lys Asp
450                 455                 460

Asp Glu Gly Asp Tyr Ala Val Gln Met Ile Trp Lys Ala Val Ala Arg
465                 470                 475                 480

Lys Ala Pro Leu Val Lys Met Lys Val His Arg Phe Gln Arg Phe Thr
                485                 490                 495

Arg Pro Phe

<210> SEQ ID NO 35
<211> LENGTH: 566
<212> TYPE: PRT
<213> ORGANISM: Oryza sativa

<400> SEQUENCE: 35

Met Ala Leu Thr Arg Arg Leu Leu Ile Asp Leu Ser Ser Arg Arg Arg
```

-continued

```
1               5                   10                  15
Leu Phe Asn Ala Gly Lys Phe Ser Thr Thr His Lys Lys Pro Val
            20                  25                  30
Leu His Glu Ala Val Ser Leu Ala Gly Phe Leu Arg Cys Ser Arg Ala
            35                  40                  45
Leu Val Ser Trp Met Val Ala Glu Arg Lys Met Gln Pro Ser Pro Ala
    50                  55                  60
Ala Pro Pro Ala Ala Glu His Arg Arg Ala Leu Leu Arg Tyr Val
65                  70                  75                  80
Val Phe Leu Ala Val Ser Leu Leu Ala Phe Ser Cys Trp Ala Leu Val
                85                  90                  95
Ser Ser Arg Ile Asp Gly Ala Val Leu Ala Ala Thr Ala Gly Gly Glu
                100                 105                 110
His Asp Asp His Asp Gly Ile Ile Val Arg Ser Ser Thr Gln Ala Glu
                115                 120                 125
Met Pro Ala Arg Gly Gly Asn Ala Thr Ser Arg Gly Ala Val Glu Val
            130                 135                 140
Gly Val Gly Thr Pro Ala Ala Met Ile Thr Arg Gln Pro Ser Ser Gly
145                 150                 155                 160
Glu Thr Thr Thr Thr Ala Ala Leu Ala Ala Thr Cys Asp Ala Glu Ser
                    165                 170                 175
Ala Leu Leu Arg Val Tyr Leu Tyr Asp Leu Pro Pro Glu Phe His Phe
                180                 185                 190
Gly Met Leu Gly Trp Asp Gly Lys Ala Ala Gly Ala Ala Trp Pro Asp
                195                 200                 205
Val Ala Gly Asp Pro Arg Ala Val Pro Arg Tyr Pro Gly Gly Leu Asn
210                 215                 220
Leu Gln His Ser Val Glu Tyr Trp Leu Thr Leu Asp Ile Leu Ser Ser
225                 230                 235                 240
Thr Thr Ser Gly Asp His Arg Arg Arg Pro Cys Thr Ala Val Arg
                245                 250                 255
Val Thr Asn Ala Ser Leu Ala Asp Val Phe Leu Val Pro Phe Phe Ala
            260                 265                 270
Ser Leu Ser Tyr Asn Arg Gln Ser Lys Ser Pro His Gly Gly His Gly
        275                 280                 285
Ser Gly Gly Arg Ser Asp Arg Gln Leu Gln Gly Glu Leu Val Arg Tyr
        290                 295                 300
Leu Ala Arg Arg Glu Glu Trp Arg Arg Trp Gly Gly Ala Asp His Leu
305                 310                 315                 320
Val Val Pro His His Pro Asn Ser Met Met Asp Ala Arg Arg Leu
                325                 330                 335
Ser Ala Ala Met Phe Val Leu Ser Asp Phe Gly Arg Tyr Pro Pro Asp
            340                 345                 350
Val Ala Asn Leu Arg Lys Asp Val Ile Ala Pro Tyr Lys His Val Val
            355                 360                 365
Pro Ser Leu Gly Asp Gly Asp Ser Pro Gly Phe Glu Gln Arg Pro Val
    370                 375                 380
Leu Ala Tyr Phe Gln Gly Ala Ile His Arg Lys Asn Gly Gly Arg Val
385                 390                 395                 400
Arg Gln Arg Leu Tyr Gln Leu Ile Lys Asp Glu Lys Asp Val His Phe
                405                 410                 415
Thr Tyr Gly Ser Val Arg Gln Asn Gly Ile Arg Arg Ala Thr Lys Gly
            420                 425                 430
```

```
Met Ala Ser Ser Lys Phe Cys Leu Asn Ile Ala Gly Asp Thr Pro Ser
        435                 440                 445

Ser Asn Arg Leu Phe Asp Ala Ile Val Ser His Cys Val Pro Val Ile
    450                 455                 460

Ile Ser Asp Asp Ile Glu Leu Pro Phe Glu Asp Val Leu Asp Tyr Ser
465                 470                 475                 480

Ala Phe Cys Val Phe Val Arg Ala Ser Asp Ala Val Lys Arg Gly Phe
                485                 490                 495

Leu Leu His Leu Leu Arg Gly Ile Ser Gln Glu Glu Trp Thr Ala Met
            500                 505                 510

Trp Arg Arg Leu Lys Glu Val Ala His His Phe Glu Tyr Gln Tyr Pro
            515                 520                 525

Ser Gln Pro Gly Asp Ala Val Gln Met Ile Trp Gly Ala Val Ala Arg
        530                 535                 540

Lys Met His Leu Val Lys Leu Gln Leu His Lys Arg Gly Arg Tyr Gln
545                 550                 555                 560

Arg Thr Phe Ser Glu Ser
                565

<210> SEQ ID NO 36
<211> LENGTH: 475
<212> TYPE: PRT
<213> ORGANISM: Oryza sativa

<400> SEQUENCE: 36

Met Pro Pro Arg Ala Arg Thr Leu Leu Met Pro Leu Ala Ala Ala Thr
1               5                   10                  15

Leu Leu Val Ala Ser Thr Ile Phe Leu Phe Ala Ala Thr Gly Ala Arg
            20                  25                  30

Trp Arg Pro Ala Asp Thr Gly Leu Pro Val Pro Ala Ala Asp Phe Ser
        35                  40                  45

Ala Ala Val Leu Glu Ser Ala Val Thr Asp Thr Thr Ala Ala Ala Lys
    50                  55                  60

Glu Leu Ser Phe Val Asp Glu Asn Gly Arg Pro Asp Asp Pro Ala Ser
65                  70                  75                  80

Ser Ser Ala Ala Ala Arg Cys Asp Pro Thr His Ala Ala Val Arg
                85                  90                  95

Val Phe Met Tyr Asp Leu Pro Pro Glu Phe His Phe Gly Ile Leu Gly
                100                 105                 110

Trp Ser Pro Pro Thr Asp Gly Ala Ala Asp Ala Ala Met Trp Pro Asp
            115                 120                 125

Val Gly Ser Gly Ala Ala Pro Arg Tyr Pro Gly Gly Leu Asn Gln
    130                 135                 140

Gln His Ser Val Glu Tyr Trp Leu Thr Leu Asp Leu Leu Ser Ser Ser
145                 150                 155                 160

Ser Pro Pro Cys Gly Ala Ala Val Arg Val Ala Asp Ser Arg Asp Ala
                165                 170                 175

Asp Val Val Phe Val Pro Phe Phe Ala Ser Leu Ser Tyr Asn Arg His
            180                 185                 190

Ser Arg Val Val Pro Pro Glu Lys Val Ser Arg Asp Lys Glu Leu Gln
        195                 200                 205

Glu Lys Leu Val Arg Tyr Leu Met Ala Gln Pro Glu Trp Lys Arg Ser
    210                 215                 220

Gly Gly Ala Asp His Val Ile Val Ala His His Pro Asn Ser Leu Leu
```

```
                225                 230                 235                 240
        His Ala Arg Ser Val Leu Phe Pro Val Val Phe Val Leu Ser Asp Phe
                        245                 250                 255
        Gly Arg Tyr His Pro Arg Val Ala Ser Leu Glu Lys Asp Val Ile Ala
                        260                 265                 270
        Pro Tyr Lys His Met Ala Lys Thr Phe Val Asn Asp Ser Ala Gly Phe
                        275                 280                 285
        Asp Asp Arg Pro Thr Leu Leu Tyr Phe Arg Gly Ala Ile Phe Arg Lys
                        290                 295                 300
        Glu Gly Gly Asn Ile Arg Gln Glu Leu Tyr Tyr Met Leu Lys Asp Glu
        305                 310                 315                 320
        Lys Asp Val Tyr Phe Ala Phe Gly Ser Val Gln Asp His Gly Ala Ser
                        325                 330                 335
        Lys Ala Ser Lys Gly Met His Ala Ser Lys Phe Cys Leu Asn Ile Ala
                        340                 345                 350
        Gly Asp Thr Pro Ser Ser Asn Arg Leu Phe Asp Ala Ile Val Ser His
                        355                 360                 365
        Cys Val Pro Val Ile Ile Ser Asp Asp Ile Glu Leu Pro Tyr Glu Asp
                        370                 375                 380
        Ala Leu Asp Tyr Ser Lys Phe Ser Ile Phe Val Arg Ser Ser Asp Ala
        385                 390                 395                 400
        Val Lys Lys Gly Tyr Leu Met Arg Leu Ile Arg Gly Val Ser Lys His
                        405                 410                 415
        Gln Trp Thr Arg Met Trp Asn Arg Leu Lys Glu Val Asp Lys His Phe
                        420                 425                 430
        Glu Tyr Gln Tyr Pro Ser Gln Lys Asp Asp Ala Val Gln Met Ile Trp
                        435                 440                 445
        Gln Ala Leu Ala Arg Lys Val Pro Ala Ile Arg Leu Lys Ser His Arg
                        450                 455                 460
        Ser Arg Arg Phe Ser Arg Tyr Asp Arg Gly Lys
        465                 470                 475

<210> SEQ ID NO 37
<211> LENGTH: 468
<212> TYPE: PRT
<213> ORGANISM: Oryza sativa

<400> SEQUENCE: 37

Met Ala Ala Ala Ala Ser Ala Ser Ala Ser Cys Arg Arg Arg Arg Pro
        1               5                   10                  15
        Ile Ala Trp Phe Phe Ala Ile Ala Ala Leu Leu Phe Phe Phe Ser Trp
                        20                  25                  30
        Tyr Leu Leu Leu Asp Ser Ala Ala Val Thr Pro Glu Pro Leu Leu Ala
                        35                  40                  45
        Ala Arg Gly Gln Gly Leu Arg Val Gly Ser Ser Gly Arg Lys Cys Asp
                        50                  55                  60
        Pro Ala Thr Ala Ala Leu Arg Val Phe Met Tyr Asp Leu Pro Ala Glu
        65                  70                  75                  80
        Phe His Phe Gly Leu Leu Asp Trp Glu Pro Gln Gly Gly Gly Gly Gly
                        85                  90                  95
        Gly Gly Gly Gly Val Trp Pro Asp Val Arg Gly Gly Val Pro Glu
                        100                 105                 110
        Tyr Pro Gly Gly Leu Asn Leu Gln His Ser Ile Glu Tyr Trp Leu Thr
                        115                 120                 125
```

Leu Asp Leu Leu Ala Ser Glu Gln Gly Ala Pro Thr Pro Cys Gly Ala
    130                 135                 140

Val Arg Val Arg His Ala Ala Ala Asp Val Val Phe Val Pro Phe
145                 150                 155                 160

Phe Ala Ser Leu Ser Phe Asn Arg His Ser Lys Val Val Pro Pro Ala
                165                 170                 175

Arg Ala Ser Glu Asp Arg Ala Leu Gln Arg Arg Leu Leu Asp Tyr Leu
            180                 185                 190

Ala Ala Arg Pro Glu Trp Arg Arg Ser Gly Gly Arg Asp His Val Val
            195                 200                 205

Leu Ala His His Pro Asn Gly Met Leu Asp Ala Arg Tyr Lys Leu Trp
    210                 215                 220

Pro Cys Val Phe Val Leu Cys Asp Phe Gly Arg Tyr Pro Pro Ser Val
225                 230                 235                 240

Ala Gly Leu Asp Lys Asp Val Ile Ala Pro Tyr Arg His Val Val Pro
                245                 250                 255

Asn Phe Ala Asn Asp Ser Ala Gly Tyr Asp Asp Arg Pro Thr Leu Leu
            260                 265                 270

Tyr Phe Gln Gly Ala Ile Tyr Arg Lys Asp Gly Gly Phe Ile Arg Gln
        275                 280                 285

Glu Leu Tyr Tyr Leu Leu Lys Asp Glu Lys Asp Val His Phe Ser Phe
    290                 295                 300

Gly Ser Val Val Gly Asn Gly Ile Glu Gln Ala Thr Gln Gly Met Arg
305                 310                 315                 320

Ala Ser Lys Phe Cys Leu Asn Ile Ala Gly Asp Thr Pro Ser Ser Asn
                325                 330                 335

Arg Leu Phe Asp Ser Ile Val Ser His Cys Val Pro Ile Ile Ile Ser
            340                 345                 350

Asp Glu Ile Glu Leu Pro Phe Glu Asp Val Leu Asp Tyr Ser Lys Phe
        355                 360                 365

Cys Ile Ile Val Arg Gly Ala Asp Ala Val Lys Lys Gly Phe Leu Met
    370                 375                 380

Asn Leu Ile Asn Gly Ile Ser Arg Glu Asp Trp Thr Arg Met Trp Asn
385                 390                 395                 400

Arg Leu Lys Glu Val Glu Arg His Phe Glu Tyr Gln Tyr Pro Ser Gln
                405                 410                 415

Asn Asp Asp Ala Val Gln Met Ile Trp Lys Ala Ile Ala Arg Lys Ala
            420                 425                 430

Pro Ser Ile Arg Leu Lys Val Asn Arg Leu Arg Arg Phe Ser Arg Phe
        435                 440                 445

Glu Thr Asn Arg Thr Asp Glu Thr Pro Thr Arg Ser Ser Trp Leu Glu
    450                 455                 460

Asn Gln Pro Ser
465

<210> SEQ ID NO 38
<211> LENGTH: 437
<212> TYPE: PRT
<213> ORGANISM: Oryza sativa

<400> SEQUENCE: 38

Met Ala Ser Pro Ser Ser Arg Ala Val Ala Val Gly Gly Ala Leu Leu
1               5                   10                  15

Leu Leu Leu Val Phe Ala Val Pro Thr Thr Phe Leu Tyr Leu Thr Ser
            20                  25                  30

```
Ala Pro Ala Ala Ser Ser Pro Ser Leu Leu Leu Asn Leu Lys Pro Phe
            35                  40                  45

Gly Ala Arg Cys Ala Pro Ala Ala Ala Ala Pro Pro Leu Arg Val
 50                  55                  60

Phe Met Tyr Asp Leu Pro Arg Arg Phe His Val Gly Met Met Asp Ala
 65                  70                  75                  80

Ser Ala Ser Gly Phe Pro Ala Trp Pro Pro Ser Ala Gly Gly Ile Arg
                 85                  90                  95

Arg Gln His Ser Val Glu Tyr Trp Met Met Ala Ser Leu Gln Gly Gly
                100                 105                 110

Gly Gly Gly Asn Gly Ser Ser Glu Glu Gly Arg Glu Ala Val
            115                 120                 125

Arg Val Thr Asp Pro Asp Ala Ala Glu Ala Phe Phe Val Pro Phe Phe
            130                 135                 140

Ser Ser Leu Ser Phe Asn Val His Gly Arg Asn Met Thr Asp Pro Glu
145                 150                 155                 160

Thr Glu Ala Asp Arg Leu Leu Gln Val Glu Leu Met Glu Ile Leu Trp
                165                 170                 175

Lys Ser Lys Tyr Trp Gln Arg Ser Ala Gly Arg Asp His Val Ile Pro
                180                 185                 190

Met His His Pro Asn Ala Phe Arg Phe Leu Arg Asp Met Val Asn Ala
            195                 200                 205

Ser Ile Leu Ile Val Ala Asp Phe Gly Arg Tyr Thr Lys Glu Leu Ala
            210                 215                 220

Ser Leu Arg Lys Asp Val Ala Pro Tyr Val His Val Val Asp Ser
225                 230                 235                 240

Phe Leu Asn Asp Asp Pro Pro Asp Pro Phe Asp Asp Arg Pro Thr Leu
                245                 250                 255

Leu Phe Phe Arg Gly Arg Thr Val Arg Lys Asp Glu Gly Lys Ile Arg
            260                 265                 270

Ala Lys Leu Ala Lys Ile Leu Lys Gly Lys Asp Gly Val Arg Phe Glu
            275                 280                 285

Asp Ser Leu Ala Thr Gly Glu Gly Ile Lys Thr Ser Thr Glu Gly Met
            290                 295                 300

Arg Ser Ser Lys Phe Cys Leu His Pro Ala Gly Asp Thr Pro Ser Ser
305                 310                 315                 320

Cys Arg Leu Phe Asp Ala Ile Val Ser His Cys Val Pro Val Ile Val
                325                 330                 335

Ser Ser Arg Ile Glu Leu Pro Phe Glu Asp Glu Ile Asp Tyr Ser Glu
            340                 345                 350

Phe Ser Leu Phe Phe Ser Val Glu Glu Ala Leu Arg Pro Asp Tyr Leu
            355                 360                 365

Leu Asn Gln Leu Arg Gln Ile Gln Lys Thr Lys Trp Val Glu Ile Trp
            370                 375                 380

Ser Lys Leu Lys Asn Val Ser His His Tyr Glu Phe Gln Asn Pro Pro
385                 390                 395                 400

Arg Lys Gly Asp Ala Val Asn Met Ile Trp Arg Gln Val Lys His Lys
                405                 410                 415

Val Pro Ala Val Asn Leu Ala Ile His Arg Asn Arg Arg Leu Lys Ile
            420                 425                 430

Pro Asp Trp Trp Gly
            435
```

<210> SEQ ID NO 39
<211> LENGTH: 29
<212> TYPE: DNA
<213> ORGANISM: artificial sequence
<220> FEATURE:
<223> OTHER INFORMATION: primer

<400> SEQUENCE: 39
ggggacaagt ttgtacaaaa aagcaggct                              29

<210> SEQ ID NO 40
<211> LENGTH: 29
<212> TYPE: DNA
<213> ORGANISM: artificial sequence
<220> FEATURE:
<223> OTHER INFORMATION: primer

<400> SEQUENCE: 40
ggggaccact ttgtacaaga aagctgggt                              29

<210> SEQ ID NO 41
<211> LENGTH: 54
<212> TYPE: DNA
<213> ORGANISM: artificial sequence
<220> FEATURE:
<223> OTHER INFORMATION: primer

<400> SEQUENCE: 41
ttaaacaagt ttgtacaaaa aagcaggctg caattaaccc tcactaaagg gaac    54

<210> SEQ ID NO 42
<211> LENGTH: 53
<212> TYPE: DNA
<213> ORGANISM: artificial sequence
<220> FEATURE:
<223> OTHER INFORMATION: primer

<400> SEQUENCE: 42
ttaaaccact ttgtacaaga aagctgggtg cgtaatacga ctcactatag ggc     53

<210> SEQ ID NO 43
<211> LENGTH: 12856
<212> TYPE: DNA
<213> ORGANISM: artificial sequence
<220> FEATURE:
<223> OTHER INFORMATION: vector

<400> SEQUENCE: 43
cgccttggcg cgccgatcat ccacaagttt gtacaaaaaa gctgaacgag aaacgtaaaa    60
tgatataaat atcaatatat taaattagat tttgcataaa aaacagacta cataatactg   120
taaaacacaa catatccagt cactatggcg gccgcattag gcaccccagg ctttacactt   180
tatgcttccg gctcgtataa tgtgtggatt ttgagttagg atttaaatac gcgttgatcc   240
ggcttactaa aagccagata acagtatgcg tatttgcgcg ctgattttg cggtataaga    300 atatatactg atatgtatac ccgaagtatg tcaaaaagag gtatgctatg aagcagcgta   360
ttacagtgac agttgacagc gacagctatc agttgctcaa gcatatatg atgtcaatat    420 ctccggtctg gtaagcacaa ccatgcagaa tgaagcccgt cgtctgcgtg ccgaacgctg   480
gaaagcggaa atcaggaag ggatggctga ggtcgcccgg tttattgaaa tgaacggctc    540
ttttgctgac gagaacaggg gctggtgaaa tgcagtttaa ggtttacacc tataaaagag   600
agagccgtta tcgtctgttt gtggatgtac agagtgatat cattgacacg cccggtcgac   660

-continued

```
ggatggtgat cccctggcc agtgcacgtc tgctgtcaga taaagtctcc cgtgaacttt    720
acccggtggt gcatatcggg gatgaaagct ggcgcatgat gaccaccgat atggccagtg    780
tgccggtctc cgttatcggg gaagaagtgg ctgatctcag ccaccgcgaa atgacatca    840 aaaacgccat taacctgatg ttctgggaa tataaatgtc aggctccctt atacacagcc    900
agtctgcagg tcgaccatag tgactggata tgttgtgttt tacagtatta tgtagtctgt    960
tttttatgca aaatctaatt taatatattg atatttatat cattttacgt ttctcgttca   1020
gctttcttgt acaaagtggt gttaacctag acttgtccat cttctggatt ggccaactta   1080
attaatgtat gaaataaaag gatgcacaca tagtgacatg ctaatcacta taatgtgggc   1140
atcaaagttg tgtgttatgt gtaattacta gttatctgaa taaaagagaa agagatcatc   1200
catatttctt atcctaaatg aatgtcacgt gtctttataa ttctttgatg aaccagatgc   1260
atttcattaa ccaaatccat atacatataa atattaatca tatataatta atatcaattg   1320
ggttagcaaa acaaatctag tctaggtgtg ttttgcgaat tgcggccgcc accgcggtgg   1380
agctcgaatt ccggtccggg tcacctttgt ccaccaagat ggaactgcgg ccgctcatta   1440
attaagtcag gcgcgcctct agttgaagac acgttcatgt cttcatcgta agaagacact   1500
cagtagtctt cggccagaat ggccatctgg attcagcagg cctagaaggc catttaaatc   1560
ctgaggatct ggtcttccta aggacccggg atatcggacc gattaaactt taattcggtc   1620
cgaagcttga agttcctatt ccgaagttcc tattctccag aaagtatagg aacttcgcat   1680
gcctgcagtg cagcgtgacc cggtcgtgcc cctctctaga gataatgagc attgcatgtc   1740
taagttataa aaaattacca catatttttt ttgtcacact tgtttgaagt gcagtttatc   1800
tatctttata catatattta aactttactc tacgaataat ataatctata gtactacaat   1860
aatatcagtg ttttagagaa tcatataaat gaacagttag acatggtcta aaggacaatt   1920
gagtattttg acaacaggac tctacagttt tatctttta gtgtgcatgt gttctccttt   1980 tttttttgcaa atagcttcac ctatataata cttcatccat tttattagta catccattta   2040
gggtttaggg ttaatggttt ttatagacta attttttag tacatctatt ttattctatt   2100
ttagcctcta aattaagaaa actaaaactc tattttagtt tttttattta ataatttaga   2160
tataaaatag aataaaataa agtgactaaa aattaaacaa ataccctta agaaattaaa   2220 aaaactaagg aaacattttt cttgtttcga gtagataatg ccagcctgtt aaacgccgtc   2280
gacgagtcta acggacacca accagcgaac cagcagcgtc gcgtcgggcc aagcgaagca   2340
gacggcacgg catctctgtc gctgcctctg gaccctctc gagagttccg ctccaccgtt   2400
ggacttgctc cgctgtcggc atccagaaat tgcgtggcgg agcggcagac gtgagccggc   2460
acggcaggcg gcctcctcct cctctcacgg caccggcagc tacgggggat tcctttccca   2520
ccgctccttc gctttccctt cctcgcccgc cgtaataaat agacaccccc tccacaccct   2580
cttttcccca cctcgtgttg ttcggagcgc acacacacac aaccagatct ccccaaatc   2640 cacccgtcgg cacctccgct tcaaggtacg ccgctcgtcc tccccccccc ccctctctac   2700
cttctctaga tcggcgttcc ggtccatgca tggttagggc ccggtagttc tacttctgtt   2760
catgtttgtg ttagatccgt gtttgtgtta gatccgtgct gctagcgttc gtacacggat   2820
gcgacctgta cgtcagacac gttctgattg ctaacttgcc agtgtttctc tttggggaat   2880
cctgggatgg ctctagccgt tccgcagacg ggatcgattt catgattttt tttgtttcgt   2940
tgcatagggt ttggtttgcc cttttccttt atttcaatat atgccgtgca cttgtttgtc   3000
```

```
gggtcatctt ttcatgcttt tttttgtctt ggttgtgatg atgtggtctg gttgggcggt    3060
cgttctagat cggagtagaa ttctgtttca aactacctgg tggatttatt aattttggat    3120
ctgtatgtgt gtgccataca tattcatagt tacgaattga agatgatgga tggaaatatc    3180
gatctaggat aggtatacat gttgatgcgg gttttactga tgcatataca gagatgcttt    3240
ttgttcgctt ggttgtgatg atgtggtgtg gttgggcggt cgttcattcg ttctagatcg    3300
gagtagaata ctgtttcaaa ctacctggtg tatttattaa ttttggaact gtatgtgtgt    3360
gtcatacatc ttcatagtta cgagtttaag atggatggaa atatcgatct aggataggta    3420
tacatgttga tgtgggtttt actgatgcat atacatgatg gcatatgcag catctattca    3480
tatgctctaa ccttgagtac ctatctatta aataaacaa gtatgtttta taattatttt    3540
gatcttgata tacttggatg atggcatatg cagcagctat atgtggattt ttttagccct    3600
gccttcatac gctatttatt tgcttggtac tgtttctttt gtcgatgctc accctgttgt    3660
ttggtgttac ttctgcaggt cgactttaac ttagcctagg atccacacga caccatgata    3720
gaggtgaaac cgattaacgc agaggatacc tatgaactaa ggcatagaat actcagacca    3780
aaccagccga tagaagcgtg tatgtttgaa agcgatttac ttcgtggtgc atttcactta    3840
ggcggctatt acggggcaa actgatttcc atagcttcat tccaccaggc cgagcactca    3900
gaactccaag gccagaaaca gtaccagctc cgaggtatgg ctaccttgga aggttatcgt    3960
gagcagaagg cgggatcgag tctaattaaa cacgctgaag aaattcttcg taagaggggg    4020
gcggacttgc tttggtgtaa tgcgcggaca tccgcctcag gctactacaa aaagttaggc    4080
ttcagcgagc agggagaggt attcgacacg ccgccagtag gacctcacat cctgatgtat    4140
aaaaggatca cataactagc tagtcagtta acctagactt gtccatcttc tggattggcc    4200
aacttaatta atgtatgaaa taaaaggatg cacacatagt gacatgctaa tcactataat    4260
gtgggcatca aagttgtgtg ttatgtgtaa ttactagtta tctgaataaa agagaaagag    4320
atcatccata tttcttatcc taaatgaatg tcacgtgtct ttataattct ttgatgaacc    4380
agatgcattt cattaaccaa atccatatac atataaatat taatcatata taattaatat    4440
caattgggtt agcaaaacaa atctagtcta ggtgtgtttt gcgaattcag agctcgaatt    4500
cattccgatt aatcgtggcc tcttgctctt caggatgaag agctatgttt aaacgtgcaa    4560
gcgctactag acaattcagt acattaaaaa cgtccgcaat gtgttattaa gttgtctaag    4620
cgtcaatttg tttacaccac aatatatcct gccaccagcc agccaacagc tccccgaccg    4680
gcagctcggc acaaaatcac cactcgatac aggcagccca tcagtccggg acggcgtcag    4740
cgggagagcc gttgtaaggc ggcagacttt gctcatgtta ccgatgctat tcggaagaac    4800
ggcaactaag ctgccgggtt tgaaacacgg atgatctcgc ggagggtagc atgttgattg    4860
taacgatgac agagcgttgc tgcctgtgat caaatatcat ctccctcgca gagatccgaa    4920
ttatcagcct tcttattcat ttctcgctta accgtgacag gctgtcgatc ttgagaacta    4980
tgccgacata ataggaaatc gctggataaa gccgctgagg aagctgagtg gcgctatttc    5040
tttagaagtg aacgttgacg atcgtcgacc gtaccccgat gaattaattc ggacgtacgt    5100
tctgaacaca gctggatact tacttgggcg attgtcatac atgacatcaa caatgtaccc    5160
gtttgtgtaa ccgtctcttg gaggttcgta tgacactagt ggttcccctc agcttgcgac    5220
tagatgttga ggcctaacat tttattagag agcaggctag ttgcttagat acatgatctt    5280
caggccgtta tctgtcaggg caagcgaaaa ttggccattt atgacgacca atgccccgca    5340
gaagctccca tctttgccgc catagacgcc gcgcccccct tttggggtgt agaacatcct    5400
```

-continued

| | |
|---|---|
| tttgccagat gtggaaaaga agttcgttgt cccattgttg gcaatgacgt agtagccggc | 5460 |
| gaaagtgcga gacccatttg cgctatatat aagcctacga tttccgttgc gactattgtc | 5520 |
| gtaattggat gaactattat cgtagttgct ctcagagttg tcgtaatttg atggactatt | 5580 |
| gtcgtaattg cttatggagt tgtcgtagtt gcttggagaa atgtcgtagt tggatgggga | 5640 |
| gtagtcatag ggaagacgag cttcatccac taaaacaatt ggcaggtcag caagtgcctg | 5700 |
| ccccgatgcc atcgcaagta cgaggcttag aaccaccttc aacagatcgc gcatagtctt | 5760 |
| ccccagctct ctaacgcttg agttaagccg cgccgcgaag cggcgtcggc ttgaacgaat | 5820 |
| tgttagacat tatttgccga ctaccttggt gatctcgcct ttcacgtagt gaacaaattc | 5880 |
| ttccaactga tctgcgcgcg aggccaagcg atcttcttgt ccaagataag cctgcctagc | 5940 |
| ttcaagtatg acgggctgat actgggccgg caggcgctcc attgcccagt cggcagcgac | 6000 |
| atccttcggc gcgattttgc cggttactgc gctgtaccaa atgcgggaca acgtaagcac | 6060 |
| tacatttcgc tcatcgccag cccagtcggg cggcgagttc catagcgtta aggtttcatt | 6120 |
| tagcgcctca aatagatcct gttcaggaac cggatcaaag agttcctccg ccgctggacc | 6180 |
| taccaaggca acgctatgtt ctcttgcttt tgtcagcaag atagccagat caatgtcgat | 6240 |
| cgtggctggc tcgaagatac ctgcaagaat gtcattgcgc tgccattctc caaattgcag | 6300 |
| ttcgcgctta gctggataac gccacggaat gatgtcgtcg tgcacaacaa tggtgacttc | 6360 |
| tacagcgcgg agaatctcgc tctctccagg ggaagccgaa gtttccaaaa ggtcgttgat | 6420 |
| caaagctcgc cgcgttgttt catcaagcct tacagtcacc gtaaccagca aatcaatatc | 6480 |
| actgtgtggc ttcaggccgc catccactgc ggagccgtac aaatgtacgg ccagcaacgt | 6540 |
| cggttcgaga tggcgctcga tgacgccaac tacctctgat agttgagtcg atacttcggc | 6600 |
| gatcaccgct tccctcatga tgtttaactc ctgaattaag ccgcgccgcg aagcggtgtc | 6660 |
| ggcttgaatg aattgttagg cgtcatcctg tgctcccgag aaccagtacc agtacatcgc | 6720 |
| tgtttcgttc gagacttgag gtctagtttt atacgtgaac aggtcaatgc cgccgagagt | 6780 |
| aaagccacat tttgcgtaca aattgcaggc aggtacattg ttcgtttgtg tctctaatcg | 6840 |
| tatgccaagg agctgtctgc ttagtgccca cttttttcgca aattcgatga gactgtgcgc | 6900 |
| gactcctttg cctcggtgcg tgtgcgacac aacaatgtgt tcgatagagg ctagatcgtt | 6960 |
| ccatgttgag ttgagttcaa tcttcccgac aagctcttgg tcgatgaatg cgccatagca | 7020 |
| agcagagtct tcatcagagt catcatccga gatgtaatcc ttccggtagg ggctcacact | 7080 |
| tctggtagat agttcaaagc cttggtcgga taggtgcaca tcgaacactt cacgaacaat | 7140 |
| gaaatggttc tcagcatcca atgtttccgc cacctgctca gggatcaccg aaatcttcat | 7200 |
| atgacgccta acgcctggca cagcggatcg caaacctggc gcggcttttg cacaaaaagg | 7260 |
| cgtgacaggt ttgcgaatcc gttgctgcca cttgttaacc cttttgccag atttggtaac | 7320 |
| tataatttat gttagaggcg aagtcttggg taaaaactgg cctaaaattg ctggggattt | 7380 |
| caggaaagta aacatcacct tccggctcga tgtctattgt agatatatgt agtgtatcta | 7440 |
| cttgatcggg ggatctgctg cctcgcgcgt ttcggtgatg acggtgaaaa cctctgacac | 7500 |
| atgcagctcc cggagacggt cacagcttgt ctgtaagcgg atgccgggag cagacaagcc | 7560 |
| cgtcagggcg cgtcagcggg tgttggcggg tgtcggggcg cagccatgac ccagtcacgt | 7620 |
| agcgatagcg gagtgtatac tggcttaact atgcggcatc agagcagatt gtactgagag | 7680 |
| tgcaccatat gcggtgtgaa ataccgcaca gatgcgtaag gagaaaatac cgcatcaggc | 7740 |

```
gctcttccgc ttcctcgctc actgactcgc tgcgctcggt cgttcggctg cggcgagcgg   7800
tatcagctca ctcaaaggcg gtaatacggt tatccacaga atcaggggat aacgcaggaa   7860
agaacatgtg agcaaaaggc cagcaaaagg ccaggaaccg taaaaaggcc gcgttgctgg   7920
cgttttccca taggctccgc ccccctgacg agcatcacaa aaatcgacgc tcaagtcaga   7980
ggtggcgaaa cccgacagga ctataaagat accaggcgtt tcccctgga agctccctcg   8040
tgcgctctcc tgttccgacc ctgccgctta ccggatacct gtccgccttt ctcccttcgg   8100
gaagcgtggc gctttctcat agctcacgct gtaggtatct cagttcggtg taggtcgttc   8160
gctccaagct gggctgtgtg cacgaacccc ccgttcagcc cgaccgctgc gccttatccg   8220
gtaactatcg tcttgagtcc aacccggtaa gacacgactt atcgccactg gcagcagcca   8280
ctggtaacag gattagcaga gcgaggtatg taggcggtgc tacagagttc ttgaagtggt   8340
ggcctaacta cggctacact agaaggacag tatttggtat ctgcgctctg ctgaagccag   8400
ttaccttcgg aaaaagagtt ggtagctctt gatccggcaa acaaaccacc gctggtagcg   8460
gtggtttttt tgtttgcaag cagcagatta cgcgcagaaa aaaaggatct caagaagatc   8520
ctttgatctt ttctacgggg tctgacgctc agtggaacga aaactcacgt taagggattt   8580
tggtcatgag attatcaaaa aggatcttca cctagatcct tttaaattaa aaatgaagtt   8640
ttaaatcaat ctaaagtata tatgagtaaa cttggtctga cagttaccaa tgcttaatca   8700
gtgaggcacc tatctcagcg atctgtctat ttcgttcatc catagttgcc tgactccccg   8760
tcgtgtagat aactacgata cgggagggct taccatctgg ccccagtgct gcaatgatac   8820
cgcgagaccc acgctcaccg gctccagatt tatcagcaat aaaccagcca gccggaaggg   8880
ccgagcgcag aagtggtcct gcaactttat ccgcctccat ccagtctatt aattgttgcc   8940
gggaagctag agtaagtagt tcgccagtta atagtttgcg caacgttgtt gccattgctg   9000
caggggggg gggggggggg gacttccatt gttcattcca cggacaaaaa cagagaaagg   9060
aaacgacaga ggccaaaaag cctcgctttc agcacctgtc gtttcctttc ttttcagagg   9120
gtatttaaaa taaaaacatt aagttatgac gaagaagaac ggaaacgcct taaaccggaa   9180
aattttcata aatagcgaaa acccgcgagg tcgccgcccc gtaacctgtc ggatcaccgg   9240
aaaggacccg taaagtgata atgattatca tctacatatc acaacgtgcg tggaggccat   9300
caaaccacgt caaataatca attatgacgc aggtatcgta ttaattgatc tgcatcaact   9360
taacgtaaaa acaacttcag acaatacaaa tcagcgacac tgaatacggg gcaacctcat   9420
gtcccccccc ccccccccc tgcaggcatc gtggtgtcac gctcgtcgtt tggtatggct   9480
tcattcagct ccggttccca acgatcaagg cgagttacat gatccccat gttgtgcaaa   9540
aaagcggtta gctccttcgg tcctccgatc gttgtcagaa gtaagttggc cgcagtgtta   9600
tcactcatgg ttatggcagc actgcataat tctcttactg tcatgccatc cgtaagatgc   9660
ttttctgtga ctggtgagta ctcaaccaag tcattctgag aatagtgtat gcggcgaccg   9720
agttgctctt gcccggcgtc aacacgggat aataccgcgc cacatagcag aactttaaaa   9780
gtgctcatca ttggaaaacg ttcttcgggg cgaaaactct caaggatctt accgctgttg   9840
agatccagtt cgatgtaacc cactcgtgca cccaactgat cttcagcatc ttttactttc   9900
accagcgttt ctgggtgagc aaaaacagga aggcaaaatg ccgcaaaaaa gggaataagg   9960
gcgacacgga aatgttgaat actcatactc ttcctttttc aatattattg aagcatttat   10020
cagggttatt gtctcatgag cggatacata tttgaatgta tttagaaaaa taaacaaata  10080
ggggttccgc gcacatttcc ccgaaaagtg ccacctgacg tctaagaaac cattattatc   10140
```

```
atgacattaa cctataaaaa taggcgtatc acgaggccct ttcgtcttca agaattggtc    10200
gacgatcttg ctgcgttcgg atattttcgt ggagttcccg ccacagaccc ggattgaagg    10260
cgagatccag caactcgcgc cagatcatcc tgtgacggaa ctttggcgcg tgatgactgg    10320
ccaggacgtc ggccgaaaga gcgacaagca gatcacgctt ttcgacagcg tcggatttgc    10380
gatcgaggat ttttcggcgc tgcgctacgt ccgcgaccgc gttgagggat caagccacag    10440
cagcccactc gaccttctag ccgacccaga cgagccaagg gatcttttg gaatgctgct     10500 ccgtcgtcag gctttccgac gtttgggtgg ttgaacagaa gtcattatcg tacggaatgc    10560
caagcactcc cgaggggaac cctgtggttg gcatgcacat acaaatggac gaacggataa    10620
accttttcac gcccttttaa atatccgtta ttctaataaa cgctctttc tcttaggttt      10680 acccgccaat atatcctgtc aaacactgat agtttaaact gaaggcggga aacgacaatc    10740
tgatcatgag cggagaatta agggagtcac gttatgaccc ccgccgatga cgcgggacaa    10800
gccgttttac gtttggaact gacagaaccg caacgttgaa ggagccactc agcaagctgg    10860
tacgattgta atacgactca ctatagggcg aattgagcgc tgtttaaacg ctcttcaact    10920
ggaagagcgg ttacccggac cgaagcttga agttcctatt ccgaagttcc tattctctag    10980
aaagtatagg aacttcagat ctcgatgctc accctgttgt ttggtgttac ttctgcaggt    11040
cgactctaga ggatccacca tgagcccaga acgacgcccg ccgcatatcc gccgtgccac    11100
cgaggcggac atgccggcgg tctgcaccat cgtcaaccac tacatcgaga caagcacggt    11160
caacttccgt accgagccgc aggaaccgca ggactgacg gacgacctcg tccgtctgcg     11220
ggagcgctat ccctggctcg tcgccgaggt ggacggcgag gtcgccggca tcgcctacgc    11280
gggcccctgg aaggcacgca acgcctacga ctggacggcc gagtcgaccg tgtacgtctc    11340
cccccgccac cagcggacgg gactgggctc cacgctctac acccacctgc tgaagtccct    11400
ggaggcacag ggcttcaaga gcgtggtcgc tgtcatcggg ctgcccaacg acccgagcgt    11460
gcgcatgcac gaggcgctcg gatatgcccc ccgcggcatg ctgcgggcgg ccggcttcaa    11520
gcacgggaac tggcatgacg tgggtttctg gcagctggac ttcagcctgc cggtaccgcc    11580
ccgtccggtc ctgcccgtca ccgagatctg atccgtcgac caacctagac ttgtccatct    11640
tctggattgg ccaacttaat taatgtatga aataaaagga tgcacacata gtgacatgct    11700
aatcactata atgtgggcat caaagttgtg tgttatgtgt aattactagt tatctgaata    11760
aaagagaaag agatcatcca tatttcttat cctaaatgaa tgtcacgtgt ctttataatt    11820
ctttgatgaa ccagatgcat ttcattaacc aaatccatat acatataaat attaatcata    11880
tataattaat atcaattggg ttagcaaaac aaatctagtc taggtgtgtt ttgcgaattg    11940
cggccgcgat ctgggaatt cccatggaca ccggtaattc ccatgatctt ctctccttca     12000
tcaatggatg ccatgtttca taacaataac accaaatgtt tgatgagcta ccaacaattg    12060
cgcaaagact atggctaagc tcgagctcgc tcgctacaag ttgttgactt tcaaatacaa    12120
gtttgttttt ggaacaccaa atattctaca tgatctttca ctaagttgcg caccactatc    12180
aaaagattat ctaggccatt attcaagtaa agagtgaaca cgtctaagac ccacaaccac    12240
accaaataga atacgcatac atgcaacata ttgtgcaaga agtatccaac tggactccca    12300
tgtattctaa aactattttc gtagagttaa agttatgaca aacttatcaa ataaaatttt    12360
gaacgctgga ccaaaacttt catctttcaa atccaccatc gtctatcctc ataaattgtt    12420
ttgattataa cacatctacg taaatcattt gttttgaaca atactaattt aattttatta    12480
```

| | |
|---|---|
| agtcaaataa cctgcttaga aaataatccc tccacctcat ttaacaattt cttgtcaaac | 12540 |
| acacaccaag aaaaaaatta atgaaagaga aagaaatga aaaggacatg gagttgaata | 12600 |
| ctagcaaaat tgattgaagg aagattcaca attgaaattg aaaccattta atttatttc | 12660 |
| gggtccataa taataaattg gtaagaataa aaacccgatc aagtccggta cagtacaatt | 12720 |
| ccactccacc aactccttac ttaaacccct atttataccc actctcatcc tcactcttcc | 12780 |
| ttcacctctc acactctctt ctctctctca aaaccctcac acaaacgctg cgtttagtgt | 12840 |
| aagaaattca atccgg | 12856 |

<210> SEQ ID NO 44
<211> LENGTH: 825
<212> TYPE: DNA
<213> ORGANISM: Zea mays

<400> SEQUENCE: 44

| | |
|---|---|
| aaatccttac agaattgctg tagtttcata gtgctagatg tggacagcaa agcgccgctg | 60 |
| tatgcttctg cttttctttt ttggtgtgtg tagccacatc ctttgttcct gcccggcgcc | 120 |
| atcccacttg gttgttttt tttatgattg aaagccttca tgcttcctcg gtcaatcacc | 180 |
| ggtgcgcact gggagcatcg ccggaaaaaa aattcttcgg ctaagagtaa cttctttctc | 240 |
| cttttcttct ctgatctcgc gagcagtgct gataacgtgt tgtaatctac ttagcggtaa | 300 |
| cgagattgag agagacaaaa tgacagaact attgtctttt tgcagagtg tcatgtattt | 360 |
| atacagggga tacaaagtct cccaaggggt gtgtcccttg ggagtaactg ccagttgatc | 420 |
| acaggacaat attttgtaac aaaacgtaca catcgtcaaa atagcgaggc atgaaactgg | 480 |
| ccttggccat ggacgcgtga agcgcgccat gcgttggata tgtggtcaat aagtatatac | 540 |
| aatcaatgt ttaacagagc tgatagtact gctttggcac attttttgtcc acgcttcatg | 600 |
| agagataaaa cacctgcacg taaattcaca tgctgcactg aaggcccgat cactgaggag | 660 |
| cgaactgccg taactccctt ctatatatac ccccagtccc tgtttcagtt ttcgtcaagc | 720 |
| tagcagcacc aagttgtcga tcacttgcct gctcttgagc tcgattaagc tatcatcagc | 780 |
| tacagcatcc gatcccaaac tgcaactgta gcagcgacaa ctgcc | 825 |

<210> SEQ ID NO 45
<211> LENGTH: 860
<212> TYPE: DNA
<213> ORGANISM: Zea mays

<400> SEQUENCE: 45

| | |
|---|---|
| ctggtaatta ttggctgtag gattctaaac agagcctaaa tagctggaat agctctagcc | 60 |
| ctcaatccaa actatgata tctatactta tgcaactcta aattttatt ctaaaagtaa | 120 |
| tatttcattt ttgtcaacga gattctctac tctattccac aatcttttga agcaatattt | 180 |
| accttaaatc tgtactctat accaataatc atatattcta ttatttattt ttatctctct | 240 |
| cctaaggagc atcccctat gtctgcatgg ccccgcctc gggtcccaat ctcttgctct | 300 |
| gctagtagca cagaagaaaa cactagaaat gacttgcttg acttagagta tcagataaac | 360 |
| atcatgttta cttaactta atttgtatcg gtttctacta tttttataat attttttgtct | 420 |
| ctatagatac tacgtgcaac agtataatca acctagttta atccagagcg aaggatttt | 480 |
| tactaagtac gtgactccat atgcacagcg ttcctttat ggttcctcac tgggcacagc | 540 |
| ataaacgaac cctgtccaat gttttcagcg cgaacaaaca gaaattccat cagcgaacaa | 600 |
| acaacataca tgcgagatga aaataaataa taaaaaaagc tccgtctcga taggccggca | 660 |

```
cgaatcgaga gcctccatag ccagttttt  ccatcggaac ggcggttcgc gcacctaatt      720
atatgcacca cacgcctata aagccaacca acccgtcgga ggggcgcaag ccagacagaa      780
gacagcccgt cagcccctct cgttttcat  ccgccttcgc ctccaaccgc gtgcgctcca      840
cgcctcctcc aggaaagcga                                                  860

<210> SEQ ID NO 46
<211> LENGTH: 899
<212> TYPE: DNA
<213> ORGANISM: Zea mays

<400> SEQUENCE: 46
gtgcagcgtg acccggtcgt gcccctctct agagataatg agcattgcat gtctaagtta       60
taaaaaatta ccacatattt ttttttgtcac acttgtttga agtgcagttt atctatcttt     120
atacatatat ttaaactta  ctctacgaat aatataatct atagtactac aataatatca     180 gtgtttaga  gaatcatata aatgaacagt tagacatggt ctaaaggaca attgagtatt     240
ttgacaacag gactctacag ttttatcttt ttagtgtgca tgtgttctcc tttttttttg     300
caaatagctt cacctatata atacttcatc catttttatta gtacatccat ttagggttta    360
gggttaatgg ttttatagga ctaattttt  tagtacatct atttattct  attttagcct     420 ctaaattaag aaaactaaaa ctctatttta gtttttttat ttaataattt agatataaaa     480
tagaataaaa taaagtgact aaaaattaaa caaatacccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggacccct ctcgagagtt ccgctccacc gttggacttg    720
ctccgctgtc ggcatccaga aattgcgtgg cggagcggca gacgtgagcc ggcacggcag    780
gcggcctcct cctcctctca cggcacggca gctacggggg attccttttcc caccgctcct    840 tcgctttccc ttcctcgccc gccgtaataa atagacaccc cctccacacc ctctttccc     899

<210> SEQ ID NO 47
<211> LENGTH: 879
<212> TYPE: DNA
<213> ORGANISM: Medicago sativa

<400> SEQUENCE: 47
aattcccatg atcttctctc cttcatcaat ggatgccatg tttcataaca ataacaccaa       60
atgtttgatg agctaccaac aattgcgcaa agactatggc taagctcgag ctcgctcgct     120
acaagttgtt gactttcaaa tacaagtttg ttttttggaac accaaatatt ctacatgatc     180
tttcactaag ttgcgcacca ctatcaaaag attatctagg ccattattca agtaaagagt     240
gaacacgtct aagacccaca accacaccaa atagaatacg catacatgca acatattgtg     300
caagaagtat ccaactggac tcccatgtat tctaaaacta ttttcgtaga gttaaagtta     360
tgacaaactt atcaaataaa aatttgaacg ctggaccaaa actttcatct ttcaaatcca     420
ccatcgtcta tcctcataaa ttgttttgat tataacacat ctacgtaaat catttgtttt     480
gaacaatact aatttaattt tattaagtca ataaccctgc ttagaaaata atccctccac     540
ctcatttaac aatttcttgt caaacacaca ccaagaaaaa aattaatgaa agagaaaaga    600
aatgaaaagg acatggagtt gaatactagc aaaattgatt gaaggaagat tcacaattga    660
aattgaaacc atttaatta  ttttcgggtc cataataata aattggtaag aataaaaacc     720
```

-continued

```
cgatcaagtc cggtacagta caattccact ccaccaactc cttacttaaa cccctattta    780
tacccactct catcctcact cttccttcac ctctcacact ctcttctctc tctcaaaacc    840
ctcacacaaa cgctgcgttt agtgtaagaa attcaatcc                           879

<210> SEQ ID NO 48
<211> LENGTH: 318
<212> TYPE: DNA
<213> ORGANISM: Solanum tuberosum

<400> SEQUENCE: 48
agacttgtcc atcttctgga ttggccaact taattaatgt atgaaataaa aggatgcaca     60
catagtgaca tgctaatcac tataatgtgg gcatcaaagt tgtgtgttat gtgtaattac    120
tagttatctg aataaaagag aaagagatca tccatatttc ttatcctaaa tgaatgtcac    180
gtgtctttat aattctttga tgaaccagat gcatttcatt aaccaaatcc atatacatat    240
aaatattaat catatataat taatatcaat tgggttagca aaacaaatct agtctaggtg    300
tgttttgcga attgcggc                                                  318

<210> SEQ ID NO 49
<211> LENGTH: 707
<212> TYPE: PRT
<213> ORGANISM: Artificial Sequence
<220> FEATURE:
<223> OTHER INFORMATION: Consensus Sequence from FIG. 15A - FIG. 15I
<220> FEATURE:
<221> NAME/KEY: misc_feature
<222> LOCATION: (4)..(73)
<223> OTHER INFORMATION: Xaa can be any naturally occurring amino acid
<220> FEATURE:
<221> NAME/KEY: misc_feature
<222> LOCATION: (81)..(82)
<223> OTHER INFORMATION: Xaa can be any naturally occurring amino acid
<220> FEATURE:
<221> NAME/KEY: misc_feature
<222> LOCATION: (102)..(111)
<223> OTHER INFORMATION: Xaa can be any naturally occurring amino acid
<220> FEATURE:
<221> NAME/KEY: misc_feature
<222> LOCATION: (139)..(180)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid
<220> FEATURE:
<221> NAME/KEY: misc_feature
<222> LOCATION: (216)..(219)
<223> OTHER INFORMATION: Xaa can be any naturally occurring amino acid
<220> FEATURE:
<221> NAME/KEY: misc_feature
<222> LOCATION: (225)..(225)
<223> OTHER INFORMATION: Xaa can be any naturally occurring amino acid
<220> FEATURE:
<221> NAME/KEY: misc_feature
<222> LOCATION: (229)..(230)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (265)..(270)
<223> OTHER INFORMATION: Xaa can be any naturally occurring amino acid
<220> FEATURE:
<221> NAME/KEY: misc_feature
<222> LOCATION: (307)..(309)
<223> OTHER INFORMATION: Xaa can be any naturally occurring amino acid
<220> FEATURE:
<221> NAME/KEY: misc_feature
```

```
<222> LOCATION: (391)..(391)
<223> OTHER INFORMATION: Xaa can be any naturally occurring amino acid
<220> FEATURE:
<221> NAME/KEY: misc_feature
<222> LOCATION: (396)..(396)
<223> OTHER INFORMATION: Xaa can be any naturally occurring amino acid
<220> FEATURE:
<221> NAME/KEY: misc_feature
<222> LOCATION: (552)..(554)
<223> OTHER INFORMATION: Xaa can be any naturally occurring amino acid
<220> FEATURE:
<221> NAME/KEY: misc_feature
<222> LOCATION: (587)..(634)
<223> OTHER INFORMATION: Xaa can be any naturally occurring amino acid
<220> FEATURE:
<221> NAME/KEY: misc_feature
<222> LOCATION: (636)..(656)
<223> OTHER INFORMATION: Xaa can be any naturally occurring amino acid
<220> FEATURE:
<221> NAME/KEY: misc_feature
<222> LOCATION: (659)..(707)
<223> OTHER INFORMATION: Xaa can be any naturally occurring amino acid

<400> SEQUENCE: 49

Met Ala Ala Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Arg Arg Arg Pro Leu Val Trp
65                  70                  75                  80

Xaa Xaa Val Phe Ala Val Val Ala Leu Leu Phe Phe Phe Ser Trp Tyr
                85                  90                  95

Leu Leu Leu Ser Ser Xaa Xaa Xaa Xaa Xaa Xaa Xaa Xaa Xaa Xaa Ala
            100                 105                 110

Ala Gly Ala Gly Ala Ala Ala Arg Pro Asn Glu Leu Leu Arg Leu Gly
        115                 120                 125

Gly Gly Gly Arg Ala Ser Asp Pro Ala Arg Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Arg Cys Asp Pro Ala Ser Ala Leu Leu Arg Val Phe
            180                 185                 190

Met Tyr Asp Leu Pro Pro Glu Phe His Phe Gly Leu Leu Gly Trp Lys
                195                 200                 205

Pro Pro Gly Xaa Gly Gly Gly Xaa Xaa Xaa Xaa Val Trp Pro Asp Val
        210                 215                 220

Xaa Arg Asp Gly Xaa Xaa Val Pro Arg Tyr Pro Gly Gly Leu Asn Leu
225                 230                 235                 240

Gln His Ser Val Glu Tyr Trp Leu Thr Leu Asp Leu Leu Ala Ser Glu
                245                 250                 255

Xaa Gly Ala Pro Thr Pro Cys Gly Xaa Xaa Xaa Xaa Xaa Xaa Ala Val
            260                 265                 270

Arg Val Thr Asp Ala Ala Asp Ala Asp Val Val Phe Val Pro Phe Phe
        275                 280                 285
```

```
Ala Ser Leu Ser Tyr Asn Arg His Ser Lys Val Val Pro Pro Ala Arg
    290                 295                 300

Gly Ser Xaa Xaa Xaa Glu Asp Arg Ala Leu Gln Glu Glu Leu Val Glu
305                 310                 315                 320

Tyr Leu Ala Ala Arg Pro Glu Trp Arg Arg Ser Gly Gly Arg Asp His
                325                 330                 335

Val Val Val Ala His His Pro Asn Ser Met Leu Asp Ala Arg Tyr Arg
            340                 345                 350

Leu Trp Pro Ala Val Phe Val Leu Ser Asp Phe Gly Arg Tyr Pro Pro
        355                 360                 365

Ser Val Ala Asn Leu Asp Lys Asp Val Ile Ala Pro Tyr Lys His Val
    370                 375                 380

Val Pro Ser Phe Val Asn Xaa Asp Ser Ala Gly Xaa Phe Asp Asp Arg
385                 390                 395                 400

Pro Thr Leu Leu Tyr Phe Gln Gly Ala Ile Tyr Arg Lys Asp Gly Gly
                405                 410                 415

Lys Ile Arg Gln Glu Leu Tyr Tyr Leu Leu Lys Asp Glu Lys Asp Val
            420                 425                 430

His Phe Ser Phe Gly Ser Val Arg Gly Asn Gly Ile Ser Gln Ala Thr
        435                 440                 445

Gln Gly Met Arg Ser Ser Lys Phe Cys Leu Asn Ile Ala Gly Asp Thr
    450                 455                 460

Pro Ser Asn Arg Leu Phe Asp Ala Ile Val Ser His Cys Val Pro
465                 470                 475                 480

Val Ile Ile Ser Asp Asp Ile Glu Leu Pro Phe Glu Asp Val Leu Asp
                485                 490                 495

Tyr Ser Lys Phe Ser Val Phe Val Arg Ser Ser Asp Ala Val Lys Lys
            500                 505                 510

Gly Phe Leu Met Asn Leu Leu Arg Gly Ile Ser Lys Glu Glu Trp Thr
        515                 520                 525

Arg Met Trp Asn Arg Leu Lys Glu Val Glu Lys His Phe Glu Tyr Gln
    530                 535                 540

Tyr Pro Ser Gln Lys Asp Asp Xaa Xaa Xaa Ala Val Gln Met Ile Trp
545                 550                 555                 560

Lys Ala Val Ala Arg Lys Val Pro Ser Ile Arg Leu Lys Ile His Arg
                565                 570                 575

Leu Arg Arg Phe Ser Arg Phe Glu Thr Asn Xaa Xaa Xaa Xaa Xaa
            580                 585                 590

Xaa Xaa Xaa Xaa Xaa Xaa Xaa Xaa Xaa Xaa Xaa Xaa Xaa Xaa Xaa Xaa
        595                 600                 605

Xaa Xaa Xaa Xaa Xaa Xaa Xaa Xaa Xaa Xaa Xaa Xaa Xaa Xaa Xaa Xaa
    610                 615                 620

Xaa Xaa Xaa Xaa Xaa Xaa Xaa Xaa Ser Xaa Xaa Xaa Xaa
625                 630                 635                 640

Xaa Xaa Xaa Xaa Xaa Xaa Xaa Xaa Xaa Xaa Xaa Xaa Xaa Xaa Xaa Xaa
                645                 650                 655

Trp Leu Xaa Xaa Xaa Xaa Xaa Xaa Xaa Xaa Xaa Xaa Xaa
            660                 665                 670

Xaa Xaa Xaa Xaa Xaa Xaa Xaa Xaa Xaa Xaa Xaa Xaa Xaa Xaa Xaa Xaa
        675                 680                 685

Xaa Xaa Xaa Xaa Xaa Xaa Xaa Xaa Xaa Xaa Xaa Xaa Xaa Xaa
    690                 695                 700
```

```
Xaa Xaa Xaa
705
```